US009717749B2

(12) United States Patent
Wilusz et al.

(10) Patent No.: US 9,717,749 B2
(45) Date of Patent: Aug. 1, 2017

(54) PRODUCTION OF STABLE NON-POLYADENYLATED RNAS

(71) Applicant: Massachusetts Institute of Technology, Cambridge, MA (US)

(72) Inventors: Jeremy E. Wilusz, Quincy, MA (US); Phillip A. Sharp, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/436,228

(22) PCT Filed: Oct. 16, 2013

(86) PCT No.: PCT/US2013/065239
§ 371 (c)(1),
(2) Date: Apr. 16, 2015

(87) PCT Pub. No.: WO2014/062801
PCT Pub. Date: Apr. 24, 2014

(65) Prior Publication Data
US 2015/0315574 A1   Nov. 5, 2015

Related U.S. Application Data

(60) Provisional application No. 61/739,153, filed on Dec. 19, 2012, provisional application No. 61/716,764, filed on Oct. 22, 2012, provisional application No. 61/714,697, filed on Oct. 16, 2012.

(51) Int. Cl.
| | |
|---|---|
| *A61K 48/00* | (2006.01) |
| *C12Q 1/68* | (2006.01) |
| *C12N 5/02* | (2006.01) |
| *C07H 21/04* | (2006.01) |
| *A61K 31/7088* | (2006.01) |
| *A61K 31/7105* | (2006.01) |
| *C12N 15/113* | (2010.01) |
| *C12N 15/67* | (2006.01) |

(52) U.S. Cl.
CPC ...... *A61K 31/7088* (2013.01); *A61K 31/7105* (2013.01); *A61K 48/00* (2013.01); *C12N 15/113* (2013.01); *C12N 15/67* (2013.01); *C12N 2310/15* (2013.01); *C12N 2310/3519* (2013.01); *C12N 2320/52* (2013.01)

(58) Field of Classification Search
None
See application file for complete search history.

(56) References Cited

U.S. PATENT DOCUMENTS

| | | |
|---|---|---|
| 6,242,187 B1 | 6/2001 | Capon et al. |
| 2011/0143436 A1 | 6/2011 | Dahl et al. |
| 2012/0142756 A1 | 6/2012 | Guild et al. |

FOREIGN PATENT DOCUMENTS

| | | |
|---|---|---|
| EP | 0 726 319 A2 | 8/1996 |
| WO | WO 2011/071931 A2 | 6/2011 |
| WO | WO 2012/075040 A2 | 6/2012 |
| WO | WO 2012/138453 A1 | 10/2012 |

OTHER PUBLICATIONS

Brown et al., Formation of triple-helical structures by the 3'-end sequences of MALAT1 and MENβ noncoding RNAs. Proc Natl Acad Sci U S A. Nov. 20, 2012;109(47):19202-7. doi: 10.1073/pnas.1217338109. Epub Nov. 5, 2012.
Tycowski et al., Conservation of a triple-helix-forming RNA stability element in noncoding and genomic RNAs of diverse viruses. Cell Rep. Jul. 26, 2012;2(1):26-32. doi:10.1016/j.celrep.2012.05.020. Epub Jul. 5, 2012.
Wilusz et al., A triple helix stabilizes the 3' ends of long noncoding RNAs that lack poly(A) tails. Genes Dev. Nov. 1, 2012;26(21):2392-407. doi: 10.1101/gad.204438.112. Epub Oct. 16, 2012.
[No Author Listed] pSTBlue-1 Vector. Novagen. TB214. 1998.
Gallie et al., RNA pseudoknot domain of tobacco mosaic virus can functionally substitute for a poly(A) tail in plant and animal cells. Genes Dev. Jul. 1990;4(7):1149-57.
Gallie et al., The role of the 3'-untranslated region of non-polyadenylated plant viral mRNAs in regulating translational efficiency. Gene. May 16, 1994;142(2):159-65.
Leathers et al., A phylogenetically conserved sequence within viral 3' untranslated RNA pseudoknots regulates translation. Mol Cell Biol. Sep. 1993;13(9):5331-47.
Pandey et al., The stem-loop structure at the 3' end of histone mRNA is necessary and sufficient for regulation of histone mRNA stability. Mol Cell Biol. Dec. 1987;7(12):4557-9.
Sunwoo et al., epsilon/beta nuclear-retained non-coding RNAs are up-regulated upon muscle differentiation and are essential components of paraspeckles. Genome Res. Mar. 2009;19(3):347-59. doi: 10.1101/gr.087775.108. Epub Dec. 22, 2008.
Tycowski et al., Conservation of a triple-helix-forming RNA stability element in noncoding and genomic RNAs of diverse viruses. Cell Rep. Jul. 26, 2012;2(1):26-32. doi: 10.1016/j.celrep.2012.05.020. Epub Jul. 5, 2012.
Yang et al., ncRNA- and Pc2 methylation-dependent gene relocation between nuclear structures mediates gene activation programs. Cell. Nov. 11, 2011;147(4):773-88. doi: 10.1016/j.cell.2011.08.054. Erratum in: Cell. Oct. 10, 2013;155(2):478.
Bartel, MicroRNAs: target recognition and regulatory functions. Cell. Jan. 23, 2009;136(2):215-33. doi: 10.1016/j.cell.2009.01.002.
Borah et al., A viral nuclear noncoding RNA binds re-localized poly(A) binding protein and is required for late KSHV gene expression. PLoS Pathog. Oct. 2011;7(10):e1002300. doi:10.1371/journal.ppat.1002300. Epub Oct. 13, 2011.
Box et al., Spliceosomal cleavage generates the 3' end of telomerase RNA. Nature. Dec. 18, 2008;456(7224):910-4. doi:10.1038/nature07584. Epub Dec. 3, 2008.

(Continued)

*Primary Examiner* — Doug Schultz
(74) *Attorney, Agent, or Firm* — Wolf, Greenfield & Sacks, P.C.

(57) ABSTRACT

The invention relates in aspects to hybrid RNAs lacking a poly-A tail and nucleic acid vectors for expressing the RNA. The hybrid RNAs in some instances have a 3' terminal stabilizing triple helical structure. Related methods for expressing said RNAs in vivo and in vitro are also disclosed.

21 Claims, 67 Drawing Sheets

(56) References Cited

OTHER PUBLICATIONS

Braun et al., GW182 proteins directly recruit cytoplasmic deadenylase complexes to miRNA targets. Mol Cell. Oct. 7, 2011;44(1):120-33. doi: 10.1016/j.molcel.2011.09.007.
Choi et al., Widespread Rna 3'-end oligouridylation in mammals. RNA. Mar. 2012;18(3):394-401. doi:10.1261/rna.029306.111. Epub Jan. 30, 2012.
Colgan et al., Mechanism and regulation of mRNA polyadenylation. Genes Dev. Nov. 1, 1997;11(21):2755-66.
Das et al., Atomic accuracy in predicting and designing noncanonical RNA structure. Nat Methods. Apr. 2010;7(4):291-4. doi:10.1038/nmeth.1433. Epub Feb. 28, 2010.
Das et al., Automated de novo prediction of native-like RNA tertiary structures. Proc Natl Acad Sci U S A. Sep. 11, 2007;104(37):14664-9. Epub Aug. 28, 2007.
Eibmann et al., Loss of the abundant nuclear non-coding Rna MALAT1 is compatible with life and development. RNA Biol. Aug. 2012;9(8):1076-87. doi: 10.4161/rna.21089. Epub Aug. 1, 2012.
Felsenfeld et al., Formation Of A Three-Stranded Polynucleotide Molecule. J. Am. Chem. So.c 1957;79(8):2023-2024.
Fukaya et al., PABP is not essential for microRNA-mediated translational repression and deadenylation in vitro. EMBO J. Nov. 25, 2011;30(24):4998-5009. doi: 10.1038/emboj.2011.426.
Kudla et al., High guanine and cytosine content increases mRNA levels in mammalian cells. PLoS Biol. Jun. 2006;4(6):e180. Epub May 23, 2006.
Li et al., Methylation protects miRNAs and siRNAs from a 3'-end uridylation activity in Arabidopsis. Curr Biol. Aug. 23, 2005;15(16):1501-7.
Lutz et al., Alternative mRNA polyadenylation in eukaryotes: an effective regulator of gene expression. Wiley Interdiscip Rev RNA. Jan.-Feb. 2011;2(1):23-31. doi: 10.1002/wrna.47.
Marzluff et al., Metabolism and regulation of canonical histone mRNAs: life without a poly(A) tail. Nat Rev Genet. Nov. 2008;9(11):843-54. doi: 10.1038/nrg2438.
Mishima et al., Translational inhibition by deadenylation-independent mechanisms is central to microRNA-mediated silencing in zebrafish. Proc Natl Acad Sci U S A. Jan. 24, 2012;109(4):1104-9. doi: 10.1073/pnas.1113350109. Epub Jan. 9, 2012.
Mitton-Fry et al., Poly(A) tail recognition by a viral RNA element through assembly of a triple helix. Science. Nov. 26, 2010;330(6008):1244-7. doi: 10.1126/science.1195858.
Miyagawa et al., Identification of cis- and trans-acting factors involved in the localization of MALAT-1 noncoding RNA to nuclear speckles. RNA. Apr. 2012;18(4):738-51. doi: 10.1261/rna.028639.111. Epub Feb. 21, 2012.
Moore et al., Accurate cleavage and polyadenylation of exogenous RNA substrate. Cell. Jul. 1985;41(3):845-55.
Moretti et al., PABP and the poly(A) tail augment microRNA repression by facilitated miRISC binding. Nat Struct Mol Biol. May 27, 2012;19(6):603-8. doi: 10.1038/nsmb.2309.
Mukherji et al., MicroRNAs can generate thresholds in target gene expression. Nat Genet. Aug. 21, 2011;43(9):854-9. doi: 10.1038/ng.905.
Mullen et al., Degradation of histone mRNA requires oligouridylation followed by decapping and simultaneous degradation of the mRNA both 5' to 3' and 3' to 5'. Genes Dev. Jan. 1, 2008;22(1):50-65. doi: 10.1101/gad.1622708.
Proudfoot, New perspectives on connecting messenger RNA 3' end formation to transcription. Curr Opin Cell Biol. Jun. 2004;16(3):272-8.
Rissland et al., Decapping is preceded by 3' uridylation in a novel pathway of bulk mRNA turnover. Nat Struct Mol Biol. Jun. 2009;16(6):616-23. doi:10.1038/nsmb.1601. Epub May 10, 2009.
Sachs et al., A single domain of yeast poly(A)-binding protein is necessary and sufficient for RNA binding and cell viability. Mol Cell Biol. Sep. 1987;7(9):3268-76.
Serganov et al., Structural basis for discriminative regulation of gene expression by adenine- and guanine-sensing mRNAs. Chem Biol. Dec. 2004;11(12):1729-41.
Shen et al., Uridine addition after microRNA-directed cleavage. Science. Nov. 5, 2004;306(5698):997.
Song et al., 3' Terminal oligo U-tract-mediated stimulation of decapping. RNA. Dec. 2007;13(12):2356-65. Epub Oct. 17, 2007.
Wilusz et al., 3' end processing of a long nuclear-retained noncoding RNA yields a tRNA-like cytoplasmic RNA. Cell. Nov. 28, 2008;135(5):919-32. doi: 10.1016/j.cell.2008.10.012.
Wilusz et al., An unexpected ending: noncanonical 3' end processing mechanisms. RNA. Feb. 2010;16(2):259-66. doi: 10.1261/rna.1907510. Epub Dec. 9, 2009.
Wilusz et al., Long noncoding RNAs: functional surprises from the RNA world. Genes Dev. Jul. 1, 2009;23(13):1494-504. doi:10.1101/gad.1800909.
Wilusz et al., tRNAs marked with CCACCA are targeted for degradation. Science. Nov. 11, 2011;334(6057):817-21. doi:10.1126/science.1213671.
Wu et al., Poly A-transcripts expressed in HeLa cells. PLoS One. Jul. 30, 2008;3(7):e2803. doi: 10.1371/journal.pone.0002803.
Wyers et al., Cryptic pol II transcripts are degraded by a nuclear quality control pathway involving a new poly(A) polymerase. Cell. Jun. 3, 2005;121(5):725-37.
Yang et al., Genomewide characterization of non-polyadenylated RNAs. Genome Biol. 2011;12(2):R16. doi:10.1186/gb-2011-12-2-r16. Epub Feb. 16, 2011.
Zhang et al., lncRNA Malat1 is dispensable for mouse development but its transcription plays a cis-regulatory role in the adult. Cell Rep. Jul. 26, 2012;2(1):111-23. doi: 10.1016/j.celrep.2012.06.003. Epub Jun. 28, 2012.
Zhao et al., Formation of mRNA 3' ends in eukaryotes: mechanism, regulation, and interrelationships with other steps in mRNA synthesis. Microbiol Mol Biol Rev. Jun. 1999;63(2):405-45.

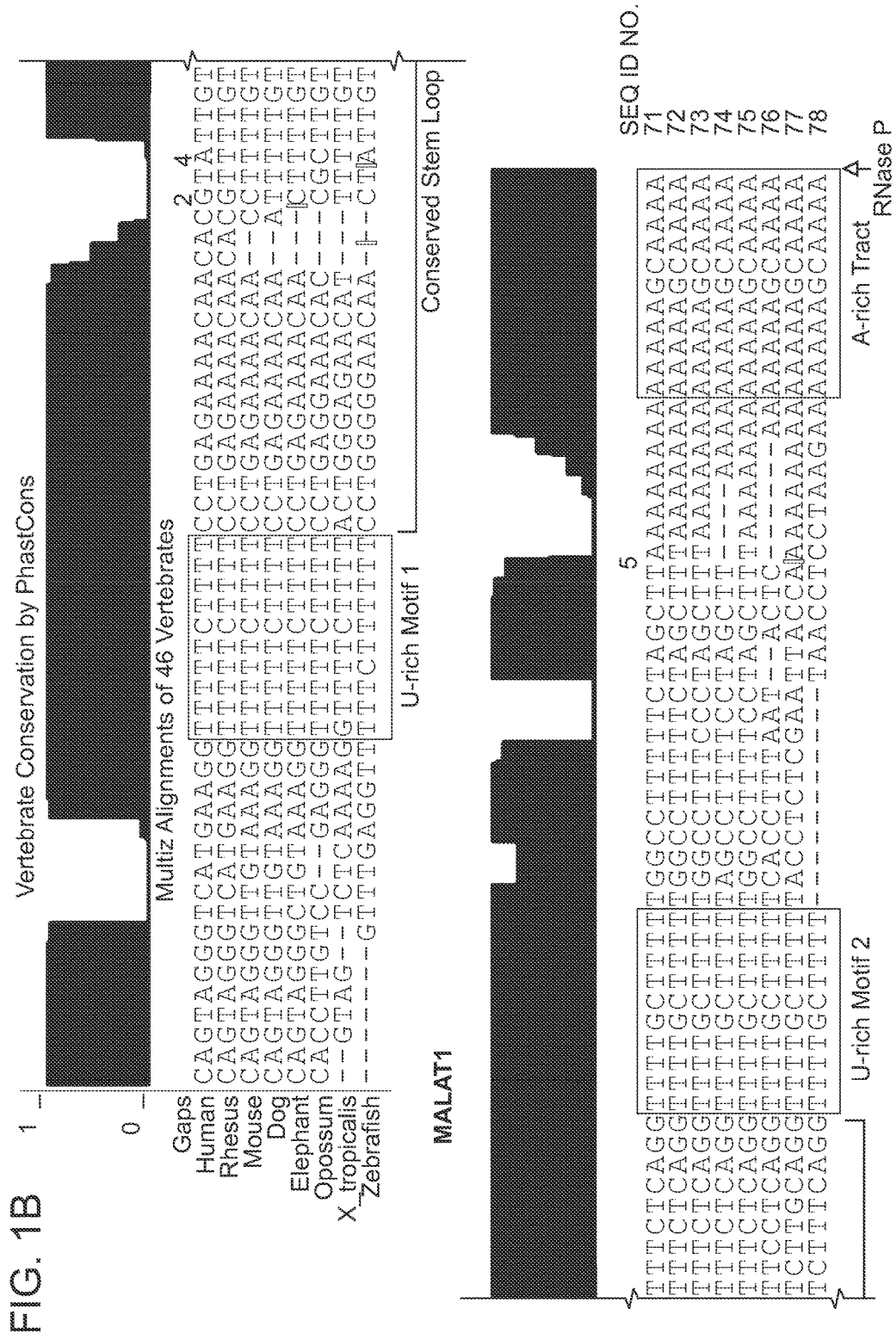

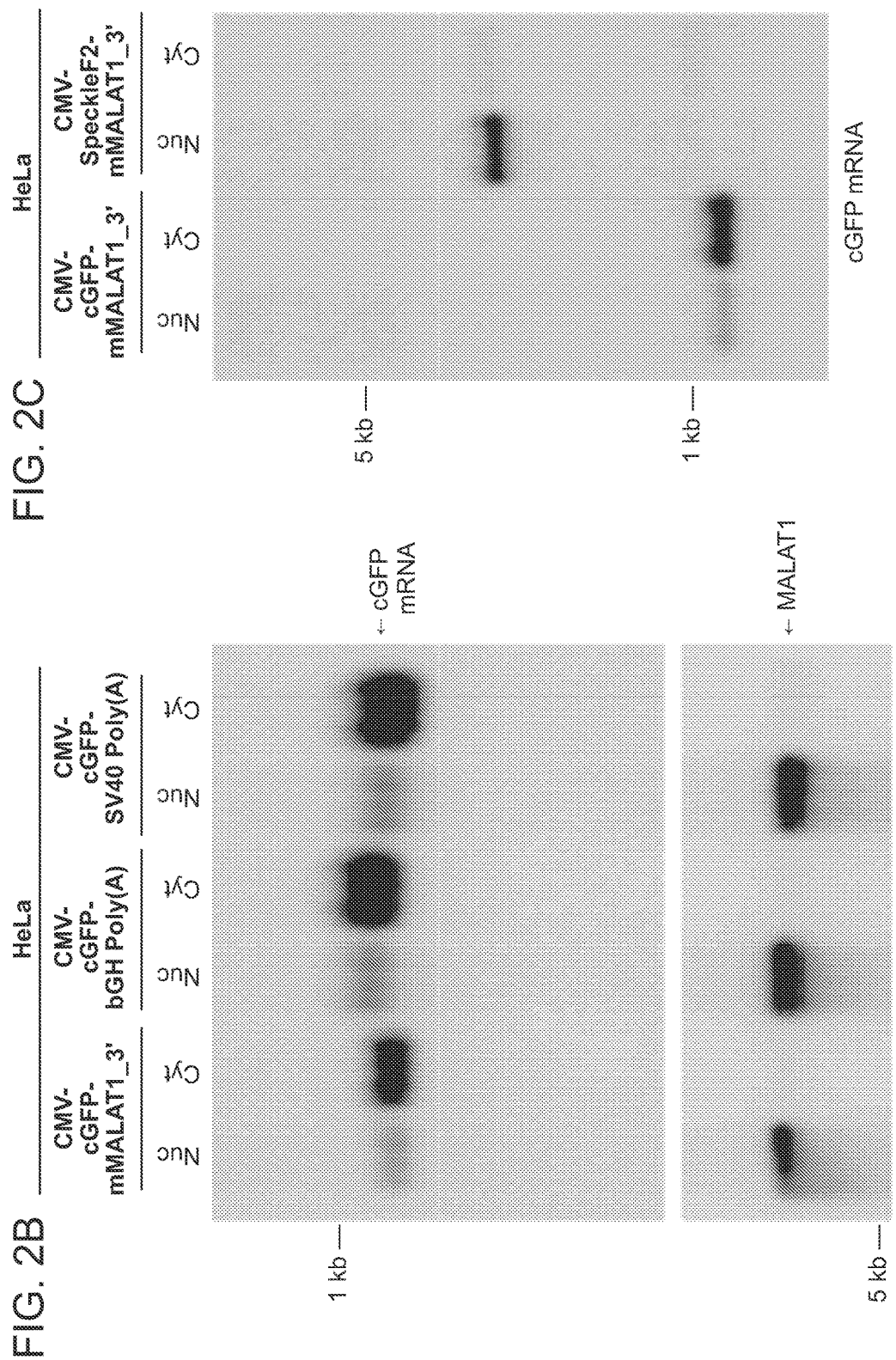

FIG. 2D

```
                                                                                                        SEQ ID No.
WT         gattcgtcagtagggttgtaaaggtttttcctgagaaacaacctttgttt                                              
Mut U1     gattcgtcagtagggttgtaaaggtttAAAAAtcctgagaaacaacctttgttt                                          
Mut U2     gattcgtcagtagggttgtaaaggtttttcctgagaaacaacctttgttt                                              
Mut U1/U2  gattcgtcagtagggttgtaaaggtttAAAAAttcctgagaaacaacctttgttt                                         
Comp. 14   **************************aaaggttttttcttcctgagaaa**********tt                                  
                                              U-rich Motif 1    Conserved Stem Loop tctcaggttttgcttttggccttccctagctttaaaaaaaaaaaaagcaaaa              85
           tctcaggttttgcttttggccttccctagctttaaaaaaaaaaaaagcaaaa              86
           tctcaggtttAAAAAttggccttccctagctttaaaaaaaaaaaaagcaaaa              87
           tctcaggtttAAAAAttggccttccctagctttaaaaaaaaaaaaagcaaaa              88
           tctcaggttttgctttt*************aaaaaaaaaaaaagcaaaa                 89
                U-rich Motif 2                  A-rich Tract
```

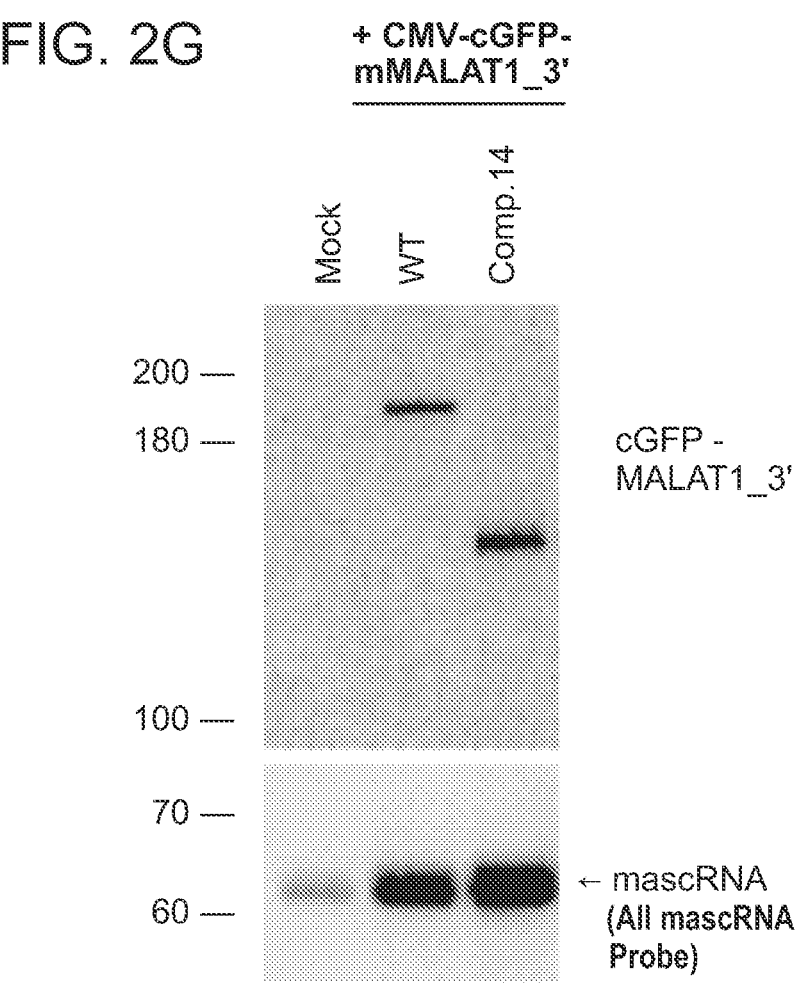

FIG. 3B

| | | SEQ ID NO. |
|---|---|---|
| WT MALAT1 | ttttgcttttggcctttcccctagctttaaaaaaaaaaagcaaaa | 102 |
| Mut U2-CG | ttttCGttttggcctttcccctagctttaaaaaaaaaaagcaaaa | 103 |
| Mut A-CG | ttttgcttttggcctttcccctagctttaaaaaaaaaaaaCGaaaa | 104 |
| Mut U2/A-CG | ttttCGttttggcctttcccctagctttaaaaaaaaaaaaCGaaaa | 105 |
| Mut U2-AA | ttttgcAAttggcctttcccctagctttaaaaaaaaaaagcaaaa | 106 |
| Mut A-AA | ttttgcttttggcctttcccctagctttaaaaaaaaaaTTgcaaaa | 107 |
| Mut U2/A-AA | ttttgcAAttggcctttcccctagctttaaaaaaaaaaTTgcaaaa | 108 |
| Mut U2-CGAAAA | ttttCGAAAAtggcctttcccctagctttaaaaaaaaaaagcaaaa | 109 |
| Mut A-CGAAAA | ttttgcttttggcctttcccctagctttaaaaaaaaTTTTTCGaaaa | 110 |
| Mut U2/A-CGAAAA | ttttCGAAAAtggcctttcccctagctttaaaaaaaaTTTTTCGaaaa | 111 |

U-rich Motif 2      A-rich Tract

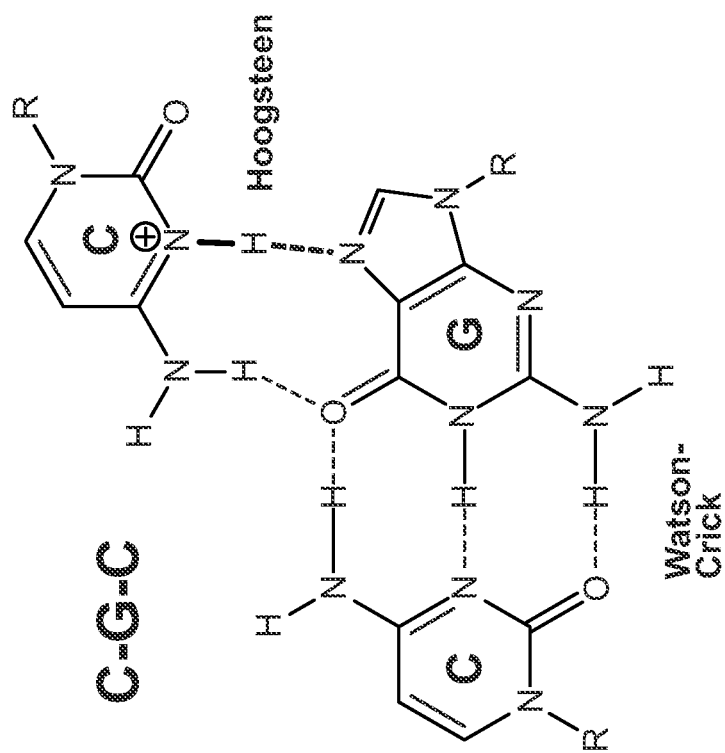
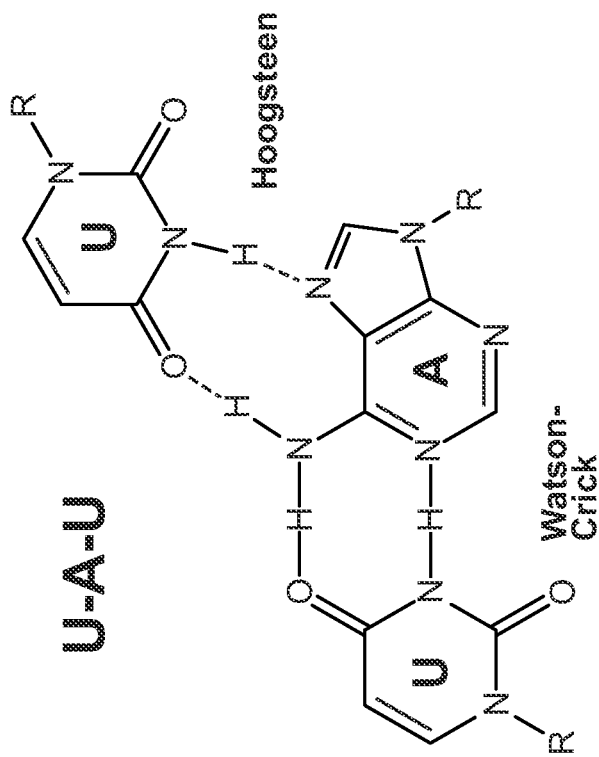
FIG. 4B

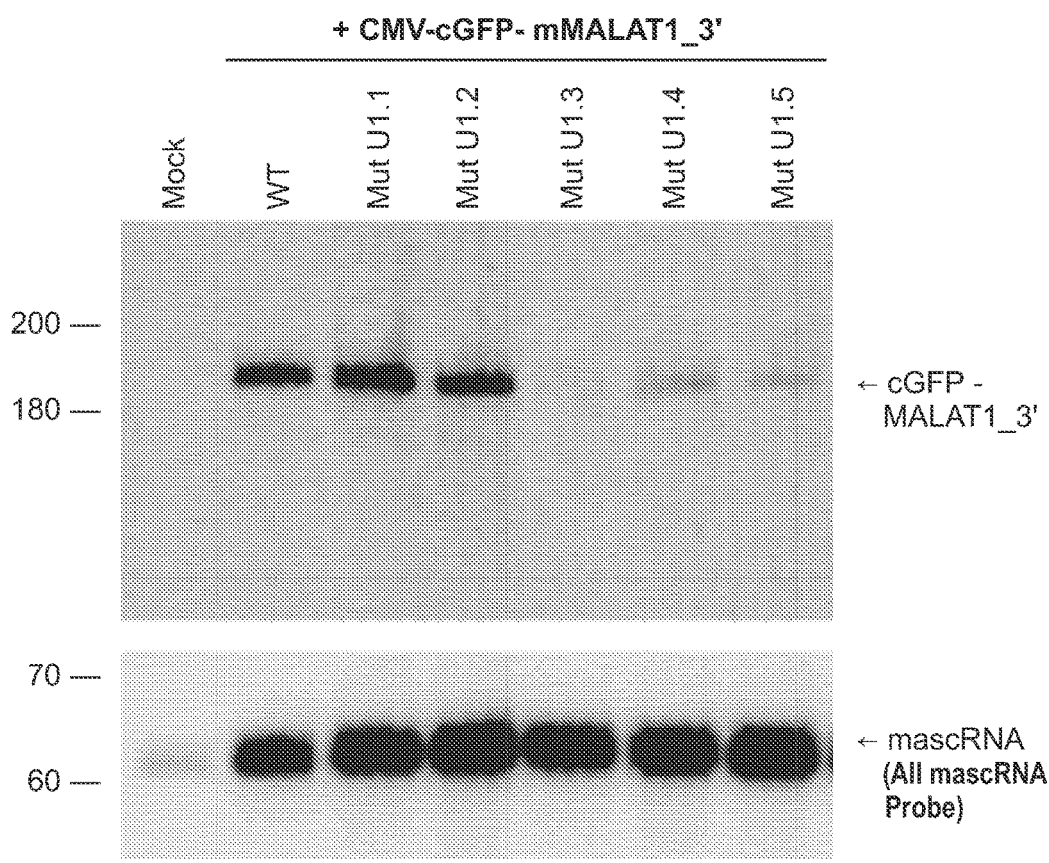

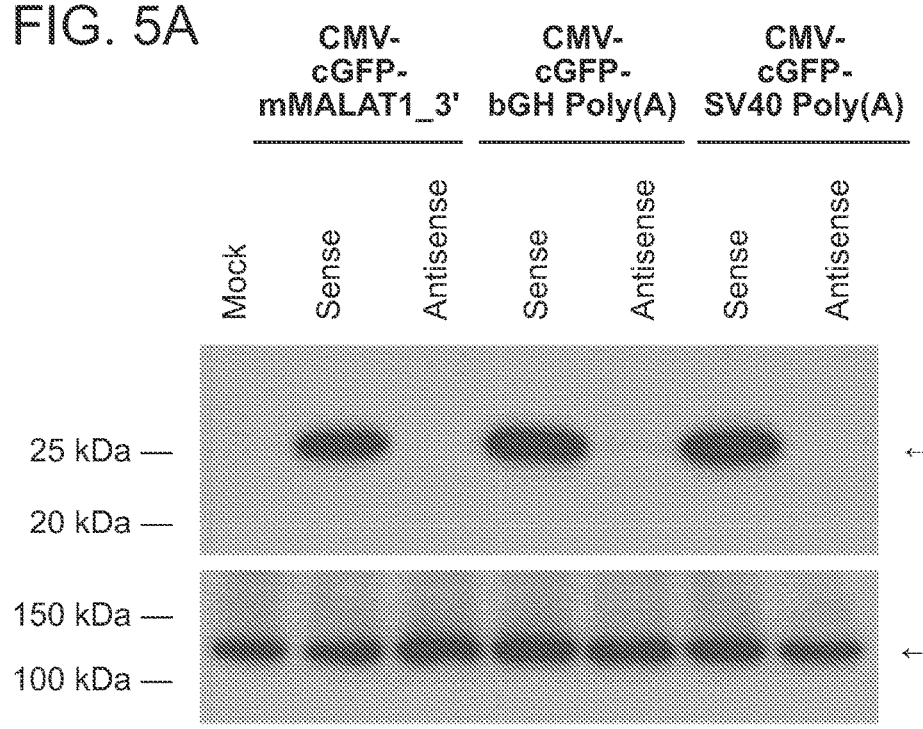

FIG. 5E

```
                                                                                                           SEQ ID NO.
WT       gattcgtcagtaggttgtaaggttttttctttttcctgagaaacaacctttgt~~                                              85
Comp.14  ***********************aaaggttttttctttttcctgagaaa****~~                                            118
Comp.15  ***********************************CCCAAttttttctttGAATTCTCT**~~                                    119
Comp.25  ***********************************CCCAAtttttttctttGAAgagaaa**~~                                   120
Comp.26  ***********************************CCCAAtttttttctttGAAgagaaa**~~                                   121
Comp.27  ***********************aaaggttttttctttttGAAgagaaa**~~                                              122
                                             └─U-rich Motif 1─┘ └─Conserved Stem Loop─┘
```

```
                                                                                                           SEQ ID NO.
tttctcaggttttgcttttttt*****************************ttaaaaaaaaaagcaaaa                                      85
tttctcaggttttgcttttttt*************cctagctttaaaaaaaaaaagcaaaa                                              118
AGAGAATTCttttgctttttt********************************CTTCaaaaaagcaaaa                                     119
tttctcTTCttttgcttttttt*******************************CTTCaaaaaagcaaaa                                     120
tttctcTTCttttgcttttttt*******************************CTTCaaaaaagcaaaa                                     121
tttctcTTCttttgcttttttt***************************aaaaaaaagcaaaa                                           122
└──U-rich Motif 2──┘                                            └─A-rich Tract─┘
```

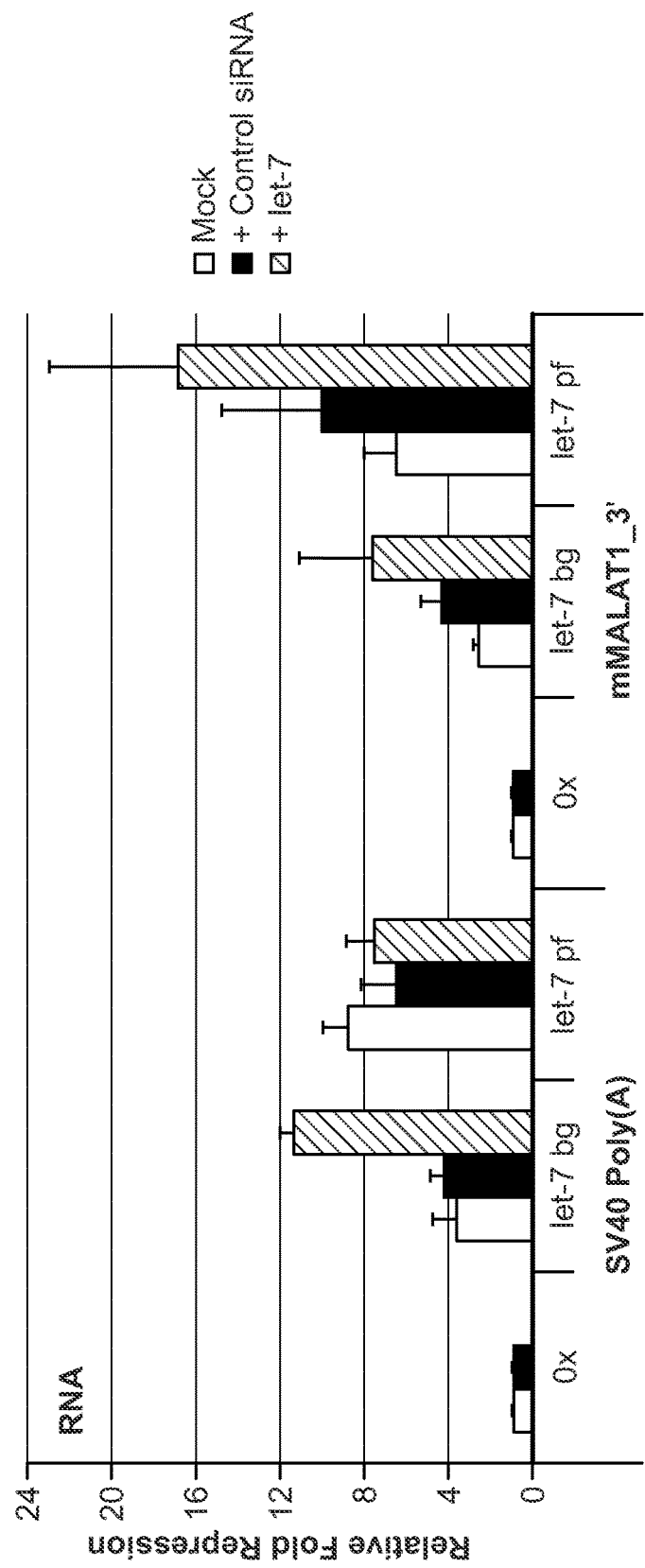

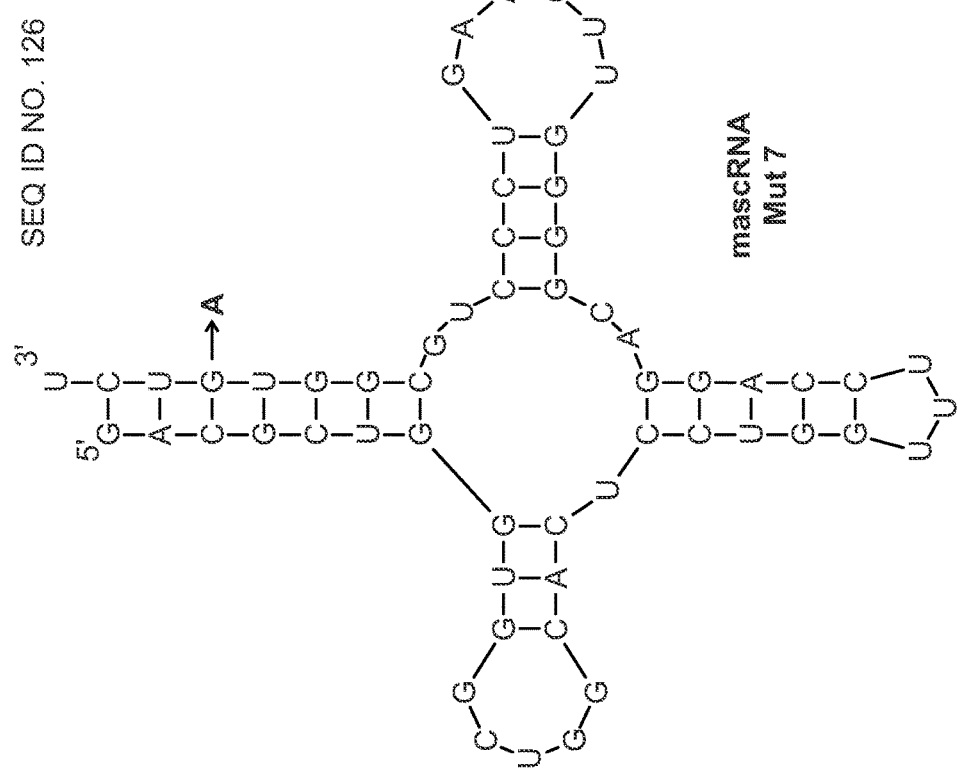
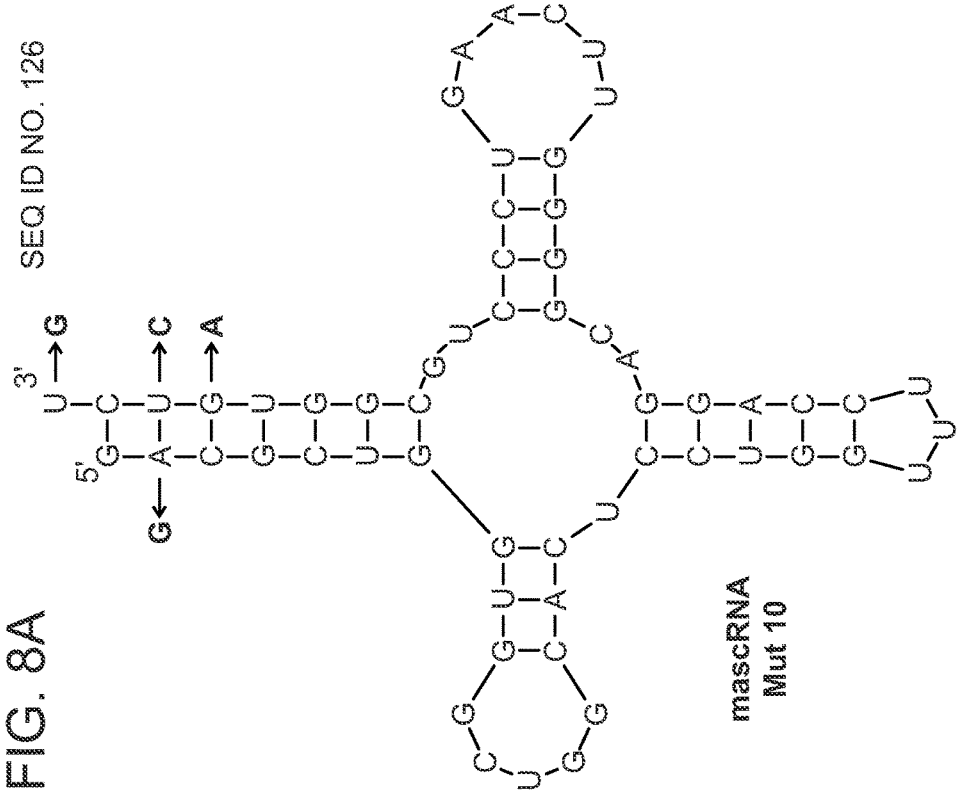
FIG. 8A

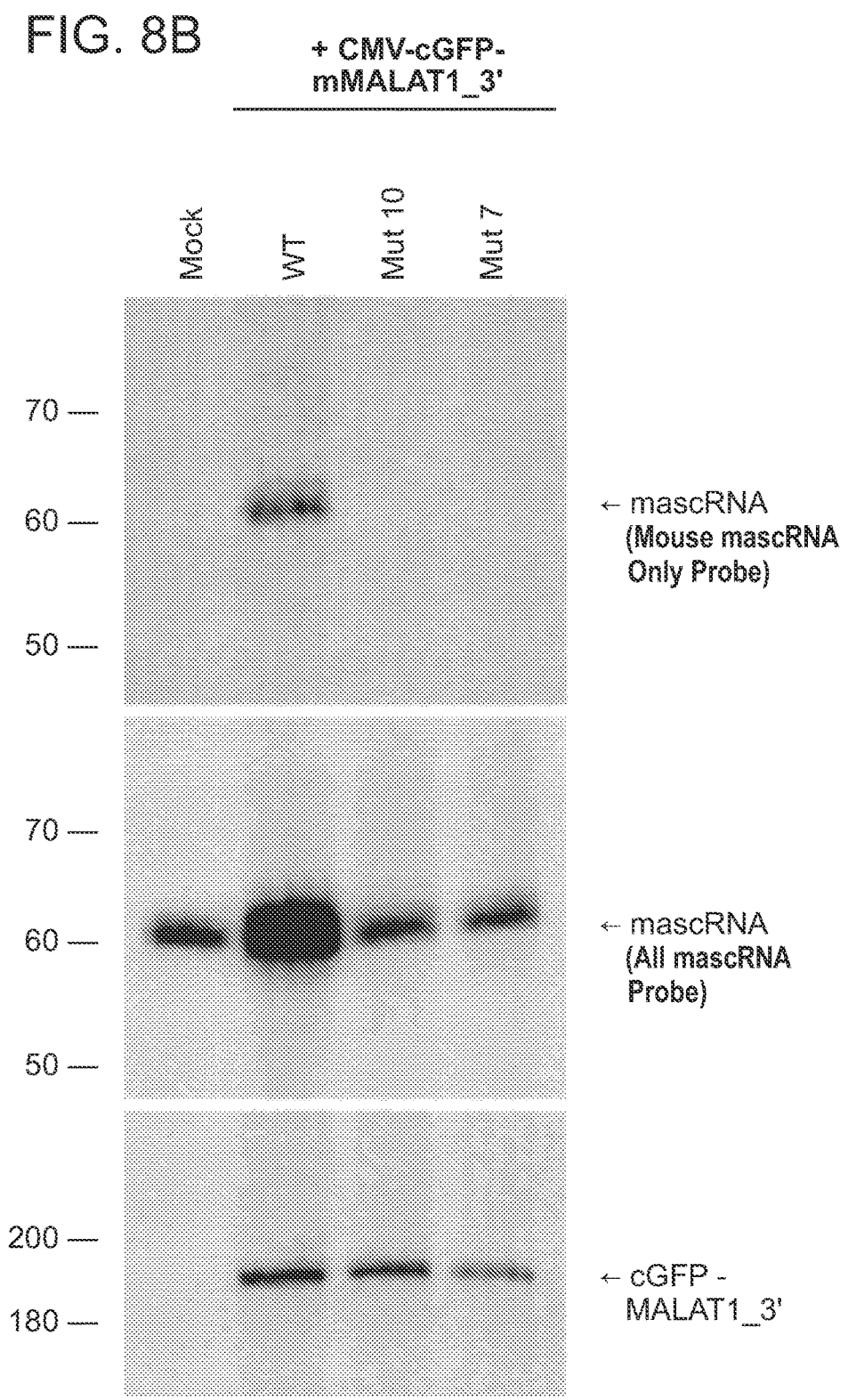

FIG. 8C

| | | SEQ ID NO. |
|---|---|---|
| Mut 10 Vector | TTCAAGTCCCTGCGGTACCGttgctt | 127 |
| 6 Clones | TTCAAGTCCCTGCGGTACCGCCACCA | 128 |
| 4 Clones | TTCAAGTCCCTGCGGTACCGCCACC | 129 |
| 2 Clones | TTCAGGTCCCTGCGGTACCGCCACCA | 130 |
| 1 Clone | TTCAAGTCCCTGCGGTACCGCCACCAG | 131 |

FIG. 8D

| | | SEQ ID NO. |
|---|---|---|
| Mut 7 Vector | TTCAAGTCCCTGCGGTATCTttgctt | 132 |
| Clone #1 | tTCAAGTCCCTGCGGTATCTAAAACTCTTTTTT | 133 |
| Clone #2 | TTCAAGTCCCTGCGGTATCTTTTAAATTTTTTTT | 134 |
| Clone #3 | TTCAAGTCCCTGCGGTATCTTTTTTTTTTTCTT | 135 |
| Clone #4 | TTCAAGTCCCTGCGGTATCTTTTTTTTTTATTTCTT | 136 |
| Clone #5 | TTCAAGTCCCTGCGGTATCTC | 137 |
| Clone #6 | TTCAAGTCCCTGCGGTATCTCCA | 138 |

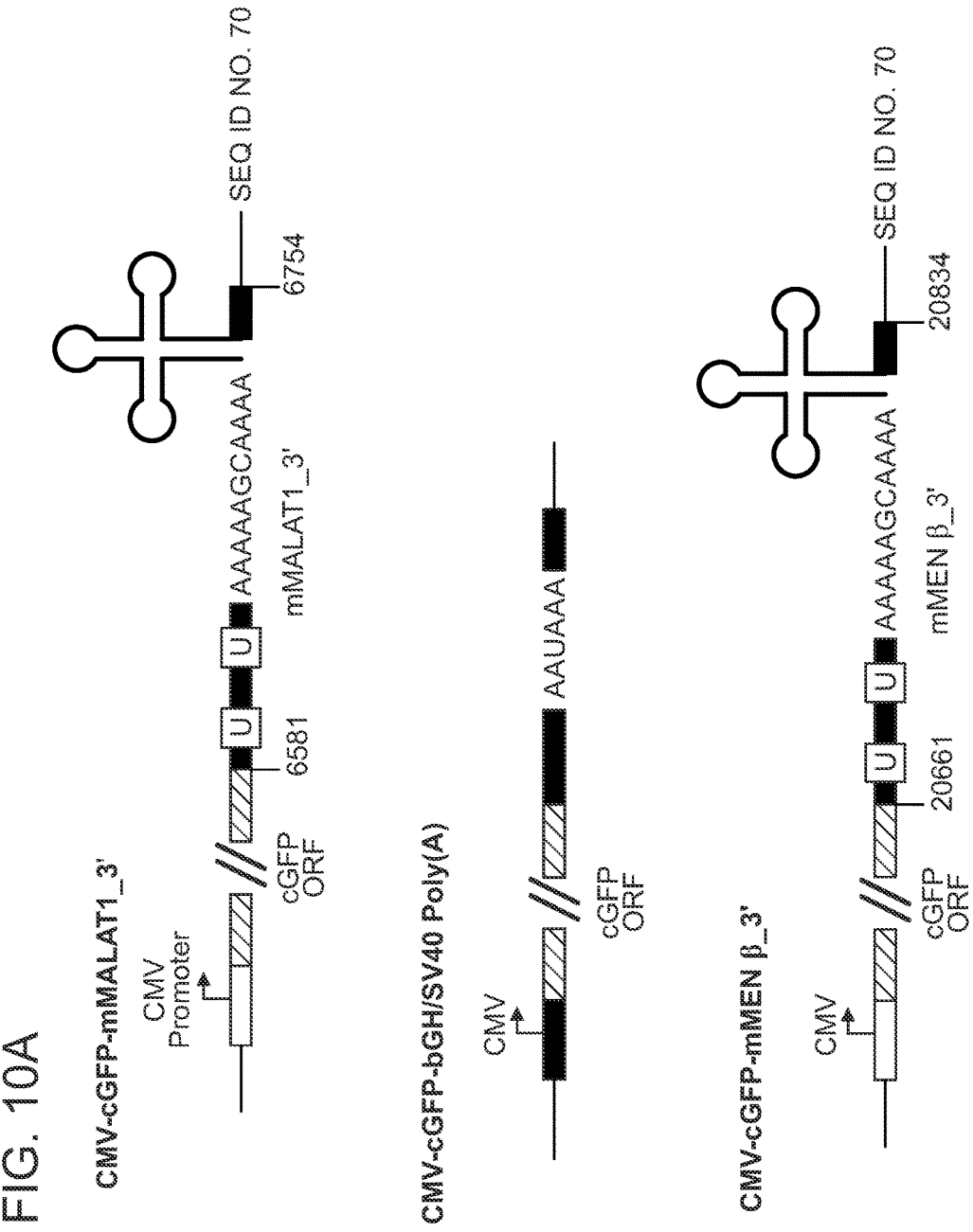

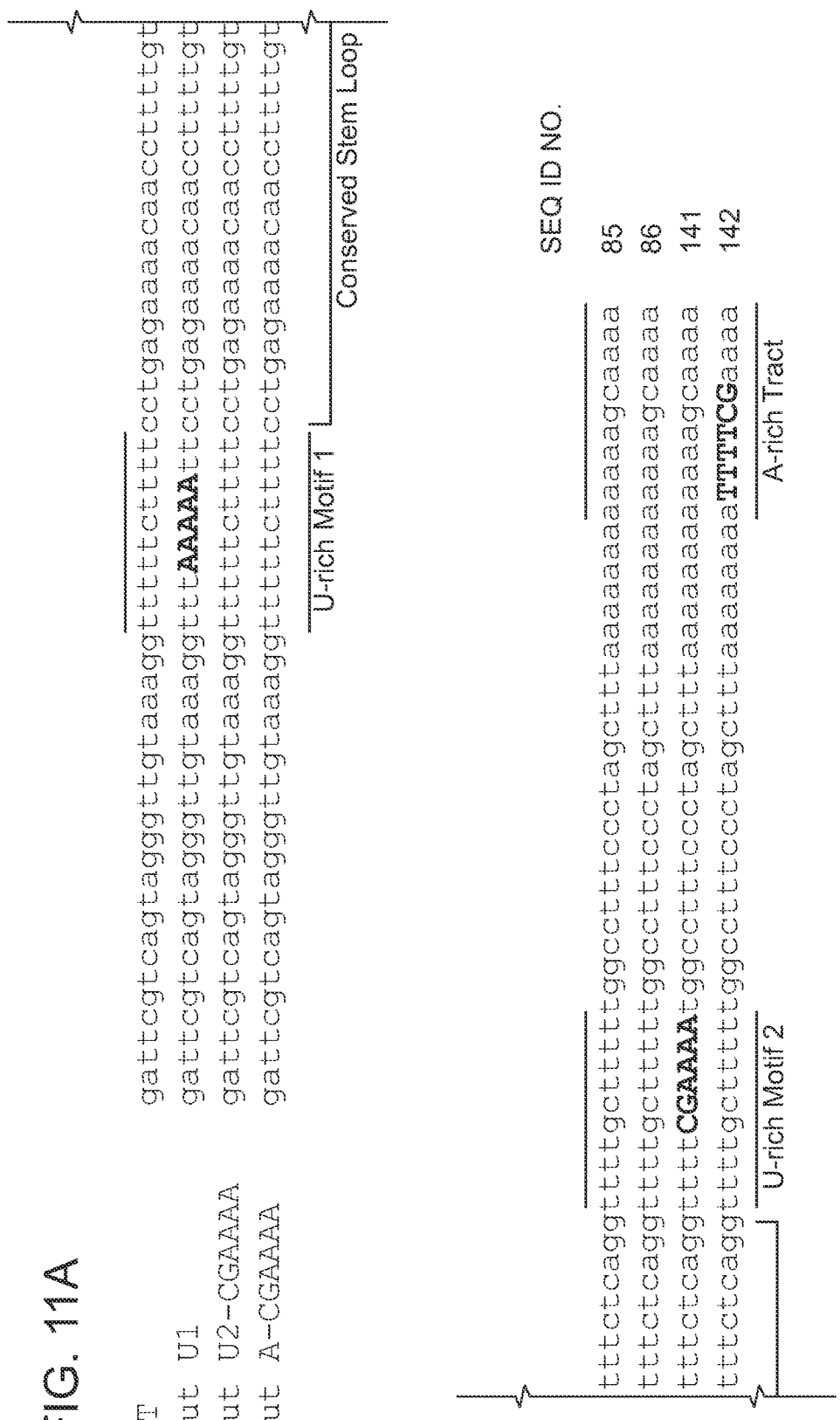

FIG. 11C

```
Genome    gattcgtcagtaggttgtaaggttttcttcctgagaaacaacctttgt
RACE #1   gattcgtcagtaggttgtaaggttttcttcctgagaaacaacctttgt
RACE #2   gattcgtcagtaggttgtaaggttttcttcctgagaaacaacctttgt
RACE #3   gattcgtcagtaggttgtaaggttttcttcctgagaaacaaccttttt
                                 └─── U-rich Motif 1 ──┘└Conserved Stem Loop┘
```

```
                                                                    SEQ ID NO.
                                           aaaaaagcaaaa              85
tttctcaggttttggcctttccctagcttta                                     143
tttctcaggtttttttttttt                                                144
tttttttttttt                                                         145
└── U-rich Motif 2 ──┘                     └─ A-rich Tract ─┘
```

| | Stable? | SEQ ID NO. |
|---|---|---|
| tttgctttttggcctttccctagctttaaaaaaaaaaaaagcaaaa | Yes | 146 |
| tttgctttt*****ggcctttccctagctttaaaaaaaaaaaaagcaaaa | Yes | 147 |
| tttgctttt**********aaaaaaaaaaaaagcaaaa | No | 148 |
| tttgctttttggcctttccctagcttt*****aaaaaaaaaaaaagcaaaa | No | 149 |
| tttgctttt*************tagcttt***aaaaaaaaaaaaagcaaaa | No | 150 |
| tttgctttt********************aaaaaaaaaaaaagcaaaa | No | 151 |
| tttgctttttggcctttccctagcttt**********aaaaaaaaaaaaagcaaaa | Yes | 152 |
| tttgctttt***ggcctttccctagcttt********aaaaaaaaaaaaagcaaaa | Yes | 153 |
| tttgctttt*************************aaaaaaaaaaaaagcaaaa | No | 154 |
| tttgctttt******************tagcttt***aaaaaaaaaaaaagcaaaa | Yes | 155 |
| tttgctttt*****************************aaaaaaaaaaaaagcaaaa | Yes | 156 |
| tttgctttt*********************tagcttt***aaaaaaaaaaaaagcaaaa | Yes | 157 |
| tttgctttt*********************************aaaaaaaaaaaaagcaaaa | Yes | 158 |
| tttgctttt*********************************aaaaaaaaaaaaagcaaaa | No | 159 |
| tttgctttt*********************************aaaaaaaaaaaaagcaaaa | Yes | 160 |

U-rich Motif 2 ... A-rich Tract

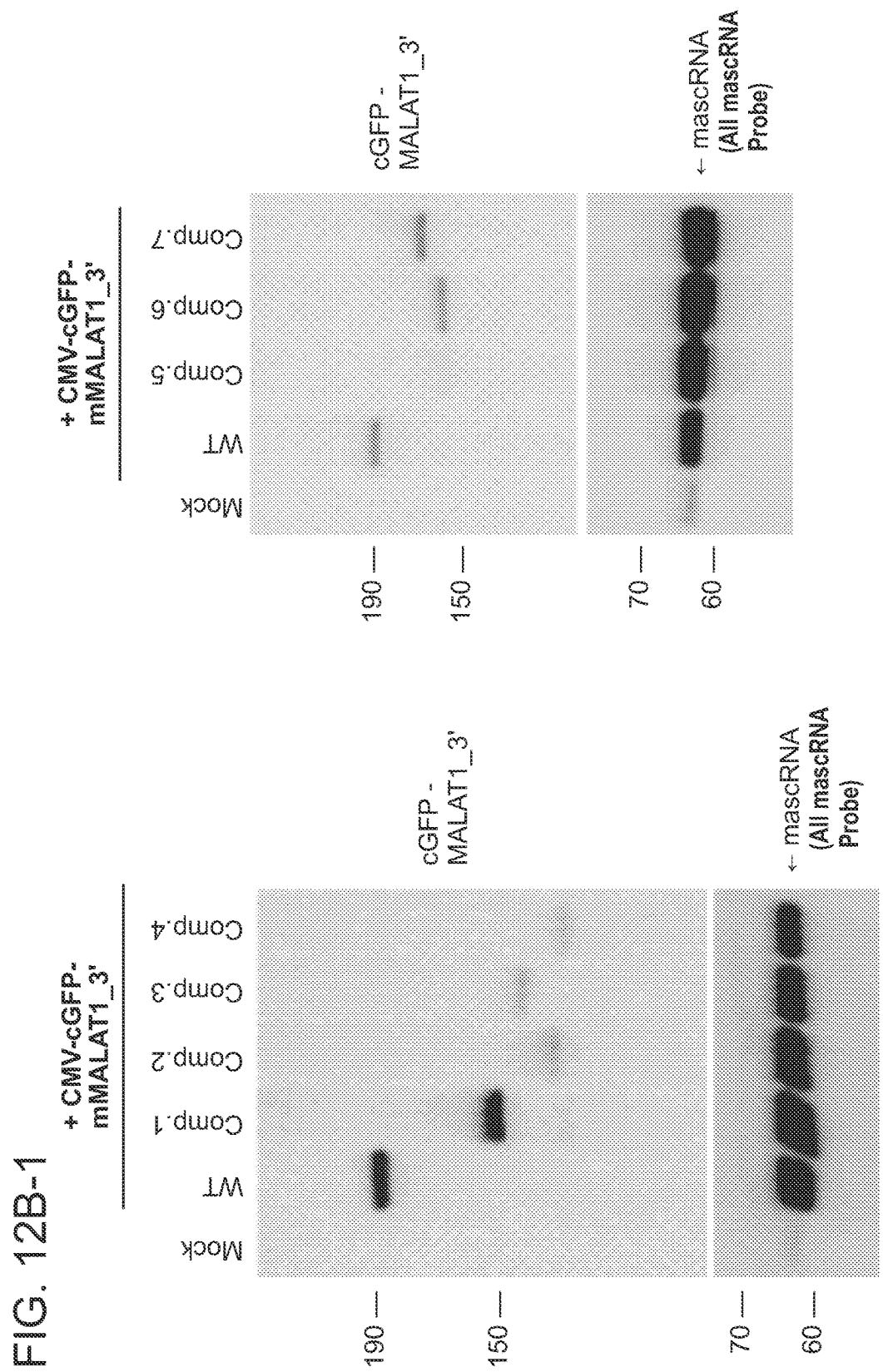

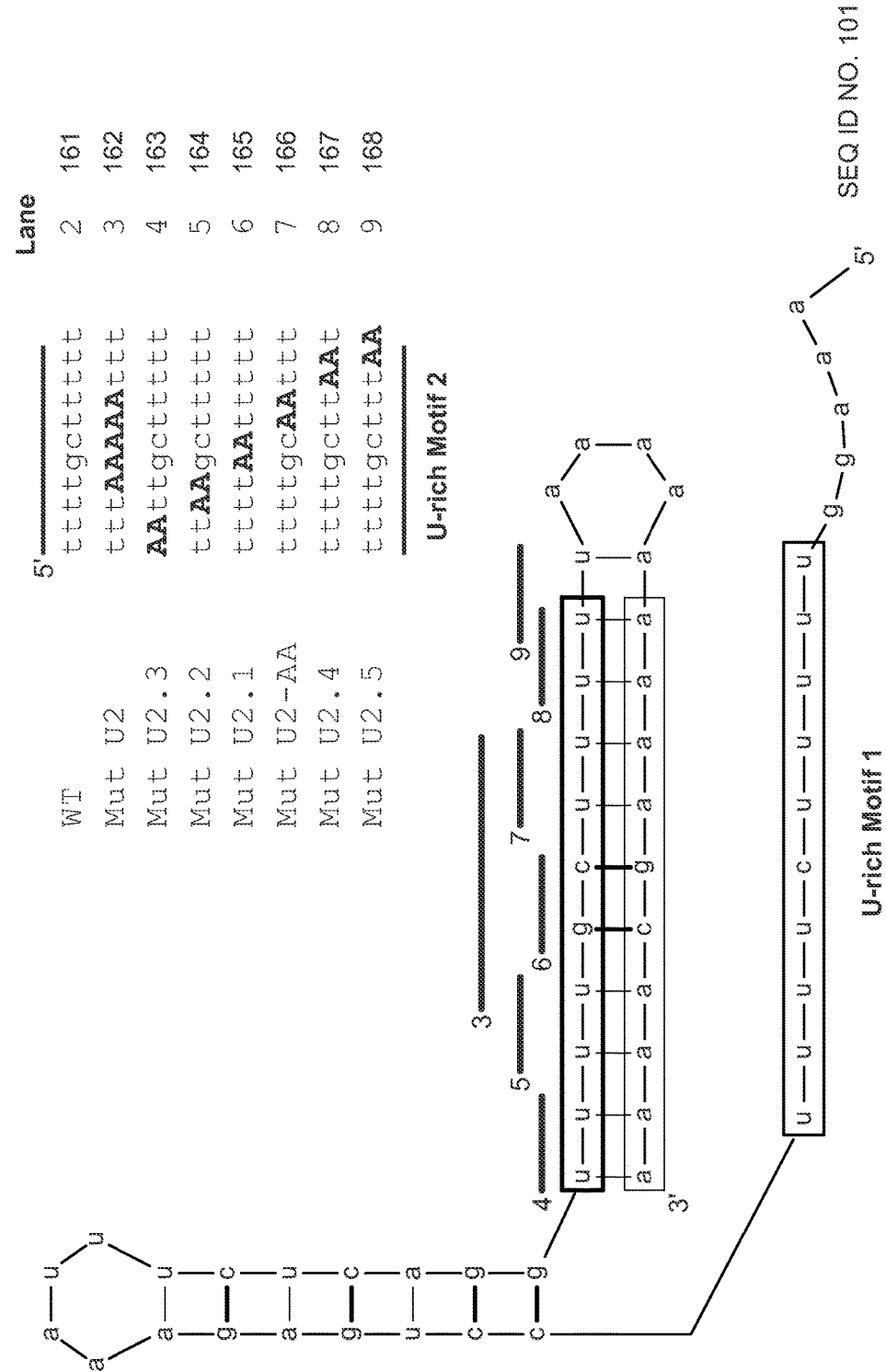

FIG. 17A
CMV-cGFP-mMALAT1_3'
SEQ ID NO. 70
CMV-cGFP-Riboswitch-masc
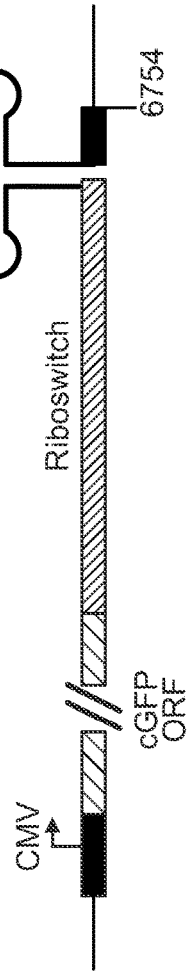
| Riboswitch | Senses | Size (nt) |
|---|---|---|
| V. vulnificus add | Adenine | 71 |
| B. subtilis xpt | Guanine | 68 |
| V. cholera Vc2 | Cyclic di-GMP | 98 |
| T. tengcongensis SAM | S-adenosylmethionine (SAM) | 132 |
| T. tengcongensis glmS | Glucosamine-6 phosphate (GlcN6P) | 125 |

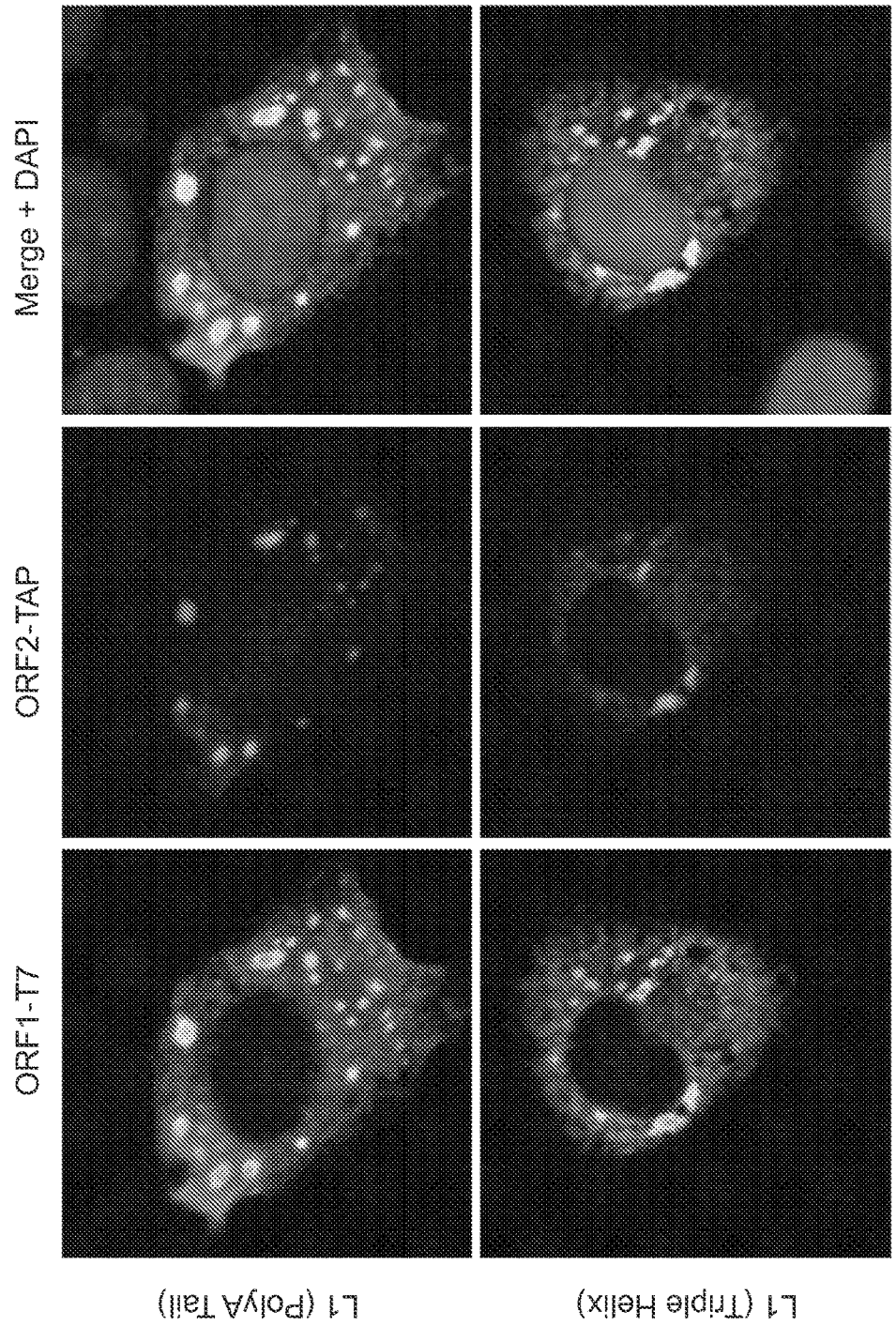

SEQUENCE LISTING

<160> NUMBER OF SEQ ID NOS: 174

<210> SEQ ID NO 1
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 1

```
gattcgtcag tagggttgta aaggtttttc ttttcctgag aaaacaacct tttgttttct      60
caggttttgc ttttttggcct ttccctagct ttaaaaaaaa aaaagcaaaa gacgctggtg    120
gctggcactc ctggtttcca ggacggggtt caagtccctg cggtgtcttt gctt          174
```

<210> SEQ ID NO 2
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 2
gattcgtcag tagggttgta aaggttttc ttttcctgag aaaacaacct tttgttttct      60
caggttttgc tttttggcct ttccctagct ttaaaaaaaa aaaagcaaaa gacgctggtg     120
gctggcactc ctggtttcca ggacggggtt caagtccctg cggtatcttt gctt           174

<210> SEQ ID NO 3
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 3
gattcgtcag tagggttgta aaggttttc ttttcctgag aaaacaacct tttgttttct      60
caggttttgc tttttggcct ttccctagct ttaaaaaaaa aaaagcaaaa ggcgctggtg     120
gctggcactc ctggtttcca ggacggggtt caagtccctg cggtaccgtt gctt           174

<210> SEQ ID NO 4
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 4
gattcgtcag tagggttgta aaggtttaaa aattcctgag aaaacaacct tttgttttct      60
caggttttgc tttttggcct ttccctagct ttaaaaaaaa aaaagcaaaa gacgctggtg     120
gctggcactc ctggtttcca ggacggggtt caagtccctg cggtgtcttt gctt           174

<210> SEQ ID NO 5
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 5
gattcgtcag tagggttgta aaggttttc ttttcctgag aaaacaacct tttgttttct      60
caggtttaaa aatttggcct ttccctagct ttaaaaaaaa aaaagcaaaa gacgctggtg     120
gctggcactc ctggtttcca ggacggggtt caagtccctg cggtgtcttt gctt           174

<210> SEQ ID NO 6
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 6
gattcgtcag tagggttgta aaggtttaaa aattcctgag aaaacaacct tttgttttct      60
caggtttaaa aatttggcct ttccctagct ttaaaaaaaa aaaagcaaaa gacgctggtg     120
gctggcactc ctggtttcca ggacggggtt caagtccctg cggtgtcttt gctt           174

<210> SEQ ID NO 7
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 7

```
gattcgtcag tagggttgta aaggttttta ttttcctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174
```

<210> SEQ ID NO 8
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 8

```
gattcgtcag tagggttgta aaggtttaac ttttcctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174
```

<210> SEQ ID NO 9
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 9

```
gattcgtcag tagggttgta aaggttttc aattcctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174
```

<210> SEQ ID NO 10
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 10

```
gattcgtcag tagggttgta aaggttttc ttaacctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174
```

<210> SEQ ID NO 11
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 11

```
gattcgtcag tagggttgta aaggtaattc ttttcctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174
```

```
<210> SEQ ID NO 12
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 12
gattcgtcag tagggttgta aaggttttc ttttcctgag aaaacaacct tttgttttct     60
caggttttaa ttttggcct ttccctagct ttaaaaaaaa aaaagcaaaa gacgctggtg    120
gctggcactc ctggtttcca ggacgggtt caagtccctg cggtgtcttt gctt          174

<210> SEQ ID NO 13
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 13
gattcgtcag tagggttgta aaggttttc ttttcctgag aaaacaacct tttgttttct     60
caggttaagc ttttggcct ttccctagct ttaaaaaaaa aaaagcaaaa gacgctggtg    120
gctggcactc ctggtttcca ggacgggtt caagtccctg cggtgtcttt gctt          174

<210> SEQ ID NO 14
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 14
gattcgtcag tagggttgta aaggttttc ttttcctgag aaaacaacct tttgttttct     60
caggaattgc ttttggcct ttccctagct ttaaaaaaaa aaaagcaaaa gacgctggtg    120
gctggcactc ctggtttcca ggacgggtt caagtccctg cggtgtcttt gctt          174

<210> SEQ ID NO 15
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 15
gattcgtcag tagggttgta aaggttttc ttttcctgag aaaacaacct tttgttttct     60
caggttttgc ttaatggcct ttccctagct ttaaaaaaaa aaaagcaaaa gacgctggtg   120
gctggcactc ctggtttcca ggacgggtt caagtccctg cggtgtcttt gctt          174

<210> SEQ ID NO 16
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 16
gattcgtcag tagggttgta aaggttttc ttttcctgag aaaacaacct tttgttttct     60
caggttttgc tttaaggcct ttccctagct ttaaaaaaaa aaaagcaaaa gacgctggtg   120
gctggcactc ctggtttcca ggacgggtt caagtccctg cggtgtcttt gctt          174
```

```
<210> SEQ ID NO 17
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 17
gattcgtcag tagggttgta aaggtttttc ttttcctgag aaaacaacct tttgttttct      60
caggttttcg ttttttggcct ttccctagct ttaaaaaaaa aaaagcaaaa gacgctggtg    120
gctggcactc ctggtttcca ggacggggtt caagtccctg cggtgtcttt gctt           174

<210> SEQ ID NO 18
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 18
gattcgtcag tagggttgta aaggtttttc ttttcctgag aaaacaacct tttgttttct      60
caggttttgc ttttttggcct ttccctagct ttaaaaaaaa aaaacgaaaa gacgctggtg    120
gctggcactc ctggtttcca ggacggggtt caagtccctg cggtgtcttt gctt           174

<210> SEQ ID NO 19
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 19
gattcgtcag tagggttgta aaggtttttc ttttcctgag aaaacaacct tttgttttct      60
caggttttcg ttttttggcct ttccctagct ttaaaaaaaa aaaacgaaaa gacgctggtg    120
gctggcactc ctggtttcca ggacggggtt caagtccctg cggtgtcttt gctt           174

<210> SEQ ID NO 20
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 20
gattcgtcag tagggttgta aaggtttttc ttttcctgag aaaacaacct tttgttttct      60
caggttttgc aatttggcct ttccctagct ttaaaaaaaa aaaagcaaaa gacgctggtg    120
gctggcactc ctggtttcca ggacggggtt caagtccctg cggtgtcttt gctt           174

<210> SEQ ID NO 21
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 21
gattcgtcag tagggttgta aaggtttttc ttttcctgag aaaacaacct tttgttttct      60
caggttttgc ttttttggcct ttccctagct ttaaaaaaaa aattgcaaaa gacgctggtg    120
gctggcactc ctggtttcca ggacggggtt caagtccctg cggtgtcttt gctt           174
```

```
<210> SEQ ID NO 22
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 22
gattcgtcag tagggttgta aaggtttttc ttttcctgag aaaacaacct tttgttttct      60
caggttttgc aatttggcct ttccctagct ttaaaaaaaa aattgcaaaa gacgctggtg     120
gctggcactc ctggtttcca ggacggggtt caagtccctg cggtgtcttt gctt           174

<210> SEQ ID NO 23
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 23
gattcgtcag tagggttgta aaggtttttc ttttcctgag aaaacaacct tttgttttct      60
caggttttcg aaaatggcct ttccctagct ttaaaaaaaa aaaagcaaaa gacgctggtg     120
gctggcactc ctggtttcca ggacggggtt caagtccctg cggtgtcttt gctt           174

<210> SEQ ID NO 24
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 24
gattcgtcag tagggttgta aaggtttttc ttttcctgag aaaacaacct tttgttttct      60
caggttttgc tttttggcct ttccctagct ttaaaaaaaa ttttcgaaaa gacgctggtg     120
gctggcactc ctggtttcca ggacggggtt caagtccctg cggtgtcttt gctt           174

<210> SEQ ID NO 25
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 25
gattcgtcag tagggttgta aaggtttttc ttttcctgag aaaacaacct tttgttttct      60
caggttttcg aaaatggcct ttccctagct ttaaaaaaaa ttttcgaaaa gacgctggtg     120
gctggcactc ctggtttcca ggacggggtt caagtccctg cggtgtcttt gctt           174

<210> SEQ ID NO 26
<211> LENGTH: 135
<212> TYPE: DNA
<213> ORGANISM: Artificial Sequence
<220> FEATURE:
<223> OTHER INFORMATION: synthetic oligonucleotide

<400> SEQUENCE: 26
aaaggttttt cttttcctga tcaggttttg cttttttggcc tttccctagc tttaaaaaaa     60
aaaaagcaaa agacgctggt ggctggcact cctggtttcc aggacggggt tcaagtccct    120
gcggtgtctt tgctt                                                      135
```

<210> SEQ ID NO 27
<211> LENGTH: 118
<212> TYPE: DNA
<213> ORGANISM: Artificial Sequence
<220> FEATURE:
<223> OTHER INFORMATION: synthetic oligonucleotide

<400> SEQUENCE: 27
aaaggttttt cttttcctga tcaggttttg cttttaaaa aaaaaaaagc aaaagacgct      60
ggtggctggc actcctggtt tccaggacgg ggttcaagtc cctgcggtgt ctttgctt     118

<210> SEQ ID NO 28
<211> LENGTH: 128
<212> TYPE: DNA
<213> ORGANISM: Artificial Sequence
<220> FEATURE:
<223> OTHER INFORMATION: synthetic oligonucleotide

<400> SEQUENCE: 28
aaaggttttt cttttcctga tcaggttttg cttttggcc tttccctagc tttaaaagc      60 aaaagacgct ggtggctggc actcctggtt tccaggacgg ggttcaagtc cctgcggtgt    120
ctttgctt                                                             128

<210> SEQ ID NO 29
<211> LENGTH: 118
<212> TYPE: DNA
<213> ORGANISM: Artificial Sequence
<220> FEATURE:
<223> OTHER INFORMATION: synthetic oligonucleotide

<400> SEQUENCE: 29
aaaggttttt cttttcctga tcaggttttg cttttttagc tttaaaagc aaaagacgct      60 ggtggctggc actcctggtt tccaggacgg ggttcaagtc cctgcggtgt ctttgctt     118

<210> SEQ ID NO 30
<211> LENGTH: 137
<212> TYPE: DNA
<213> ORGANISM: Artificial Sequence
<220> FEATURE:
<223> OTHER INFORMATION: synthetic oligonucleotide

<400> SEQUENCE: 30
gattcgtcag tagggttgta aaggttttc ttttcctgat caggttttgc tttttaaaa      60 aaaaaaagca aaagacgctg gtggctggca ctcctggttt ccaggacggg gttcaagtcc    120
ctgcggtgtc tttgctt                                                   137

<210> SEQ ID NO 31
<211> LENGTH: 138
<212> TYPE: DNA
<213> ORGANISM: Artificial Sequence
<220> FEATURE:
<223> OTHER INFORMATION: synthetic oligonucleotide

<400> SEQUENCE: 31
aaaggttttt cttttcctga gaaacaacc tttgttttc tcaggttttg cttttaaaa      60 aaaaaaagc aaaagacgct ggtggctggc actcctggtt tccaggacgg ggttcaagtc    120
cctgcggtgt ctttgctt                                                  138

<210> SEQ ID NO 32
<211> LENGTH: 148
<212> TYPE: DNA
<213> ORGANISM: Artificial Sequence
<220> FEATURE:
<223> OTHER INFORMATION: synthetic oligonucleotide

<400> SEQUENCE: 32

```
aaaggttttt cttttcctga gaaaacaacc ttttgttttc tcaggttttg cttttttggcc      60
tttccctagc tttaaaaagc aaaagacgct ggtggctggc actcctggtt tccaggacgg     120
ggttcaagtc cctgcggtgt ctttgctt                                        148
```

<210> SEQ ID NO 33
<211> LENGTH: 131
<212> TYPE: DNA
<213> ORGANISM: Artificial Sequence
<220> FEATURE:
<223> OTHER INFORMATION: synthetic oligonucleotide

<400> SEQUENCE: 33

```
aaaggttttt cttttcctga gaaaacaacc ttttgttttc tcaggttttg cttttttaaaa     60
agcaaaagac gctggtggct ggcactcctg gtttccagga cggggttcaa gtccctgcgg    120
tgtctttgct t                                                         131
```

<210> SEQ ID NO 34
<211> LENGTH: 134
<212> TYPE: DNA
<213> ORGANISM: Artificial Sequence
<220> FEATURE:
<223> OTHER INFORMATION: synthetic oligonucleotide

<400> SEQUENCE: 34

```
aaaggttttt cttttcctga gaaaacaatt gttttctcag ttttgctttt taaaaaaaa       60
aaaagcaaaa gacgctggtg gctggcactc ctggtttcca ggacggggtt caagtccctg    120
cggtgtcttt gctt                                                      134
```

<210> SEQ ID NO 35
<211> LENGTH: 130
<212> TYPE: DNA
<213> ORGANISM: Artificial Sequence
<220> FEATURE:
<223> OTHER INFORMATION: synthetic oligonucleotide

<400> SEQUENCE: 35

```
aaaggttttt cttttcctga gaaaacgttt tctcaggttt tgcttttttaa aaaaaaaaaa     60
gcaaaagacg ctggtggctg gcactcctgg tttccaggac ggggttcaag tccctgcggt    120
gtctttgctt                                                           130
```

<210> SEQ ID NO 36
<211> LENGTH: 138
<212> TYPE: DNA
<213> ORGANISM: Artificial Sequence
<220> FEATURE:
<223> OTHER INFORMATION: synthetic oligonucleotide

<400> SEQUENCE: 36

```
aaaggttttt cttttcctga gaaaacaacc ttttgttttc tcaggttttg cttttttagc      60
tttaaaaagc aaaagacgct ggtggctggc actcctggtt tccaggacgg ggttcaagtc    120
cctgcggtgt ctttgctt                                                  138
```

```
<210> SEQ ID NO 37
<211> LENGTH: 126
<212> TYPE: DNA
<213> ORGANISM: Artificial Sequence
<220> FEATURE:
<223> OTHER INFORMATION: synthetic oligonucleotide

<400> SEQUENCE: 37
aaaggttttt cttttcctga gaaatttctc aggttttgct ttttaaaaaa aaaaaagcaa      60
aagacgctgg tggctggcac tcctggtttc caggacgggg ttcaagtccc tgcggtgtct     120
ttgctt                                                                126

<210> SEQ ID NO 38
<211> LENGTH: 122
<212> TYPE: DNA
<213> ORGANISM: Artificial Sequence
<220> FEATURE:
<223> OTHER INFORMATION: synthetic oligonucleotide

<400> SEQUENCE: 38
aaaggttttt cttttcctga gatctcaggt tttgcttttt aaaaaaaaaa aagcaaaaga      60
cgctggtggc tggcactcct ggtttccagg acggggttca agtccctgcg gtgtctttgc     120
tt                                                                    122

<210> SEQ ID NO 39
<211> LENGTH: 123
<212> TYPE: DNA
<213> ORGANISM: Artificial Sequence
<220> FEATURE:
<223> OTHER INFORMATION: synthetic oligonucleotide

<400> SEQUENCE: 39
aaaggttttt cttttcctga gaaatttctc aggttttgct ttttaaaaaa aaagcaaaag      60
acgctggtgg ctggcactcc tggtttccag gacggggttc aagtccctgc ggtgtctttg     120
ctt                                                                   123

<210> SEQ ID NO 40
<211> LENGTH: 123
<212> TYPE: DNA
<213> ORGANISM: Artificial Sequence
<220> FEATURE:
<223> OTHER INFORMATION: synthetic oligonucleotide

<400> SEQUENCE: 40
cccaattttt cttttgaatt ctctagagaa ttcttttgct ttttcttcaa aaagcaaaag      60
acgctggtgg ctggcactcc tggtttccag gacggggttc aagtccctgc ggtgtctttg     120
ctt                                                                   123

<210> SEQ ID NO 41
<211> LENGTH: 123
<212> TYPE: DNA
<213> ORGANISM: Artificial Sequence
<220> FEATURE:
<223> OTHER INFORMATION: synthetic oligonucleotide

<400> SEQUENCE: 41
cccaattttt cttttgaaga gaaatttctc ttcttttgct ttttcttcaa aaagcaaaag      60
acgctggtgg ctggcactcc tggtttccag gacggggttc aagtccctgc ggtgtctttg     120
ctt                                                                   123
```

```
<210> SEQ ID NO 42
<211> LENGTH: 123
<212> TYPE: DNA
<213> ORGANISM: Artificial Sequence
<220> FEATURE:
<223> OTHER INFORMATION: synthetic oligonucleotide

<400> SEQUENCE: 42
cccaattttt cttttgaaga gaatttctc ttcttttgct ttttaaaaaa aaagcaaaag    60
acgctggtgg ctggcactcc tggtttccag gacggggttc aagtccctgc ggtgtctttg   120
ctt                                                                 123

<210> SEQ ID NO 43
<211> LENGTH: 123
<212> TYPE: DNA
<213> ORGANISM: Artificial Sequence
<220> FEATURE:
<223> OTHER INFORMATION: synthetic oligonucleotide

<400> SEQUENCE: 43
aaaggttttt cttttgaaga gaatttctc ttcttttgct ttttcttcaa aaagcaaaag    60
acgctggtgg ctggcactcc tggtttccag gacggggttc aagtccctgc ggtgtctttg   120
ctt                                                                 123

<210> SEQ ID NO 44
<211> LENGTH: 138
<212> TYPE: DNA
<213> ORGANISM: Artificial Sequence
<220> FEATURE:
<223> OTHER INFORMATION: synthetic oligonucleotide

<400> SEQUENCE: 44
aaaggttttt cttttcctga gaaaacaacc ttttgttttc tcaggttttg cccctaaaa    60 aaaaaaaagc aaaagacgct ggtggctggc actcctggtt tccaggacgg ggttcaagtc   120
cctgcggtgt ctttgctt                                                 138

<210> SEQ ID NO 45
<211> LENGTH: 138
<212> TYPE: DNA
<213> ORGANISM: Artificial Sequence
<220> FEATURE:
<223> OTHER INFORMATION: synthetic oligonucleotide

<400> SEQUENCE: 45
aaaggttttt cttttcctga gaaaacaacc ttttgttttc tcaggttttg cttttaaaa    60 aaaaggggc aaaagacgct ggtggctggc actcctggtt tccaggacgg ggttcaagtc    120
cctgcggtgt ctttgctt                                                 138

<210> SEQ ID NO 46
<211> LENGTH: 138
<212> TYPE: DNA
<213> ORGANISM: Artificial Sequence
<220> FEATURE:
<223> OTHER INFORMATION: synthetic oligonucleotide

<400> SEQUENCE: 46
aaaggttttt cttttcctga gaaaacaacc ttttgttttc tcaggttttg cccctaaaa    60 aaaaggggc aaaagacgct ggtggctggc actcctggtt tccaggacgg ggttcaagtc    120
cctgcggtgt ctttgctt                                                 138
```

```
<210> SEQ ID NO 47
<211> LENGTH: 138
<212> TYPE: DNA
<213> ORGANISM: Artificial Sequence
<220> FEATURE:
<223> OTHER INFORMATION: synthetic oligonucleotide

<400> SEQUENCE: 47
aaaggtcccc cttttcctga gaaaacaacc ttttgttttc tcaggttttg cccctaaaa        60 aaaagggggc aaaagacgct ggtggctggc actcctggtt tccaggacgg ggttcaagtc      120
cctgcggtgt ctttgctt                                                    138

<210> SEQ ID NO 48
<211> LENGTH: 122
<212> TYPE: DNA
<213> ORGANISM: Artificial Sequence
<220> FEATURE:
<223> OTHER INFORMATION: synthetic oligonucleotide

<400> SEQUENCE: 48
aacttgttta ttgcagctta taatggttac aaataaagca atagcatcac aaatttcaca       60
aataaagcat ttttttcact gcattctagt tgtggtttgt ccaaactcat caatgtatct     120
ta                                                                    122

<210> SEQ ID NO 49
<211> LENGTH: 228
<212> TYPE: DNA
<213> ORGANISM: Artificial Sequence
<220> FEATURE:
<223> OTHER INFORMATION: synthetic oligonucleotide

<400> SEQUENCE: 49
cgactgtgcc ttctagttgc cagccatctg ttgtttgccc ctcccccgtg ccttccttga       60
ccctggaagg tgccactccc actgtccttt cctaataaaa tgaggaaatt gcatcgcatt     120
gtctgagtag gtgtcattct attctggggg gtggggtggg gcaggacagc aaggggagg      180 attgggaaga caatagcagg catgctgggg atgcggtggg ctctatgg                  228

<210> SEQ ID NO 50
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 50
ggcacggagc cgccgcaggt gtttcttttc ctgaccgcgg ctcatggccg cgctcaggtt       60 ttgctttca cctttgtctg agagaacgaa cgtgagcagg aaaaagcaaa aggcactggt     120
ggcggcacgc ccgcacctcg ggccagggtt cgagtccctg cagtaccgtg cttc           174

<210> SEQ ID NO 51
<211> LENGTH: 174
<212> TYPE: DNA
<213> ORGANISM: Artificial Sequence
<220> FEATURE:
<223> OTHER INFORMATION: synthetic oligonucleotide
```

<400> SEQUENCE: 51
gattcgtcag tagggttgta aaggttttc ttttcctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174

<210> SEQ ID NO 52
<211> LENGTH: 76
<212> TYPE: DNA
<213> ORGANISM: Artificial Sequence
<220> FEATURE:
<223> OTHER INFORMATION: synthetic oligonucleotide

<400> SEQUENCE: 52
ggacaaaaac gagacgctgg tggctggcac tcctggtttc caggacgggg ttcaagtccc    60
tgcggtgtct ttgctt                                                    76

<210> SEQ ID NO 53
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 53
gattcgtcag tagggttgta aaggttttc ttttcctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174

<210> SEQ ID NO 54
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 54
gattcgtcag tagggttgta aaggtttaaa aattcctgag aaaacaacct tttgttttct    60
caggttttgc tttttggcct ttccctagct ttaaaaaaaa aaaagcaaaa gacgctggtg   120
gctggcactc ctggtttcca ggacggggtt caagtccctg cggtgtcttt gctt         174

<210> SEQ ID NO 55
<211> LENGTH: 174
<212> TYPE: DNA
<213> ORGANISM: Artificial Sequence
<220> FEATURE:
<223> OTHER INFORMATION: synthetic oligonucleotide

<400> SEQUENCE: 55
gattcgtcag tagggttgta aaggttttc ttttcctgag aaaacaacct tttgttttct    60
caggttttcg aaaatggcct ttccctagct ttaaaaaaaa aaaagcaaaa gacgctggtg   120
gctggcactc ctggtttcca ggacggggtt caagtccctg cggtgtcttt gctt         174

<210> SEQ ID NO 56
<211> LENGTH: 174
<212> TYPE: DNA
<213> ORGANISM: Artificial Sequence
<220> FEATURE:
<223> OTHER INFORMATION: synthetic oligonucleotide

```
<400> SEQUENCE: 56
gattcgtcag tagggttgta aaggtttttc ttttcctgag aaaacaacct tttgttttct     60
caggttttgc ttttggcct ttccctagct ttaaaaaaaa ttttcgaaaa gacgctggtg     120
gctggcactc ctggtttcca ggacggggtt caagtccctg cggtgtcttt gctt          174

<210> SEQ ID NO 57
<211> LENGTH: 135
<212> TYPE: DNA
<213> ORGANISM: Artificial Sequence
<220> FEATURE:
<223> OTHER INFORMATION: synthetic oligonucleotide

<400> SEQUENCE: 57
ggcttcatat aatcctaatg atatggtttg ggagtttcta ccaagagcct taaactcttg     60
attatgaagt cgacgctggt ggctggcact cctggtttcc aggacggggt tcaagtccct    120
gcggtgtctt tgctt                                                    135

<210> SEQ ID NO 58
<211> LENGTH: 132
<212> TYPE: DNA
<213> ORGANISM: Artificial Sequence
<220> FEATURE:
<223> OTHER INFORMATION: synthetic oligonucleotide

<400> SEQUENCE: 58
ggatcatata atcgcgtgga tatggcacgc aagtttctac cgggcaccgt aaatgtccga     60
ctatggtcga cgctggtggc tggcactcct ggtttccagg acggggttca agtccctgcg    120
gtgtctttgc tt                                                       132

<210> SEQ ID NO 59
<211> LENGTH: 162
<212> TYPE: DNA
<213> ORGANISM: Artificial Sequence
<220> FEATURE:
<223> OTHER INFORMATION: synthetic oligonucleotide

<400> SEQUENCE: 59
ggaaaaatgt cacgcacagg gcaaaccatt cgaaagagtg ggacgcaaag cctccggcct     60
aaaccagaag acatggtagg tagcgggggtt accgatggga cgctggtggc tggcactcct   120
ggtttccagg acggggttca agtccctgcg gtgtctttgc tt                       162

<210> SEQ ID NO 60
<211> LENGTH: 196
<212> TYPE: DNA
<213> ORGANISM: Artificial Sequence
<220> FEATURE:
<223> OTHER INFORMATION: synthetic oligonucleotide

<400> SEQUENCE: 60
ttaaaatctc ttatcaagag aggtggaggg actggcccga tgaaacccgg caaccagcct     60
tagggcatgg tgccaattcc tgcagcggtt tcgctgaaag atgagagatt cttgtagtct    120
cttcttttag cggacgctgg tggctggcac tcctggtttc caggacgggg ttcaagtccc    180
tgcggtgtct ttgctt                                                   196

<210> SEQ ID NO 61
<211> LENGTH: 189
<212> TYPE: DNA
<213> ORGANISM: Artificial Sequence
```

<220> FEATURE:
<223> OTHER INFORMATION: synthetic oligonucleotide

<400> SEQUENCE: 61
ccggctttaa gttgacgagg gcagggttta tcgagacatc ggcgggtgcc ctgcggtctt    60
cctgcgaccg ttagaggact ggtaaaacca caggcgactg tggcatagag cagtccgggc   120
aggaagacgc tggtggctgg cactcctggt ttccaggacg gggttcaagt ccctgcggtg   180
tctttgctt                                                            189

<210> SEQ ID NO 62
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 62
gcaaagacac cgcagggact tgaac                                          25

<210> SEQ ID NO 63
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 63
gcaaagacac cgcagggatt tgaacccogt cctggaaacc aggagtgcca                50

<210> SEQ ID NO 64
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 64
tccatgccgt gggtgatgcc                                                20

<210> SEQ ID NO 65
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 65
ctaagatgct agcttggcca agtctgttat g                                   31

<210> SEQ ID NO 66
<211> LENGTH: 45
<212> TYPE: DNA
<213> ORGANISM: Artificial Sequence
<220> FEATURE:
<223> OTHER INFORMATION: synthetic oligonucleotide

<400> SEQUENCE: 66
gctaatcttc tctgtatcgt tccaattta gtatatgtgc tgccg                     45

<210> SEQ ID NO 67
<211> LENGTH: 21
<212> TYPE: DNA
<213> ORGANISM: Artificial Sequence

```
<220> FEATURE:
<223> OTHER INFORMATION: synthetic oligonucleotide

<400> SEQUENCE: 67
gccggtggag tggcggccct c                                              21

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 68
cgcgcttctc gttggggtcc                                                20

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 69
ttcgtactgt tccacgatgg                                                20

<210> SEQ ID NO 70
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 70
aaaaagcaaa a                                                         11

<210> SEQ ID NO 71
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 71
cagtagggtc atgaaggttt ttcttttcct gagaaaacaa cacgtattgt tttctcaggt    60
tttgcttttt ggccttttc tagcttaaaa aaaaaaaag caaaa                     105

<210> SEQ ID NO 72
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 72
cagtagggtc atgaaggttt ttcttttcct gagaaaacaa cacgttttgt tttctcaggt    60
tttgcttttt ggccttttc tagctttaaa aaaaaaaag caaaa                     105

<210> SEQ ID NO 73
<211> LENGTH: 103
<212> TYPE: DNA
<213> ORGANISM: Artificial Sequence
<220> FEATURE:
<223> OTHER INFORMATION: synthetic oligonucleotide
```

<400> SEQUENCE: 73
cagtagggtt gtaaaggttt ttcttttcct gagaaaacaa cctttttgttt tctcaggttt    60 tgcttttttgg cctttcccta gctttaaaaa aaaaaaagca aaa    103

<210> SEQ ID NO 74
<211> LENGTH: 99
<212> TYPE: DNA
<213> ORGANISM: Artificial Sequence
<220> FEATURE:
<223> OTHER INFORMATION: synthetic oligonucleotide

<400> SEQUENCE: 74
cagtagggtt gtaaaggttt ttcttttcct gagaaaacaa attttttgttt tctcaggttt    60 tgcttttttag cctttttccta gcttaaaaaa aaagcaaaa    99

<210> SEQ ID NO 75
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 75
cagtagggct gtaaaggttt ttcttttcct gagaaaacaa cttttgtttt ctcaggtttt    60 gcttttttggc ctttttcctag ctttaaaaaa aaaaagcaa aa    102

<210> SEQ ID NO 76
<211> LENGTH: 92
<212> TYPE: DNA
<213> ORGANISM: Artificial Sequence
<220> FEATURE:
<223> OTHER INFORMATION: synthetic oligonucleotide

<400> SEQUENCE: 76
caccttgtcc gagggttttt cttttcctga ggaaacaccg cttgtttcct caggttttgc    60 ttttttcacct ttaatactca aaaaaagcaa aa    92

<210> SEQ ID NO 77
<211> LENGTH: 98
<212> TYPE: DNA
<213> ORGANISM: Artificial Sequence
<220> FEATURE:
<223> OTHER INFORMATION: synthetic oligonucleotide

<400> SEQUENCE: 77
gtagtctcaa aaggttttct tttactggga gaacattttt tgttcttgca ggttttgctt    60
tttacctctc gaattaccaa aaaaaaaaaa aagcaaaa    98

<210> SEQ ID NO 78
<211> LENGTH: 84
<212> TYPE: DNA
<213> ORGANISM: Artificial Sequence
<220> FEATURE:
<223> OTHER INFORMATION: synthetic oligonucleotide

<400> SEQUENCE: 78
gtttgaggtt tttctttttt cctgggggaa caactattgt tctttcaggt tttgcttttt    60
aacctcctaa gaaaaaaagc aaaa    84

```
<210> SEQ ID NO 79
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 79
cggagccgcc gcaggtgttt cttttactga gtgcagccca tggccgcact caggttttgc    60
ttttcacctt cccatctgtg aaagagtgag caggaaaaag caaaa                   105

<210> SEQ ID NO 80
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 80
cggagccgcc gcaggtgttt cttttactga gtgtggccca tggccgcact caggttttgc    60
ttttcacctt ctgatctgtg aaagagtgag caggaaaaag caaaa                   105

<210> SEQ ID NO 81
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 81
cggagccgcc gcaggtgttt cttttcctga ccgcggctca tggccgcgct caggttttgc    60
ttttcacctt tgtctgagag aacgtgagca ggaaaaagca aaa                     103

<210> SEQ ID NO 82
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 82
tggagccgcc gcaggtgttt cttttactgg atgaggctca tggccacatt caggttttgc    60
ttttcacctt tgagtctgtg cgaaaacaag gaggaaaaag caaaa                   105

<210> SEQ ID NO 83
<211> LENGTH: 105
<212> TYPE: DNA
<213> ORGANISM: Artificial Sequence
<220> FEATURE:
<223> OTHER INFORMATION: synthetic oligonucleotide

<400> SEQUENCE: 83
cggagccgcc gcaggtgttt cttttactga acgcagctca tggcagcgtt caggttttgc    60
ttttcacctt tgagtctgtg agaaaatgag caggaaaaag caaaa                   105

<210> SEQ ID NO 84
<211> LENGTH: 101
<212> TYPE: DNA
<213> ORGANISM: Artificial Sequence
<220> FEATURE:
<223> OTHER INFORMATION: synthetic oligonucleotide
```

<400> SEQUENCE: 84
ggcagccccc gcgggtgttt cttttactga ggctgccctg cagcctcagg ttttgctttt    60 caccccttaac tttgtgaaag aaagagcgcc aaaaagcaaa a                        101

<210> SEQ ID NO 85
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 85
gattcgtcag tagggttgta aaggtttttc ttttcctgag aaaacaacct tttgttttct    60
caggttttgc ttttggcct ttccctagct ttaaaaaaaa aaaagcaaaa                110

<210> SEQ ID NO 86
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 86
gattcgtcag tagggttgta aaggtttaaa aattcctgag aaaacaacct tttgttttct    60
caggttttgc ttttggcct ttccctagct ttaaaaaaaa aaaagcaaaa                110

<210> SEQ ID NO 87
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 87
gattcgtcag tagggttgta aaggtttttc ttttcctgag aaaacaacct tttgttttct    60
caggtttaaa aatttggcct ttccctagct ttaaaaaaaa aaaagcaaaa                110

<210> SEQ ID NO 88
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 88
gattcgtcag tagggttgta aaggtttaaa aattcctgag aaaacaacct tttgttttct    60
caggtttaaa aatttggcct ttccctagct ttaaaaaaaa aaaagcaaaa                110

<210> SEQ ID NO 89
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 89
aaaggttttt cttttcctga gaaatttctc aggttttgct tttaaaaaa aaagcaaaa       59

<210> SEQ ID NO 90
<211> LENGTH: 17
<212> TYPE: DNA
<213> ORGANISM: Artificial Sequence

```
<220> FEATURE:
<223> OTHER INFORMATION: synthetic oligonucleotide

<400> SEQUENCE: 90
aaaaagcaaa agacgcg                                                  17

<210> SEQ ID NO 91
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 91
aaaaagcaaa attttttt                                                 18

<210> SEQ ID NO 92
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 92
aaaaagcaat ttttt                                                    15

<210> SEQ ID NO 93
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 93
aaaaagcaaa atctt                                                    15

<210> SEQ ID NO 94
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 94
aaaaagcaaa aatattt                                                  17

<210> SEQ ID NO 95
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 95
aaaaagcaaa aaaaaaat                                                 19

<210> SEQ ID NO 96
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 96
aaaaagcaaa aaaaaatt                                                 19
```

```
<210> SEQ ID NO 97
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 97
aaaaagcaaa atttt                                                          15

<210> SEQ ID NO 98
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 98
aaaaagcaaa aaaaaaa                                                        17

<210> SEQ ID NO 99
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 99
aaaaagcttt tttttttttt ttttt                                               25

<210> SEQ ID NO 100
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 100
aaaaagcttt ttt                                                            13

<210> SEQ ID NO 101
<211> LENGTH: 59
<212> TYPE: RNA
<213> ORGANISM: Artificial Sequence
<220> FEATURE:
<223> OTHER INFORMATION: synthetic oligonucleotide

<400> SEQUENCE: 101
aaagguuuuu cuuuuccuga gaaauuucuc agguuuugcu uuuuaaaaaa aaagcaaaa          59

<210> SEQ ID NO 102
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 102
ttttgctttt tggcctttcc ctagctttaa aaaaaaaaaa gcaaaa                        46

<210> SEQ ID NO 103
<211> LENGTH: 46
<212> TYPE: DNA
<213> ORGANISM: Artificial Sequence
<220> FEATURE:
<223> OTHER INFORMATION: synthetic oligonucleotide
```

<400> SEQUENCE: 103
ttttcgtttt tggcctttcc ctagctttaa aaaaaaaaaa gcaaaa    46

<210> SEQ ID NO 104
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 104
ttttgctttt tggcctttcc ctagctttaa aaaaaaaaaa cgaaaa    46

<210> SEQ ID NO 105
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 105
ttttcgtttt tggcctttcc ctagctttaa aaaaaaaaaa cgaaaa    46

<210> SEQ ID NO 106
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 106
ttttgcaatt tggcctttcc ctagctttaa aaaaaaaaaa gcaaaa    46

<210> SEQ ID NO 107
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 107
ttttgctttt tggcctttcc ctagctttaa aaaaaaaatt gcaaaa    46

<210> SEQ ID NO 108
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 108
ttttgcaatt tggcctttcc ctagctttaa aaaaaaaatt gcaaaa    46

<210> SEQ ID NO 109
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 109
ttttcgaaaa tggcctttcc ctagctttaa aaaaaaaatt gcaaaa    46

```
<210> SEQ ID NO 110
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 110
ttttgctttt tggcctttcc ctagctttaa aaaaaatttt cgaaaa                          46

<210> SEQ ID NO 111
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 111
ttttcgaaaa tggcctttcc ctagctttaa aaaaaatttt cgaaaa                          46

<210> SEQ ID NO 112
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 112
cctttctttt ttggaaa                                                         17

<210> SEQ ID NO 113
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 113 cctttttattt ttggaaa                                                        17

<210> SEQ ID NO 114
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 114 cctttttcaat ttggaaa                                                        17

<210> SEQ ID NO 115
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 115
ccttaacttt ttggaaa                                                         17

<210> SEQ ID NO 116
<211> LENGTH: 17
<212> TYPE: DNA
<213> ORGANISM: Artificial Sequence
<220> FEATURE:
<223> OTHER INFORMATION: synthetic oligonucleotide
```

<400> SEQUENCE: 116
ccaattcttt ttggaaa                                                      17

<210> SEQ ID NO 117
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 117
cctttcttta atggaaa                                                      17

<210> SEQ ID NO 118
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 118
aaaggttttt cttttcctga gaaatttctc agttttgctt ttttaaaaaa aaagcaaaa        59

<210> SEQ ID NO 119
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 119 cccaatttt ctttgaatt ctctagagaa ttcttttgct ttttcttcaa aaagcaaaa          59

<210> SEQ ID NO 120
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 120 cccaatttt cttttgaaga gaaatttctc ttcttttgct ttttcttcaa aaagcaaaa         59

<210> SEQ ID NO 121
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 121 cccaatttt cttttgaaga gaaatttctc ttcttttgct ttttaaaaaa aaagcaaaa         59

<210> SEQ ID NO 122
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 122
aaaggttttt cttttgaaga gaaatttctc ttcttttgct ttttcttcaa aaagcaaaa        59

```
<210> SEQ ID NO 123
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 123
acuccaucau ccaacauacc aa                                              22

<210> SEQ ID NO 124
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 124
ugagguagua gguuguaugg uu                                              22

<210> SEQ ID NO 125
<211> LENGTH: 50
<212> TYPE: RNA
<213> ORGANISM: Artificial Sequence
<220> FEATURE:
<223> OTHER INFORMATION: synthetic oligonucleotide

<400> SEQUENCE: 125
acuccaucua gcaacauacc aacuuaagac uccaucuagc aacauaccaa                50

<210> SEQ ID NO 126
<211> LENGTH: 58
<212> TYPE: RNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (2)..(2)
<223> OTHER INFORMATION: n represents a or g
<220> FEATURE:
<221> NAME/KEY: misc_feature
<222> LOCATION: (55)..(55)
<223> OTHER INFORMATION: n represents a or g
<220> FEATURE:
<221> NAME/KEY: misc_feature
<222> LOCATION: (56)..(56)
<223> OTHER INFORMATION: n represents c or u
<220> FEATURE:
<221> NAME/KEY: misc_feature
<222> LOCATION: (58)..(58)
<223> OTHER INFORMATION: n represents g or u

<400> SEQUENCE: 126
gncgcuggug gcuggcacuc cugguuucca ggacgggguu caaguccug cggunncn        58

<210> SEQ ID NO 127
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 127
ttcaagtccc tgcggtaccg ttgctt                                          26
```

```
<210> SEQ ID NO 128
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 128
ttcaagtccc tgcggtaccg ccacca                                        26

<210> SEQ ID NO 129
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 129
ttcaagtccc tgcggtaccg ccacc                                         25

<210> SEQ ID NO 130
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 130
ttcaggtccc tgcggtaccg ccacca                                        26

<210> SEQ ID NO 131
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 131
ttcaagtccc tgcggtaccg ccaccag                                       27

<210> SEQ ID NO 132
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 132
ttcaagtccc tgcggtatct ttgctt                                        26

<210> SEQ ID NO 133
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 133
tcaagtccct gcggtaaaac tcttttttt                                     29

<210> SEQ ID NO 134
<211> LENGTH: 29
<212> TYPE: DNA
<213> ORGANISM: Artificial Sequence
<220> FEATURE:
<223> OTHER INFORMATION: synthetic oligonucleotide
```

-continued

```
<400> SEQUENCE: 134
ttcaagtccc tgcggtttaa attttttt                                          29

<210> SEQ ID NO 135
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 135
ttcaagtccc tgcggtatct tttttttct t                                       31

<210> SEQ ID NO 136
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 136
ttcmgtccct gcggtatttt tatttttttt atttctt                                37

<210> SEQ ID NO 137
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 137
ttcaagtccc tgcggtatct c                                                 21

<210> SEQ ID NO 138
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 138
ttcaagtccc tgcggtatct cca                                               23

<210> SEQ ID NO 139
<211> LENGTH: 13
<212> TYPE: DNA
<213> ORGANISM: Artificial Sequence
<220> FEATURE:
<223> OTHER INFORMATION: synthetic oligonucleotide

<400> SEQUENCE: 139
aaaaaaagca aaa                                                          13

<210> SEQ ID NO 140
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 140
ggacaaaaac ga                                                           12
```

```
<210> SEQ ID NO 141
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 141
gattcgtcag tagggttgta aaggttttc ttttcctgag aaaacaacct tttgttttct     60
caggttttcg aaaatggcct ttccctagct ttaaaaaaaa aaaagcaaaa                110

<210> SEQ ID NO 142
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 142
gattcgtcag tagggttgta aaggttttc ttttcctgag aaaacaacct tttgttttct     60
caggttttgc ttttggcct ttccctagct ttaaaaaaaa ttttcgaaaa                 110

<210> SEQ ID NO 143
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 143
gattcgtcag tagggttgta aaggttttc ttttcctgag aaaacaacct tttgttttct     60 caggttttt tttttttttt t                                                81

<210> SEQ ID NO 144
<211> LENGTH: 69
<212> TYPE: DNA
<213> ORGANISM: Artificial Sequence
<220> FEATURE:
<223> OTHER INFORMATION: synthetic oligonucleotide

<400> SEQUENCE: 144
gattcgtcag tagggttgta aaggttttc ttttcctgag aaaacaacct tttgtttttt     60
ttttttttt                                                             69

<210> SEQ ID NO 145
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 145
gattcgtcag tagggttgta aaggttttc ttttcctgag aaaacaacct ttttt           55

<210> SEQ ID NO 146
<211> LENGTH: 110
<212> TYPE: DNA
<213> ORGANISM: Artificial Sequence
<220> FEATURE:
<223> OTHER INFORMATION: synthetic oligonucleotide
```

<400> SEQUENCE: 146
gattcgtcag tagggttgta aaggttttc ttttcctgag aaacaacct tttgttttct    60 caggttttgc ttttggcct ttccctagct ttaaaaaaa aaaagcaaaa             110

<210> SEQ ID NO 147
<211> LENGTH: 71
<212> TYPE: DNA
<213> ORGANISM: Artificial Sequence
<220> FEATURE:
<223> OTHER INFORMATION: synthetic oligonucleotide

<400> SEQUENCE: 147
aaaggttttt cttttcctga tcaggttttg cttttggcc tttccctagc tttaaaaaaa    60
aaaaagcaaa a                                                       71

<210> SEQ ID NO 148
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 148
aaaggttttt cttttcctga tcaggttttg cttttttaaaa aaaaaaagc aaaa         54

<210> SEQ ID NO 149
<211> LENGTH: 64
<212> TYPE: DNA
<213> ORGANISM: Artificial Sequence
<220> FEATURE:
<223> OTHER INFORMATION: synthetic oligonucleotide

<400> SEQUENCE: 149
aaaggttttt cttttcctga tcaggttttg cttttggcc tttccctagc tttaaaaagc    60
aaaa                                                               64

<210> SEQ ID NO 150
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 150
aaaggttttt cttttcctga tcaggttttg cttttttagc tttaaaaagc aaaa         54

<210> SEQ ID NO 151
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 151
gattcgtcag tagggttgta aaggttttc ttttcctgat caggttttgc ttttaaaaa    60 aaaaaagca aa                                                       73

<210> SEQ ID NO 152
<211> LENGTH: 74
<212> TYPE: DNA
<213> ORGANISM: Artificial Sequence
<220> FEATURE:
<223> OTHER INFORMATION: synthetic oligonucleotide

```
<400> SEQUENCE: 152
aaaggttttt cttttcctga gaaacaacc ttttgttttc tcaggttttg cttttaaaa        60 aaaaaaaagc aaaa                                                        74

<210> SEQ ID NO 153
<211> LENGTH: 84
<212> TYPE: DNA
<213> ORGANISM: Artificial Sequence
<220> FEATURE:
<223> OTHER INFORMATION: synthetic oligonucleotide

<400> SEQUENCE: 153
aaaggttttt cttttcctga gaaacaacc ttttgttttc tcaggttttg cttttggcc        60 tttccctagc tttaaaaagc aaaa                                             84

<210> SEQ ID NO 154
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 154
aaaggttttt cttttcctga gaaacaacc ttttgttttc tcaggttttg cttttaaaa        60 agcaaaa                                                                67

<210> SEQ ID NO 155
<211> LENGTH: 70
<212> TYPE: DNA
<213> ORGANISM: Artificial Sequence
<220> FEATURE:
<223> OTHER INFORMATION: synthetic oligonucleotide

<400> SEQUENCE: 155
aaaggttttt cttttcctga gaaacaatt gttttctcag ttttgctttt taaaaaaaa        60 aaaagcaaaa                                                             70

<210> SEQ ID NO 156
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 156
aaaggttttt cttttcctga gaaacgttt tctcaggttt tgcttttttaa aaaaaaaaa       60 gcaaaa                                                                 66

<210> SEQ ID NO 157
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 157
aaaggttttt cttttcctga gaaacaacc ttttgttttc tcaggttttg ctttttagc        60 tttaaaaagc aaaa                                                        74
```

```
<210> SEQ ID NO 158
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 158
aaaggttttt ctttcctga gaaatttctc aggttttgct ttttaaaaaa aaaaaagcaa        60
aa                                                                     62

<210> SEQ ID NO 159
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 159
aaaggttttt ctttcctga gatctcaggt tttgctttt aaaaaaaaaa aagcaaaa          58

<210> SEQ ID NO 160
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 160
aaaggttttt ctttcctga gaaatttctc aggttttgct ttttaaaaaa aaagcaaaa        59

<210> SEQ ID NO 161
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 161
ttttgctttt t                                                           11

<210> SEQ ID NO 162
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 162
tttaaaaatt t                                                           11

<210> SEQ ID NO 163
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 163
aattgctttt t                                                           11

<210> SEQ ID NO 164
<211> LENGTH: 11
<212> TYPE: DNA
<213> ORGANISM: Artificial Sequence
```

```
<220> FEATURE:
<223> OTHER INFORMATION: synthetic oligonucleotide

<400> SEQUENCE: 164
ttaagctttt t                                                          11

<210> SEQ ID NO 165
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 165
ttttaatttt t                                                          11

<210> SEQ ID NO 166
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 166
ttttgcaatt t                                                          11

<210> SEQ ID NO 167
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 167
ttttgcttaa t                                                          11

<210> SEQ ID NO 168
<211> LENGTH: 11
<212> TYPE: DNA
<213> ORGANISM: Artificial Sequence
<220> FEATURE:
<223> OTHER INFORMATION: synthetic oligonucleotide

<400> SEQUENCE: 168
ttttgcttta a                                                          11

<210> SEQ ID NO 169
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 169
ccacctacgg caagctgacc                                                 20

<210> SEQ ID NO 170
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 170
ggtagcgggc gaagcact                                                   18
```

```
<210> SEQ ID NO 171
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 171
cttggagccg tacatgaact gagg                                          24

<210> SEQ ID NO 172
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 172
gcgcctgagc accatttagc                                               20

<210> SEQ ID NO 173
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 173
gcgctttggc ttgggtcatc                                               20

<210> SEQ ID NO 174
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 174
aaaaaaaaaa aaaaa                                                    15
```

PRODUCTION OF STABLE NON-POLYADENYLATED RNAS

This application is a national stage filing under U.S.C. §371 of PCT International Application PCT/US2013/065239, which claims priority under 35 U.S.C. §119(e) to U.S. Provisional Application Ser. No. 61/714,697, entitled "PRODUCTION OF STABLE NON-POLYADENYLATED RNAS" filed on Oct. 16, 2012, U.S. Provisional Application Ser. No. 61/716,764, entitled "PRODUCTION OF STABLE NON-POLYADENYLATED RNAS" filed on Oct. 22, 2012, and U.S. Provisional Application Ser. No. 61/739,153, entitled "PRODUCTION OF STABLE NON-POLYADENYLATED RNAS" filed on Dec. 19, 2012, which are herein incorporated by reference in their entirety.

FEDERALLY SPONSORED RESEARCH

This invention was made with government support under Grant Nos. GM34277 and CA133404 awarded by the National Institutes of Health. The government has certain rights in this invention.

BACKGROUND OF INVENTION

Processing the 3' end of a nascent transcript is critical for termination of RNA polymerase and for ensuring the proper functionality of the mature RNA. During normal development and in the progression of diseases such as cancer, 3' end cleavage site usage frequently changes, resulting in additional sequence motifs being included (or excluded) at the 3' ends of mature RNAs that can affect the transcripts' stability, subcellular localization, or function (reviewed in Lutz and Moreira 2011). Virtually all long RNA polymerase II (Pol II) transcripts terminate in a poly-A tail that is generated by endonucleolytic cleavage followed by the addition of adenosine (A) residues in a non-templated fashion (Moore and Sharp 1985; reviewed in Colgan and Manley 1997; Zhao et al. 1999; Proudfoot 2004). However, recent large-scale studies of the human transcriptome indicate that transcription is pervasive throughout the genome (reviewed in Wilusz et al. 2009) and suggest that a significant fraction (possibly >25%) of long Pol II transcripts present in cells may lack a canonical poly-A tail (Cheng et al. 2005; Wu et al. 2008; Yang et al. 2011a). Although some of these transcripts are likely degradation intermediates, there are well-characterized stable Pol II transcripts that lack a poly-A tail, such as replication-dependent histone mRNAs. Following U7 snRNA guided endonucleolytic cleavage at their 3' end, histone mRNAs have a highly conserved stem-loop structure in their 3' untranslated regions (UTRs) that is functionally analogous to a poly-A tail as it ensures RNA stability and enhances translational efficiency (reviewed in Marzluff et al. 2008).

Recent work has identified additional Pol II transcripts that are subjected to noncanonical 3' end processing mechanisms (reviewed in Wilusz and Spector 2010). In particular, enzymes with well-known roles in other RNA processing events, such as pre-mRNA splicing (Box et al. 2008) and tRNA biogenesis, have been shown to cleave certain nascent transcripts to generate mature 3' ends. In its well-characterized role, RNase P endonucleolytically cleaves tRNA precursors to produce the mature 5' termini of functional tRNAs (reviewed in Kirsebom 2007). It was shown that RNase P also generates the mature 3' end of the long noncoding RNA MALAT1 (metastasis-associated lung adenocarcinoma transcript 1), also known as NEAT2, despite the presence of a nearby polyadenylation signal (Wilusz et al. 2008). Cleavage by RNase P simultaneously generates the mature 3' end of the ~6.7-kb MALAT1 noncoding RNA and the 5' end of a small tRNA-like transcript. Additional enzymes involved in tRNA biogenesis, including RNase Z and the CCA-adding enzyme, further process the small RNA to generate the mature 61-nucleotide (nt) transcript known as mascRNA (MALAT1-associated small cytoplasmic RNA) (Wilusz et al. 2008).

The long MALAT1 transcript is retained in the nucleus in nuclear speckles (Hutchinson et al. 2007), where it has been proposed to regulate alternative splicing (Tripathi et al. 2010), transcriptional activation (Yang et al. 2011b), and the expression of nearby genes in cis (Nakagawa et al. 2012; Zhang et al. 2012). Although the MALAT1 locus appears to be dispensable for mouse development (Eissmann et al. 2012; Nakagawa et al. 2012; Zhang et al. 2012), MALAT1 is over-expressed in many human cancers (Ji et al. 2003; Lin et al. 2007; Lai et al. 2011), suggesting it may have an important function during cancer progression. Further, chromosomal translocation breakpoints (Davis et al. 2003; Kuiper et al. 2003; Rajaram et al. 2007) as well as point mutations and short deletions (Ellis et al. 2012) associated with cancer have been identified within MALAT1.

Despite lacking a canonical poly-A tail, MALAT1 is among the most abundant long noncoding RNAs in mouse and human cells. In fact, MALAT1 is expressed at a level comparable or higher than many protein-coding genes, including β-actin or GAPDH (Zhang et al. 2012).

SUMMARY OF INVENTION

The invention in some aspects relates to hybrid RNAs, expression vectors for expressing the RNAs and methods of use thereof. The hybrid RNAs include a stabilizing 3' end that replaces the poly-A tail of an endogenous RNA. Thus, in some aspects, the invention is a hybrid nucleic acid including an RNA molecule, lacking a poly-A tail, linked to a terminal sequence.

In other aspects a method for generating functional RNAs that are not mRNAs is provided. In some embodiments the functional RNA that is not an mRNA is an antisense RNA that may base pair with a target mRNA and regulate expression of target mRNA. The regulation may be up-regulation or down-regulation.

In some embodiments the terminal sequence is a heterologous RNA stabilizing terminal sequence that has a triple helix conformation. In other embodiments the terminal sequence is a heterologous RNA stabilizing terminal sequence that is a MALAT1 terminal sequence or a MEN β terminal sequence. In yet other embodiments the terminal sequence is a heterologous RNA stabilizing terminal sequence that is a U-rich sequence, an A-rich sequence, a U-rich and A-rich sequence, or a C-rich and G-rich sequence.

In other embodiments the terminal sequence has a ligand binding domain. For instance the ligand binding domain may be a tissue specific element. In some embodiments the tissue is a cancerous tissue and the tissue specific element is involved in regulation of translation in the cancerous tissue.

The RNA molecule may be any type of RNA molecule. For instance, the RNA molecule may be cytoplasmic RNA, a nuclear RNA, a mRNA, or a noncoding RNA. In some embodiments the RNA molecule is a eukaryotic RNA, a mammalian RNA, a plant RNA, or more specifically a human RNA. In some instances the RNA molecule corresponds to a reporter molecule.

A vector having a nucleic acid corresponding to an RNA molecule, a promoter upstream of the nucleic acid corresponding to the RNA molecule and a nucleic acid corresponding to a terminal sequence downstream of the nucleic acid corresponding to the RNA molecule is provided according to other aspects of the invention. In some embodiments the vector is a plasmid.

In some embodiments the nucleic acid corresponding to the RNA molecule is nucleic acid encoding a reporter protein, such as, for example, green fluorescent protein.

In other embodiments the vector includes a nucleic acid sequence that produces any of the hybrid nucleic acids described herein.

The promoter in some embodiments is a heterologous promoter. In other embodiments the promoter is a CMV promoter.

In other aspects of the invention a method for enhancing translation of an RNA is provided. The method involves expressing in a cell an isolated cytoplasmic RNA lacking a poly A tail, wherein the cytoplasmic RNA has a 3' terminal sequence effective for enhancing translation of the RNA in the cell.

In some embodiments the isolated cytoplasmic RNA lacking a poly A tail, having a 3' terminal sequence is a hybrid nucleic acid as described herein. In other embodiments any of the vectors described herein are administered to the cell to express the isolated cytoplasmic RNA lacking a poly A tail.

A method for expressing an RNA lacking a poly-A tail, by expressing in a cell an isolated nucleic acid comprising an RNA having a 3' heterologous terminal sequence and lacking a poly A tail is provided according to other aspects of the invention. In some embodiments the isolated nucleic acid is any of the hybrid nucleic acids described herein. In other embodiments any of the vectors described herein are administered to the cell to express the isolated nucleic acid.

In some embodiments the nucleic acid includes at least one chemical or natural modification.

In other aspects the invention is a method for purifying RNA. The method comprises the steps of subjecting a mixture of an isolated nucleic acid comprising an RNA having a 3' heterologous terminal sequence and lacking a poly A tail to an affinity purification step or a size exclusion purification step in order to obtain a purified RNA lacking a poly A tail.

In some embodiments the isolated nucleic acid is a hybrid nucleic acid as disclosed anywhere within the patent application. In other embodiments the purified RNA is used in an in vitro, ex vivo or in vivo method.

A method for treating a disease in a subject by administering to the subject an isolated nucleic acid comprising an RNA having a 3' heterologous terminal sequence and lacking a poly A tail in an effective amount to express a protein in the subject, wherein the protein is useful in the treatment of disease in the subject is provided according to other aspects of the invention. In some embodiments the disease is a disease associated with loss of function, such as muscular dystrophy or cystic fibrosis. In other embodiments the disease is a disease selected from the group of cancer, autoimmunity, cardiovascular disease, neurodegenerative disease, and skin disease.

According to other aspects the invention is a method for tissue generation involving expressing in a cell an isolated nucleic acid comprising an RNA having a 3' heterologous terminal sequence and lacking a poly A tail, growing the cell on a scaffold under growth conditions to form a tissue. In some embodiments the tissue is implanted in a body.

The invention also encompasses a tissue generated according to the methods described herein.

In other aspects of the invention a method for producing a stem cell is provided. The method involves expressing in a population of differentiated cells an isolated nucleic acid comprising an RNA having a 3' heterologous terminal sequence and lacking a poly A tail, wherein the RNA encodes a reprogramming protein, growing the differentiated cells under conditions for promoting reprogramming to form a pluripotent stem cell.

A pluripotent stem cell produced according to the methods described herein is provided according to other aspects of the invention.

A method for producing a differentiated cell is provided according to aspects of the invention. The method involves expressing in a population of stem cells an isolated nucleic acid comprising an RNA having a 3' heterologous terminal sequence and lacking a poly A tail, wherein the RNA encodes a differentiation protein, growing the stem cells under conditions for promoting differentiation to form a differentiated cell.

The invention in other aspects is a method of correcting a genetic defect in a subject in need thereof, by administering to the subject a therapeutically effective amount of an isolated cell which comprises an isolated nucleic acid comprising an RNA having a 3' heterologous terminal sequence and lacking a poly A tail, wherein the RNA encodes a protein for correcting the genetic defect. In some embodiments the genetic defect is selected from the group consisting of: a genetic defect that causes an immune system disorder; a genetic defect that causes a neurological disorder; a genetic defect that causes a cardiac disorder; a genetic defect that causes a circulatory disorder and a genetic defect that causes a respiratory disorder.

A method of treating a genetic disorder in a subject in need thereof by administering to the subject a therapeutically effective amount of an isolated cell which comprises an isolated nucleic acid comprising an RNA having a 3' heterologous terminal sequence and lacking a poly A tail, wherein the RNA encodes a replacement protein, wherein a lack of the replacement protein is associated with the genetic disorder is provided in other aspects of the invention.

The invention in other aspects is a hybrid nucleic acid of an RNA molecule, lacking a poly-A tail, linked to a heterologous RNA stabilizing terminal sequence, wherein the RNA molecule encodes an immunogenic protein. A method for vaccinating a subject by administering to a subject the hybrid nucleic acid in an effective amount to elicit an adaptive immune response to the immunogenic protein is provided in other embodiments.

In other aspects the invention is a non-human animal, comprising: an exogenous RNA molecule, lacking a poly-A tail, linked to a heterologous RNA, and a stabilizing terminal sequence in one or more cells of the animal. In some embodiments the RNA molecule encodes a therapeutic protein or an immunogenic protein.

This invention is not limited in its application to the details of construction and the arrangement of components set forth in the following description or illustrated in the drawings. The invention is capable of other embodiments and of being practiced or of being carried out in various ways. Each of the above embodiments and aspects may be linked to any other embodiment or aspect. Also, the phraseology and terminology used herein is for the purpose of description and should not be regarded as limiting. The use of "including," "comprising," or "having," "containing,"

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 1A-1E show that the 3' end of MALAT1 is highly conserved and cleaved by RNase P. (1A) Although there is a polyadenylation signal at the 3' end of the MALAT1 locus, MALAT1 is primarily processed via an upstream cleavage mechanism that is mediated by the tRNA biogenesis machinery. RNase P cleavage simultaneously generates the mature 3' end of MALAT1 and the 5' end of mascRNA. The tRNA-like small RNA is subsequently cleaved by RNase Z and subjected to CCA addition. The sequence shown is SEQ ID NO. 70. (1B) Immediately upstream of the MALAT1 RNase P cleavage site (denoted by arrow) is a highly evolutionarily conserved A-rich tract. Further upstream are two near perfectly conserved U-rich motifs separated by a predicted stem-loop structure. The sequences shown are SEQ ID NOs. 71 through 78 from top to bottom. (1C) Similar motifs are present upstream of the MEN β RNase P cleavage site. The sequences shown are SEQ ID NOs. 79 through 84 from top to bottom. (1D) The CMV-cGFP-mMALAT1_3' sense expression plasmid was generated by placing nt 6581-6754 of mouse MALAT1 downstream of the cGFP open reading frame. No polyadenylation signal is present at the 3' end. The sequence shown is SEQ ID NO. 70. (1E) After transfecting the plasmids into HeLa cells, Northern blots were performed to detect expression of mascRNA and cGFPMALAT1_3' RNA. To verify that the 3' end of cGFP MALAT1_3' RNA was accurately generated and that no additional nucleotides were added post-transcriptionally, RNase H digestion was performed prior to Northern blot analysis.

FIGS. 2A-2G show that the U-rich motifs inhibit uridylation and degradation of the 3' end of MALAT1. (2A) Schematics of cGFP expression plasmids used in this study. The sequence shown is SEQ ID NO. 70. To generate a cGFP transcript ending in a canonical poly-A tail, the mMALAT1_3' region was replaced with either the bovine growth hormone (bGH) or the SV40 polyadenylation signal (middle). To generate a nuclear-retained cGFP transcript, nt 1676 to 3598 of mMALAT1 was placed upstream of cGFP (bottom). (2B) Transfected HeLa cells were fractionated to isolate nuclear and cytoplasmic total RNA, which was then subjected to Northern blot analysis with a probe to the cGFP ORF. A probe to endogenous MALAT1 was used as a control for fractionation efficiency. (2C) The SpeckleF2-MALAT1_3' transcript was efficiently retained in the nucleus. (2D) Mutations or deletions (denoted in red) were introduced into the mMALAT1_3' region of the CMV-cGFP-mMALAT1_3' expression plasmid. The sequences shown are SEQ ID NOs. 85 through 89 from top to bottom. (2E) The wild type (WT) or mutant plasmids were transfected into HeLa cells and Northern blots performed. RNase H treatment was performed prior to the Northern blot that detected cGFP-MALAT1_3' RNA. (2F) A ligation-mediated 3' RACE approach was used to examine the 3' ends of cGFP-MALAT1_3' RNA transcripts undergoing degradation. Nucleotides added post-transcriptionally are in red. The sequences shown are SEQ ID NOs. 90 through 100 from top to bottom. (2G) RNase H treatment followed by Northern blotting was used to show that the cGFP-MALAT1_3' (comp 14 shown in FIG. 2D) transcript is stable. As 51 nt were deleted to generate the Comp. 14 transcript, a band of only 139-nt is expected.

FIGS. 3A-3E show base pairing between U-rich Motif 2 and the A-rich tract is necessary but not sufficient for MALAT1 stability. (3A) Predicted secondary structure of the 3' end of the mature Comp.14 transcript (SEQ ID NO. 101). Denoted in purple are base pairs between U-rich Motif 2 and the A-rich tract that were mutated in panels C, D, and E. (3B) Mutations (denoted in red) were introduced into the CMV-cGFP-mMALAT1_3' expression plasmid. The sequences shown are SEQ ID NOs. 102 through 111 from top to bottom. The atomic structure of the helix may vary in detail from the predicted structure shown but formation of the secondary structure is strongly supported. The full 174-nt mMALAT1_3' region was present in these plasmids, although only the region between U-rich Motif 2 and the A-rich tract is shown. (3C-E) The wild type (WT) or mutant plasmids were transfected into HeLa cells and Northern blots performed. RNase H treatment was performed prior to the Northern blots detecting cGFP-MALAT1_3'RNA.

FIGS. 4A-4F show that a triple helix forms at the 3' end of MALAT1 (4A) Base triples (denoted by dashed lines) form at the 3' end of the mature Comp.14 transcript. The sequence shown is SEQ ID NO. 101. This structure is similar to that shown in FIG. 3A except that the orientation of the conserved stem loop has been rotated by 90 degrees. This predicted structure may vary in detail from the atomic structure when available but formation of the triple helix is strongly supported. The U-A•U base triples that were mutated in panel E are denoted in purple. (4B) U-A•U and C-G•C base triples form via Hoogsteen hydrogen bonds to the major grove of a Watson-Crick base paired helix. (4C) Rosetta model of the MALAT1 Comp.14 3' end in cartoon representation. Bases 1 through 5 are not included to achieve modeling convergence. As in panel A, U-rich Motif 1 is in green, U-rich Motif 2 is in red, and the A-rich tract is in blue. Remaining bases are in gray. (4D) Close-up view of the triple helix surrounding the non-bonded base C-11 (numbering as in panel A). Bases are shown in stick representation with Watson-Crick hydrogen bonds in black, Hoogsteen hydrogen bonds in red. (4E) Four of the U-A•U base triples were progressively converted to C-G•C base triples in the CMV-cGFP-mMALAT1_3' expression plasmid. In the name of each construct, * represents the Hoogsteen hydrogen bonds. The wild type (WT) or mutant plasmids were then transfected into HeLa cells and Western blots performed to detect cGFP protein expression. Vinculin was used as a loading control. (4F) Mutations (denoted in red) were introduced into the CMV-cGFP-mMALAT1_3' expression plasmid. The full 174-nt mMALAT1_3' region was present in these plasmids, although only the region around U-rich Motif 1 is shown. Note that the 5' end of each transcript is on the right side to allow a direct comparison with the structure in panel A. The sequences shown are SEQ ID NOs. 112 through 117 from top to bottom. The WT or mutant plasmids were then transfected into HeLa cells and Northern blots performed.

FIGS. 5A-5I show that the MALAT1 triple helix functions as a translational enhancer element. (5A) Plasmids expressing cGFP transcripts ending in the designated 3' end sequences were transfected into HeLa cells. The mMALAT1_3' region and the polyadenylation signals were inserted in either the sense or antisense direction as denoted. Western blots were performed to detect cGFP protein expression. Vinculin was used as a loading control. (5B) Schematic of the two-color fluorescent reporter expression system. (5C) The two-color expression plasmids were transiently transfected into HeLa cells and flow cytometry used to measure mCherry and eYFP protein expression in single cells. Shown are box plots of the ratios of mCherry to eYFP protein expression measured in individual transfected cells (horizontal line, median; box, 25th through 75th percentile; error bars, 1.5× interquartile range) from a representative experiment (n=3). (5D) QPCR was used to measure the ratio of mCherry mRNA to eYFP mRNA in populations of cells transfected with the two-color expression plasmids. The data were normalized to the polyadenylated construct and are shown as mean and standard deviation values of three independent experiments. (5E) Mutations or deletions (denoted in red) were introduced into the mMALAT1_3' region of the CMV-cGFP-mMALAT1_3' expression plasmid. The sequences shown are SEQ ID NOs. 85, and 118 through 122 from top to bottom. (5F) The wild type (WT) or mutant plasmids were then transfected into HeLa cells and Northern blots performed. RNase H treatment was performed prior to the Northern blot that detects cGFP-MALAT1_3'RNA. (5G) Western blotting was used to detect cGFP expression in the transfected HeLa cells. (5H) Transfected HeLa cells were fractionated to isolate nuclear and cytoplasmic total RNA, which was then subjected to Northern blot analysis. (5I) Nucleotides that function in promoting translation (denoted in purple) flank the triple helical region at the 3' end of MALAT1. The sequence shown is SEQ ID NO. 101.

FIGS. 7A-7C show that a transcript ending in the MALAT1 triple helix is efficiently repressed by microRNAs in vivo. (7A) Inserted into the 3' UTR of mCherry was either a sequence perfectly complementary to let-7 or two bulged let-7 binding sites. The let-7 microRNA sequence is shown in blue. The sequences shown are SEQ ID NOs. 123 through 125, and 124 repeated twice from top to bottom. (7B) HeLa cells were transfected with two-color fluorescent reporter plasmids ending in either the SV40 polyadenylation signal or the mMALAT1_3' region, with or without (denoted 0x) microRNA binding sites. In addition, 40 nM of control siRNA or exogenous let-7 microRNA was co-transfected as indicated. Flow cytometry was then used to measure mCherry and eYFP protein levels. Relative fold repression was calculated as the ratio of the mean mCherry to the mean eYFP signal of the targeted construct normalized to the equivalent ratio for the non-targeted (0x) reporter. Data are shown as mean and standard deviation values of three independent experiments. (7C) QPCR was used to measure mCherry and eYFP transcript levels across the population of cells and relative fold repression of mCherry RNA expression was calculated analogously to above. Data are shown as mean and standard deviation values of three independent experiments.

FIGS. 8A-8D show that structurally unstable mascRNA mutants are marked at their 3' ends for degradation in vivo. (8A) It was shown that tRNAs (and tRNA-like transcripts) that have GG at their 5' ends and contain an unstable acceptor stem are targeted for rapid degradation by the addition of CCACCA by the CCA-adding enzyme (Wilusz et al. 2011). The sequences shown are both SEQ ID NO. 126. Using purified CCA-adding enzyme, allowed, for conversion of mascRNA from a CCA to a CCACCA target in vitro through the introduction of four mutations (denoted in red) in the acceptor stem (generating the Mut 10 transcript). In contrast, a mascRNA mutant that has an unstable acceptor stem but GA at its 5' end (Mut 7) remained a CCA target in vitro. To confirm these sequence requirements for CCACCA addition in vivo, CMV-cGFP-mMALAT1_3' plasmids were generated that express these two mutant mascRNA transcripts. (8B) The wild-type (WT) or mutant expression plasmids were transfected into HeLa cells and Northern blots used to detect expression of mascRNA and cGFP-MALAT1_3' RNA. None of the mascRNA mutations affected RNase P cleavage as cGFP-MALAT1_3' RNA was efficiently produced from both mutant plasmids (bottom). In contrast, neither mutant mascRNA transcript was detectable by Northern blot analysis (top), indicating that both were efficiently degraded post-RNase P cleavage. (8C) By performing a ligation-based 3' RACE PCR approach, it was found that CCACC(A) was added to the mascRNA Mut 10 transcript in vivo. Nucleotides added post-transcriptionally are shown in red. The sequences shown are SEQ ID NOs. 127 through 131 from top to bottom. (8D) In contrast and consistent with the previous in vitro results (Wilusz et al. 2011), no mascRNA Mut 7 transcripts ending in CCACCA were detected. Instead, it was often observed that short U-rich tails added to the 3' end of the Mut 7 transcript, implicating uridylation in the degradation process. The sequences shown are SEQ ID NOs. 132 through 138 from top to bottom. For several of the RACE clones, the U-rich tails began within the acceptor stem, indicating that a 3'-5' exonuclease likely stalled within this double-stranded region and the U-rich tail was added to provide a new single-stranded tail for an exonuclease to recognize and re-start the decay process. This shows that short single-stranded tails are added to the 3' ends of structurally unstable tRNAs and tRNA-like transcripts by multiplying mechanisms in vivo, resulting in transcript degradation.

FIGS. 10A-10C show that the 3' end of MEN β is cleaved by RNase P and supports efficient translation. (10A) Schematic of expression plasmids used. Inserted downstream of the cGFP open reading frame was the mMALAT1_3' region (top), the SV40 or bGH polyadenylation signal (middle), or a 174-nt region from the 3' end of the mouse MEN β locus that includes the MEN β tRNA-like structure as well as the conserved upstream U- and A-rich motifs (bottom). The sequences shown are both SEQ ID NO. 139. (10B) After transfecting the plasmids into HeLa cells, Northern blots were performed to detect expression of mascRNA and the cGFP mRNA. To verify the accuracy of cGFP mRNA 3' end processing with the various constructs, RNase H digestion was performed prior to Northern blot analysis. Smears were observed for the cGFP transcripts ending in the SV40 or bGH poly-A sites, indicative of variations in the length of the poly-A tails added. In contrast, defined bands of the expected size (190-nt) were observed for cGFP transcripts ending in the 3' ends of MALAT1 or MEN 13, indicating that no additional nucleotides are added post-RNase P cleavage. (10C) Western blots were performed to detect cGFP protein expression from the transfected plasmids. Vinculin was used as a loading control. Results show that the 3' ends of MALAT1 and MEN β support similar levels of translation.

FIGS. 11A-11C show that the U- and A-rich motifs are critical for stabilizing the 3' end of MALAT1 in the nucleus. (11A) Mutations (denoted in red) in U-rich Motif 1, U-rich Motif 2, or the A-rich tract were introduced into the CMV-SpeckleF2-mMALAT1_3' expression plasmid, which generates a nuclear-retained long transcript as shown in FIG. 2C. The sequences shown are SEQ ID NOs. 85, 86, 141, and 142 from top to bottom. (11B) The wild-type (WT) or mutant CMV-SpeckleF2-mMALAT1_3' expression plasmids were transfected into HeLa cells. As a control, the CMV-cGFP-mMALAT1_3' expression plasmid was also used (Lane 2). Northern blots were then performed to detect expression of mascRNA and the SpeckleF2-MALAT1_3' transcript (or the cGFP-MALAT1_3'-transcript in Lane 2). To verify that the 3' end of the long SpeckleF2-MALAT1_3' transcript was accurately generated and that no additional nucleotides were added post-transcriptionally, RNase H digestion was performed prior to Northern blot analysis. As the SpeckleF2-MALAT1_3' mutant transcripts were undetectable by Northern by analysis, we conclude that the U- and A-rich motifs are all required for stabilizing MALAT1 in the nucleus. (11C) A ligation-mediated 3' RACE approach was used to examine the 3' ends of SpeckleF2-MALAT1_3' transcripts undergoing degradation. Three clones (out of 15 sequenced) were detected that represent uridylated decay intermediates, suggesting that uridylation also occurs in the nucleus. The sequences shown are SEQ ID NOs. 85 and 143 through 145 from top to bottom. Interestingly, these 3 uridylated transcripts had been significantly degraded from the 3' end prior to the addition of the short U-tails.

FIGS. 12A1-12B-2 show a mutational analysis, which suggests that the motifs at the 3' end of MALAT1 cooperate to ensure transcript stability. (12A1 and 12A-2) CMV-cGFP-mMALAT1_3' expression plasmids containing various deletions in the 3' end region of MALAT1 were generated. * denotes nucleotides that were deleted in each construct. The sequences shown are SEQ ID NOs. 146 through 160 from top to bottom. (12B-1 and 12B-2) The various CMV-cGFP-mMALAT1_3' plasmids containing the compound mutations were transfected into HeLa cells and total RNA isolated 24 hr later. Northern blots were then performed to detect expression of mascRNA or cGFP-MALAT1. RNase H digestion was performed prior to Northern blot analysis for cGFP-MALAT1 RNA to validate the accuracy of RNase P processing for each construct. Interestingly, the cGFP-MALAT1_3' transcript was stable, suggesting that only 10 nt of the conserved stem loop are required for RNA stability. However, when attempting to delete additional nucleotides from the Comp.1 transcript (to generate Comp.2, Comp.3, Comp.4, or Comp.5), the cGFP-MALAT1_3' transcript became unstable. Nevertheless, if 18 or more nucleotides were present in the conserved stem loop (Comp.12), then additional nucleotides could be deleted from other parts of the 3' end of MALAT1. It was found that nucleotides in the conserved stem loop and in the region between U-rich Motif 2 and the A-rich tract redundantly cooperate to ensure MALAT1 RNA stability, likely by ensuring that a threshold of structural stability is reached. However, it is important to point out that triple helix formation plays a much more critical role in ensuring MALAT1 3' end stability.

FIGS. 13A-13B show that base pairing between U-rich Motif 2 and the A-rich tract is necessary for stabilizing the 3' end of MALAT1. (13A) Mutations in U-rich Motif 2 were introduced into the CMV-cGFP-mMALAT1_3' plasmid to disrupt select base pairs between U-rich Motif 2 and the A-rich tract. The full 174-nt mMALAT1_3' region is present in these plasmids, although only U-rich Motif 2 is shown. In the secondary structure prediction of mMALAT1_3' Comp.14, the nucleotides that were mutated in each lane in panel B are denoted in purple. The sequences shown are SEQ ID NOs. 161 through 168 and 101 from top to bottom. (13B) The wild type (WT) or mutant plasmids were transfected into HeLa cells and Northern blots performed. RNase H treatment was performed prior to the Northern blot detecting cGFP-MALAT1_3' RNA. With the exception of the U-A base pair farthest from the MALAT1 3' end (Mut U2.5, Lane 9), all the base pairs between U-rich Motif 2 and the A-rich tract play a significant role in stabilizing the MALAT1 3' end in vivo.

FIGS. 17A-17C show that other highly structured RNA tails can stabilize the 3' ends of long transcripts. (17A) To test if other highly structured RNA tails may be sufficient to stabilize the 3' end of the long cGFP transcript, the region of MALAT1 upstream of the RNase P cleavage site (which contains the U- and A-rich motifs that form the triple helix) was replaced with the sequences of well-characterized riboswitches (Serganov et al. 2004; Klein and Ferre-D'Amare 2006; Montange and Batey 2006; Sudarsan et al. 2008). The sequence shown is SEQ ID NO. 139. As the mascRNA tRNA-like structure is present immediately downstream of the 3' end of the riboswitch, RNase P cleavage generates a mature cGFP transcript ending in the riboswitch sequence in vivo. (17B) CMV-cGFP plasmids ending in the mMALAT1_3' region or a riboswitch+mascRNA were transfected into HeLa cells and Northern blots performed. RNase H treatment was performed prior to the Northern blot detecting cGFP mRNA. Of the 5 riboswitches tested, it was found that only the *T. tengcongensis* glmS catalytic riboswitch, which senses glucosamine-6 phosphate, was able to stabilize the 3' end of the cGFP message, although much more weakly than the MALAT1 triple helix. (17C) Western blots indicated that the *T. tengcongensis* glmS riboswitch also weakly supports translation The structural motifs tested show that this in vivo expression system provides an ideal method to screen for RNA sequences that are sufficient to stabilize the 3' ends of RNA transcripts.

FIGS. 20A-20E are a schematic and set of graphs demonstrating that a triple helix can be placed on the 3' end of multiple different mRNAs and support translation. (20A) Schematic of L1 mRNA (modified from Beck et al. 2011). Although L1 mRNA normally ends in a poly(A) tail (top, shown as SEQ ID NO. 174), an additional construct was generated in which the L1 polyadenylation signal was replaced with the mMALAT1_3' region to allow the mature L1 transcript to end in a triple helix (bottom). (20B) HeLa cells were transfected with a control vector expressing GFP or an episome-based vector expressing L1 mRNA ending in a poly(A) tail or a triple helix. A Northern blot using 15 µg of total RNA per lane was performed to detect expression of L1 mRNA. (20C) To verify that the 3' end of the L1 mRNA was accurately generated, RNase H digestion was performed prior to Northern blot analysis. Whereas a single band is observed for L1 mRNA ending in a triple helix, L1 mRNA ending in a poly(A) tail gives a smear that runs from approximately 300-400 nt. (20D) Western blots were performed to detect expression of ORF1 and ORF2 proteins from the transfected expression vectors. p110 was used as a loading control. (20E) Immunofluorescence was used to detect expression of ORF1 and ORF2 proteins in transfected HeLa cells.

DETAILED DESCRIPTION

Normally, long RNA polymerase II transcripts end in post-transcriptionally added polyadenylate (poly-A) tails that are required for RNA stability and efficient protein translation. When a poly-A tail is not present, the transcript is generally rapidly degraded in cells. Described herein is a method for generating transcripts that lack poly-A tails and yet are stable and efficiently translated. The invention is based at least in part on the discovery that the poly-A tail of RNA could be replaced by a functional terminal domain or sequence that enhances the stability of the RNA in the absence of the poly-A tail and in some instances even enhances the translation of the protein encoded within the RNA.

For instance, the use of sequences derived from the MALAT1 long noncoding RNA and the MEN β long noncoding RNA, as well as mutations and modifications thereof, which when transcribed into RNA, fold into a triple helical structure followed by a tRNA-like structure, is demonstrated in the Examples provided herein. The MALAT1 locus is misregulated in many human cancers and produces an abundant long nuclear-retained noncoding RNA. Despite being transcribed by RNA polymerase II, the 3' end of MALAT1 is not produced by canonical cleavage/polyadenylation but instead by recognition and cleavage of a tRNA-like structure by RNase P. Mature MALAT1 thus lacks a poly-A tail, yet is expressed at a level higher than many protein-coding genes in vivo. The tRNA-like structure is recognized and efficiently cleaved at its 5' end by the endonuclease RNase P, resulting in a mature transcript that is not poly-A, but instead has a triple helix at its 3' end in vivo.

Figure 1A:
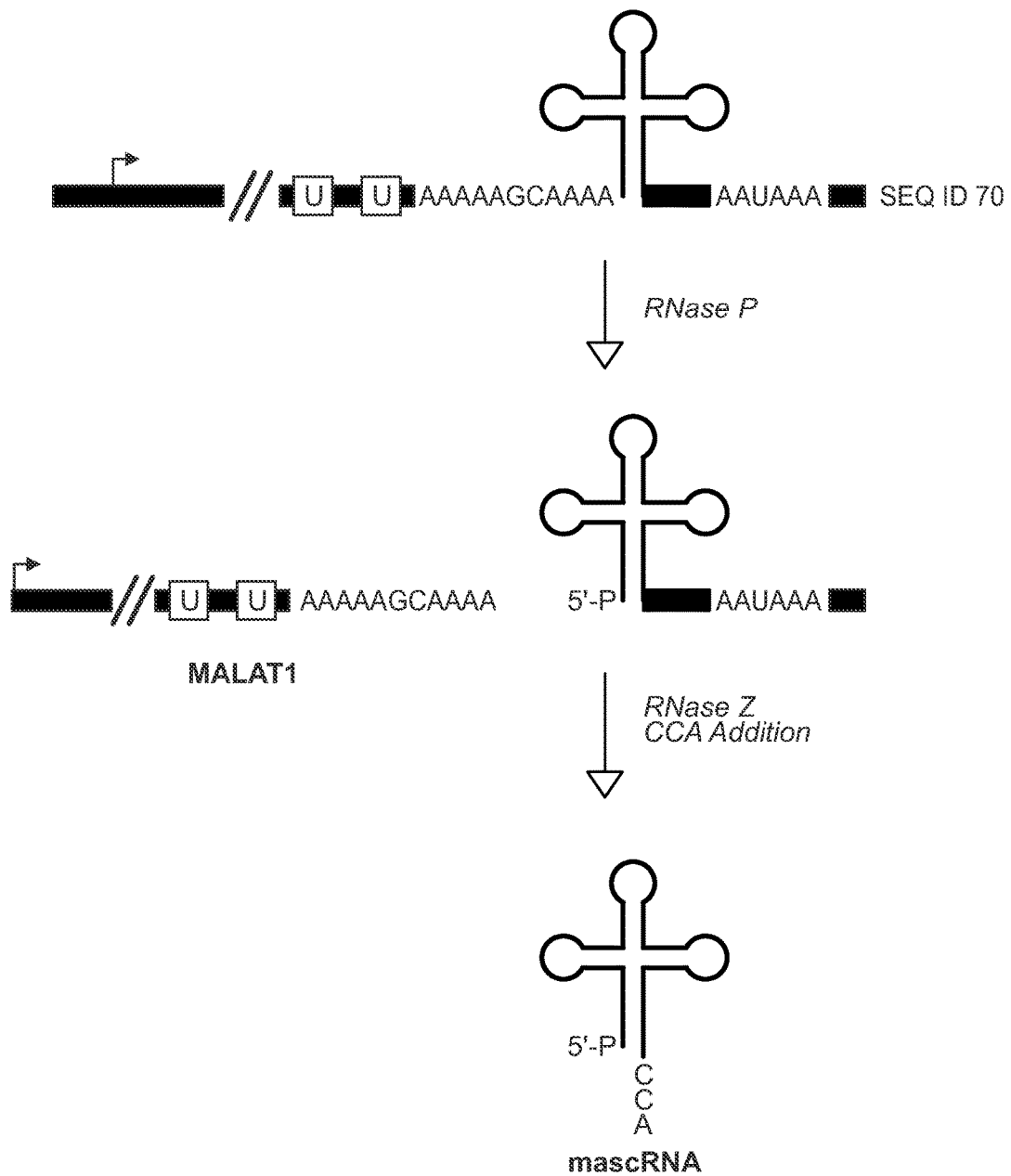
Figure 1C:
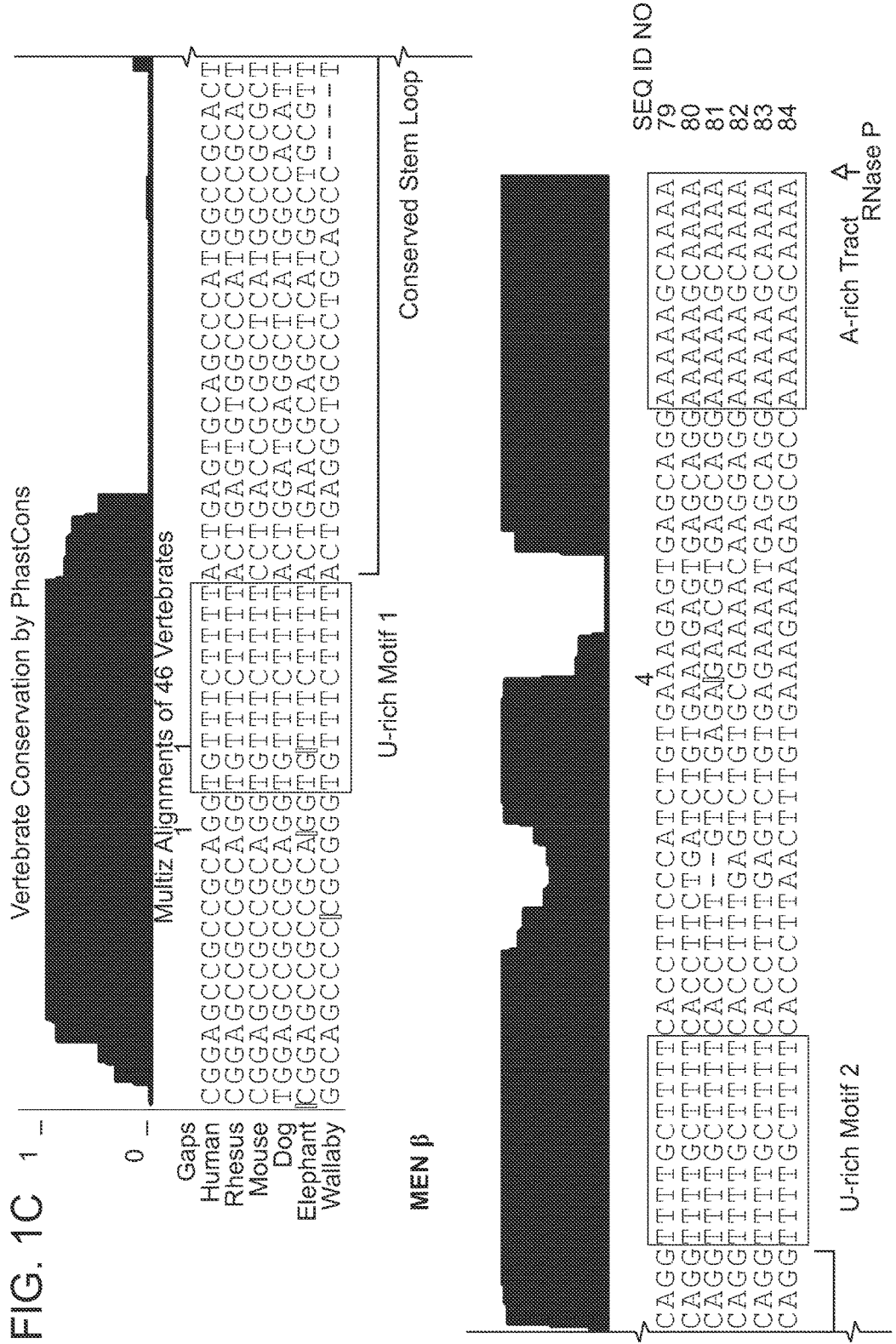

Cleavage by RNase P simultaneously generates the mature 3' end of the ~6.7-kb MALAT1 noncoding RNA and the 5' end of a small tRNA-like transcript (FIG. 1A). The mature MALAT1 transcript has a short A-rich tract on its 3' end (Wilusz et al. 2008; Wilusz and Spector 2010). Rather than being added on post-transcriptionally, as occurs during polyadenylation, the MALAT1 poly-A tail-like moiety is encoded in the genome and thus part of the nascent transcript (FIG. 1A). From human to fish, this A-rich motif along with two upstream U-rich motifs and a stem loop structure is highly evolutionarily conserved (FIG. 1B). Similar highly conserved A- and U-rich motifs are present at the 3' end of the MEN β long nuclear-retained noncoding RNA, also known as NEAT1_2, which is also processed at its 3' end by RNase P (Sunwoo et al. 2009) (FIG. 1C). However, the function of these motifs as well as the molecular mechanism by which the 3' ends of MALAT1 and MEN β are protected to allow the transcripts to accumulate to high levels was not known prior to the invention.

In some aspects the invention relates to hybrid RNAs, expression vectors for expressing the RNAs and methods of use thereof. The hybrid RNAs effectively recapitulate MALAT1 3' end processing in vivo, with, for example, highly conserved A- and U-rich motifs forming a triple helical structure at their 3' ends. Formation of the triple helix does not affect RNase P processing or mascRNA biogenesis, but is instead important for protecting the 3' end of MALAT1 from 3'-5' exonucleases. Surprisingly, when the 3' end of MALAT1 or MEN β was placed downstream of an open reading frame as shown in the Examples, the transcript was efficiently translated in vivo despite the absence of a poly-A tail. The triple helix structure thus strongly promotes both RNA stability and translation, suggesting that these long noncoding RNAs may interact with the protein synthesis machinery or even be translated under certain conditions. In addition, mutational analysis was used to show that the RNA stability and translational control functions can be separated. As this expression system provides a unique way to generate a stable transcript lacking a poly-A tail in vivo, we explored the role of the poly-A tail in microRNA-mediated repression. These and other research methods are encompassed by the invention. These results provide important new insights into how MALAT1, MEN β, and likely other transcripts that lack a poly-A tail are stabilized, regulated, and thus able to perform important cellular functions.

The triple helical structure is sufficient to efficiently stabilize the 3' end of the mature non-poly-A RNA in vivo. In addition, transcripts ending in a triple helix are efficiently translated to produce protein in vivo. The terminal sequence or domain can be used to construct a variety of stable RNA molecules which lack a poly-A tail. These stable RNA molecules can be produced in vivo from an expression vector. As demonstrated in the examples below the transcribed RNA is then delivered to the cytoplasm and efficiently produces protein. In some instance nuclear RNA is used according to the invention. In those instances the RNA remains in the nucleus, where it is functional.

As the sequence upstream of the tRNA-like structure/RNase P cleavage site can be replaced with any other sequence, the methods of the invention may be used to generate mature RNAs that have any desired sequence at their 3' ends. These sequences may, for example, regulate RNA stability and/or translation in response to a certain stimulus, resulting in regulated gene expression. The methods and constructs described herein enable the study of the effects of the poly A tail, as well as alternative mechanisms of expression and in some instance the design of in vivo regulated expression mechanisms.

Thus, the invention in some embodiments is a hybrid nucleic acid composed of an RNA molecule linked to a heterologous RNA stabilizing terminal sequence. The RNA molecule may be any form of naturally occurring or synthetic RNA but it lacks a poly-A tail. A poly-A tail as used herein, refers to a nucleic acid of 8, 9, 10, 11, 12 or more contiguous A's. Typically RNA that is exported from the nucleus to the cytoplasm, cytoplasmic RNA, includes a poly-A tail. Without a poly-A tail the RNA is highly unstable. By replacing the poly-A tail with the terminal sequence of the invention, the RNA is stabilized and translation is enhanced, resulting in the production of specific protein from the RNA. The RNA molecule includes for example a mRNA or a noncoding RNA as well as cytoplasmic and nuclear RNA. An mRNA typically corresponds to a protein. Depending on the purpose of the methods of the invention, the protein corresponding to the RNA may be a therapeutic or diagnostic protein or a reporter or other research protein, such as green fluorescent protein.

The RNA molecule may be an RNA molecule corresponding to an RNA molecule from any type of species or organism and including any chemical or natural modification thereof. For example the RNA may be a eukaryotic RNA, a mammalian RNA, a plant RNA or more specifically a human RNA. The particular type of RNA will depend on the use for the RNA. For example if the RNA will be used to study the effects of the expression of a particular protein in a mammalian cell, then the RNA may correspond to that type of mammal. In other circumstances the RNA may be expressed in a human in vivo for therapeutic purposes. In that case it is desirable to express a human RNA.

Chemical and natural modifications are well known in the art. Such modifications include, for example, modifications designed to increase binding to a target strand (i.e., increase their melting temperatures), to assist in identification of the oligonucleotide or an oligonucleotide-target complex, to increase cell penetration, to stabilize against nucleases and other enzymes that degrade or interfere with the structure or activity of the oligonucleotides, to provide a mode of disruption (a terminating event) once sequence-specifically bound to a target, and to improve the pharmacokinetic properties of the oligonucleotide.

Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50%, 60%, 70%, 80%, or 90% or more in translation relative to the lack of the modification—e.g., in a rabbit reticulocyte in vitro translation assay), the modification may not be suitable for the methods and compositions described herein.

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Substituted sugar moieties include, but are not limited to one of the following at the 2' position: H (deoxyribose); OH (ribose); F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted CI to CIO alkyl or C2 to CIO alkenyl and alkynyl.

A chemically or naturally modified RNA may include, for example, at least one nucleotide modified at the 2' position of the sugar, most preferably a 2'-O-alkyl, 2'-O-alkyl-O-alkyl or 2'-fluoro-modified nucleotide or an end cap. In other embodiments, RNA modifications include 2'-fluoro, 2'-amino and 2' O-methyl modifications on the ribose of pyrimidines, abasic residues or an inverted base at the 3' end of the RNA.

The RNAs useful according to the invention may include a single modified nucleoside. In other embodiments the RNA may include at least two modified nucleosides, at least 3, at least 4, at least 5, at least 6, at least 7, at least 8, at least 9, at least 10, at least 15, at least 20 or more nucleosides, up to the entire length of the oligonucleotide.

Nucleosides or nucleobases include the natural purine bases adenine (A) and guanine (G), and the pyrimidine bases thymine (T), cytosine (C) and uracil (U). Modified nucleosides include other synthetic and natural nucleobases such as inosine, xanthine, hypoxanthine, nubularine, isoguanisine, tubercidine, 2-(halo)adenine, 2-(alkyl)adenine, 2-(propyl) adenine, 2 (amino)adenine, 2-(aminoalkyll)adenine, 2 (aminopropyl)adenine, 2 (methylthio) N6 (isopentenyl)adenine, 6 (alkyl)adenine, 6 (methyl)adenine, 7 (deaza)adenine, 8 (alkenyl)adenine, 8-(alkyl)adenine, 8 (alkynyl)adenine, 8 (amino)adenine, 8-(halo)adenine, 8-(hydroxyl) adenine, 8 (thioalkyl) adenine, 8-(thiol)adenine, N6-(isopentyl)adenine, N6 (methyl)adenine, N6,N6 (dimethyl) adenine, 2-(alkyl)guanine, 2 (propyl)guanine, 6-(alkyl) guanine, 6 (methyl)guanine, 7 (alkyl)guanine, 7 (methyl) guanine, 7 (deaza)guanine, 8 (alkyl)guanine, 8-(alkenyl) guanine, 8 (alkynyl)guanine, 8-(amino)guanine, 8 (halo) guanine, 8-(hydroxyl)guanine, 8 (thioalkyl)guanine, 8-(thiol)guanine, N (methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl)cytosine, 5 (propynyl) cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl) uracil, 5 (guanidiniumalkyl)uracil, 5 (1,3-diazole-1-alkyl) uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo) uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl) pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio) pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio) pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 aminocarbonylethylenyl)-2,4-(dithio)pseudouracil, 1 (aminoalkylaminocarbonylethylenyl)-pseudouracil, 1 (aminoalkylaminocarbonylethylenyl)-2(thio)-pseudouracil, 1(aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, diiluorotolyl, 4-(iluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino) purine, 5 substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolopyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof.

The terminal sequence of the hybrid RNA or vector for expressing the RNA typically is a heterologous RNA stabilizing terminal sequence which has a triple helix structure. As used herein the term "heterologous" when used in the context of the 3' end of the RNA or "RNA stabilizing terminal sequence" refers to any nucleotide sequence that is not the naturally occurring sequence found at the 3' end of the naturally occurring RNA. The poly-A tail at the 3' ends of long RNA polymerase II transcripts functions to ensure that the mature RNA is stable, exported to the cytoplasm, and efficiently translated (reviewed in Zhao et al. 1999). It has been demonstrated according to the invention that the triple helical structures at the 3' ends of the MALAT1 and MEN β long noncoding RNAs can functionally replace a poly-A tail. It has also been demonstrated that similar triple helical structures can replace a poly-A tail. In addition to supporting transcript stability, these triple helices support efficient export (FIG. 2B) and translation (FIG. 5) of a reporter transcript. The endogenous noncoding RNAs in the examples are, however, not exported as nuclear retention signals elsewhere in the transcripts (FIG. 2C) somehow override any export signals present at the 3' ends. The various functions ascribed to the triple helical region have been separated from one another based on the identification of mutations that generate a stable and exported transcript that is not efficiently translated.

PAN (polyadenylated nuclear) RNA, an abundant long noncoding RNA generated by Kaposi's sarcoma-associated herpes virus, has previously been shown to also have a triple helix at its 3' end (Mitton-Fry et al. 2010). Unlike MALAT1 and MEN β, PAN RNA is subjected to canonical cleavage/polyadenylation and binds PABP (Borah et al. 2011). Nevertheless, 5 consecutive U-A•U base triples form between part of the PAN RNA poly-A tail and a U-rich region approximately 120 nt upstream of the poly-A tail (Mitton-Fry et al. 2010). Formation of this triple helix inhibits RNA decay and has been proposed to be required for nuclear retention of PAN RNA. In contrast, we find that the MALAT1/MEN β triple helices are not critical for nuclear retention (FIG. 2B). Using the PAN RNA triple helix structure as a guide, recent computational work identified six additional transcripts that likely form triple helices, although two of them were simply PAN RNA homologs in related gammaherpesviruses (Tycowski et al. 2012). The MALAT1 and MEN β triple helices were not identified in this study, likely due to the subtle differences in these structures compared to the PAN RNA triple helix. Considering that base triples can be formed by nucleotides far away from one another in a transcript's primary sequence (or even be encoded on separate independent transcripts), additional functional RNA triple helices are contemplated according to the invention and are encompassed by the invention.

Thus, in addition to the histone stem-loop structure and the MALAT1/MEN β triple helices, other RNA structural motifs may be able to functionally replace a poly-A tail. For example, it is known that tRNA-like structures stabilize the 3' ends of several single-stranded RNA viruses, such as Turnip Yellow Mosaic Virus and bacteriophage Qβ (reviewed in Fechter et al. 2001). The work presented in the Examples involves screens for other stabilizing RNA structures. Using those screens modified CMV-cGFP-mMALAT1_3' expression plasmids have been generated by replacing the region of MALAT1 upstream of the RNase P cleavage site with the sequences of various riboswitches, RNA elements which bind cellular metabolites and often fold into elaborate structures (reviewed in Serganov and Patel 2012) (data shown in the Examples). As the mascRNA tRNA-like structure is present immediately downstream of the 3' end of the riboswitch, RNase P cleavage generates a mature cGFP transcript ending in the riboswitch sequence in vivo. Interestingly, the *T. tengcongensis* glmS catalytic riboswitch, which senses glucosamine-6 phosphate (Klein and Ferre-D'Amare 2006), was able to stabilize the 3' end of the cGFP message and support translation, although the effects were weaker than that obtained with the MALAT1 triple helix. Nevertheless, these results demonstrate that there are indeed various RNA sequences that are sufficient to stabilize the 3' ends of non-polyadenylated transcripts. The invention also includes methods for in vivo screening to identify additional sequences.

Thus, the heterologous RNA stabilizing terminal sequence may be a MALAT1 terminal sequence or a MEN β terminal sequence or functional variants thereof. Variants may result from alternative splicing or allelic variation of genes provided in herein. In general, homologues and alleles typically will share at least 90% nucleotide identity and/or at least 95% amino acid identity to the sequences of known triple helix forming nucleic acids and polypeptides, respectively, in some instances will share at least 95% nucleotide identity and/or at least 97% amino acid identity, in other instances will share at least 97% nucleotide identity and/or at least 98% amino acid identity, in other instances will share at least 99% nucleotide identity and/or at least 99% amino acid identity, and in other instances will share at least 99.5% nucleotide identity and/or at least 99.5% amino acid identity. Homology can be calculated using various, publicly available software tools known in the art, such as those developed by NCBI (Bethesda, Md.) that are available through the internet. Exemplary tools include the BLAST system (e.g., using the default nucleic acid (Blastn) or protein (Blastp) search parameters) available from the website of the National Center for Biotechnology Information (NCBI) at the National Institutes of Health.

Alternatively the heterologous RNA stabilizing terminal sequence may be a U-rich or A-rich sequence or a combination thereof. A U-rich sequence as used herein refers to a set of nucleotide sequences that includes at least 5 U's in close proximity and in some embodiments 5 consecutive U's. An A-rich sequence as used herein refers to a set of nucleotide sequences that includes at least 5 A's in close proximity and in some embodiments 5 consecutive A's. The terminal sequence may include multiple U-rich and/or A-rich sequences or motifs. For example a terminal sequence may include 2, 3, or 4 U-rich sequences and/or 2, 3, or 4 A-rich sequences or any combination thereof. Preferably the U-rich and/or A-rich sequences are arranged in a manner that would produce triple helix structure.

The terminal sequence may similarly be composed of a C-rich and/or G-rich sequence. A C-rich sequence as used herein refers to a set of nucleotide sequences that includes at least 5 C's in close proximity and in some embodiments 5 consecutive C's. An G-rich sequence as used herein refers to a set of nucleotide sequences that includes at least 5 G's in close proximity and in some embodiments 5 consecutive G's. The terminal sequence may include multiple C-rich and/or G-rich sequences or motifs. For example a terminal sequence may include 2, 3, or 4 C-rich sequences and/or 2, 3, or 4 G-rich sequences or any combination thereof. Preferably the C-rich and/or G-rich sequences are arranged in a manner that would produce triple helix structure.

The terminal sequence may also have a ligand binding domain. A ligand binding domain is a domain that is sensitive to the presence or absence of a ligand. When the ligand is present the RNA may be activated or inhibited. Alternatively, when the ligand is absent the RNA may be activated or inhibited, depending on the particular ligand and element in the RNA. In some instances the ligand binding domain has a tissue specific element. For instance the ligand may be specific for a particular type of cancer and may be activated or inhibited in the presence of that particular type of cancer.

The RNAs of the invention can be expressed using a vector. In order to effect expression of the gene the nucleic acid may be delivered in a vector and/or operably linked to a heterologous promoter and transcription terminator. An expression vector is one into which a desired sequence may be inserted, e.g., by restriction and ligation such that it is operably joined to regulatory sequences and may be expressed as an RNA transcript. Vectors may further contain one or more marker sequences suitable for use in the identification of cells that have or have not been transformed or transfected with the vector or for studying the expression and effect of the terminal sequences and hybrid RNA. Markers include, for example, genes encoding proteins that increase or decrease either resistance or sensitivity to antibiotics or other compounds, genes that encode enzymes whose activities are detectable by standard assays known in the art (e.g., β-galactosidase or alkaline phosphatase), and genes that visibly affect the phenotype of transformed or transfected cells, hosts, colonies or plaques (e.g., green fluorescent protein).

Methods for identifying and obtaining nucleic acid sequences for use in the methods disclosed herein are routine in the art. For example, the skilled artisan may search Entrez Gene database using a GeneID or GeneAlias of a target to identify RNA sequences for creation of the hybrid RNA or vectors described herein. In most cases, links to commercial suppliers (e.g., Open Biosystems) of cDNA's containing the transcripts are provided in the Entrez Gene webinterface, which can be utilized to procure a copy cDNA clone. In other cases, commercial sources (e.g., Sigma Aldrich) can be contacted directly.

A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. An expression vector is one into which a desired DNA sequence may be inserted by restriction and ligation such that it is operably joined to regulatory sequences and may be expressed as an RNA transcript.

As used herein, a coding sequence and regulatory sequences are said to be "operably joined" when they are covalently linked in such a way as to place the expression or transcription of the coding sequence under the influence or control of the regulatory sequences. As used herein, "operably joined" and "operably linked" are used interchangeably and should be construed to have the same meaning. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region is operably joined to a coding sequence if the promoter region is capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

In some embodiments, a virus vector for delivering a nucleic acid molecule is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., Virology 219:220-227, 1996; Eloit et al., J. Virol. 7:5375-5381, 1997; Chengalvala et al., Vaccine 15:335-339, 1997), a modified retrovirus (Townsend et al., J. Virol. 71:3365-3374, 1997), a nonreplicating retrovirus (Irwin et al., J. Virol. 68:5036-5044, 1994), a replication defective Semliki Forest virus (Zhao et al., Proc. Natl. Acad. Sci. USA 92:3009-3013, 1995), canarypox virus and highly attenuated vaccinia virus derivative (Paoletti, Proc. Natl. Acad. Sci. USA 93:11349-11353, 1996), non-replicative vaccinia virus (Moss, Proc. Natl. Acad. Sci. USA 93:11341-11348, 1996), replicative vaccinia virus (Moss, Dev. Biol. Stand. 82:55-63, 1994), Venezuelan equine encephalitis virus (Davis et al., J. Virol. 70:3781-3787, 1996), Sindbis virus (Pugachev et al., Virology 212:587-594, 1995), lentiviral vectors (Naldini L, et al., Proc Natl Acad Sci USA. 1996 Oct. 15; 93(21):11382-8) and Ty virus-like particle (Allsopp et al., Eur. J. Immunol 26:1951-1959, 1996).

Another virus useful for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (i.e., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991).

In another embodiment, the nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the myosin heavy chain promoter, albumin promoter, lymphoid-specific promoters, neuron specific promoters, pancreas specific promoters, and mammary gland specific promoters. Developmentally-regulated promoters are also encompassed, for example the murine hox promoters and the a-fetoprotein promoter.

The invention also includes methods for enhancing translation of an RNA or for expressing an RNA. The methods are achieved by expressing a hybrid RNA, as described herein in a cell or organism in vivo.

The methods may be useful for treating disease in a subject, also referred to as an organism. As used herein, a subject is a mammal such as a human, non-human primate, cow, horse, pig, sheep, goat, dog, cat, or rodent. In all embodiments human subjects are preferred. A disease treatable according to the methods of the invention is any disease in which it is desirable to express a stable version of a RNA and optionally a protein corresponding to the RNA.

The nucleic acids of the invention are typically isolated nucleic acids. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

Aspects of the invention relate to methods for altering phenotypic properties of a cell or cells. The methods involve administration of an RNA of the invention to a cell, resulting in the expression of a desired protein in a cell or tissue, which may result in the upregulation, down regulation, activation, or deactivation of other proteins, nucleic acids, or factors or even to change the differentiated phenotype of a cell to that of another, desired cell type. Since the methods of the invention involve the administration of RNA rather than DNA or protein, the methods do not cause permanent modification of the genome or have the potential for unintended mutagenic effects.

Thus, aspects of the invention involve induction of protein expression in cells in vitro, in vivo, or ex vivo to modify the cells. Traditional methods for introducing agents or inducing gene expression has utilized exogenous DNA, or recombinant viral vectors. Gene therapy methods, however, have potential risks. The methods of the invention avoid gene therapy associated risks and provide effective and specific protein expression.

In some embodiments, the present invention provides methods for treating disease using the nucleic acids of the invention. The type of disease to be treated will depend on the RNA being expressed and vice versa. Diseases treatable according to the invention include but are not limited to proliferative diseases, autoimmunity, neurodegenerative diseases, cardiovascular diseases, myopathy, liposomal storage diseases, skin diseases, diseases associated with genetic defects or loss of function, and infectious diseases.

The RNAs of the invention are also useful for expressing a protein in a cell in order to alter one or more phenotypic properties of the cell. For instance, the protein may be involved in tissue generation or regeneration, or it may be a therapeutic protein or inhibitory protein for the treatment of a disease. For example the protein may be useful in the treatment of cancer or other proliferative disorders, neurodegenerative diseases, autoimmunity, cardiovascular diseases, muscle diseases and disorders.

Thus, the methods are useful for delivering RNA encoding a protein of interest to a cell for treatment of diseases and disorders in a subject. For example the methods may be used in methods for protein replacement therapy in vivo. In some embodiments, an RNA of the invention encoding a protein of interest can be delivered to a tissue and/or organ for in vivo protein expression in a method for treatment of a variety of different diseases where protein expression is desirable. For example diseases involving loss-of-function such as, muscular dystrophy, cystic fibrosis or other diseases involving low levels of protein expression of a particular protein are treatable according to the invention.

Thus, in some embodiments, the methods and compositions are useful in a method for the treatment of muscular dystrophy. Muscular dystrophy represents a family of inherited diseases of the muscles. Some forms affect children (e.g., Duchenne dystrophy) and are lethal within two to three decades. Adult forms tend to be more slowly progressive. The genes for several dystrophies have been identified, including Duchenne dystrophy (caused by mutations in the dystrophin gene) and the teenage and adult onset Miyoshi dystrophy or its variant, limb girdle dystrophy 2B or LGMD-2B (caused by mutations in the dysferlin gene). These are "loss of function" mutations that prevent expression of the relevant protein in muscle and thereby cause muscle dysfunction. A nucleic acid of the invention is delivered to one or more muscle tissue targets to replace a defective protein associated with the disease. For example, an RNA encoding the Dystrophin protein may be delivered for the treatment of Duchenne/Becker Muscular Dystrophy. Alternatively an RNA encoding a Emerin and/or Lamin protein can be administered to a subject having Emery-Dreyfuss muscular dystrophy.

The RNA may be delivered systemically or locally to achieve the therapeutic benefit. Local administration involves, for instance, delivering an RNA encoding dystrophin and/or Emerin and/or Lamin protein to a muscle tissue particularly associated with the condition. For example the diseases are associated with insufficient respiration due to a weakened thoracic diaphragm and inability to ambulate due to weak postural muscles. For diaphragmatic injection, a thoracoscopic approach may be used to deliver RNA into a diaphragm muscle. Alternatively direct injection into skeletal muscles, for example, direct injection into a pelvic girdle and shoulder girdle muscles associated with maintenance of posture and gross arm movements, respectively can be performed.

For the treatment of cystic fibrosis, an RNA encoding a CFTR protein can be administered to the tissue of the subject, such as the diaphragm. In some embodiments, an RNA encoding CFTR can be delivered by direct parenchymal injection and/or intrabronchial injection.

The methods are also useful for treating cardiovascular disease. Cardiovascular diseases include but are not limited to congestive heart failure, cardiomyopathy, myocardial infarction, tissue ischemia, cardiac ischemia, vascular disease, acquired heart disease, congenital heart disease, atherosclerosis, cardiomyopathy, dysfunctional conduction systems, dysfunctional coronary arteries, pulmonary heard hypertension, coronary artery disease, myocardial infarction, myocardial ischemia, atherosclerosis, cardiomyopathy, idiopathic cardiomyopathy, cardiac arrhythmias, muscular dystrophy, muscle mass abnormality, muscle degeneration, infective myocarditis, drug- or toxin-induced muscle abnormalities, hypersensitivity myocarditis, and autoimmune endocarditis.

A number of proteins are known to be useful in the treatment of heart disease. The RNA of the invention can be administered to produce these proteins in vivo to treat the disease. Examples of proteins useful for treating cardiovascular disease include but are not limited to VEGF polypeptides, e.g., human VEGF (hVEGF), alpha 1 anti-trypsin polypeptide, any cardiotrophic factors or growth factor to promote survival and/or growth of cardiac cells, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, products of the BMP or cripto pathway and cellular differentiation agents, such as cytokines and growth factors. Cardiotrophic factors are well known in the art and include but are not limited to cardiotrophic agents, creatine, carnitine, and taurine. The RNA can be delivered locally or systemically, as in the treatment of any of the diseases described herein. Examples of some local methods of delivery include administration to a subject via endomyocardial, epimyocardial, intraventricular, intracoronary, retrosinus, intra-arterial, intra-pericardial, or intravenous administration route.

In some instances, the disease treatable according to the invention is a loss-of-function disease. A loss-of-function disease is a disease associated with a mutation in a gene which causes a reduced or abolished protein function. "Loss-of-function" as used herein refers to a reduction or elimination of the normal activity of a gene or gene product. Loss of activity can be due to a decrease in transcription and/or processing of the RNA, a decrease in translation, stability, transport, or activity of the gene product, or any combination thereof. The loss of function genes include but are not limited to tumor suppressor genes, or mutations in genes responsible for DNA repair, cell division cycle checkpoints, cell motility, transcriptional regulation, and apoptosis. Tumor-suppressor genes and genes suspected of being tumor-suppressor genes include, but are not limited to, BRCA1, BRCA2, MLH1, MSH2, MSH6, EPHA3, EPHA4, APHB2, INI1, AXIN1, AXIN2, MLL3, EP300, NF1, TP53, APC, VHL, SMAD2, SMAD4, KEAP1, CDKN2A, RB I, MEN, NF2/SCH, PTCH, TGFBR1, TGFBR2, ACVR1B, AVCR2, MRE11, MAP2K4, and LKB1/STK11. Loss of function diseases include, a-thalassemia, beta-thalassemia, Turner Syndrome, Retinoblastoma.

The methods of the invention also encompass the use of the RNA for treating neurodegenerative disorders. As used herein the term "neurodegenerative disease" or "neurodegenerative disorder" implies any disorder that might be reversed, deterred, managed, treated, improved, or eliminated with agents that stimulate the generation of new neurons. Examples of neurodegenerative disorders include: (i) chronic neurodegenerative diseases such as familial and sporadic amyotrophic lateral sclerosis (FALS and ALS, respectively), familial and sporadic Parkinson's disease, Huntington's disease, familial and sporadic Alzheimer's disease, multiple sclerosis, olivopontocerebellar atrophy, multiple system atrophy, progressive supranuclear palsy, diffuse Lewy body disease, corticodentatonigral degeneration, progressive familial myoclonic epilepsy, strionigral degeneration, torsion dystonia, familial tremor, Down's Syndrome, Gilles de la Tourette syndrome, Hallervorden Spatz disease, diabetic peripheral neuropathy, dementia pugilistica, AIDS Dementia, age related dementia, age associated memory impairment, and amyloidosis related neurodegenerative diseases such as those caused by the prion protein (PrP) which is associated with transmissible spongiform encephalopathy (Creutzfeldt Jakob disease, Gerstmann Straussler Scheinker syndrome, scrapic, and kuru), and those caused by excess cystatin C accumulation (hereditary cystatin C angiopathy); and (ii) acute neurodegenerative disorders such as traumatic brain injury (e.g., surgery related brain injury), cerebral edema, peripheral nerve damage, spinal cord injury, Leigh's disease, Guillain-Barre syndrome, lysosomal storage disorders such as lipofuscinosis, Alper's disease, vertigo as result of CNS degeneration; pathologies arising with chronic alcohol or drug abuse including, for example, the degeneration of neurons in locus coeruleus and cerebellum; pathologies arising with aging including degeneration of cerebellar neurons and cortical neurons leading to cognitive and motor impairments; and pathologies arising with chronic amphetamine abuse including degeneration of basal ganglia neurons leading to motor impairments; pathological changes resulting from focal trauma such as stroke, focal ischemia, vascular insufficiency, hypoxic-ischemic encephalopathy, hyperglycemia, hypoglycemia or direct trauma; pathologies arising as a negative side-effect of therapeutic drugs and treatments (e.g., degeneration of cingulate and entorhinal cortex neurons in response to anticonvulsant doses of antagonists of the NMDA class of glutamate receptor), and Wernicke Korsakoff's related dementia. Neurodegenerative diseases affecting sensory neurons include Friedreich's ataxia, diabetes, peripheral neuropathy, and retinal neuronal degeneration. Other neurodegenerative diseases include nerve injury or trauma associated with spinal cord injury. Neurodegenerative diseases of limbic and cortical systems include cerebral amyloidosis, Pick's atrophy, and Retts syndrome. The foregoing examples are not meant to be comprehensive but serve merely as an illustration of the term "neurodegenerative disorder."

Parkinson's disease is a disturbance of voluntary movement in which muscles become stiff and sluggish. Symptoms of the disease include difficult and uncontrollable rhythmic twitching of groups of muscles that produces shaking or tremors. Currently, the disease is caused by degeneration of pre-synaptic dopaminergic neurons in the brain and specifically in the brain stem. As a result of the degeneration, an inadequate release of the chemical transmitter dopamine occurs during neuronal activity.

Amyotrophic lateral sclerosis (ALS), also called Lou Gehrig's disease, is a progressive, fatal neurological disease. ALS occurs when specific nerve cells in the brain and spinal cord that control voluntary movement gradually degenerate and causes the muscles under their control to weaken and waste away, leading to paralysis. ANG, encoding a 14 kDa angiogenic ribonuclease, is a loss-of-function gene identified in ALS. The methods of the invention contemplate delivery of the 14 kDa angiogenic ribonuclease in the treatment of ALS using the RNA of the invention.

Currently, Parkinson's disease is treated with several different compounds and combinations. Levodopa (L-dopa), which is converted into dopamine in the brain, is often given to restore muscle control. Perindopril, an ACE inhibitor that crosses the blood-brain barrier, is used to improve patients' motor responses to L-dopa. Carbidopa is administered with L-dopa in order to delay the conversion of L-dopa to dopamine until it reaches the brain, and it also lessens the side effects of L-dopa. Other drugs used in Parkinson's disease treatment include dopamine mimickers Mirapex (pramipexole dihydrochloride) and Requip (ropinirole hydrochloride), and Tasmar (tolcapone), a COMT inhibitor that blocks a key enzyme responsible for breaking down levodopa before it reaches the brain.

Alzheimer's disease is a degenerative brain disorder characterized by cognitive and noncognitive neuropsychiatric symptoms. Psychiatric symptoms are common in Alzheimer's disease, with psychosis (hallucinations and delusions) present in approximately fifty percent of affected patients. Similar to schizophrenia, positive psychotic symptoms are common in Alzheimer's disease. Delusions typically occur more frequently than hallucinations. Alzheimer's patients may also exhibit negative symptoms, such as disengagement, apathy, diminished emotional responsiveness, loss of volition, and decreased initiative. Indeed, antipsychotic agents that are used to relieve psychosis of schizophrenia are also useful in alleviating psychosis in Alzheimer's patients. As used herein, the term "dementia" refers to the loss, of cognitive and intellectual functions without impairment of perception or consciousness. Dementia is typically characterized by disorientation, impaired memory, judgment, and intellect, and a shallow labile affect.

Autism (also referred to as Autism Spectrum Disorder, or ASD) is a disorder that seriously impairs the functioning of individuals. It is characterized by self-absorption, a reduced ability to communicate with or respond to the outside world, rituals and compulsive phenomena, and mental retardation. Autistic individuals are also at increased risk of developing seizure disorders, such as epilepsy. While the actual cause of autism is unknown, it appears to include one or more genetic factors, as indicated by the fact that the concordance rate is higher in monozygotic twins than in dizygotic twins, and may also involve immune and environmental factors, such as diet, toxic chemicals and infections.

Proteins useful for treating neurodegenerative disorders include but are not limited to presenilin protein, and ANG. Presenilin protein is useful in the treatment of Alzheimer's disease.

An RNA encoding a protein of interest may also be used in the treatment of a skin disorder, such as for instance, vitiligo, eczema (often associated with loss of function of filaggrin gene), albinism, e.g., Hermansky-Pudlak syndrome (associated with mutations in HPS1 and HPS3 genes, among others), Incontinentia pigmenti (associated with mutations in the 1 KB KG gene), Oculocutaneous albinism (associated with mutations in one or more of MC1R, OCA2, SLC45A2, TYR, SLC45A2 and TYRP1 genes), Waardenburg syndrome (associated with mutations in EDN3, EDNRB, MITF, PAX3, SNAI2, and SOX10 genes), or Xeroderma pigmentosum (associated with mutations in ERCC2, ERCC3, POLH, XPA, and XPC genes). Accordingly, the present invention relates to treatment of such disorders by in vivo expression of a protein associated with the skin disorder. Optionally, the administration may be topical to the skin.

The methods and compositions described herein are useful in the treatment of proliferative diseases. In some embodiments, the proliferative disease is a solid tumor. In some embodiments, the proliferative disease is a hematological malignancy. In certain embodiments, the proliferative disease is a benign neoplasm. In other embodiments, the neoplasm is a malignant neoplasm. In certain embodiments, the proliferative disease is a cancer. In some embodiments at least some of the tumor cells overexpresses a protein relative, e.g., to cells of the type from which the tumor is believed to have arisen and/or typical values observed in normal cells. In that case the methods of the invention may be utilized for instance to deliver a protein which interferes with or interrupts the expression or activity of the overexpressed protein. Alternatively or in addition the methods may involve the delivery of an RNA molecule having a ligand binding domain, wherein the ligand is the overexpressed protein and the protein produced in response to contact with overexpressed protein may be useful in killing the cells or otherwise treating the cancer. In other instances the cancer cell may underexpress a protein. In that instance the methods of the invention may result in the increased delivery and expression of the protein.

In some embodiments, the tumor is a malignancy (e.g., sarcoma, adenocarcinoma, or carcinoma) of one of the various organ systems, such as those of lung, breast, lymphoid, gastrointestinal (e.g., colon), and genitourinary (e.g., renal, urothelial, or testicular tumors) tracts, pancrease, pharynx, prostate, and ovary. In some embodiments, the tumor can be a tumor having a stromal layer. In some embodiments, the cancer is non-small cell lung cancer. In some embodiments, the cancer is an adenocarcinoma. In some embodiments, the cancer is pancreatic ductal adenocarcinoma (PDAC). Examples of adenocarcinomas include, but are not limited to colorectal cancers, renal-cell carcinoma, liver cancer, non-small cell carcinoma of the lung, and cancer of the small intestine. Additional exemplary solid tumors include: fibrosarcoma, myxosarcoma, liposarcoma, chondrosarcoma, osteogenic sarcoma, chordoma, angiosarcoma, endotheliosarcoma, lymphangiosarconia, lymphangioendotheliosarcoma, synovioma, mesothelioma, Ewing's tumor, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, lung cancer, bladder carcinoma, epithelial carcinoma, glioma, astrocytoma, meduilobias oma, craniopharyngioma, ependymoma, pinealoma, hemangiohlastoma, acoustic neuroma, oligodendroglioma, meningioma, melanoma, neuroblastoma, and retinoblastoma.

The RNA may be used alone or in conjunction with a standard chemotherapeutic agent. In some instances, the protein expressed by the RNA is one which contributes to the chemotherapeutic sensitivity phenotype of the cancer cell. For instance, the protein may cause a resistant cancer cell to become sensitive to a chemotherapeutic agent. Alternatively the protein may be useful for preventing the cancer cell from developing a chemotherapy resistant phenotype. As used herein a "chemotherapeutic agent" refers to any chemical or biological agent with therapeutic utility in the treatment of diseases characterized by abnormal cell growth. Such diseases include tumors, neoplasms and cancer as well as diseases characterized by hyperplastic growth. Chemotherapeutic agents include but are not limited to alkylating/ alkaloid agents, antimetabolites, hormones or hormone analogs, and miscellaneous antineoplastic drugs. Chemotherapeutic agents are well known in the art (e.g. see Slapak and Kufe, Principles of Cancer Therapy, Chapter 86 in Harrison's Principles of Internal Medicine, 14th edition; Perry et al, Chemotherapy, Ch. 17 in Abeloff, Clinical Oncology 2 nd ed., 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Thus, the RNAs of the invention may encode any protein useful in a cell. The specific type of RNA/protein used in the manipulation of a cell or the treatment of a disease will depend on the type of disease. Exemplary proteins and genes encoding the proteins useful for expression in the methods of the invention include but are not limited to VEGF proteins, alpha 1 anti-trypsin polypeptide, cardiotrophic factors such as creatine, carnitine, and taurine, growth factor to promote survival and/or growth of cardiac cells, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, products of the BMP or cripto pathway and cellular differentiation agents, such as cytokines growth factors, TDGF1, vWF, GATA-4, GATA-6, Nkx2.5, Mef2-c, LGMD-2B, dysferlin, dystrophin, emerin, lamin A/C, alpha-1anti-trypsin, CFTR, ANG, ppresenilin, IS11, SERCA 1a or 2a, phospholamban, beta-ARK, beta-adrenergic receptor, Akt, adenyl cyclase V1, neuregulin 1, ErbB4, Periostin, HAND1, E2F4, Skp2, BRCA1, BRCA2, MLH1, MSH2, MSH6, EPHA3, EPHA4, APHB2, INl1, AXIN1, AXIN2, MLL3, EP300, NF1, TP53, APC, VHL, SMAD2, SMAD4, KEAP1, CDKN2A, RB I, MEN, NF2/ SCH, PTCH, TGFBR1, TGFBR2, ACVR1B, AVCR2, MRE11, MAP2K4, LKB1/STK11, HERG, KCNQ1, SCN5A, ANK2, KCNE1, KCNE2, KCNJ2, CACNA1c, SCN4B SERCA, KCNQ2, SCN1B, and KCNE3.

The methods described herein encompass in vivo, in vitro and ex-vivo applications. As discussed above, a protein of interest may be expressed therapeutically in a target tissue or organ by in vivo administration of an RNA composition to a subject. The invention also encompasses therapeutic methods involving contacting one or more cells with an RNA composition ex-vivo, and then administering such cells to a subject for therapeutic, diagnostic or research purposes. The cells may be first removed from the subject, in a traditional ex vivo approach, transfected by any method capable of transporting the RNA into the cell e.g., electroporation or lipofection, and re-introduced to the subject. Alternatively, the cells may be obtained from a different source and then introduced into the subject for the first time after the RNA is introduced into the cell.

The invention is also useful in the development of animal models for research. For example the RNAs of the invention can be administered to animals to generate animal models for the study of whole-organ and systemic pathophysiology, as well as drug screening and testing. The methods include the development of both small- and large-animal models, such as murine, primate and porcine models, for testing and/or the development of therapeutics.

Thus, the invention provides methods of producing non-human vertebrates, e.g., non-human mammals. The non-human vertebrates of the invention can be used for a wide variety of purposes. In some embodiments, a non-human vertebrate is used as a model for a condition in order to facilitate study of the condition. In some embodiments, a non-human vertebrate is used as a model for a condition for which a preventive or therapeutic drug is sought. If a candidate drug reduces the extent to which the condition is present in the animal model or progresses or causes the condition to reverse (partially or totally), the candidate drug is a drug to be administered to treat the condition.

The invention also encompasses regenerative medicine methodologies. For example, a population of cells capable of forming a tissue may be treated in some embodiments with an RNA which encodes a protein that contributes to the formation of the tissue by the population of cells. The population of cells may be treated with the RNA in vivo or they may be treated in vitro immediately prior to implantation or they may be treated in vitro, seeded on a scaffold and grown in culture prior to implantation. In some embodiments, a cell population is a stem cell population.

Thus, the invention encompasses methods of tissue generation, tissue regeneration and tissue engineering. "Tissue regeneration" refers to the regrowth of a cell population, organ or tissue after disease or trauma. The term "tissue generation" refers to the growth of a tissue from an initial cell population.

Tissue engineering involves the generation of tissue or tissue structures using cells and scaffold or support materials. Such engineered tissue or tissue structures are useful for therapeutic purposes to improve or replace biological functions, such as for instance, in the repair or replacement of portions of, or whole tissues (e.g., skin, heart, cardiac tissue, bone, cartilage, pancreas, liver, kidney, blood vessels, bladder, etc.), or in assays for identifying agents which modify the function of parts of, or entire organs without the need to obtain such organs from a subject.

A "scaffold" or "support" refers to any suitable carrier material to which cells generated using the methods and compositions described herein are able to attach themselves or adhere. The scaffold or support may be flat or it may have a three-dimensional form. The scaffold can be a polymer with a surface that can be shaped into a desired structure that requires repairing or replacing, such that it provides the supportive framework that allows cells to attach to it, and grow on it. The scaffold can be in any desired geometric conformation, for example, a flat sheet, a spiral, a cone, or a v-like structure. Cultured populations of cells can then be grown on the scaffold, which provides the appropriate interstitial distances required for cell-cell interaction and a an appropriate size and shape for later implantation. Typically if the scaffold is to be implanted in a subject, the scaffold will be a biocompatible scaffold. A "biocompatible scaffold" is non-toxic, such that it does not cause toxic effects once implanted in the subject.

The scaffold can be designed to assist in the control of a cell undergoing differentiation or transdifferentiation. For instance, the scaffold, may include environmental cues to control and direct the differentiation of cells into a specific tissue. A scaffold engineered to provide environmental cues can include, for instance, a nanometer to micrometer to millimeter to macroscopic length, and/or be based on factors such as, but not limited to, material mechanical properties, material solubility, spatial patterning of bioactive compounds, spatial patterning of topological features, soluble bioactive compounds, mechanical perturbation (cyclical or static strain, stress, shear, etc.), electrical stimulation, and thermal perturbation.

The scaffold typically is polymeric. Examples of polymers useful in the generation of a scaffold include, but are not limited to, polylactic acid (PLA), poly-L-lactic acid (PLLA), poly-D-lactic acid (PDLA), polyglycolide, polyglycolic acid (PGA), polylactide-co-glycolide (PLGA), polydioxanone, polygluconate, polylactic acid-polyethylene oxide copolymers, modified cellulose, collagen, polyhydroxybutyrate, polyhydroxpriopionic acid, polyphosphoester, poly(alpha-hydroxy acid), polycaprolactone, polycarbonates, polyamides, polyanhydrides, polyamino acids, polyorthoesters, polyacetals, polycyanoacrylates, degradable urethanes, aliphatic polyester polyacrylates, polymethacrylate, acyl substituted cellulose acetates, non-degradable polyurethanes, polystyrenes, polyvinyl chloride, polyvinyl flouride, polyvinyl imidazole, chlorosulphonated polyolifins, polyethylene oxide, polyvinyl alcohol, Teflon™, nylon silicon, and shape memory materials, such as poly(styrene-block-butadiene), polynorbornene, hydrogels, metallic alloys, and oligo(e-caprolactone)diol as switching segment/oligo(p-dioxyanone)diol as physical crosslink. Other suitable polymers can be obtained by reference to The Polymer Handbook, 3rd edition (Wiley, N.Y., 1989), the contents of which are herein incorporated in their reference by entirety.

The polymers may also be coated or mixed with biopolymers such as extracellular matrix (ECM) proteins (e.g., collagen, fibronectin, laminin, etc. to direct cell adhesion and function), growth factors (e.g., nerve growth factor, bone morphogenic proteins, vascular endothelial growth factor, etc.), lipids, fatty acids, steroids (e.g., glycerides, non-glycerides, saturated and unsaturated fatty acids, cholesterol, corticosteroids, sex steroids, etc.), sugars and other biologically active carbohydrates (e.g., monosaccharides, oligosaccharides, sucrose, glucose, glycogen, etc.), proteoglycans (protein cores with attached side chains of chondroitin sulfate, dermatan sulfate, heparin, heparan sulfate, and/or keratan sulfate); glycoproteins [e.g., selectins, immunoglobulins, hormones (e.g., anabolic steroids, sex hormones, human chorionic gonadotropin, insulin, angiotensin, etc.), Alpha-fetoprotein and Erythropoietin (EPO), etc.]; proteolipids (e.g., N-myristoylated, palmitoylated and prenylated proteins); and glycolipids (e.g., glycoglycerolipids, glycosphingolipids, glycophosphatidylinositols, etc.), nucleic acids (e.g., DNA, RNA, etc.), hormones, cell surface ligands and receptors (e.g., integrins, selectins, cadherins, etc.), cytoskeletal filaments, motor proteins (e.g., intermediate filaments, microtubules, actin filaments, dynein, kinesin, myosin, etc.), silks, enzymes (types: oxidoreductases, transferases, hydrolases, lyases, isomerases, ligases; examples: trypsin, collegenases, matrix metallproteinases, etc.), polyprotein (e.g., poly(lysine), polylactic and polyglycolic acids and poly-L-lysine) or any combination thereof.

The cells may be treated with the RNA of the invention prior to being seeded on the scaffold. Alternatively the cells may be treated with the RNA after they are seeded onto the scaffold in addition to or rather than being pretreated with the RNA. In some embodiments the RNA of the invention is attached to or incorporated within the scaffold. Additionally, therapeutic agents may be incorporated into or onto the scaffold. Alternatively the cells seeded on the scaffold may be treated with therapeutic agents in addition to the RNA of the invention.

Therapeutic agents include but are not limited to antivirals; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; biocidal/biostatic sugars such as dextran, glucose, etc.; amino acids; peptides; vitamins; inorganic elements; co-factors for protein synthesis; hormones; endocrine tissue or tissue fragments; synthesizers; enzymes such as alkaline phosphatase, collagenase, peptidases, oxidases, etc.; angiogenic agents; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; demineralized bone powder; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digestors; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

The developmental potential of cells can be altered using the RNA compositions of the invention. For instance, the ability to express a protein from an exogenous RNA of the invention allows both the alteration or reversal of the developmental potential of a cell, i.e., the reprogramming of the cell, and the directed differentiation of a cell to a more differentiated phenotype. An important component of the process of altering the developmental potential of a cell is the requirement for sustained and prolonged expression of one or more developmental potential reprogramming factors in the cell. Typically, this sustained expression can be achieved using exogenous DNA or viral vectors. However, it has been discovered that the RNA of the invention can be directly delivered to the cells, bypassing the need for using DNA or viral vectors.

Thus, the RNA of the invention may be used to produce pluripotent stem cells from cells which have a differentiated phenotype. To achieve this embodiment the RNA is delivered to the cell having a differentiated phenotype. Once the RNA is within the cell, it is translated into a reprogramming factor which causes the cells to produce a less differentiated phenotype. The resultant cell, which has a greater developmental potential, than the untreated cell, may then become the source of stem cells for further manipulations.

The stem cells produced as described above, or any other source of stem cells may also be treated according to the invention in order to produce a more differentiated cell. For example, the stem cell may be manipulated by the induction of protein expression to make the stem cell differentiate into a desired cell type. This type of directed differentiation is used to create cells having a desired phenotype. The stem cells are treated with the RNA of the invention, which is translated into a differentiation factor which causes the cells to produce a differentiated phenotype.

Thus, using the technology described herein stem cells can be generated from a differentiated cell, and stem cells can be differentiated into to one or more desired cell types. A "stem cell" as used herein is an undifferentiated or partially differentiated cell that has the ability to self-renew and has the developmental potential to differentiate into multiple cell types. A pluripotent cell is a cell with the developmental potential, under different conditions, to differentiate to cell types characteristic of all three germ cell layers, i.e., endoderm (e.g., gut tissue), mesoderm (including blood, muscle, and vessels), and ectoderm (such as skin and nerve).

A multipotent cell is a cell that has the developmental potential to differentiate into cells of one or more germ layers, but not all three. These cells include, for instance, adult stem cells, such as for example, hematopoietic stem cells and neural stem cells. Stem cells may have a propensity for a differentiated phenotype. However, these cells can be induced to reverse and re-express the stem cell phenotype. This process is referred to as "dedifferentiation" or "reprogramming".

Stem cells are undifferentiated cells defined by their ability at the single cell level to both self-renew and differentiate to produce progeny cells, including self-renewing progenitors, non-renewing progenitors, and terminally differentiated cells. Stem cells, depending on their level of differentiation, are also characterized by their ability to differentiate in vitro into functional cells of various cell lineages from multiple germ layers (endoderm, mesoderm and ectoderm), as well as to give rise to tissues of multiple germ layers following transplantation. Stem cells may be embryonic stem cells or somatic stem cells. The term "embryonic stem cell" is typically used to refer to a pluripotent stem cell of the inner cell mass of the embryonic blastocyst that can give rise during development to all derivatives of the three primary germ layers: ectoderm, endoderm and mesoderm. In contrast, a "somatic stem cell" as used herein refers to any pluripotent or multipotent stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. In contrast, "differentiated cells" are somatic cells that are not pluripotent.

The term "reprogramming" as used herein refers to a process that reverses the developmental potential of a cell or population of cells (e.g., a somatic cell). Thus, reprogramming refers to a process of driving a cell to a state with higher developmental potential, i.e., backwards to a less differentiated state. The cell to be reprogrammed can be either partially or terminally differentiated prior to reprogramming. In some embodiments reprogramming encompasses a complete or partial reversion of the differentiation state, i.e., an increase in the developmental potential of a cell, to that of a cell having a pluripotent state. In some embodiments, reprogramming encompasses driving a somatic cell to a pluripotent state, such that the cell has the developmental potential of an embryonic stem cell, i.e., an embryonic stem cell phenotype. In some embodiments, reprogramming also encompasses a partial reversion of the differentiation state or a partial increase of the developmental potential of a cell, such as a somatic cell or a unipotent cell, to a multipotent state. Reprogramming also encompasses partial reversion of the differentiation state of a cell to a state that renders the cell more susceptible to complete reprogramming to a pluripotent state when subjected to additional manipulations.

A "reprogramming factor" as used herein, refers to a developmental potential altering factor, the expression of which contributes to the reprogramming of a cell, e.g. a somatic cell, to a less differentiated or undifferentiated state, e.g. to a cell of a pluripotent state or partially pluripotent state. Reprogramming factors include but are not limited to OCT4, SOX1, SOX 2, SOX 3, SOX15, SOX 18, NANOG, KLF1, KLF 2, KLF 4, KLF 5, NR5A2, c-MYC, l-MYC, n-MYC, REM2, TERT, and LIN28.

As used herein, the term "differentiation factor" refers to a developmental potential altering factor, as that term is defined herein, such as a protein, RNA, or small molecule, that induces a cell to differentiate to a desired cell-type, i.e., a differentiation factor reduces the developmental potential of a cell. Differentiation to a specific cell type may involve simultaneous and/or successive expression of more than one differentiation factor. This can be achieved by delivering one or more RNAs encoding one or more differentiation factors to the cell, and optionally delivering one or more differentiation factors to the cell in the form of a protein.

In some aspects, the invention relates to cells manipulated according to the methods of the invention. Such cells, are isolated cells. The term "isolated cell" refers to a cell that has been removed from an organism in which it was originally found, or a descendant of such a cell. These cells may be later introduced into a second organism or re-introduced into the organism from which it (or the cell or population of cells from which it descended) was isolated. However, such cells, once manipulated according to the methods of the invention are still considered to be isolated cells. Stem cells can be isolated based on the presence or absence of specific markers of interest. For example, agents can be used to recognize stem cell markers, for instance labeled antibodies that recognize and bind to cell-surface markers or antigens on desired stem cells can be used to separate and isolate the desired stem cells using fluorescent activated cell sorting (FACS), panning methods, magnetic particle selection, particle sorter selection and other methods known to persons skilled in the art, including density separation.

In some embodiments the stem cells treated according to the invention are cancer stem cells. Cancer stem cells are present in some human tumors. These cells represent a small minority of the total cellular mass of the tumor but are believed to be the subpopulation of tumor cells responsible for growth of the tumor. Cancer stem cells proliferate extensively and give rise to additional tumor stem cells as well as to other tumor cells that lack tumorigenic potential. An additional trait of cancer stem cells is their resistance to therapeutics, such as chemotherapy. It is the small fraction of tumor stem cells and their immediate daughter cell population that proliferates and ultimately proves fatal. The cancer stem cells of the invention may be used to study factors which reverse or otherwise interfere with the chemotherapy resistance of the cell.

Stem cells may be obtained from any mammalian species, e.g. human, primate, equine, bovine, porcine, canine, feline, rodent, e.g. mice, rats, hamster, etc.

The differentiated or pluripotent cell populations treated according to the methods of the invention can be manipulated under standard conditions for these cell types. The treatment of the cells may be performed in vitro, ex vivo, or in vivo. For instance the cells may be present in the body or in a culture medium. The manipulations may be performed under high or low-oxygen conditions.

A "culture medium" contains nutrients that maintain cell viability and support proliferation. A typical culture medium includes: salts, buffers, amino acids, glucose or other sugar(s), antibiotics, serum or serum replacement, and/or other components such as peptide growth factors, etc. Cell culture media for use in deriving and maintaining pluripotent cells are known in the art. Culture medium may also include cell specific growth factors, such as angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor-alpha, cytokine-induced neutrophil chemotactic factor 1, cytokine-induced neutrophil, chemotactic factor 2-alpha, cytokine-induced neutrophil chemotactic factor 2-beta, beta-endothelial cell growth factor, endothelia 1, epidermal growth factor, epithelial-derived neutrophil attractant, fibroblast growth factor 4, fibroblast growth factor 5, fibroblast growth factor 6 fibroblast growth factor 7, fibroblast growth factor 8, fibroblast growth factor b, fibroblast growth factor c, fibroblast growth factor 9, fibroblast growth factor 10, fibroblast growth factor acidic, fibroblast growth factor basic, glial cell line-derived neutrophil factor receptor-alpha-1, glial cell line-derived neutrophil factor receptor-alpha-2, growth related protein, growth related protein-alpha, growth related protein-beta, growth related protein-gamma, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-alpha, nerve growth factor, nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-alpha, platelet derived growth factor receptor-beta, pre-B cell growth stimulating factor, stem cell factor, stem cell factor receptor, transforming growth factor-alpha, transforming growth factor-beta, transforming growth factor-beta-1, transforming growth factor-beta-1-2, transforming growth factor-beta-2, transforming growth factor-beta-3, transforming growth factor-beta-5, latent transforming growth factor-beta-1, transforming growth factor-beta-binding protein I, transforming growth factor-beta-binding protein II, transforming growth factor-beta-binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

The differentiation state of the cell can be assessed using any methods known in the art for making such assessments. For instance, the differentiation state of a cell treated according to the methods described herein may be compared with an untreated cell or cells treated with DNA using viral vectors to deliver DNA resulting in the expression of the same reprogramming or differentiation factors.

The methods of the invention are also useful for vaccination. The RNA of the invention may be used to express an antigen to a cell or a subject. For example, the RNA delivered to the cell may encode an antigen, e.g., an antigen against which an immune response is desired. Exemplary antigens include proteins or fragments thereof from a pathogenic organism, e.g., a bacterium or virus or other microorganism, as well as proteins or fragments thereof from a cell, e.g., a cancer cell. The antigen may be simply an immunogenic protein or fragment thereof or it may be a fusion protein encompassing an antigenic protein or fragment thereof fused with a carrier peptide. The carrier peptide, may be a second antigenic peptide or it may be non-immunogenic.

The antigen may be a complete protein or an epitope, such as a MHC Class I epitope, a MHC Class II epitope, or a B or T cell epitope. A T cell epitope presented by MHC Class I molecules can be a peptide of approximately 8 to 11 amino acids. A T cell epitope presented by MHC Class II molecules can be longer than a MHC Class I molecule. Epitopes may be predicted using a variety of web-based prediction tools, such as, http://tools.immuneepitope.org/main/html/tcell_tools.html.

Viral antigens are immunogenic proteins or fragments thereof derived from viruses. Several important viruses in chronic human viral infections include but are not limited to HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. Useful antigens include HBV surface antigen or HBV core antigen; ppUL83 or pp 89 of CMV; antigens of gp120, gp41 or p24 proteins of HIV-1; ICP27, gD2, gB of HSV; or influenza hemagglutinin or nucleoprotein (Anthony, L S et al., Vaccine 1999; 17:373-83). Other viruses include Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, Drosophila C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus—pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolas, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, or the Yug Bogdanovac virus.

Bacterial antigens are derived from bacterium, such as *Acetobacter aurantius, Acinetobacter baumannii, Actinomyces israelii, Agrobacterium radiobacter, Agrobacterium tumefaciens, Azorhizobium caulinodans, Azotobacter vinelandii, Anaplasma phagocytophilum, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaminogenicus (Prevotella melaminogenica), Bartonella henselae, Bartonella quintana, Bordetella bronchiseptica, Bordetella pertussis, Borrelia burgdorferi, Brucella abortus, Brucella melitensis, Brucella suis, Burkholderia, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae (Chlamydia pneumoniae), Chlamydophila psittaci (Chlamydia psittaci), Clostridium botulinum, Clostridium difficile, Clostridium perfringens* (previously called *Clostridium welchii*), *Clostridium tetani, Corynebacterium diphtheria, Corynebacterium fusiforme, Coxiella burnetii, Ehrlichia chaffeensis, Enterobacter cloacae, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus ducreyi, Haemophilus influenza, Haemophilus parainfluenzae, Haemophilus pertussis, Haemophilus vaginalis, Helicobacter pylori, Klebsiella pneumonia, Lactobacillus acidophilus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheria, Mycobacterium intracellulare, Mycobacterium leprae, Mycobacterium lepraemurium, Mycobacterium phlei,*

*Mycobacterium smegmatis, Mycobacterium tuberculosis, Mycoplasma fermentans, Mycoplasma genitalium, Mycoplasma hominis, Mycoplasma penetrans, Mycoplasma pneumonia, Lactobacillus Bulgaricus, Neisseria gonorrhoeae, Neisseria meningitides, Pasteurella multocida, Pasteurella tularensis, Peptostreptococcus, Porphyromonas gingivalis, Pseudomonas aeruginosa, Rhizobium radiobacter, Rickettsia prowazekii, Rickettsia psittaci, Rickettsia Quintana, Rickettsia rickettsii, Rickettsia trachomas, Rochalimaea henselae, Rochalimaea quintana, Rothia dentocariosa, Salmonella enteritidis, Salmonella typhi, Salmonella typhimurium, Serratia marcescens, Shigella dysenteriae, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumonia, Streptococcus pyogenes, Streptococcus rattus, Streptococcus salivarius, Streptococcus sanguis, Streptococcus sobrinus, Treponema pallidum, Treponema denticola, Vibrio cholera, Vibrio comma, Vibrio parahaemolyticus, Vibrio vulnificus, Yersinia enterocolitica, Yersinia pestis,* or *Yersinia pseudotuberculosis.*

Fungal antigens are derived from fungi such as *Absidia corymbifera, Ajellomyces capsulatus, Ajellomyces dermatitidis, Arthroderma benhamiae, Arthroderma fulvum, Arthroderma gypseum, Arthroderma incurvatum, Arthroderma otae, Arthroderma vanbreuseghemii, Aspergillus flavus, Aspergillus fumigates, Aspergillus niger, Blastomyces dermatitidis, Candida albicans, Candida glabrata, Candida guilliermondii, Candida krusei, Candida parapsilosis, Candida tropicalis, Candida pelliculosa, Cladophialophora carrionii, Coccidioides immitis, Cryptococcus neoformans, Cunninghamella sp., Epidermophyton floccosum, Exophiala dermatitidis, Filobasidiella neoformans, Fonsecaea pedrosoi, Fusarium solani, Geotrichum candidum, Histoplasma capsulatum, Hortaea werneckii, Issatschenkia orientalis, Madurella grisae, Malassezia furfur, Malassezia globosa, Malassezia obtuse, Malassezia pachydermatis, Malassezia restricta, Malassezia slooffiae, Malassezia sympodialis, Microsporum canis, Microsporum fulvum, Microsporum gypseum, Mucor circinelloides, Nectria haematococca, Paecilomyces variotii, Paracoccidioides brasiliensis, Penicillium marneffei, Pichia anomala, Pichia guilliermondii, Pneumocystis carinii, Pseudallescheria boydii, Rhizopus oryzae, Rhodotorula rubra, Scedosporium apiospermum, Schizophyllum commune, Sporothrix schenckii, Trichophyton mentagrophytes, Trichophyton rubrum, Trichophyton verrucosum, Trichophyton violaceum, Trichosporon asahii, Trichosporon cutaneum, Trichosporon inkin,* and *Trichosporon mucoides.*

Parasitic antigens include but are not limited to immunogenic proteins or fragments thereof from the parasite *Acanthamoeba,* African trypanosomiasis, *Echinocococcus granulosus, Echinococcus multicularis, Entamoeba histolytica, Trypanosoma cruzi, Ascaris lumbricoides, Angiostrongylus cantonensis,* anisakid nematode, *Babesia microti, Balantidium coli, Cimex lectularius, Balamuthia mandrillaris, Baylisascaris, Schistosoma mansoni, S. haematobium, S. japonicum, Schistosoma masoni, Schistosoma intercalatum, B. hominis,* body lice, *Capillaria hepatica, Capillaria philippinensis, Austrobilharzia variglandis, Chilomastix mesnili, Endolimax nana, Entamoeba coli, Entamoeba dispar, Entamoeba hartmanni, Entamoeba polecki, Iodamoeba buetschlii, C. sinensis, Ancylostoma braziliense, A. caninum, A. ceylanicum, Uncinaria stenocephala,* lice, *Cryptosporidium, Cyclospora cayetanensis, Taenia, Cystoisospora belli, Dientamoeba fragilis, Diphyllobothrium latum, Dipylidium caninum, Dracunculus medinensis, Giardia intestinalis, Brugia malayi, Entamoeba histolytica, Enterobius vermicularis, Fasciola hepatica, Fasciola gigantica, Fasciolopsis buski, Toxoplasma gondii, Trichinella spiralis, Giardia lamblia, Giardia duodenalis, Gnathostoma spinigerum, Heterophyes heterophyes, Hymenolepis nana, Leishmania promastigotes, Pediculus humanus capitis, Pediculus humanus corporis, Pthirus pubis, Loa loa, Plasmodium vivax, Plasmodium ovale, Plasmodium falciparum, Plasmodium malariae, Plasmodium yoelii, Plasmodium bubalis, Plasmodium juxtanucleare, Plasmodium circumflexum, Plasmodium relictum, Plasmodium relictum, Plasmodium vaughani, Plasmodium minasense, Plasmodium agamae, Plasmodium dominicum, Brachiola algerae, B. connori, B. vesicularum, Encephalitozoon cuniculi, E. hellem, E. intestinalis, Enterocytozoon bieneusi Microsporidium ceylonensis, M. africanum, Nosema ocularum, Pleistophora sp., Trachipleistophora hominis, T. anthropophthera, Vittaforma corneae, Sarcoptes scabiei* var. *hominis, Dermatobia hominis, Naegleria fowleri, Toxocara canis, Toxocara cati, Onchocerca volvulus, Opisthorchis felineus, Paragonimus westermani, Pneumocystis jirovecii, Sappinia diploidea, Sappinia pedata, Trypanosoma brucei, Trichuris trichiura, Ascaris lumbricoides, Anclostoma duodenale, Necator americanus, Strongyloides stercoralis, Strongyloides fiilleborni, Capillaria philippinensis, Taenia saginata, Taenia solium, Taenia asiatica, Toxoplasma gondii, Trichinella,* or *Trichomonas vaginalis.*

A cancer antigen is a protein or a fragment thereof that is specific to an individual tumor. For example, proteins that are overexpressed in a tumor sample, as compared to a control sample from the same individual or a normal tissue or a known standard control value are considered to be tumor-specific antigens. An RNA encoding a tumor specific antigen can be administered to a cell to produce the tumor specific antigen. Tumor specific antigens or cancer antigens or fragments thereof can comprise, for example, an antigen selected from HER2, BRCA1, prostate-specific membrane antigen (PSMA), MART-1/MelanA, prostatic serum antigen (PSA), squamous cell carcinoma antigen (SCCA), ovarian cancer antigen (OCA), pancreas cancer associated antigen (PaA), MUC-1, MUC-2, MUC-3, MUC-18, carcino-embryonic antigen (CEA), polymorphic epithelial mucin (PEM), Thomsen-Friedenreich (T) antigen, gp100, tyrosinase, TRP-1, TRP-2, NY-ESO-1, CDK-4, b-catenin, MUM-1, Caspase-8, KIAA0205, HPVE7, SART-1, SART-2, PRAME, BAGE-1, DAGE-1, RAGE-1, NAG, TAG-72, CA125, mutated p21ras, mutated p53, HPV16 E7, RCC-3.1.3, MAGE-1, MAGE-2, MAGE-3, MAGE-4, MAGE-11, GAGE-I, GAGE-6, GD2, GD3, GM2, TF, sTn, gp75, EBV-LMP 1, EBV-LMP 2, HPV-F4, HPV-F6, HPV-F7, alpha-fetoprotein (AFP), CO17-1A, GA733, gp72, p-HCG, gp43, HSP-70, p17 mel, HSP-70, gp43, HMW, HOJ-1, HOM-MEL-55, NY-COL-2, HOM-HD-397, HOM-RCC-1.14, HOM-HD-21, HOM-NSCLC-11, HOM-MEL-2.4, HOM-TES-11, melanoma gangliosides, TAG-72, prostatic acid phosphatase, protein MZ2-E, folate-binding-protein LK26, truncated epidermal growth factor receptor (EGFR), GM-2 and GD-2 gangliosides, polymorphic epithelial mucin, folate-binding protein LK26, pancreatic oncofetal antigen, cancer antigen 15-3, cancer antigen 19-9, cancer antigen 549, cancer antigen 195 or a fragment thereof.

The RNA of the invention may also encode an Alzheimer's disease antigen or a fragment thereof. An Alzheimer's disease antigen is an antigen selectively expressed in a subject with Alzheimer's disease. An antigen that is selectively expressed in a subject with Alzheimer's disease is an antigen which is expressed in a subject having Alzheimer's disease but not expressed or expressed to a lower level in a subject without Alzheimer's disease. Alternatively it is an antigen overexpressed in a subject with Alzheimer's disease relative to a subject that does not have Alzheimer's disease. The Alzheimer's disease antigen can be, for example, A68, A1340, A1342 or a fragment thereof.

Delivery vehicles or transfection reagents such as liposomes, nanocapsules, microparticles, microspheres, lipid particles, vesicles, and the like, may be used for the introduction of the nucleic acids of the present invention into cells and organisms. In particular, the nucleic acids may be formulated for delivery either encapsulated in a lipid particle, a liposome, a vesicle, a nanosphere, or a nanoparticle or the like.

Transfection reagents include but are not limited to cationic lipids, such as lipofectin, cationic glycerol derivatives, and polycationic molecules, such as polylysine. Examples of commercially available transfection reagents include, for example Lipofectamine™ (Invitrogen; Carlsbad, Calif.), Lipofectamine 2000™ (Invitrogen; Carlsbad, Calif.), 293fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega Madison, Wis.), TransFast™ Transfection Reagent (Promega Madison, Wis.), Tfx™-20 Reagent (Promega Madison, Wis.), Tfx™-50 Reagent (Promega Madison, Wis.), DreamFect™ (OZ Biosciences; Marseille, France), EcoTransfect (OZ Biosciences; Marseille, France), TransPass³ Dl Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFecf™ (B-Bridge International, Mountain View, Calif., USA) or non-cationic lipid-based carriers (e.g., Transit-TKOTM™, Minis Bio LLC, Madison, Wis.).

Such formulations may be preferred for the introduction of pharmaceutically acceptable formulations of the nucleic acids disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 .ANG., containing an aqueous solution in the core.

In some embodiments, the nucleic acids may be delivered to the organism or subject using a nanoparticle or microparticle. The terms nanoparticle or microparticle, as used herein refer to particles having an average particle size (i.e. diameter) of nanometers or less or of micrometers or less respectively. The terms include all forms of particles including solid and porous particles as well as hollow spheres and capsules as well as hybrid and multi-phase particles. For instance, the particles may comprises a polymeric shell (nanocapsule), a polymer matrix (nanosphere) or a block copolymer, which may be cross-linked or else surrounded by a lipid layer or bilayer.

The nucleic acids of the invention may be incorporated in, dispersed on, conjugated to or otherwise attached to the particles.

Numerous polymers have been proposed for synthesis of polymer-agent conjugates including polyaminoacids, polysaccharides such as dextrin or dextran, and synthetic polymers such as N-(2-hydroxypropyl)methacrylamide (HPMA) copolymer. Suitable methods of preparation are described in the art, for example, in Veronese et al. (1999) IL Farmaco 54:497-516. Other suitable polymers can be any known in the art of pharmaceuticals and include, but are not limited to, naturally-occurring polymers such as hydroxyethyl starch, proteins, glycopeptides and lipids. The synthetic polymers can also be linear or branched, substituted or unsubstituted, homopolymeric, co-polymers, or block co-polymers of two or more different synthetic monomers.

Nanocapsules can generally entrap substances in a stable and reproducible way. To avoid side effects due to intracellular polymeric overloading, such ultrafine particles (sized around 0.1 µm) could be designed using polymers able to be degraded in vivo. Biodegradable polyalkyl-cyanoacrylate nanoparticles that meet these requirements are contemplated for use.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Materials and Methods:
Expression Plasmid Construction
To generate the CMV-cGFP-mMALAT1_3' expression constructs, a previously described plasmid was modified (Gutschner et al. 2011) in which the CMV promoter and the cGFP open reading frame were cloned into the multicloning site of the pCRII-TOPO vector (Life Technologies). The mMALAT1_3' region (nt 6581 to 6754 of GenBank accession number EF177380) was inserted downstream of cGFP into the NotI cloning site in the sense direction (to generate CMV-cGFP-mMALAT1_3' Sense) or in the antisense direction (to generate CMV-cGFP-mMALAT1_3' Antisense). The NotI cloning site was similarly used to generate CMV-cGFP expression plasmids ending in the SV40 polyadenylation signal, the bGH polyadenylation signal, the mMEN β_3' region, and all of the mutant mMALAT1_3' regions. To generate the CMV-SpeckleF2-mMALAT1_3' expression plasmid, nt 1676 to 3598 of mouse MALAT1 was inserted into the EcoRV and BstEII cloning sites of the CMV-cGFP-mMALAT1_3' Sense plasmid. The sequences of the inserts for all plasmids are provided in Table 1 (SEQ ID NO. 1-61 from top to bottom).

TABLE 1

| cGFP Plasmids | Sequence inserted downstream of cGFP Open Reading Frame (unless ORF not present as noted by * in plasmid name) |
|---|---|
| pCRII-TOPO CMV-cGFP-mMALAT1_3' WT Sense (SEQ ID NO. 1) | gattcgtcagtagggttgtaaaggttttctttcctgagaaaacaacctttgtttctcaggtttt gcttttggcctttccctagctttaaaaaaaaaaagcaaaagacgctggtggctggcactcctggtt tccaggacggggttcaagtccctgcggtgtctttgctt |
| pCRII-TOPO CMV-cGFP-mMALAT1_3' Mut 7 Sense (SEQ ID NO. 2) | gattcgtcagtagggttgtaaaggttttctttcctgagaaaacaacctttgtttctcaggtttt gcttttggcctttccctagctttaaaaaaaaaaagcaaaagacgctggtggctggcactcctggtt tccaggacggggttcaagtccctgcggtAttctttgctt |
| pCRII-TOPO CMV-cGFP-mMALAT1_3' Mut 10 Sense (SEQ ID NO. 3) | gattcgtcagtagggttgtaaaggttttctttcctgagaaaacaacctttgtttctcaggtttt gcttttggcctttccctagctttaaaaaaaaaaagcaaaagGcgctggtggctggcactcctggtt tccaggacggggttcaagtccctgcggttACcCttgctt |
| pCRII-TOPO CMV-cGFP-mMALAT1_3' Mut U1 Sense (SEQ ID NO. 4) | gattcgtcagtagggttgtaaaggtttAAAAAttcctgagaaaacaacctttgtttctcaggtttt gcttttggcctttccctagctttaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U2 Sense (SEQ ID NO. 5) | gattcgtcagtagggttgtaaaggttttctttcctgagaaaacaacctttgtttctcaggtttAAAAAtttggcctttccctagctttaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U1/U2 Sense (SEQ ID NO. 6) | gattcgtcagtagggttgtaaaggtttAAAAAttcctgagaaaacaacctttgtttctcaggtttAAAAAtttggcctttccctagctttaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U1.1 Sense (SEQ ID NO. 7) | gattcgtcagtagggttgtaaaggttttAttttcctgagaaaacaacctttgtttctcaggtttt gcttttggcctttccctagctttaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U1.2 Sense (SEQ ID NO. 8) | gattcgtcagtagggttgtaaaggtttAActtttcctgagaaaacaacctttgtttctcaggtttt gcttttggcctttccctagctttaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U1.3 Sense (SEQ ID NO. 9) | gattcgtcagtagggttgtaaaggttttcAAttcctgagaaaacaacctttgtttctcaggtttt gcttttggcctttccctagctttaaaaaaaaaaagcaaaagacgctggtggctggcactcctggtt tccaggacggggttcaagtccctgcggtgtctttgctt |

TABLE 1-continued

| cGFP Plasmids | Sequence inserted downstream of cGFP Open Reading Frame (unless ORF not present as noted by * in plasmid name) |
|---|---|
| pCRII-TOPO CMV-cGFP-mMALAT1_3' Mut U1.4 Sense (SEQ ID NO. 10) | gattcgtcagtagggttgtaaaggttttttcttAAcctgagaaaacaaccttttgttttctcaggtttt gcttttttggcctttccctagctttaaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U1.5 Sense(SEQ ID NO. 11) | gattcgtcagtagggttgtaaaggtAAttcttttcctgagaaaacaaccttttgttttctcaggtttt gcttttttggcctttccctagctttaaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U2.1 Sense (SEQ ID NO. 12) | gattcgtcagtagggttgtaaaggttttttcttttcctgagaaaacaaccttttgttttctcaggtttt AAttttttggcctttccctagctttaaaaaaaaaaaagcaaaagacgctggtggctggcactcctggtt tccaggacggggttcaagtccctgcggtgtctttgctt |
| pCRII-TOPO CMV-cGFP-at MALAT1_3' Mut U2.2 Sense (SEQ ID NO. 13) | gattcgtcagtagggttgtaaaggttttttcttttcctgagaaaacaaccttttgttttctcaggttAA gcttttttggcctttccctagctttaaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U2.3 Sense(SEQ ID NO. 14) | gattcgtcagtagggttgtaaaggttttttcttttcctgagaaaacaaccttttgttttctcaggAAtt gcttttttggcctttccctagctttaaaaaaaaaaaagcaaaagacgctggtggctggcactcctggtt tccaggacggggttcaagtccctgcggtgtctttgctt |
| pCRII-TOPO CMV-cGFP-at MALAT1_3' Mut U2.4 Sense (SEQ ID NO. 15) | gattcgtcagtagggttgtaaaggttttttcttttcctgagaaaacaaccttttgttttctcaggtttt gcttAAtggcctttccctagctttaaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U2.5 Sense(SEQ ID NO. 16) | gattcgtcagtagggttgtaaaggttttttcttttcctgagaaaacaaccttttgttttctcaggtttt gcttttAAggcctttccctagctttaaaaaaaaaaaagcaaaagacgctggtggctggcactcctggtt tccaggacggggttcaagtccctgcggtgtctttgctt |
| pCRII-TOPO CMV-cGFP-mMALAT1_3' Mut U2-CG Sense (SEQ ID NO. 17) | gattcgtcagtagggttgtaaaggttttttcttttcctgagaaaacaaccttttgttttctcaggtttt CGttttttggcctttccctagctttaaaaaaaaaaaagcaaaagacgctggtggctggcactcctggtt tccaggacggggttcaagtccctgcggtgtctttgctt |
| pCRII-TOPO CMV-cGFP-at MALAT1_3' Mut A-CG Sense (SEQ ID NO. 18) | gattcgtcagtagggttgtaaaggttttttcttttcctgagaaaacaaccttttgttttctcaggtttt gcttttttggcctttccctagctttaaaaaaaaaaaaCGaaaagacgctggtggctggcactcctggtt tccaggacggggttcaagtccctgcggtgtctttgctt |
| pCRII-TOPO CMV-cGFP-mMALAT1_3' Mut U2/A-CG Sense (SEQ ID NO. 19) | gattcgtcagtagggttgtaaaggttttttcttttcctgagaaaacaaccttttgttttctcaggtttt CGttttttggcctttccctagctttaaaaaaaaaaaaCGaaaagacgctggtggctggcactcctggtt tccaggacggggttcaagtccctgcggtgtctttgctt |
| pCRII-TOPO CMV-cGFP-mMALAT1_3' Mut U2-AA Sense (SEQ ID NO. 20) | gattcgtcagtagggttgtaaaggttttttcttttcctgagaaaacaaccttttgttttctcaggtttt gcAAtttggcctttccctagctttaaaaaaaaaaaagcaaaagacgctggtggctggcactcctggtt tccaggacggggttcaagtccctgcggtgtctttgctt |
| pCRII-TOPO CMV-cGFP-at MALAT1_3' Mut A-AA Sense (SEQ ID NO. 21) | gattcgtcagtagggttgtaaaggttttttcttttcctgagaaaacaaccttttgttttctcaggtttt gcttttttggcctttccctagctttaaaaaaaaaaaTTgcaaaagacgctggtggctggcactcctggtt tccaggacggggttcaagtccctgcggtgtctttgctt |

TABLE 1-continued

| cGFP Plasmids | Sequence inserted downstream of cGFP Open Reading Frame (unless ORF not present as noted by * in plasmid name) |
|---|---|
| pCRII-TOPO CMV-cGFP-mMALAT1_3' Mut U2/A-AA Sense (SEQ ID NO. 22) | gattcgtcagtagggttgtaaaggttttcttttcctgagaaaacaaccttttgttttctcaggtttt gc<u>AA</u>ttttggcctttccctagctttaaaaaaaaa<u>TT</u>gcaaaagacgctggtggctggcactcctggtt tccaggacggggttcaagtccctgcggtgtctttgctt |
| pCRII-TOPO CMV-cGFP-mMALAT1_3' Mut U2-CGAAAA Sense (SEQ ID NO. 23) | gattcgtcagtagggttgtaaaggttttcttttcctgagaaaacaaccttttgttttctcaggtttt <u>CCAAAA</u>tggcctttccctagctttaaaaaaaaaaaagcaaaagacgctggtggctggcactcctggtt tccaggacggggttcaagtccctgcggtgtctttgctt |
| pCRII-TOPO CMV-cGFP-mMALAT1_3' Mut A-CGAAAA Sense (SEQ ID NO. 24) | gattcgtcagtagggttgtaaaggttttcttttcctgagaaaacaaccttttgttttctcaggtttt gcttttggcctttccctagctttaaaaaaaa<u>TTTTCG</u>aaaagacgctggtggctggcactcctggtt tccaggacggggttcaagtccctgcggtgtctttgctt |
| pCRII-TOPO CMV-cGFP-mMALAT1_3' Mut U2/A-CGAAAA Sense (SEQ ID NO. 25) | gattcgtcagtagggttgtaaaggttttcttttcctgagaaaacaaccttttgttttctcaggtttt <u>CGAAAA</u>ggcctttccctagctttaaaaaaaat<u>TTTTCG</u>aaaagacgctggtggctggcactcctggtt tccaggacggggttcaagtccctgcggtgtctttgctt |
| pCRII-TOPO CMV-cGFP-mMALAT1_3' Comp.1 Sense (SEQ ID NO. 26) | <u>******************</u>aaaggttttcttttcctga<u>******************</u>tcaggtttt gcttttggcctttccctagctttaaaaaaaaaaaagcaaaagacgctggtggctggcactcctggtt tccaggacggggttcaagtccctgcggtgtctttgctt |
| pCRII-TOPO CMV-cGFP-mMALAT1_3' Comp.2 Sense (SEQ ID NO. 27) | <u>******************</u>aaaggttttcttttcctga<u>****************</u>tcaggtttt gcttttt<u>**************</u>aaaaaaaaaaaagcaaaagacgctggtggctggcactcctggtt tccaggacggggttcaagtccctgcggtgtctttgctt |
| pCRII-TOPO CMV-cGFP-mMALAT1_3' Comp.3 Sense (SEQ ID NO. 28) | <u>******************</u>aaaggttttcttttcctga<u>****************</u>tcaggtttt gcttttggcctttccctagcttt<u>****</u>aaaaagcaaaagacgctggtggctggcactcctggtt tccaggacggggttcaagtccctgcggtgtctttgctt |
| pCRII-TOPO CMV-cGFP-mMALAT1_3' Comp.4 Sense (SEQ ID NO. 29) | <u>******************</u>aaaggttttcttttcctga<u>****************</u>tcaggtttt gcttttt<u>******</u>tagcttt<u>****</u>aaaaagcaaaagacgctggtggctggcactcctggtt tccaggacggggttcaagtccctgcggtgtctttgctt |
| pCRII-TOPO CMV-cGFP-mMALAT1_3' Comp.5 Sense (SEQ ID NO. 30) | gattcgtcagtagggttgtaaaggttttcttttcctga<u>******************</u>tcaggtttt gcttttt<u>**************</u>aaaaaaaaaaaagcaaaagacgctggtggctggcactcctggtt tccaggacggggttcaagtccctgcggtgtctttgctt |
| pCRII-TOPO CMV-cGFP-mMALAT1_3' Comp.6 Sense (SEQ ID NO. 31) | <u>******************</u>aaaggttttcttttcctgagaaaacaaccttttgttttctcaggtttt gcttttt<u>**************</u>aaaaaaaaaaaagcaaaagacgctggtggctggcactcctggtt tccaggacggggttcaagtccctgcggtgtctttgctt |
| pCRII-TOPO CMV-cGFP-mMALAT1_3' Comp.7 Sense (SEQ ID NO. 32) | <u>******************</u>aaaggttttcttttcctgagaaaacaaccttttgttttctcaggtttt gcttttttggcctttccctagcttt<u>****</u>aaaaagcaaaagacgctggtggctggcactcctggtt tccaggacggggttcaagtccctgcggtgtctttgctt |
| pCRII-TOPO CMV-cGFP-mMALAT1_3' Comp.8 Sense (SEQ ID NO. 33) | <u>******************</u>aaaggttttcttttcctgagaaaacaaccttttgttttctcaggtttt gctttttt<u>******************</u>aaaaagcaaaagacgctggtggctggcactcctggtt tccaggacggggttcaagtccctgcggtgtctttgctt |

TABLE 1-continued

| cGFP Plasmids | Sequence inserted downstream of cGFP Open Reading Frame (unless ORF not present as noted by * in plasmid name) |
|---|---|
| pCRII-TOPO CMV-cGFP-mMALAT1_3' Comp.9 Sense (SEQ ID NO. 34) | ****************aaaggttttctttttcctgagaaaacaattgttttctcaggtttt gcttttt*************aaaaaaaaaaaagcaaaagacgctggtggctggcactcctggtt tccaggacggggttcaagtccctgcggtgtctttgctt |
| pCRII-TOPO CMV-cGFP-mMALAT1_3' Comp.10 Sense (SEQ ID NO. 35) | ****************aaaggttttctttttcctgagaaaac****gttttctcaggtttt gcttttt*************aaaaaaaaaaaagcaaaagacgctggtggctggcactcctggtt tccaggacggggttcaagtccctgcggtgtctttgctt |
| pCRII-TOPO CMV-cGFP-mMALAT1_3' Comp.11 Sense (SEQ ID NO. 36) | ****************aaaggttttctttttcctgagaaaacaaccttttgttttctcaggtttt gcttttt******tagctttt*****aaaaagcaaaagacgctggtggctggcactcctggtt tccaggacggggttcaagtccctgcggtgtctttgctt |
| pCRII-TOPO CMV-cGFP-mMALAT1_3' Comp.12 Sense (SEQ ID NO. 37) | ****************aaaggttttctttttcctgagaaa********tttctcaggtttt gcttttt*************aaaaaaaaaaaagcaaaagacgctggtggctggcactcctggtt tccaggacggggttcaagtccctgcggtgtctttgctt |
| pCRII-TOPO CMV-cGFP-mMALAT1_3' Comp.13 Sense (SEQ ID NO. 38) | ****************aaaggttttctttttcctgaga***********tctcaggtttt gcttttt*************aaaaaaaaaaaagcaaaagacgctggtggctggcactcctggtt tccaggacggggttcaagtccctgcggtgtctttgctt |
| pCRII-TOPO CMV-cGFP-mMALAT13' Comp.14 Sense (SEQ ID NO. 39) | ****************aaaggttttctttttcctgagaaa********tttctcaggtttt gcttttt****************aaaaaaaaagcaaaagacgctggtggctggcactcctggtt tccaggacggggttcaagtccctgcggtgtctttgctt |
| pCRII-TOPO CMV-cGFP-mMALAT1_3' Comp.15 Sense (SEQ ID NO. 40) | ****************CCCAAttttctttttGAATTCTCT*******AGAGAATTCtttt gcttttt****************CTTCaaaaagcaaaagacgctggtggctggcactcctggtt tccaggacggggttcaagtccctgcggtgtctttgctt |
| pCRII-TOPO CMV-cGFP-mMALAT1_3' Comp.25 Sense (SEQ ID NO. 41) | ****************CCCAAttttctttttGAATTCTCT*******AGAGAATTCtttt gcttttt****************CTTCaaaaagcaaaagacgctggtggctggcactcctggtt tccaggacggggttcaagtccctgcggtgtctttgctt |
| pCRII-TOPO CMV-cGFP-mMALAT1_3' Comp.26 Sense (SEQ ID NO. 42) | ****************CCCAAttttctttttGAAgagaaa********tttctcTTCtttt gcttttt****************aaaaaaaagcaaaagacgctggtggctggcactcctggtt tccaggacggggttcaagtccctgcggtgtctttgctt |
| pCRII-TOPO CMV-cGFP-mMALAT1_3' Comp.27 Sense (SEQ ID NO. 43) | ****************aaaggttttctttttGAAgagaaa********tttctcTTCtttt gcttttt****************CTTCaaaaagcaaaagacgctggtggctggcactcctggtt tccaggacggggttcaagtccctgcggtgtctttgctt |
| pCRII-TOPO CMV-cGFP-mMALAT1_3' U*A-C Sense (SEQ ID NO. 44) | ****************aaaggttttctttttcctgagaaaacaaccttttgttttctcaggtttt gcCCCCt*************aaaaaaaaaaaagcaaaagacgctggtggctggcactcctggtt tccaggacggggttcaagtccctgcggtgtctttgctt |
| pCRII-TOPO CMV-cGFP-mMALAT1_3' U*G-U Sense (SEQ ID NO. 45) | ****************aaaggttttctttttcctgagaaaacaaccttttgttttctcaggtttt gcttttt*************aaaaaaaaGGGGgcaaaagacgctggtggctggcactcctggtt tccaggacggggttcaagtccctgcggtgtctttgctt |

TABLE 1-continued

| cGFP Plasmids | Sequence inserted downstream of cGFP Open Reading Frame (unless ORF not present as noted by * in plasmid name) |
|---|---|
| pCRII-TOPO CMV-cGFP-mMALAT1_3′ U*G-C Sense(SEQ ID NO. 46) | ****************aaaggttttttcttttcctgagaaaacaaccttttgttttctcaggtttt gcCCCCt*************aaaaaaaaGGGGgcaaaagacgctggtggctggcactcctggtt tccaggacggggttcaagtccctgcggtgtctttgctt |
| pCRII-TOPO CMV-cGFP-mMALAT1_3′ C*G-C Sense(SEQ ID NO. 47) | ****************aaaggtCCCCcttttcctgagaaaacaaccttttgttttctcaggtttt gcCCCCt*************aaaaaaaaCGCGgcaaaagacgctggtggctggcactcctggtt tccaggacggggttcaagtccctgcggtgtctttgctt |
| pCRII-TOPO CMV-cGFP-SV40 Poly(A) Sense(SEQ ID NO. 48) | aacttgtttattgcagcttataatggttacaaataaagcaatagcatcacaaatttcacaaataaagc atttttttcactgcattctagttgtggtttgtccaaactcatcaatgtatctta |
| pCRII-TOPO CMV-cGFP-bGH Poly(A) Sense(SEQ ID NO. 49) | cgactgtgccttctagttgccagccatctgttgtttgcccctcccccgtgccttccttgaccctggaa ggtgccactcccactgtcctttcctaataaaatgaggaaattgcatcgcattgtctgagtaggtgtca ttctattctggggggtggggtggggcaggacagcaaggggggaggattgggaagacaatagcaggcatg ctggggatgcggtgggctctatgg |
| pCRII-TOPO CMV-cGFP-mMEN β_3′ Sense(SEQ ID NO. 50) | ggcacggagccgccgcaggtgtttcttttcctgaccgcggctcatggccgcgctcaggttttgctttt cacctttgtctgagagaacgaacgtgagcaggaaaaagcaaaaggcactggtggcggcacgcccgcac ctcgggccagggttcgagtccctgcagtaccgtgcttc |
| *pCRII-TOPO CMV-mMALAT1_3′ Sense(SEQ ID NO. 51) | gattcgtcagtagggttgtaaaggttttcttttcctgagaaaacaaccttttgttttctcaggtttt gcttttggcctttcctagctttaaaaaaaaaaaagcaaaagacgctggtggctggcactcctggtt tccaggacggggttcaagtccctgcggtgtctttgctt |
| *pCRII-TOPO CMV-mmascRNA Sense(SEQ ID NO. 52) | GGACAAAACGAgacgctggtggctggcactcctggtttccaggacggggttcaagtccctgcggtgt ctttgctt |
| pCRII-TOPO CMV-SpeckleF2-mMALAT1_3′ WT Sense(SEQ ID NO. 53) | gattcgtcagtagggttgtaaaggttttcttttcctgagaaaacaaccttttgttttctcaggtttt gcttttggcctttcctagctttaaaaaaaaaaaagcaaaagacgctggtggctggcactcctggtt tccaggacggggttcaagtccctgcggtgtctttgctt |
| pCRII-TOPO CMV-SpeckleF2-mMALAT1_3′ Mut U1 Sense(SEQ ID NO. 54) | gattcgtcagtagggttgtaaaggtttAAAAAttcctgagaaaacaaccttttgttttctcaggtttt gcttttggcctttcctagctttaaaaaaaaaaaagcaaaagacgctggtggctggcactcctggtt tccaggacggggttcaagtccctgcggtgtctttgctt |
| pCRII-TOPO CMV-SpeckleF2-mMALAT1_3′ Mut U2-CGAAAA Sense(SEQ ID NO. 55) | gattcgtcagtagggttgtaaaggttttcttttcctgagaaaacaaccttttgttttctcaggtttt CCAAAAtggcctttcctagctttaaaaaaaaaaaagcaaaagacgctggtggctggcactcctggtt tccaggacggggttcaagtccctgcggtgtctttgctt |
| pCRII-TOPO CMV-SpeckleF2-mMALAT1_3′ MutA-CGAAAA Sense(SEQ ID NO. 56) | gattcgtcagtagggttgtaaaggttttcttttcctgagaaaacaaccttttgttttctcaggtttt gcttttggcctttcctagctttaaaaaaaaTTTTCGaaaagacgctggtggctggcactcctggtt tccaggacggggttcaagtccctgcggtgtctttgctt |

TABLE 1-continued

| cGFP Plasmids | Sequence inserted downstream of cGFP Open Reading Frame (unless ORF not present as noted by * in plasmid name) |
|---|---|
| pCRII-TOPO CMV-cGFP-V. vulnificus add-masc Sense(SEQ ID NO. 57) | Ggcttcatataatcctaatgatatggtttgggagtttctaccaagagccttaaactcttgattatgaa gtcgacgctggtggctggcactcctggtttccaggacggggttcaagtccctgcggtgtctttgctt |
| pCRII-TOPO CMV-cGFP-B. subtilis xpt-masc Sense(SEQ ID NO. 58) | Ggatcatataatcgcgtggatatggcacgcaagtttctaccgggcaccgtaaatgtccgactatggtc gacgctggtggctggcactcctggtttccaggacggggttcaagtccctgcggtgtctttgctt |
| pCRII-TOPO CMV-cGFP-V. cholera Vc2-masc Sense(SEQ ID NO. 59) | ggaaaaatgtcacgcacagggcaaaccattcgaaagagtgggacgcaaagcctccggcctaaaccaga agacatggtaggtagcggggttaccgatgggacgctggtggctggcactcctggtttccaggacgggg ttcaagtccctgcggtgtctttgctt |
| pCRII-TOPO CMV-cGFP-T. tengcongensis SAM-masc Sense(SEQ ID NO. 60) | ttaaaatctcttatcaagagaggtggagggactggcccgatgaaaccggcaaccagccttagggcat ggtgccaattcctgcagcggtttcgctgaaagatgagagattcttgtagtctcttcttttagcggacg ctggtggctggcactcctggtttccaggacggggttcaagtccctgcggtgtctttgctt |
| pCRII-TOPO CMV-cGFP-T. tengcongensis glm-masc Sense(SEQ ID NO. 61) | ccggctttaagttgacgagggcagggtttatcgagacatcggcgggtgccctgcggtcttcctgcgac cgttagaggactggtaaaaccacaggcgactgtggcatagagcagtccgggcaggaagacgctggtgg ctggcactcctggtttccaggacggggttcaagtccctgcggtgtctttgctt |

Transfections and RNA Analysis

HeLa cells were grown at 37° C., 5% $CO_2$ in Dulbecco's modified Eagle's medium (DMEM) containing high glucose (Life Technologies), supplemented with penicillin-streptomycin and 10% fetal bovine serum. CMV-cGFP expression plasmids were transfected using Lipofectamine 2000 (Life Technologies) and total RNA was isolated using Trizol (Life Technologies) as per the manufacturer's instructions. Northern blots were performed as previously described (Wilusz et al. 2008). For RNase H treatments, 9 μg of total RNA was first mixed with 20 pmol of antisense oligo and heated to 65° C. for 10 min. After the antisense oligos were allowed to anneal by slow cooling, the RNA was treated with RNase H (New England Biolabs) at 37° C. for 30 min and then subjected to Northern blot analysis. Nuclear and cytoplasmic fractionation was performed as described previously (Wilusz et al. 2008). All oligonucleotide probe sequences are provided in Table 2 (SEQ ID NO. 62-69 from top to bottom). 3' RACE PCR using microRNA Cloning Linker 3 (Integrated DNA Technologies) was performed as previously described (Wilusz et al. 2008).

TABLE 2

| Northern Probe | Sequence |
|---|---|
| mascRNA (Mouse mascRNA Only Probe) | gcaaagacaccgcagggacttgaac (SEQ ID NO. 62) |
| mascRNA (All mascRNA Probe) | gcaaagacaccgcagggatttgaaccccgtcctggaaaccag gagtgcca (SEQ ID NO. 63) |
| cGFP Probe | Tccatgccgtgggtgatgcc (SEQ ID NO. 64) |
| Endogenous MALAT1 | Ctaagatgctagcttggccaagtctgttatg (SEQ ID NO. 65) |
| U6 snRNA | gctaatcttctctgtatcgttccaattttagtatatgtg ctgccg (SEQ ID NO. 66) |
| mCherry Probe | Gccggtggagtggcggccctc (SEQ ID NO. 67) |
| RNase H Oligo for cGFP Transcript | Cgcgcttctcgttgggtcc (SEQ ID NO. 68) |
| RNase H Oligo for mCherry Transcript | Ttcgtactgttccacgatgg (SEQ ID NO. 69) |

Protein Analysis

Western blots were performed using the Nu-PAGE Bis-Tris Electrophoresis System (Life Technologies) as per the manufacturer's instructions. The cGFP antibody was obtained from GenScript and the Vinculin antibody from Sigma-Aldrich.

Two-Color Fluorescent Reporter System

The two-color fluorescent reporter vector was previously described (Mukherji et al. 2011) and contains the SV40 polyadenylation signal in the 3' UTR of mCherry. To replace this polyadenylation signal with the mMALAT1_3' region, the EcoRV and AatII cloning sites that flank the SV40 polyadenylation signal were used. Target sites for let-7 were inserted into the 3' UTR of mCherry using HindIII and SalI cloning sites and the sequences are provided in Table 1. HeLa cells were seeded at 175,000 cells per well of a 12-well plate for 20 hours prior to transfection of equivalent amounts (250 ng) of the reporter plasmid and rtTA using Lipofectamine 2000. At the time of transfection, the media was changed to complete DMEM supplemented with 2 μg/mL doxycycline (Sigma). Where indicated, control siRNA (siGENOME Non-Targeting siRNA #2, Dharmacon) or an siRNA equivalent of murine let-7g (Dharmacon) were co-transfected at final concentrations of 40 nM. Flow cytometry or RNA isolation was performed 18-20 hours post-transfection. Flow cytometry, QPCR, and raw data processing were performed as previously described (Mukherji et al. 2011) and are further described herein.

Structural Model Prediction

De novo RNA folding was carried out using Rosetta Version 3.4 (rosettacommons.org) (Das and Baker 2007; Das et al. 2010). For a converging model of the 3' end of the MALAT1 Comp. 14 transcript, the first five nucleotides (AAGGG) were removed. Suspected helical interactions were defined (all 9 U-A•U base triples were defined) and 2,000 models were calculated. The model converged between 3-4 Å (see FIG. 14C). The full-length (59-nt) Comp. 14 3' end was subjected to the same procedure, although convergence could not be achieved due to high flexibility of the 5' end.

Flow Cytometry, QPCR, and Data Processing

Flow cytometry and raw data processing were performed as previously described (Mukherji et al. 2011). Briefly, ~100,000 cells were run on LSRII analyzer (Becton Dickinson) using FACSDiva software. Using FlowJo, the viable, single cell population was gated according to the forward and side scatter profiles. To control for background fluorescence, the mean autofluorescence plus twice the standard deviation of untransfected cells was subtracted from the eYFP and mCherry values for each cell from the transfected samples. Cells indistinguishable from background (fluorescence values less than 0 after background subtraction) were excluded from further analysis. Background subtraction and downstream analysis was performed using a custom MATLAB script (MathWorks).

Total RNA was isolated using Trizol, treated with the TURBO DNA-free kit (Life Technologies), and reverse transcribed with random hexamers using Superscript III (Life Technologies). QPCR reactions on resulting cDNAs were performed in triplicate using Power SYBR Green (Life Technologies) run on an Applied Biosystems 7500 Real-Time PCR instrument. QPCR primer sequences (SEQ ID NO 169 to SEQ ID NO. 171): eYFP Forward (5'-CCACCTACGGCAAGCTGACC), eYFP Reverse (5'-GG-TAGCGGGCGAAGCACT), mCherry Forward (5'-GAACGGCCACGAGTTCGAGA) and mCherry Reverse (5'-CTTGGAGCCGTACATGAACTGAGG).

Figure 1D:
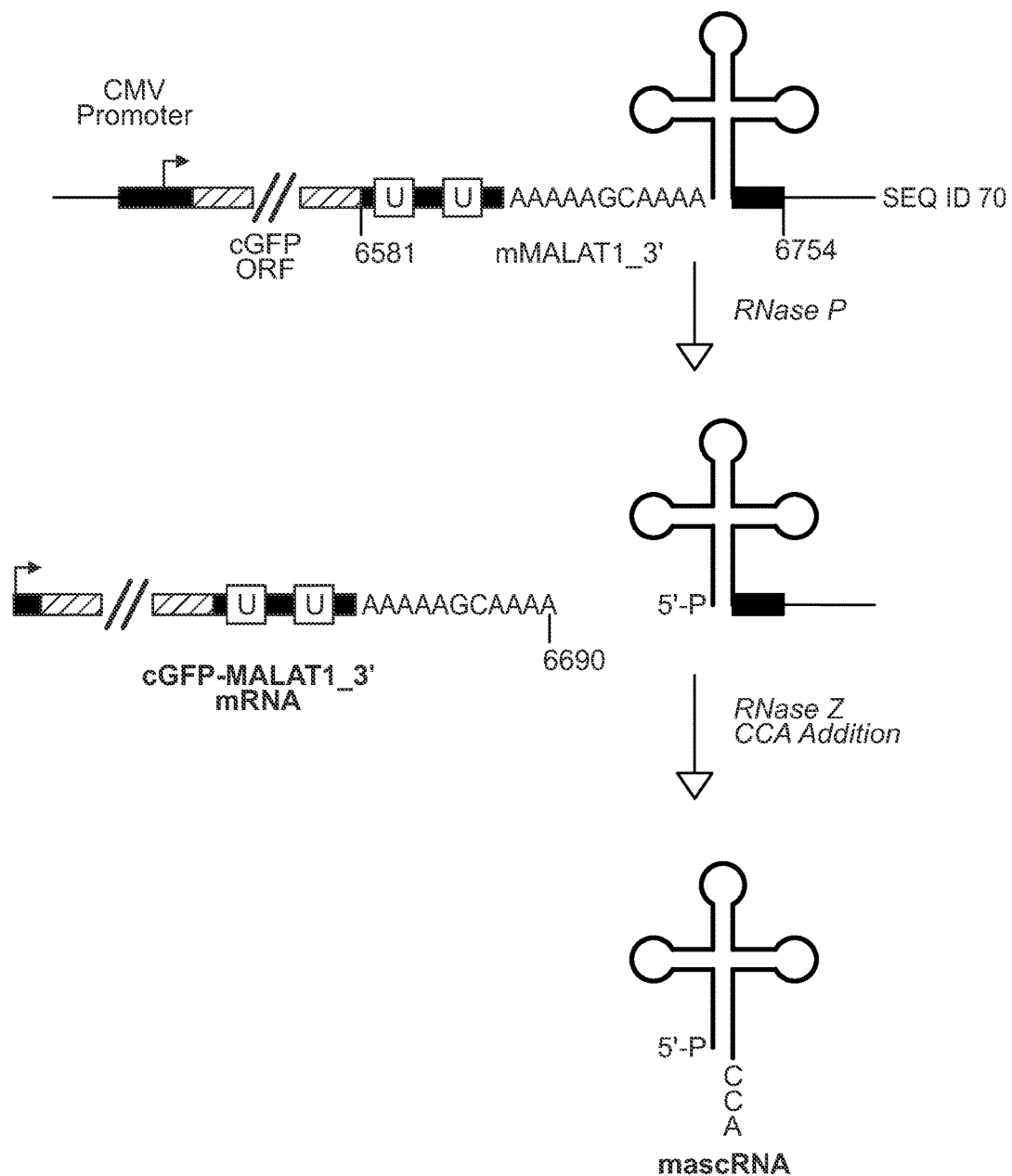

Example 1: Generation of an Expression Plasmid that Accurately Recapitulates MALAT1 3' End Processing Although it is clear that MALAT1 is cleaved to generate mascRNA (Wilusz et al. 2008), a plasmid expression system that recapitulates this processing event in vivo has not been reported. It was possible to generate such a plasmid by inserting downstream of a CMV promoter the coral green fluorescent protein (cGFP) open reading frame (ORF) followed by a 174-nt fragment of the 3' end of the mouse MALAT1 locus (nt 6581 to 6754 of mMALAT1) (FIG. 1D). This region, denoted mMALAT1_3', is highly evolutionarily conserved from humans to zebrafish (FIG. 1B) and includes the well-conserved U- and A-rich motifs, the RNase P cleavage site (after nt 6690), as well as mascRNA (nt 6691-6748). As a control, a plasmid with the mMALAT1_3' region cloned downstream of cGFP in the antisense direction was generated to verify that mascRNA expression is dependent on processing from the CMV-driven transcript.

The CMV-cGFP-mMALAT1_3' sense and antisense plasmids were transiently transfected into human HeLa cells and total RNA isolated 24 hours later. For this system to accurately recapitulate MALAT1 3' end processing, it must generate two transcripts: the ~850-nt cGFP-MALAT1_3' RNA as well as mature (61-nt) mouse mascRNA that has been processed by RNases P and Z as well as by the CCA-adding enzyme (FIG. 1D). There are four sequence changes between mouse and human mascRNA (Wilusz et al. 2008), allowing for the design oligo probes that either distinguish between the homologs (probe denoted "Mouse mascRNA Only" in FIG. 1E) or detect both mouse and human mascRNA (probe denoted "All mascRNA" in FIG. 1E) by Northern blot analysis. In cells transfected with the sense, but not antisense, expression plasmid, mature mascRNA was generated and expressed ~16-fold over the level observed in Mock treated cells (FIG. 1E). 3' RACE PCR was used to confirm that mascRNA generated from the plasmid was properly processed and had CCA post-transcriptionally added to its 3' end (data not shown). In parallel, mutant mascRNA transcripts expressed using this plasmid were subjected to CCACCA addition and rapidly degraded in vivo (FIG. 8) confirming the previous find that the CCA-adding enzyme plays a key role in tRNA quality control (Wilusz et al. 2011). These results show that this plasmid generates bona fide mascRNA.

Figure 1E:
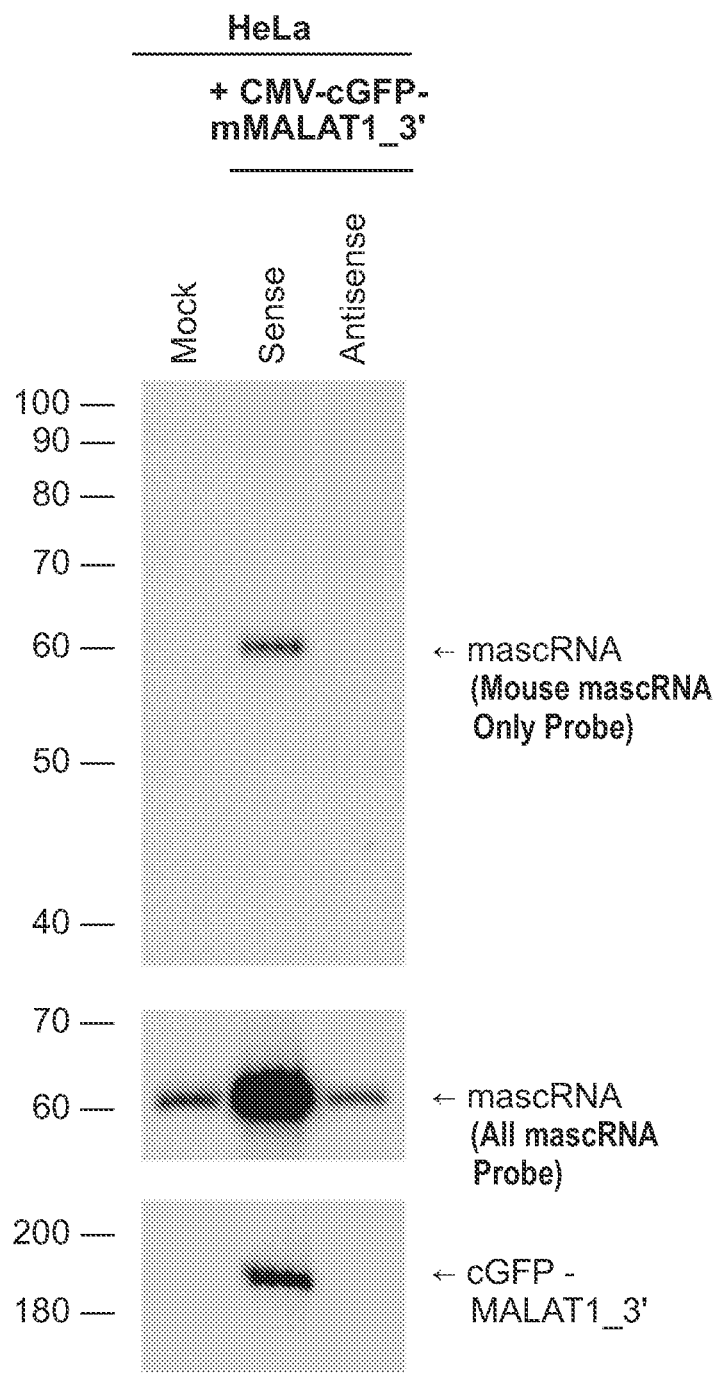

To determine if the sense plasmid expresses cGFP-MALAT1_3'RNA that is stable and properly processed by RNase P at its 3' end in vivo, total RNA from the transfections was first hybridized to an oligo complementary to near the 3' end of the cGFP ORF and subjected to RNase H digestion. Cleavage of the transcript to a smaller size allowed Northern blots with high resolution to be performed to verify the accuracy of RNase P cleavage. A single band of the expected size (190-nt) was observed with the sense, but not antisense, plasmid (FIG. 1E). These results indicate that the cGFP-MALAT1_3' sense primary transcript is efficiently cleaved by RNase P to generate both expected mature transcripts (FIG. 1D) and thus accurately recapitulates 3' end processing of MALAT1 in vivo. The antisense plasmid likely failed to produce a stable cGFP mRNA as the transcript contained no functional polyadenylation signals, causing the transcript to be rapidly degraded by nuclear surveillance pathways.

Figure 9A:
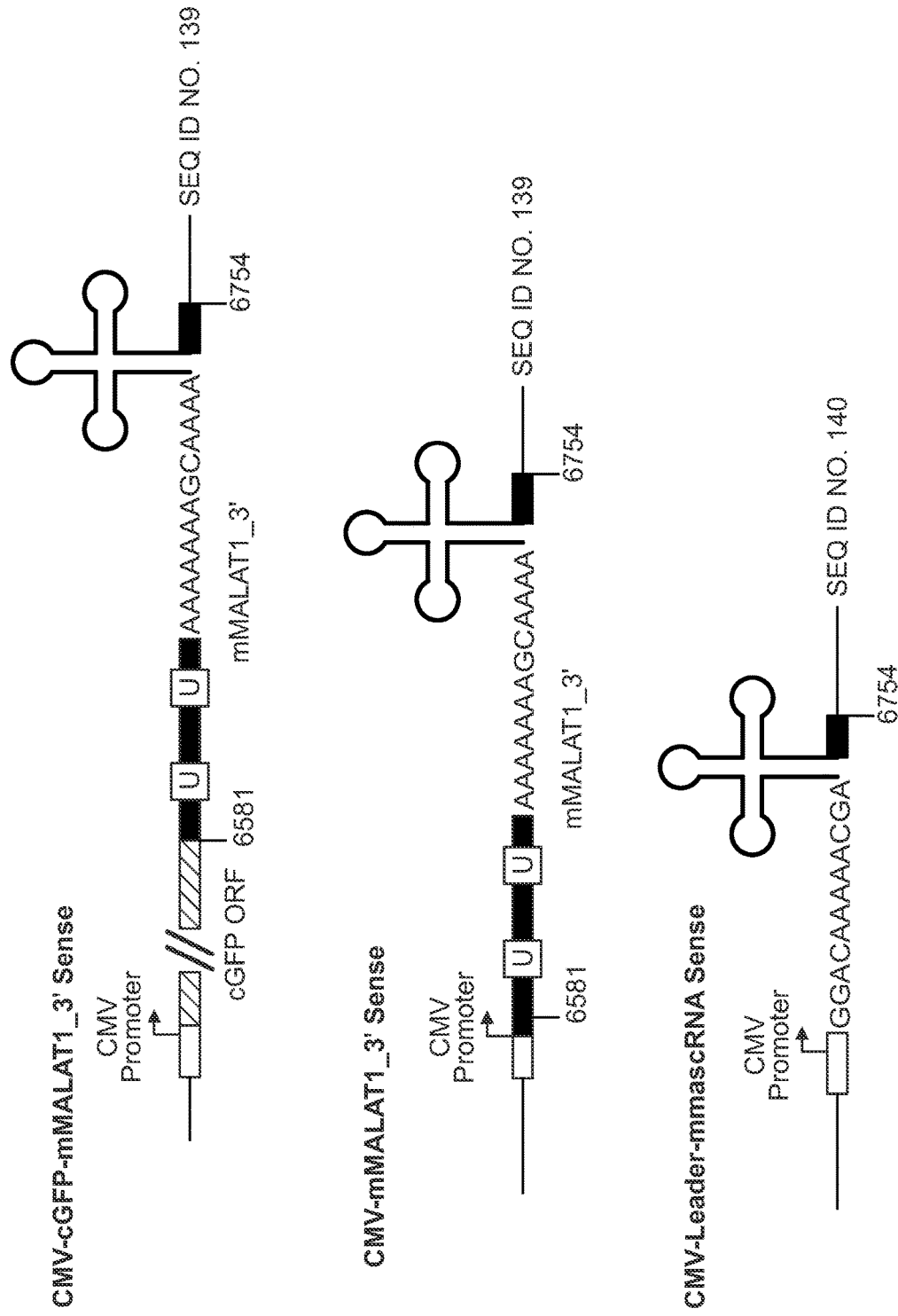
FIGS. 9A-9B show that the MALAT1 tRNA-like structure is sufficient for RNase P recruitment and mascRNA biogenesis in vivo. (9A) To identify the minimal sequence elements required for mascRNA biogenesis from a CMV-driven transcript, progressive deletions were introduced into the CMV-cGFP-mMALAT1_3' expression plasmid (top). The cGFP open reading frame was first removed to generate the CMV-mMALAT1_3' expression plasmid (middle). This plasmid still contains the complete 174-nt mMALAT1_3' fragment (nt 6581-6754), and thus includes the U- and A-rich motifs upstream of the RNase P cleavage site. To then determine if the mascRNA tRNA-like structure itself is sufficient for mascRNA biogenesis, the region upstream of the MALAT1 RNase P cleavage site was replaced with an unrelated 12-nt sequence, generating the CMV-Leader-mmascRNA expression plasmid (bottom). The 12-nt sequence is the 5' leader from S. cerevisiae pre-tRNA(Tyr). Antisense controls (not shown) for each of the plasmids were generated by placing the MALAT1/mascRNA regions in the antisense orientation. The sequences shown are SEQ ID NOs. 139, 139, and 140 from top to bottom. (9B) The expression plasmids were transfected into HeLa cells and total RNA isolated 24 hr later. Northern blots were then performed to detect mascRNA expression. U6 snRNA was used as a loading control. As mascRNA was efficiently produced from all three sense plasmids, this shows that the only region of MALAT1 that is required for mascRNA generation in vivo is the tRNA-like structure itself.
Figure 9B:
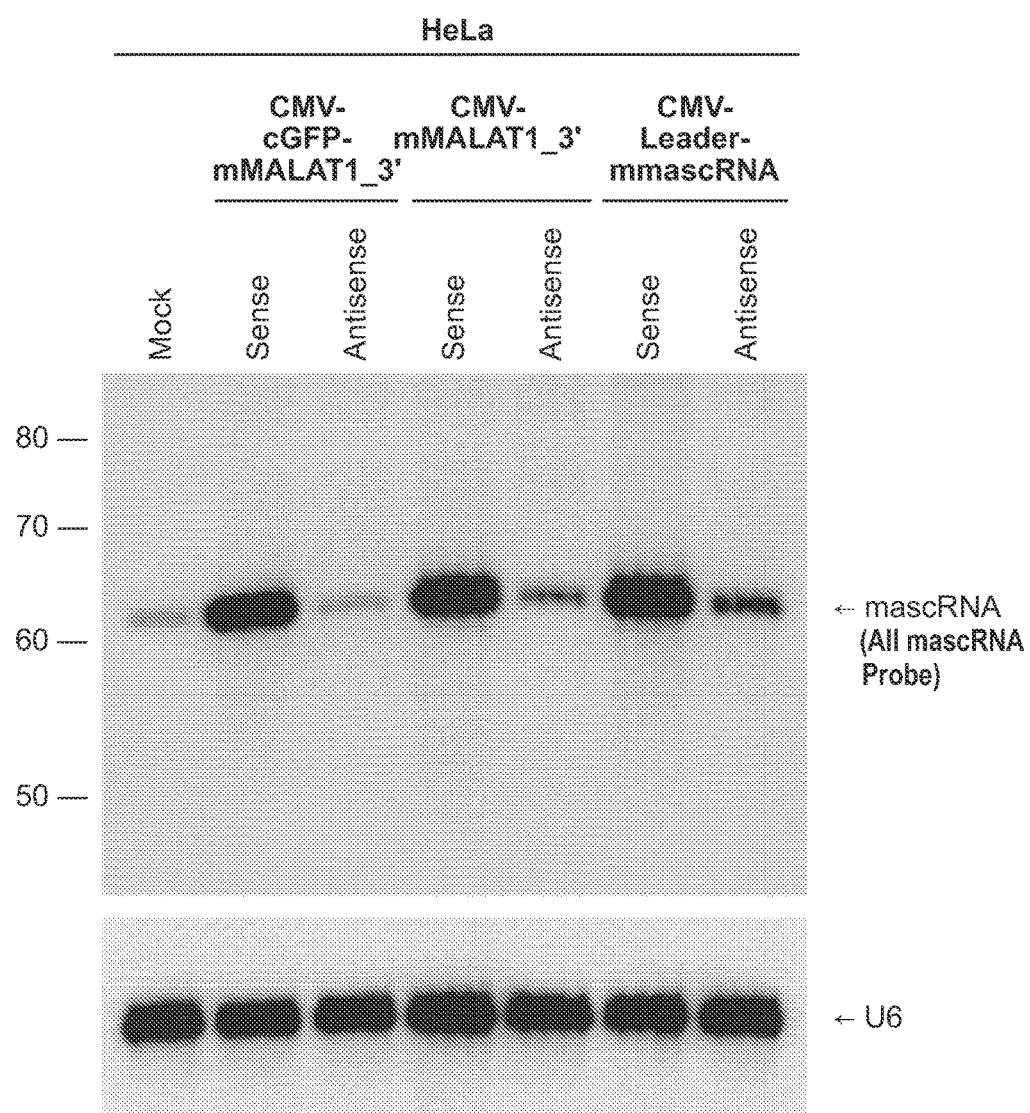
Figure 10B:
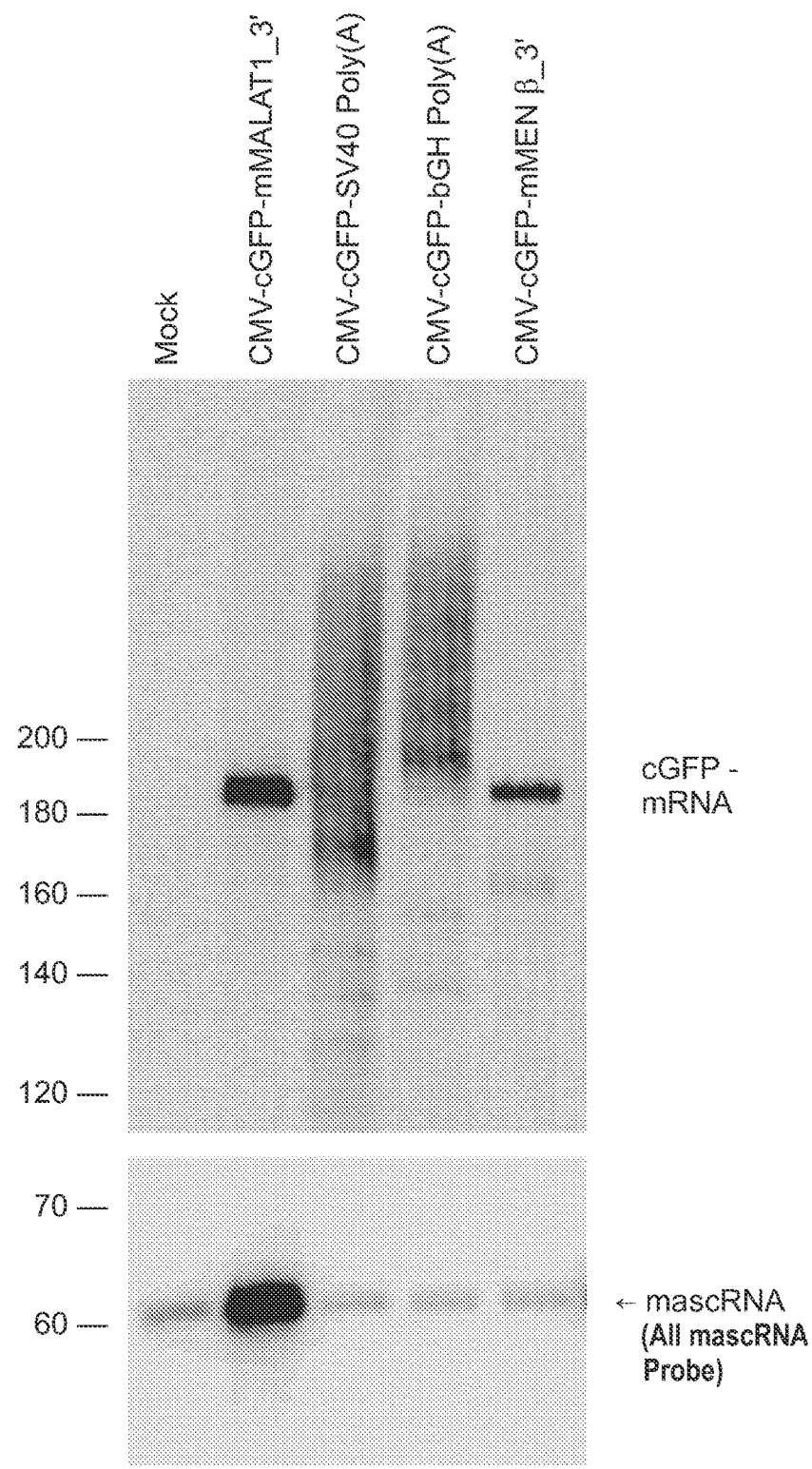

As mascRNA is efficiently produced from the CMV promoter-driven transcript (FIG. 1E), it was found that the MALAT1 promoter is not required for the recruitment of RNase P or any of the other tRNA processing factors to the nascent RNA. Further, it was found that the only region of the MALAT1 primary transcript that is required for mascRNA generation in vivo is the tRNA-like structure itself (FIG. 9). Consistent with current models of substrate recognition by RNase P (Kirsebom 2007), the enzyme will probably recognize and cleave any tRNA-like structure, regardless of the promoter used to generate the transcript. Indeed, placing the MEN β tRNA-like structure downstream of cGFP in our expression system similarly resulted in efficient RNase P cleavage (FIG. 10).

Figure 2A:
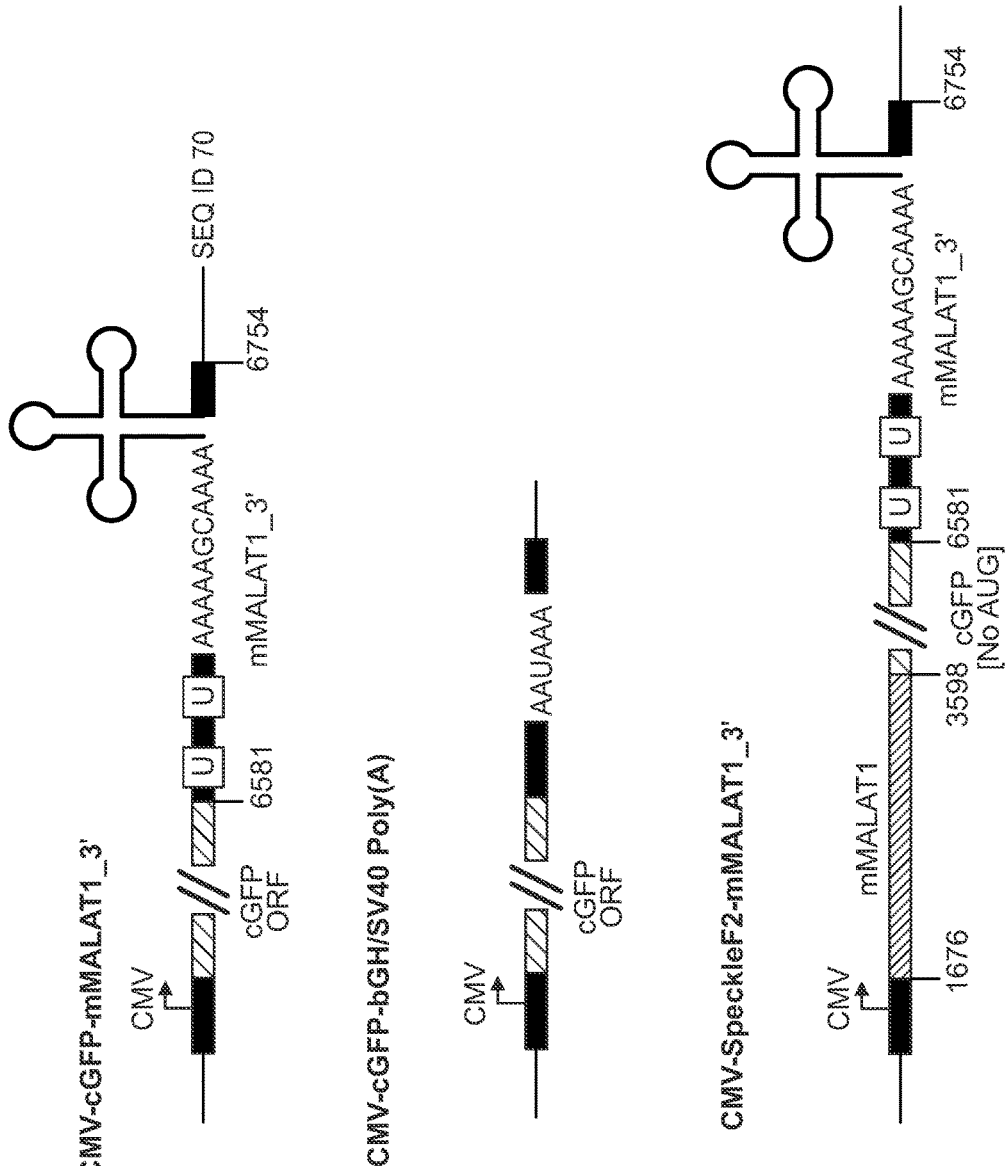

Example 2: The Conserved U-Rich Motifs Protect the 3' End of MALAT1 from Degradation As the highly conserved U- and A-rich motifs present immediately upstream of the MALAT1 RNase P cleavage site were not required for mascRNA biogenesis (FIG. 1B and FIG. 9), it was hypothesized that they may instead function to prevent nuclear export of MALAT1 and/or to stabilize the long noncoding RNA post-RNase P cleavage. Using biochemical fractionation to separate nuclear and cytoplasmic total RNA from transfected HeLa cells, it was found that the cGFP-MALAT1_3' reporter RNA was efficiently exported to the cytoplasm (FIG. 2B). In fact, the transcript was exported as efficiently as a cGFP transcript ending in a canonical poly-A tail (FIG. 2A,B). Therefore, the 3' end of MALAT1 does not function in nuclear retention. Instead, a region was identified within the body of mouse MALAT1 (nt 1676-3598) that when inserted into the expression construct (to generate the CMV-SpeckleF2-mMALAT1_3' plasmid, FIG. 2A) was sufficient to cause nuclear retention (FIG. 2C). This is consistent with previous reports that indicated that this region is important for targeting endogenous MALAT1 to nuclear speckles (Tripathi et al. 2010; Miyagawa et al. 2012).

Figure 2E:
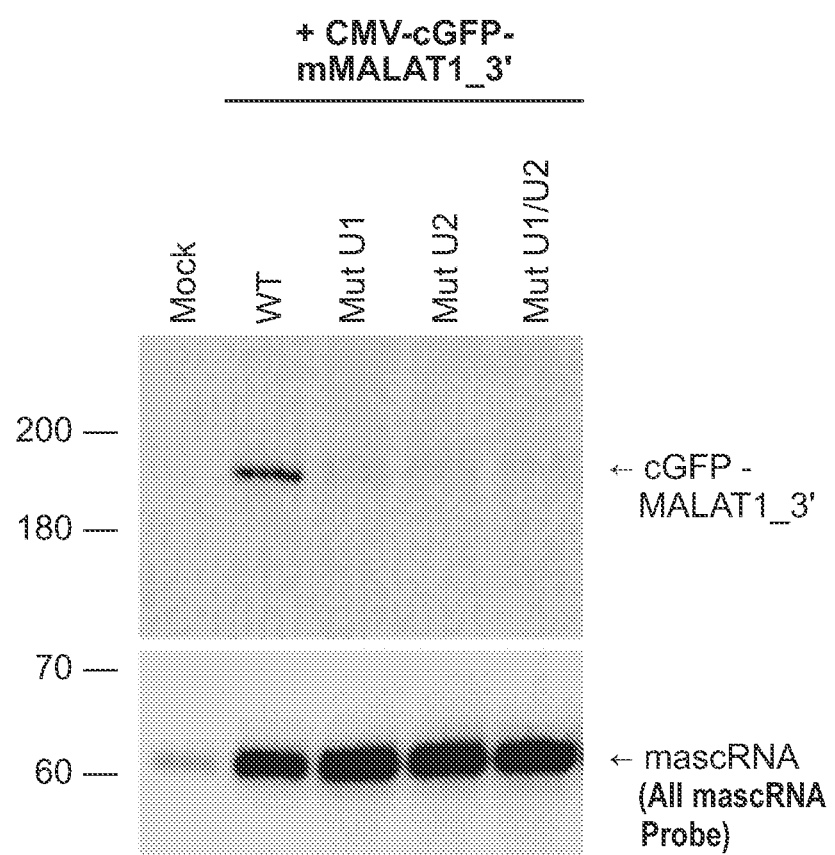
Figure 11B:
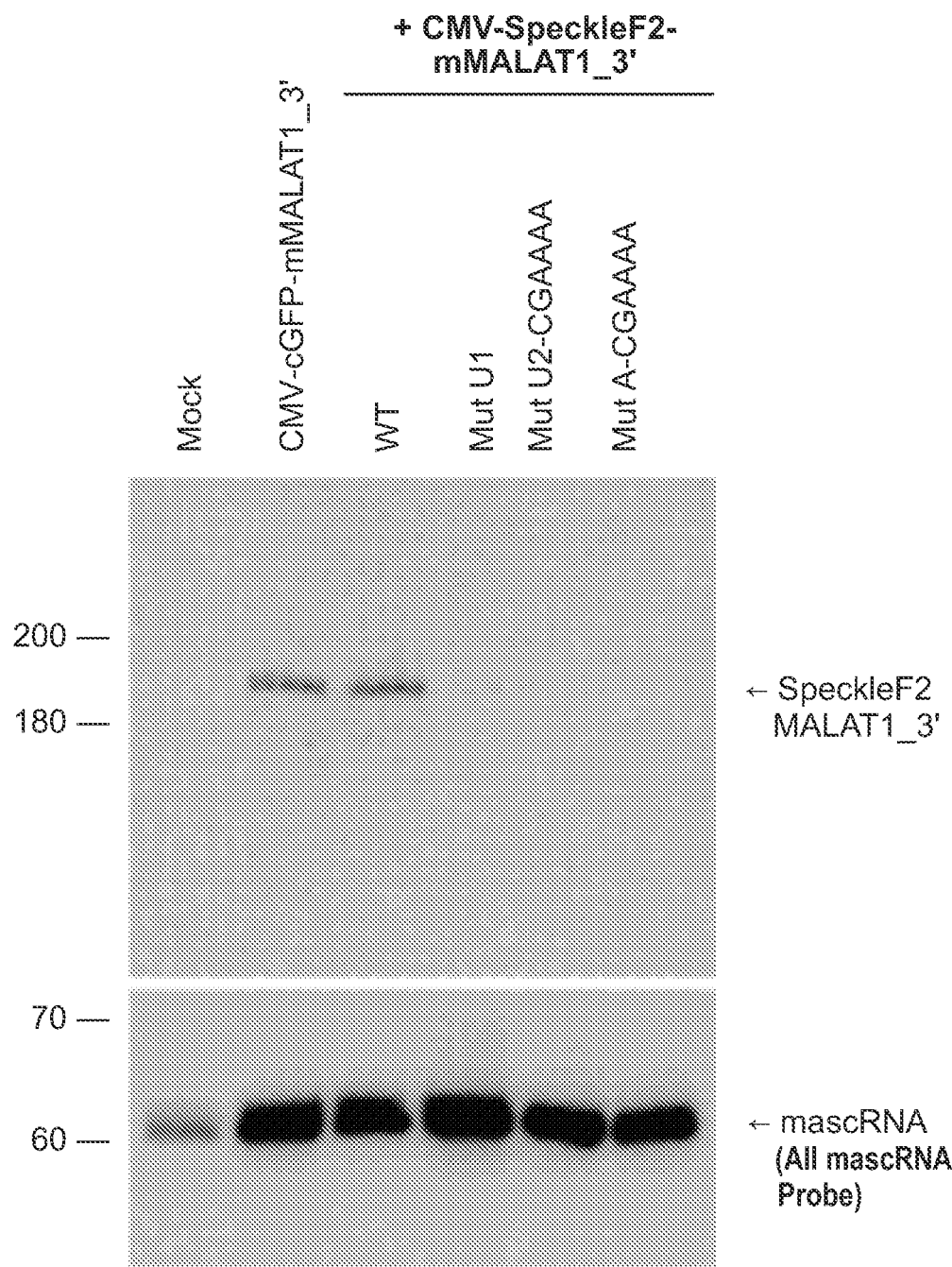

To instead explore a possible role for the highly conserved U-rich motifs in MALAT1 RNA stability, cGFP-mMALAT1_3' expression plasmids were generated and transfected, containing 5-nt mutations in U-rich Motif 1, U-rich Motif 2, or in both motifs (FIG. 2D). These mutations had no effect on RNase P cleavage or mascRNA biogenesis (FIG. 2E, bottom), but caused the mature cGFP-MALAT1_3' RNA to be efficiently degraded (FIG. 2E, top). Introducing similar mutations into the nuclear-retained reporter transcript also caused the RNA to be undetectable by Northern blot analysis (1 FIG. 11B), showing that U-rich Motifs 1 and 2 are both required for stabilizing the 3' end of MALAT1 in the nucleus and cytoplasm.

Figure 2F:
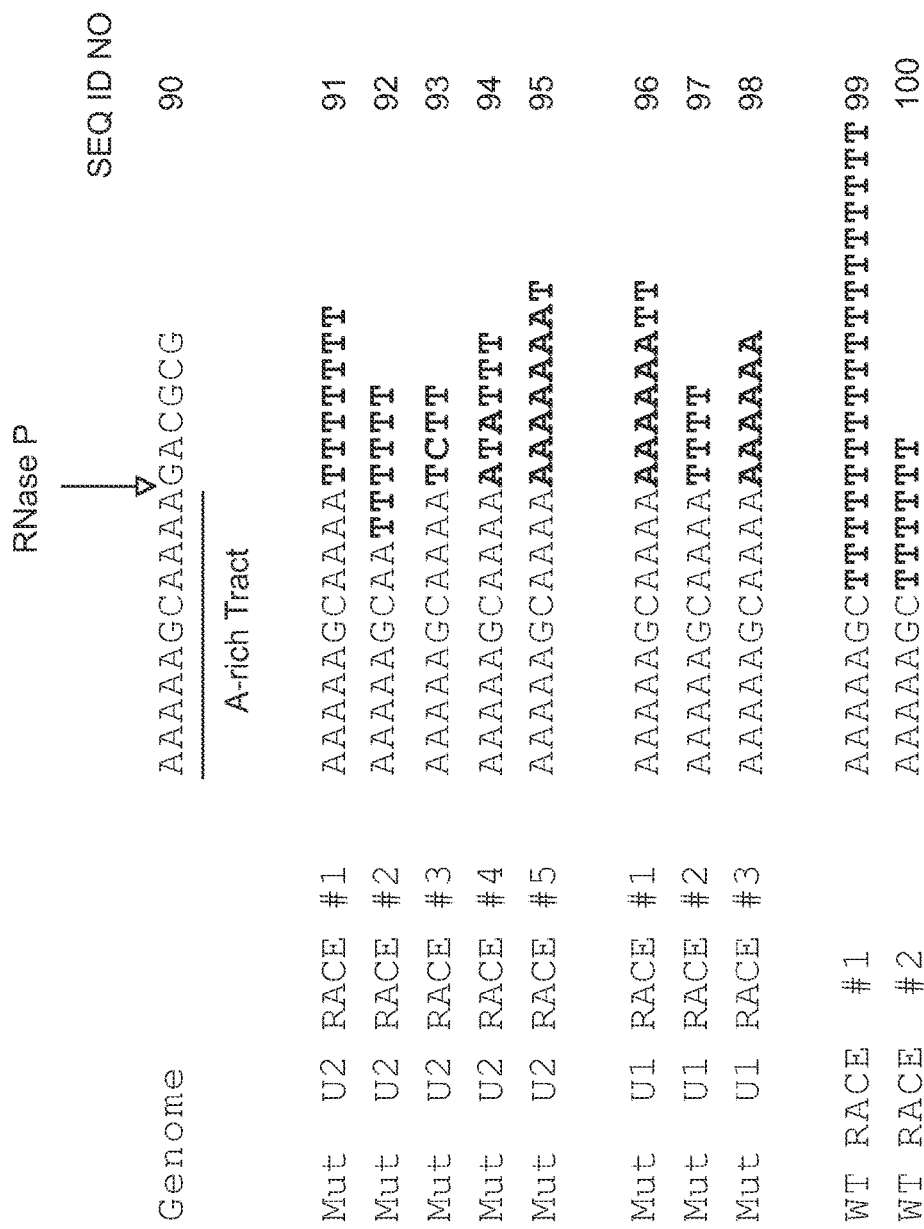

A ligation-based 3' RACE PCR approach was used to gain insight into the mechanism by which the mutant transcripts are degraded. In addition to detecting transcripts simply degraded from their 3' ends to various extents, numerous cGFP-MALAT1_3' transcripts ending in short post-transcriptionally added U-rich tails (10 out of 56 sequenced RACE clones) were surprisingly detected, implicating uridylation in the degradation of both the wild-type and mutant MALAT1 3' ends (FIG. 2F). Several degradation patterns were observed: (1) untemplated adenylation of the MALAT1 3' end prior to uridylation (e.g. Mut U1 RACE #1), (2) addition of a U-rich tail to the full-length transcript (e.g. Mut U2 RACE #1), and (3) partial degradation of the 3' end prior to uridylation (e.g. WT RACE #1) (FIG. 2F). This last pattern is particularly interesting as it suggests that a 3'-5' exonuclease stalled as it was degrading the MALAT1 3' end. The U-tail was then likely added to provide a new single-stranded tail for an exonuclease to recognize and re-start the decay process (Houseley et al. 2006). Uridylated decay intermediates were also detected using the nuclear-retained reporter transcript (FIG. 11C), indicating that uridylation likely occurs in both the nucleus and the cytoplasm. These results indicate that U-rich Motifs 1 and 2 are likely critical for stabilizing the 3' end of MALAT1 by preventing uridylation and degradation by 3'-5' exonucleases.

Example 3: A Triple Helix Forms at the 3' Ends of MALAT1 and MEN β

Figure 3A:
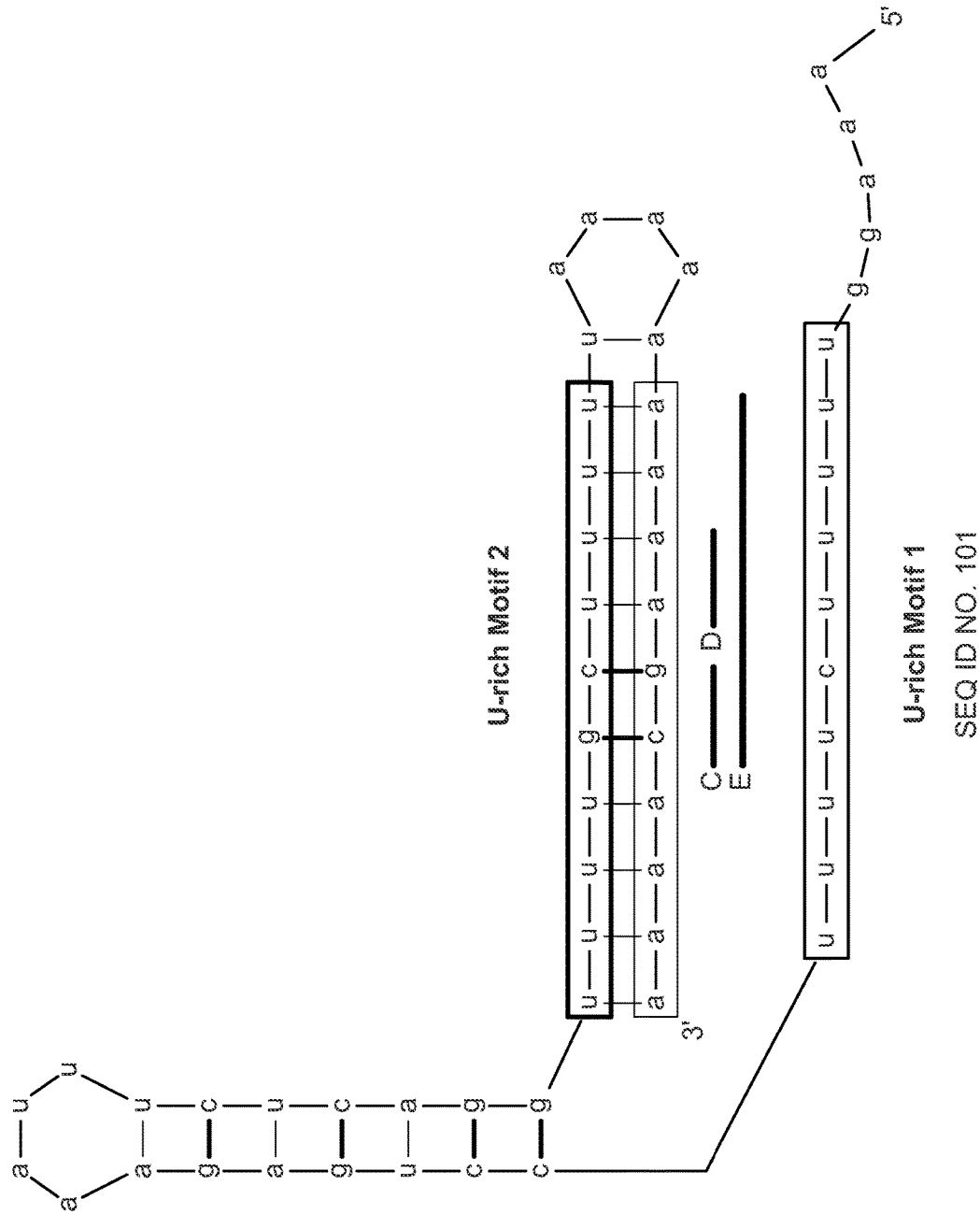
Figure 12A-1:
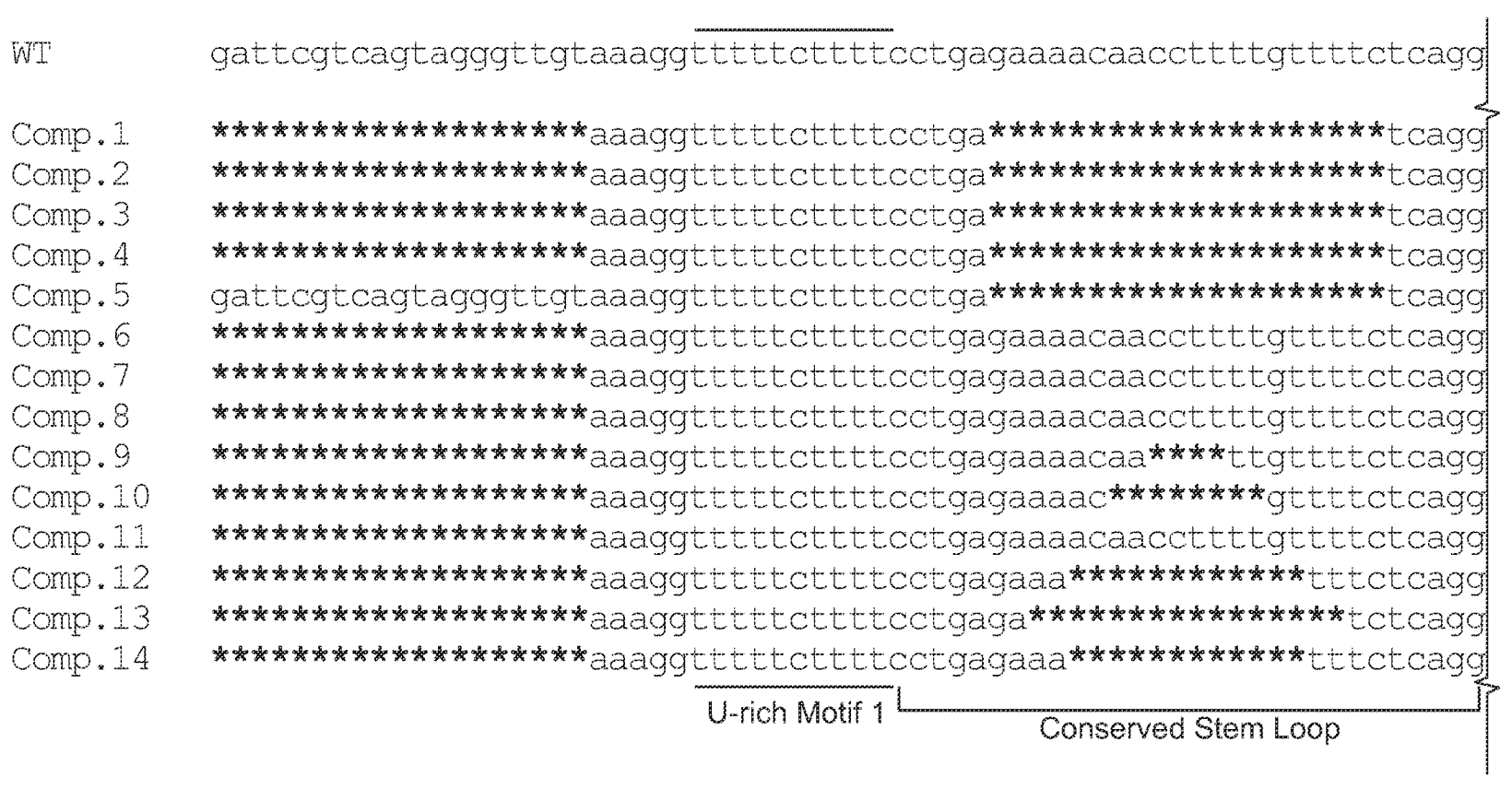
Figures 2, 12B:
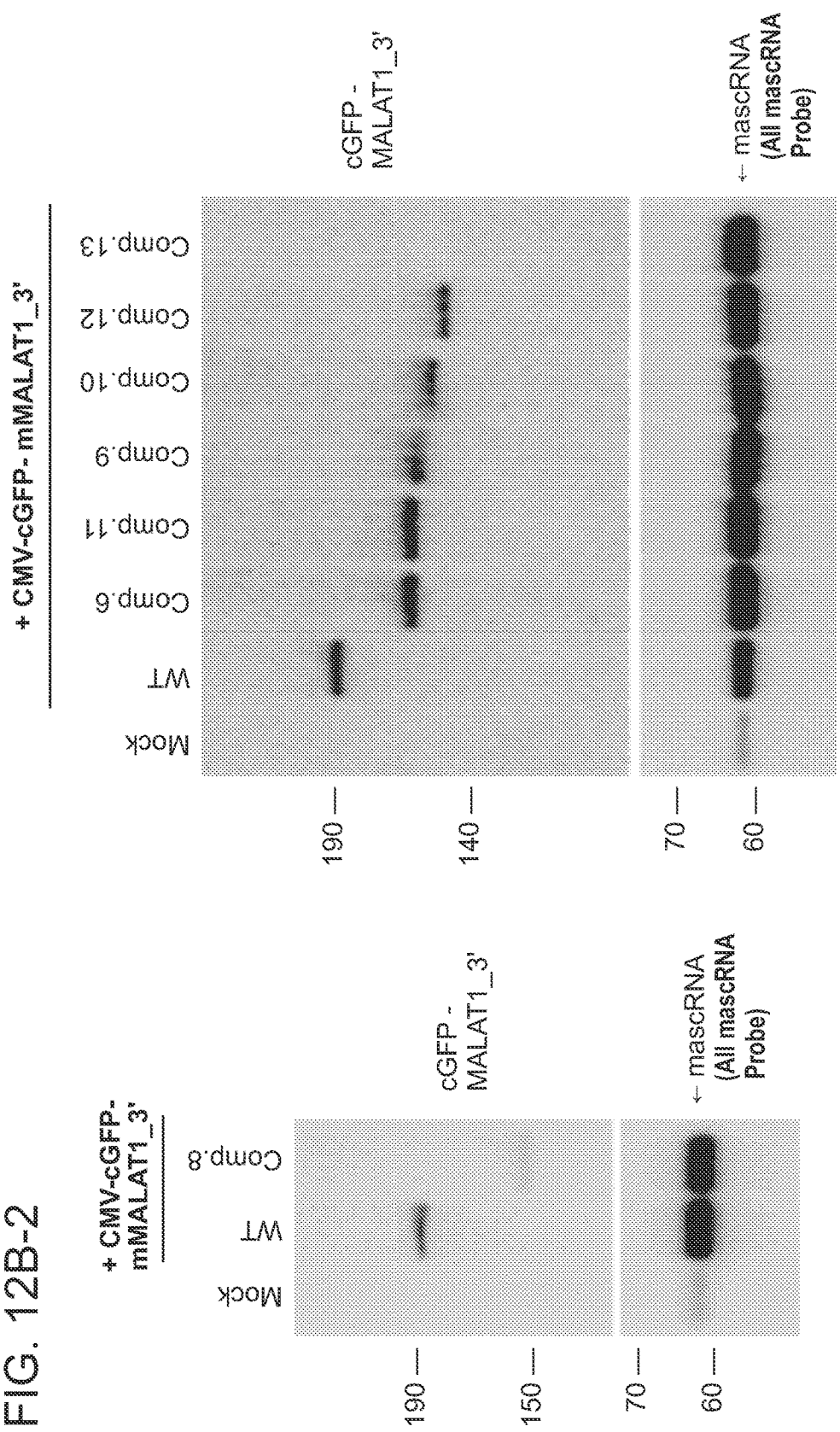
Figure 13B:
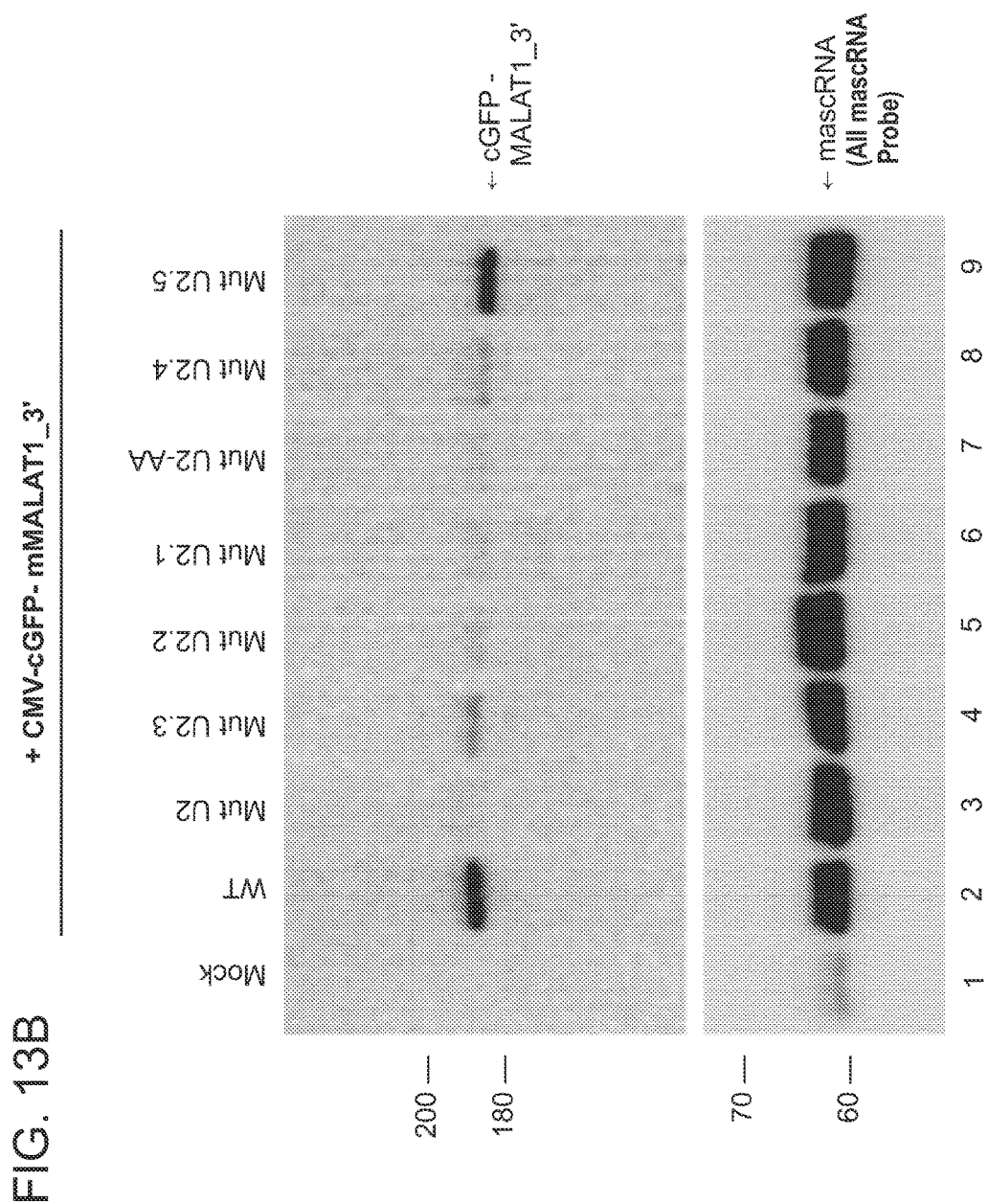

Having identified U-rich Motifs 1 and 2 as being critical for MALAT1 3' end stability, the minimal sequence elements required to stabilize the 3' end of the cGFP-MALAT1_3' transcript was investigated. Using extensive mutagenesis, it was found that 51 of the 110 nts at the 3' end of MALAT1 (Comp. 14, FIG. 2D) can be removed with little or no effect on cGFP-MALAT1_3' RNA stability (FIG. 2G and FIG. 12). Consistent with the evolutionary conservation patterns of MALAT1 (FIG. 1B) and MEN β (FIG. 1C), the well-conserved A- and U-rich motifs as well as the bottom half of the conserved stem loop are required for cGFP-MALAT1_3' stability (FIG. 2D and FIG. 3A). In contrast, more divergent regions, such as the sequences between U-rich Motif 2 and the A-rich tract, are either dispensable or have only a minor supporting role in stabilizing the 3' end of MALAT1 (FIG. 12).

Figure 3C:
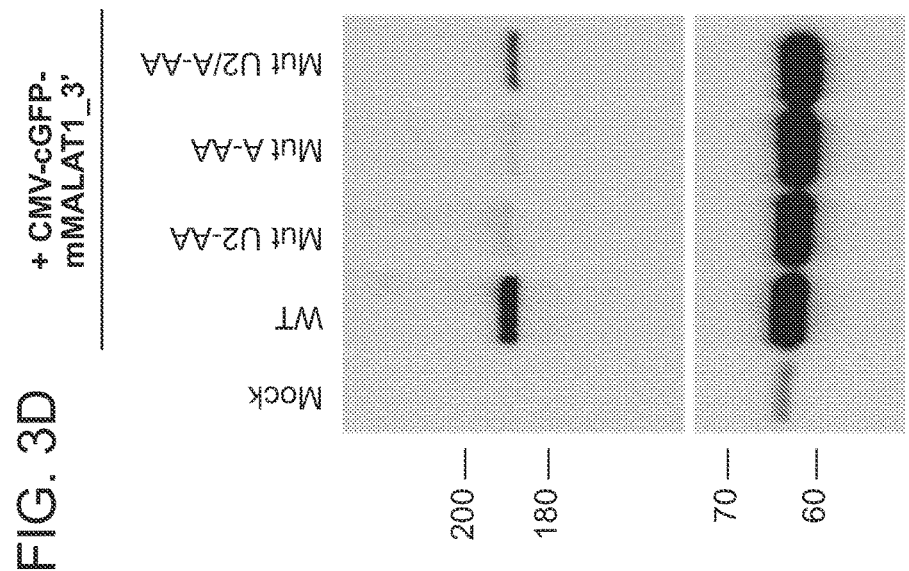
Figure 3D:
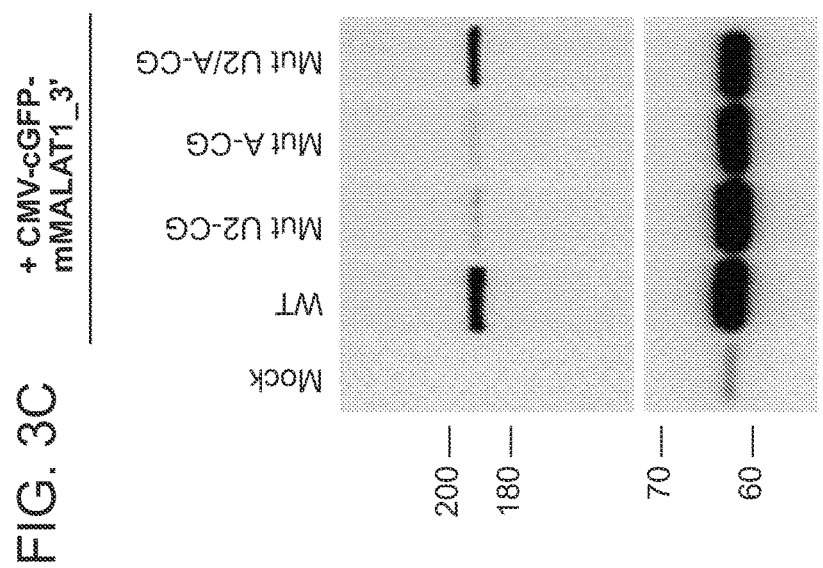
Figure 3E:
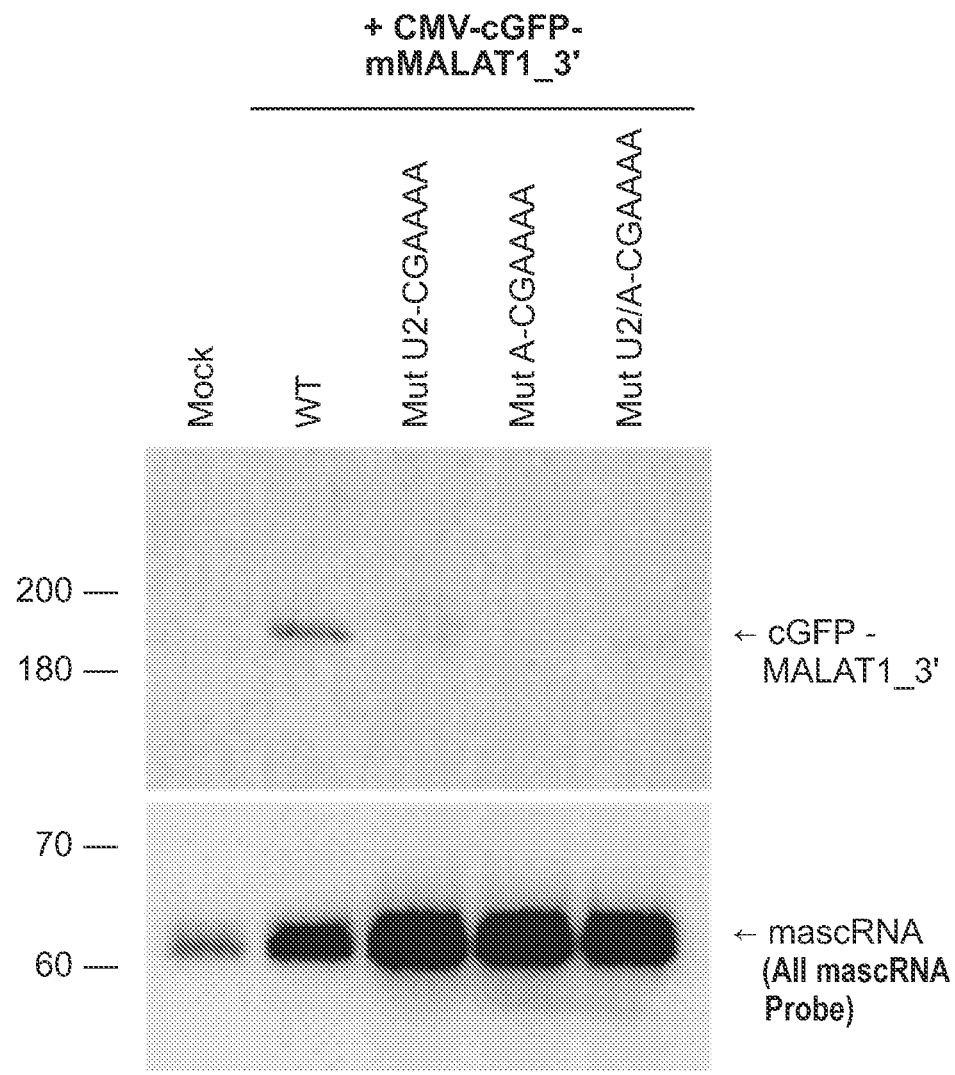
Figure 18:
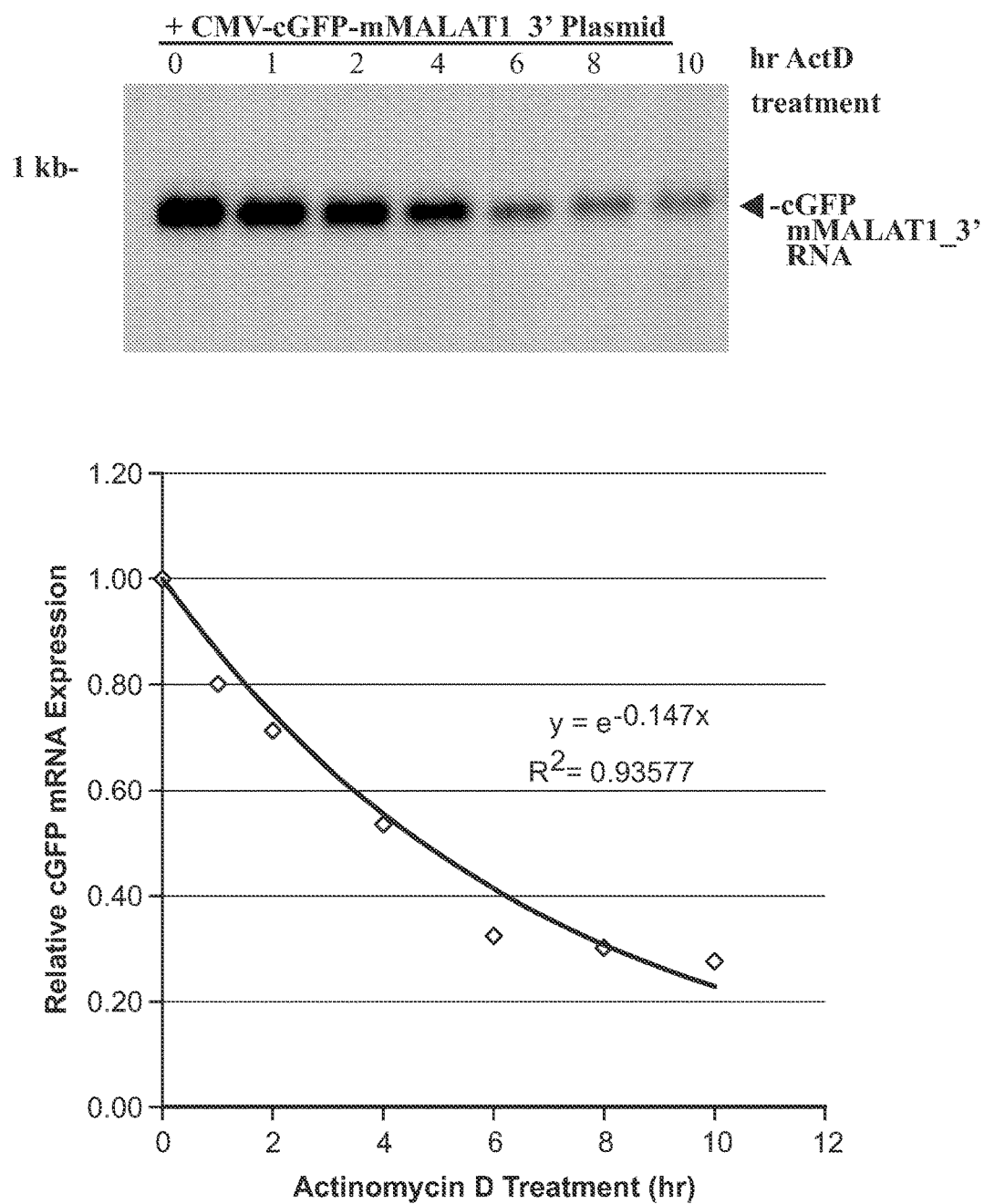
FIG. 18 shows a half-life measurement of an RNA of the invention. The top panel is a photograph of a Northern blot and the bottom panel is a graph of the data indicating the half-life of a cGFP transcript ending in a triple helix to be ~5 hr in HeLa cells.

Secondary structure prediction of the minimal functional MALAT1 3' end using Mfold indicated that the A-rich tract should base pair with U-rich Motif 2 (FIG. 3A). As these potential base pairs are perfectly conserved through evolution (FIG. 1B,C), cGFP-MALAT1_3' expression plasmids were generated in which specific base pairs were disrupted (FIG. 3B and FIG. 18). As shown in FIGS. 3C and 3D, the cGFP-MALAT1_3' RNA failed to accumulate when two mismatches were introduced in either U-rich Motif 2 or the A-rich tract. When base pairing was re-established by introduction of mutations in both motifs, a significant rescue in the level of cGFP-MALAT1_3' RNA was detected (FIG. 3C, D). This indicates that base pairing between U-rich Motif 2 and the A-rich tract is critical for stabilizing the 3' end of MALAT1. Interestingly, cGFP-MALAT1_3' ending in a short homopolymeric poly-A tail due to the GC in the A-rich tract being mutated to AA was also degraded in vivo (data not shown), showing that a short poly-A tail can not functionally replace base pairing at the 3' end of MALAT1. As expected, when 6 base pairs were disrupted, the mutated cGFP-MALAT1_3' transcript failed to accumulate in vivo (FIG. 3E). Unexpectedly, however, introduction of compensatory mutations that re-establish these 6 base pairs failed to rescue cGFP-MALAT1_3' transcript levels (FIG. 3E), indicating that base pairing between U-rich Motif 2 and the A-rich tract is necessary but not sufficient for MALAT1 stability.

Figure 4A:
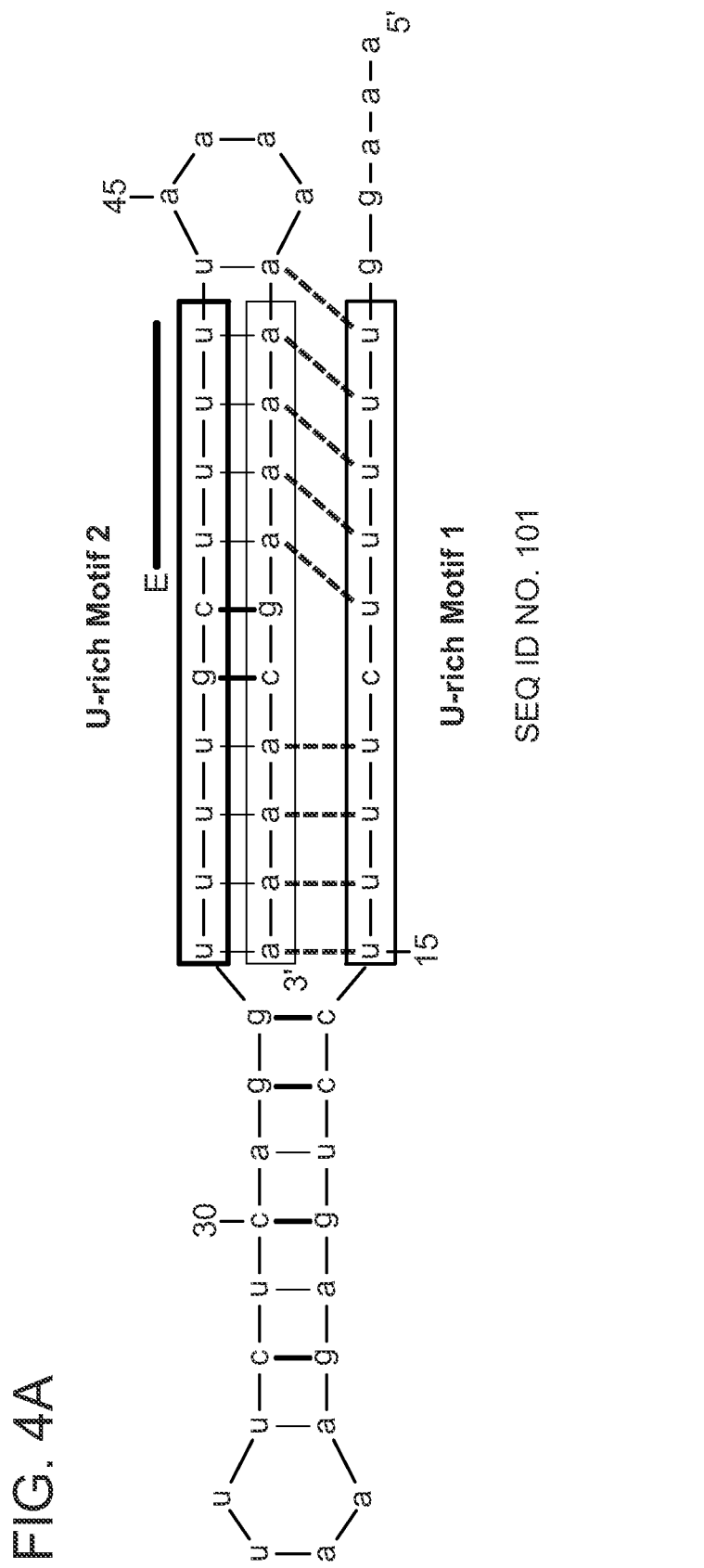

As U-rich Motif 1 is also required for MALAT1 3' end stability (FIG. 2E), is highly conserved (FIG. 1B,C), and is predicted to be in close proximity to U-rich Motif 2 and the A-rich tract (FIG. 3A), we suspected that U-rich Motif 1 may also interact with the duplex in, for example, a triple helix (FIG. 4A). Pioneering work by Felsenfeld, Davies, and Rich in 1957 first described U-A•U triple helix structures, where a poly(U) third strand forms Hoogsteen hydrogen bonds to the major groove of a Watson-Crick base paired helix of poly-A/poly(U) (Felsenfeld et al. 1957) (FIG. 4B). Naturally occurring U-A•U RNA triple helix structures have recently been identified in telomerase RNA (Qiao and Cech 2008) and at the 3' end of a noncoding RNA produced by Kaposi's sarcoma-associated herpesvirus and related gammaherpesviruses (Mitton-Fry et al. 2010; Tycowski et al. 2012). In the latter case, this structure was essential for stabilization of the RNA. C-G•C triple helices are structurally similar to U-A•U, although protonation of the cytosine in the third strand is required to fully stabilize the structure, making C-G•C triplexes favorable under acidic conditions (FIG. 4B). Importantly, at the 3' ends of MALAT1 and MEN β, the U- and A-rich motifs are properly oriented to allow an intramolecular triple helical structure to form by Hoogsteen hydrogen-bonding of U-rich Motif 1 to the major groove of the Watson-Crick base paired helix that is formed by U-rich Motif 2 and the A-rich tract (FIG. 4A).

Figure 4C:
Figure 4D:
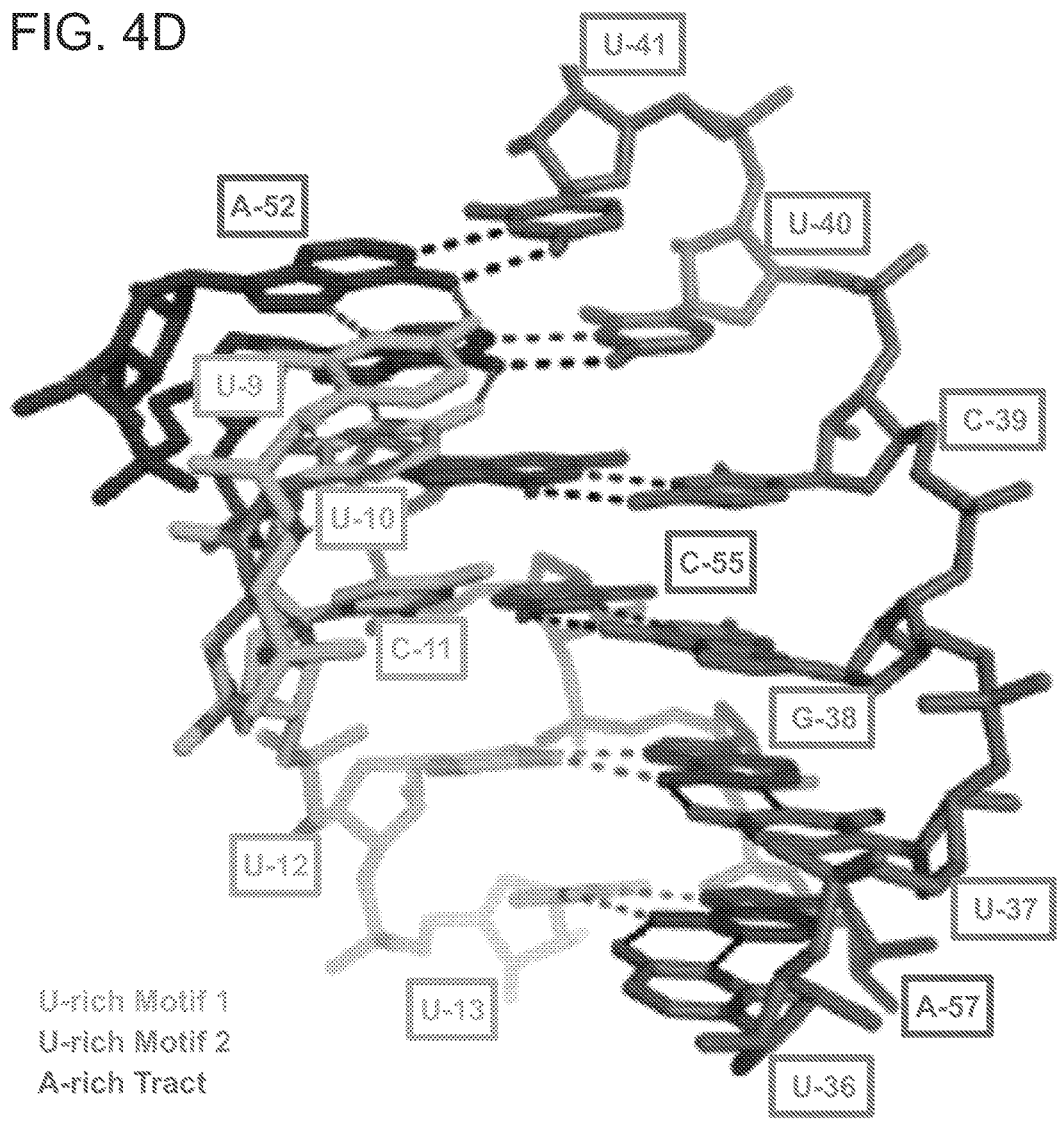
Figure 14B:
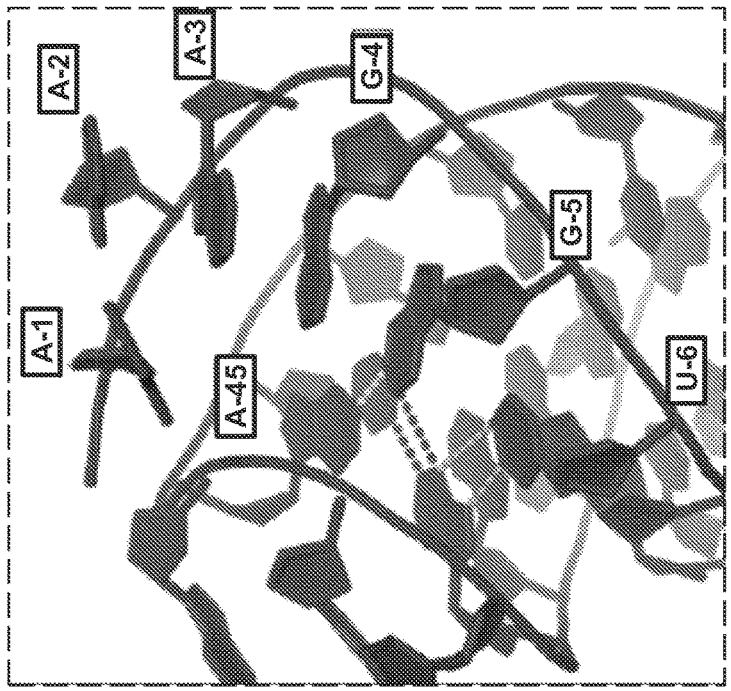
FIGS. 14A-14C show the structural modeling of the MALAT1 3' end. (14A) Overlay of five individual models of the full-length (nt 1 to 59) MALAT1 Comp.143' end. Models are shown in cartoon representation and colored in blue, red, green, orange, and magenta. (14B) Close-up view of the 5' end of the model colored in blue (from panel A). The first base triple of the triple helix is indicated through its Watson-Crick and Hoogsteen base pairs. A possible hydrogen bond between G-5 and A-45 is shown in orange, highlighting the possibility of a stabilization of the 5' end of this region through the loop between U-rich Motif 2 and the A-rich tract. (14C) Scatter plot of 2,000 MALAT1 Comp.14 3' end models (lacking nt 1-5) generated by Rosetta de novo RNA folding. The plot shows the distance (in Å) of all models to a reference model on the X-axis and the score of the individual structure of the Y-axis.
Figure 14A:
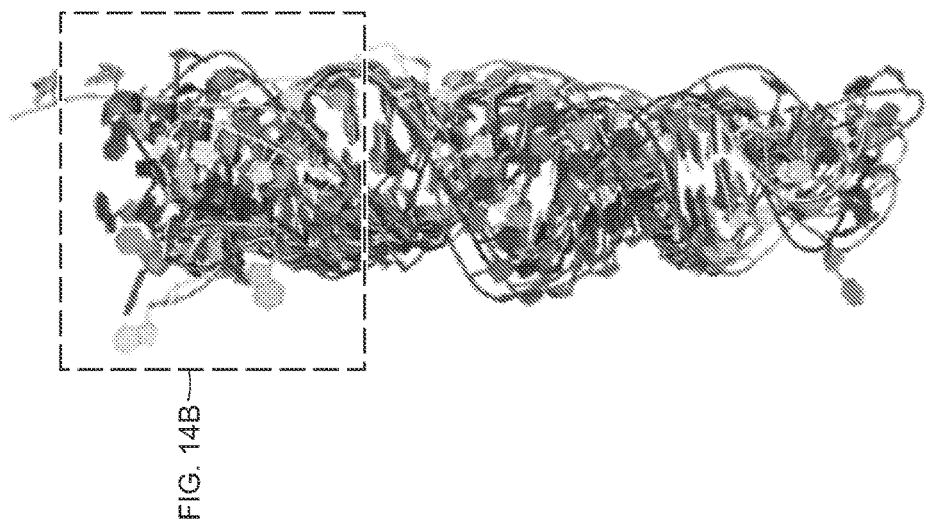
Figure 14C:
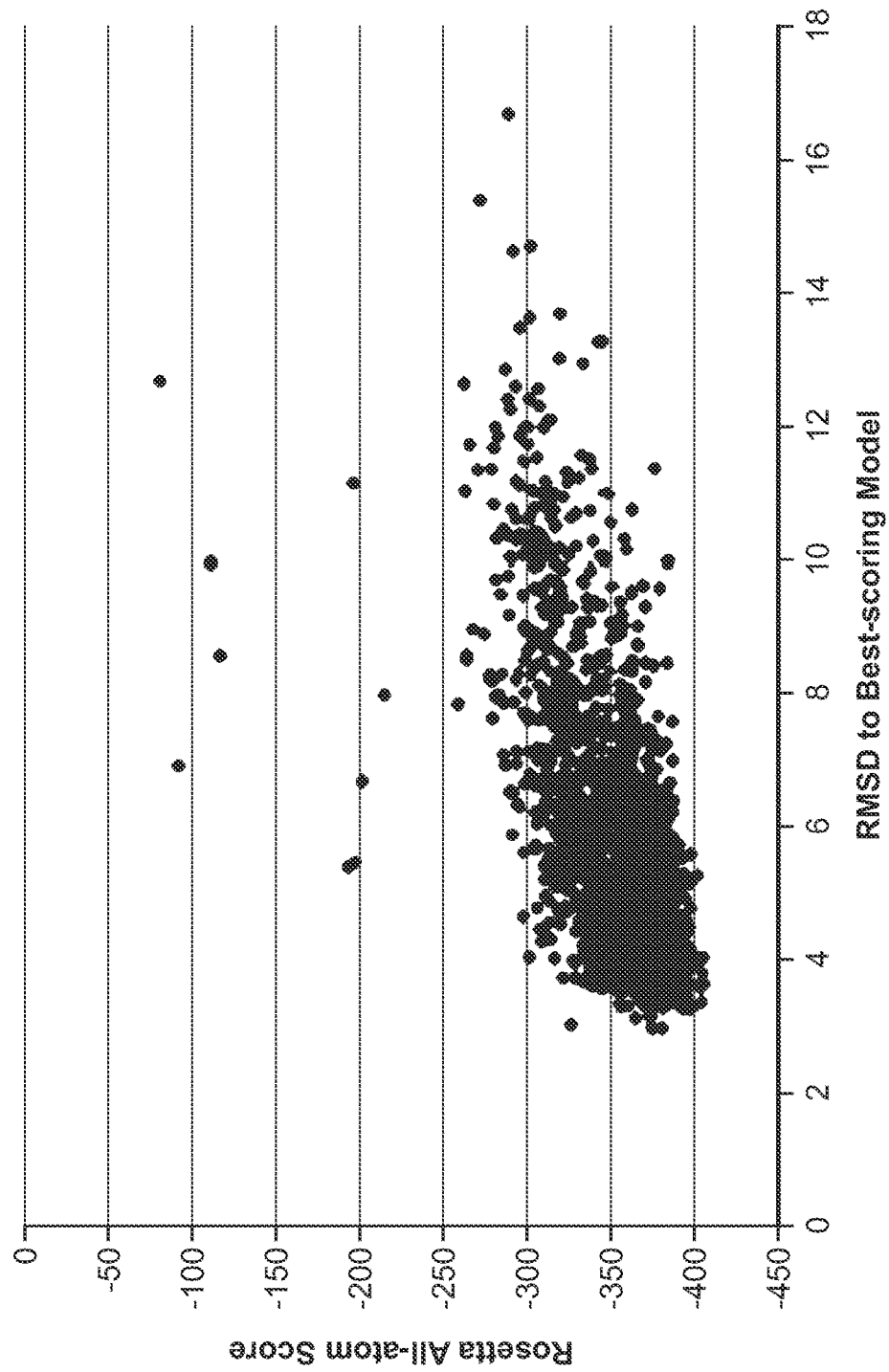

To assess the ability of the 3' end of MALAT1 to form a triple helix, a fragment assembly of RNA with full atom refinement, known as FARFAR was used (Das et al. 2010). This Rosetta-based algorithm predicts low energy tertiary RNA structures de novo to near atomic resolution (Das and Baker 2007). As shown in FIG. 4C, the 59-nt Comp. 14 mMALAT1_3' region is predicted to be able to fold into a barbell-like structure with loops at each end of a continuous Watson-Crick base paired helix, part of which further forms a triple helical structure with U-rich Motif 1 binding in the major groove. 9 U-A•U base triples are able to form by base pairing between the Hoogsteen face of the A nucleotides in the A-rich tract with the Watson-Crick face of the U nucleotides of U-rich Motif 1 (FIG. 4C,D and FIG. 14). It is unclear from the modeling if the C-G•C triple forms. Although FARFAR does not allow modeling of a protonated cytidine residue at the Hoogsteen base (FIG. 4D), other steric constraints may preclude formation of this C-G•C triple. The predicted structure lacks chain breaks and has reasonable stereochemistry, indicating that there are no structural constraints blocking the formation of the triple helix. Nicely, nucleotides that are not critical for MALAT1 3' end stability and thus deleted from the Comp. 14 transcript (FIG. 2D) are all predicted to be in loop regions at the ends of the barbell-like structure, physically separated from the core triple helix (FIG. 4A, C). Further, the structural model indicates that the 3' terminal nucleotide of MALAT1 is part of the core triple helix and thus well protected from either addition of non-templated nucleotides or exonucleases. It is likely that significant free energy would be necessary to unwind this triple helix. Consistent with this model, 3' RACE revealed that 3'-5' exonucleases often pause within this structure (FIG. 2F).

Figure 4E:
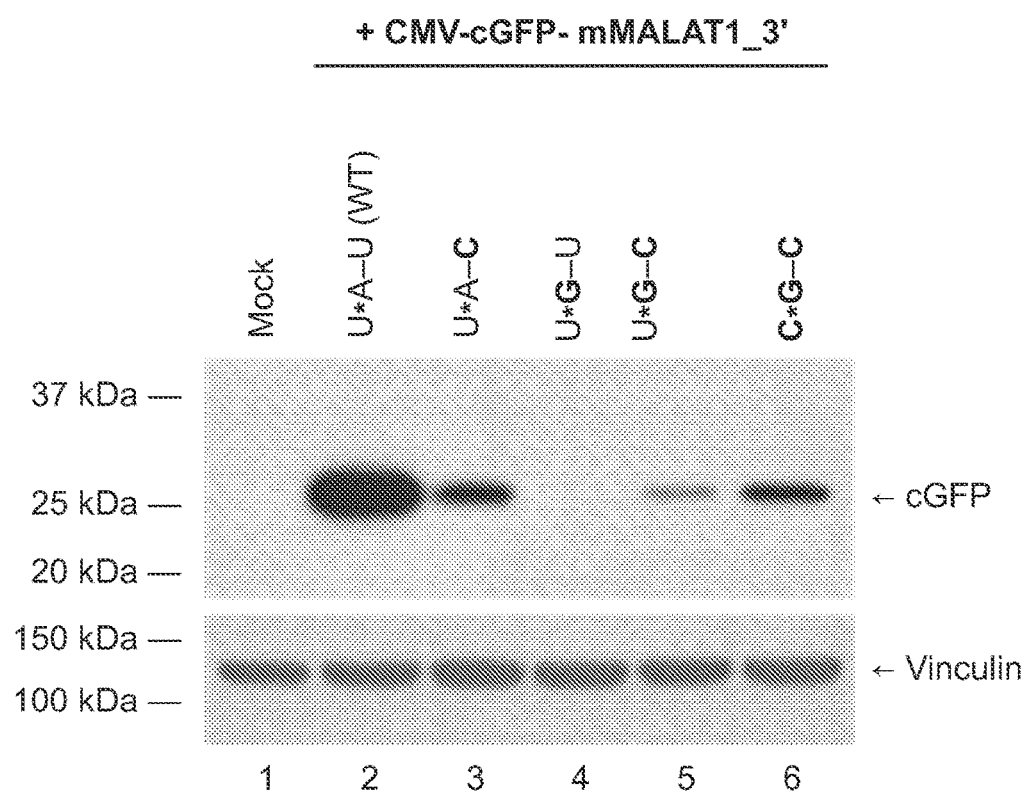

Although the structural model predicts that the triple helix structure can form, it does not prove that the triple helix does form in vivo. Nevertheless, several independent lines of evidence that support the existence and functional significance of the triple helix in vivo. First, all of the base triples are near perfectly conserved through evolution at the 3' ends of both MALAT1 (FIG. 1B) and MEN β (FIG. 1C). Second, the mutational analysis in FIG. 3 revealed that base pairing between U-rich Motif 2 and the A-rich tract is necessary but not sufficient for stabilizing the 3' end of MALAT1. Of particular interest is the Mut U2/A-CGAAAA transcript (FIG. 3B,E) in which nucleotides that form six of the base pairs between U-rich Motif 2 and the A-rich tract were swapped across the helix. These nucleotide swaps should not alter the structural integrity of the double helix, but should eliminate the potential to form base triples, providing indirect support for this structure in stabilization of MALAT1. Third, to directly test for the presence of the triple helix in vivo, we investigated the effect of converting four of the U-A•U base triples at the 3' end of MALAT1 (denoted in purple in FIG. 4A) to C-G•C base triples (FIG. 4E). Mutating the 4 consecutive A nucleotides to G (Lane 4, FIG. 4E) caused the cGFP-MALAT1_3' transcript to be unstable and not translated in vivo (see below for further information about translation). Compared to a transcript only able to form a double helix with C-G base pairs (Lane 5), significantly greater protein expression was observed when C-G•C base triples were able to form (Lane 6, FIG. 4E). This is strong evidence that a functional triple helix forms in vivo.

To then investigate if the entire triple helix structure is necessary for stabilizing the 3' end of MALAT1 in vivo, cGFP-MALAT1_3' expression plasmids were generated in which select base triples were disrupted by mutating U-rich Motif 1 (FIG. 4F). Interestingly, it was found that mutations in the middle of U-rich Motif 1 (Mut U1.1 and Mut U1.2) had no effect on cGFP-MALAT1_3' transcript levels (FIG. 4F). This result is consistent with data from FIGS. 3C and 3D where base pairing between U-rich Motif 2 and the A-rich tract in this middle region was necessary for RNA stability, but the identities of the nucleotides on either side of the double helix (and thus the ability to form a base triple or not) were not critical. In contrast, base triples at both ends of the triple helix are critical for cGFP-MALAT1_3' to be stable (Mut U1.3 to Mut U1.5, FIG. 4F). These results support a model in which U-A•U base triples at each end of the MALAT1 triple helix ensure the structural stability of the overall structure and prevent transcript degradation by 3'-5' exonucleases.

Figure 10C:
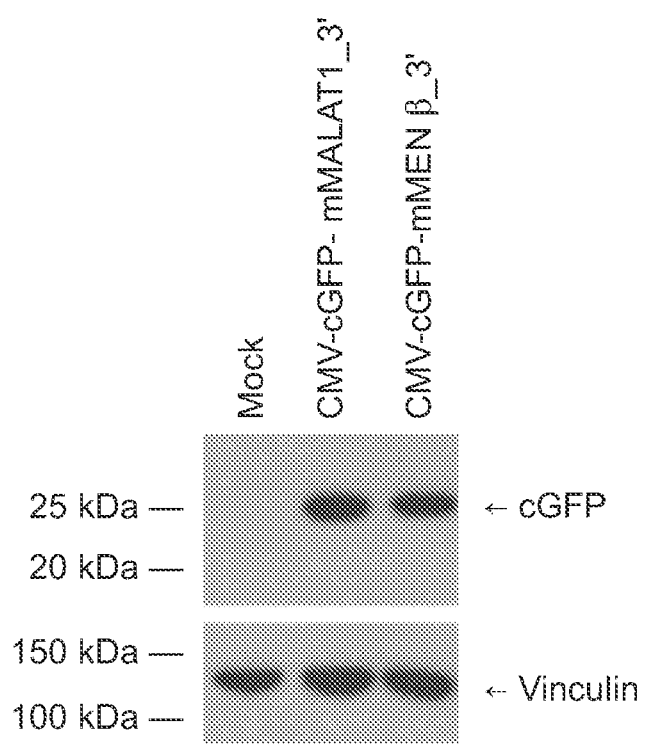

Example 4: The Triple Helix Structure Also Functions as a Translational Enhancer Element As the cGFP-MALAT1_3' reporter mRNA is stable and efficiently exported to the cytoplasm (FIG. 2B), it was investigated whether the cGFP open reading frame is translated. Surprisingly, similar levels of protein expression were observed from the cGFP transcripts ending in the mMALAT1_3' region as compared to those ending in a poly-A tail (FIG. 5A). This shows that the 3' end of MALAT1 may also function to promote translation. The 3' end of MEN β similarly supported significant cGFP protein expression (FIG. 10C). These results are particularly surprising considering that endogenous MALAT1 and MEN β are nuclear-retained transcripts and thus not thought to interact with the translation machinery.

Figure 5C:
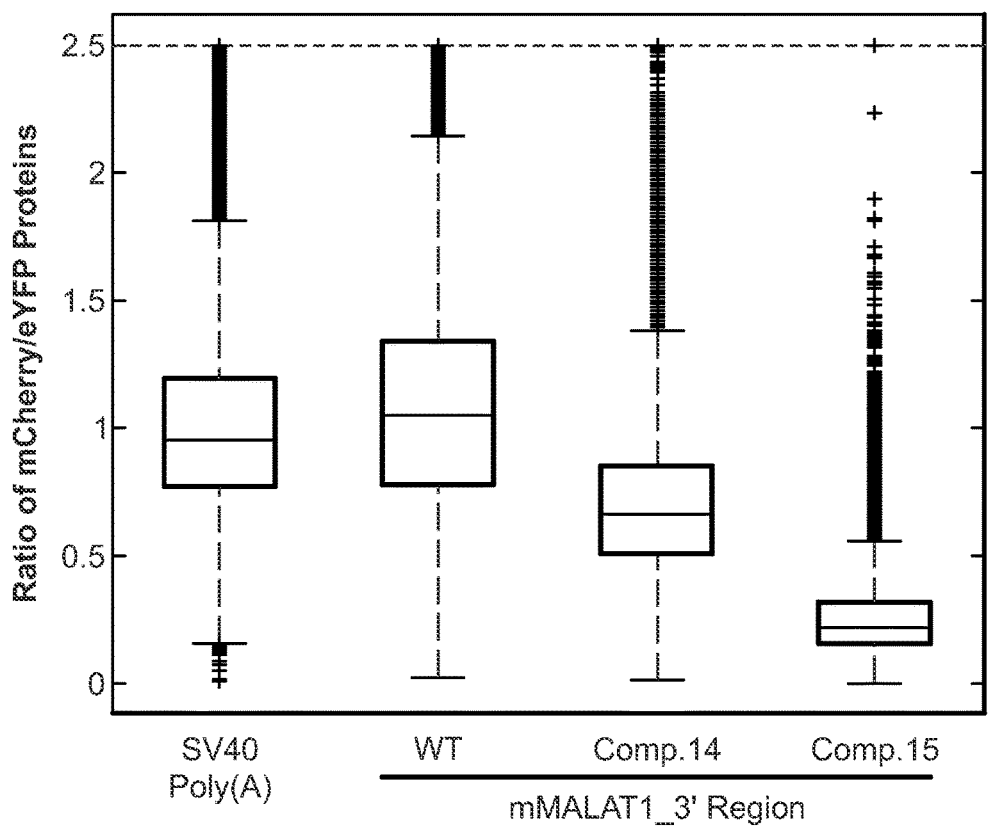
Figure 5D:
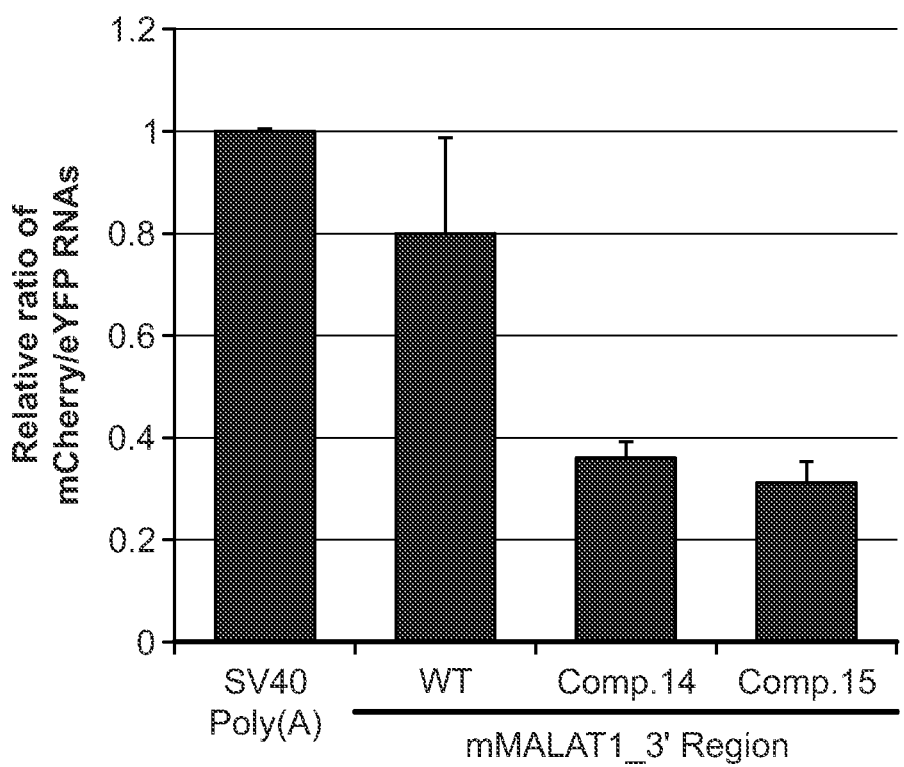
Figure 15A:
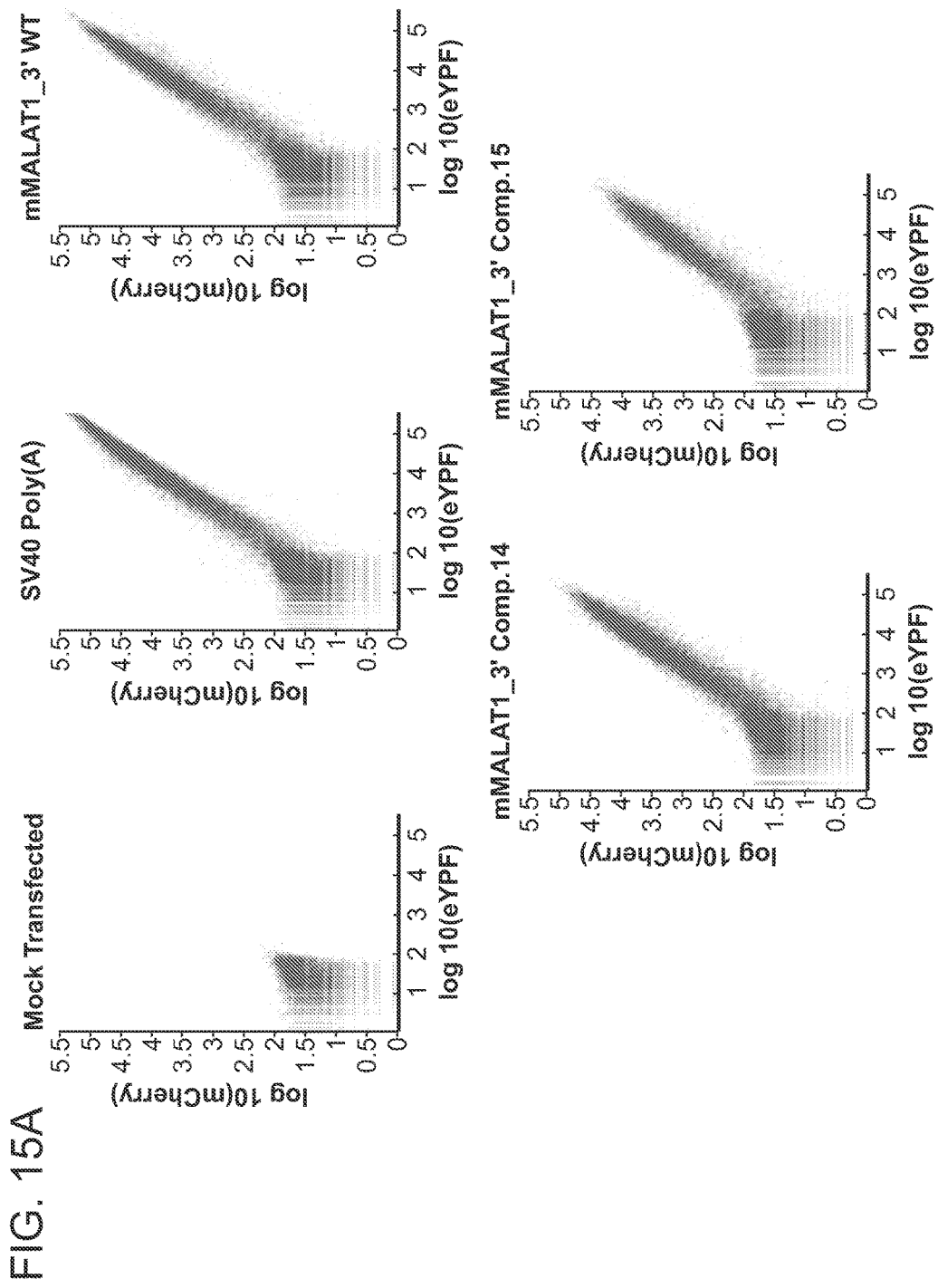
FIGS. 15A-15E show that the MALAT1 triple helix supports efficient protein translation. (15A) After transfecting HeLa cells with the designated dual-color fluorescent reporter vectors (the sequence downstream of mCherry is noted for each plot), flow cytometry was used to determine each cell's raw eYFP and mCherry intensities. The Mock Transfected sample shows the background (autofluorescence) levels of eYFP and mCherry observed. In all subsequent analyses, cells expressing background levels of fluorescence were removed as described in the Materials and Methods. (15B-D) Scatter plots comparing the eYFP and mCherry intensities for each cell transfected with dual-color vectors in which mCherry ended in the SV40 polyadenylation signal or WT/mutant mMALAT1_3' region as designated. Cells expressing only background levels of fluorescence were removed. (15E) To verify the accuracy of mCherry mRNA 3' end processing with the various constructs, RNase H digestion was performed prior to Northern blot analysis. A smear was observed for the mCherry transcript ending in the SV40 poly-A site, indicative of variations in the length of the poly-A tails added. In contrast, a defined band of the expected size (180-nt) was observed for mCherry ending in the mMALAT1_3' region, indicating that no additional nucleotides are added post-RNase P processing.
Figure 15B:
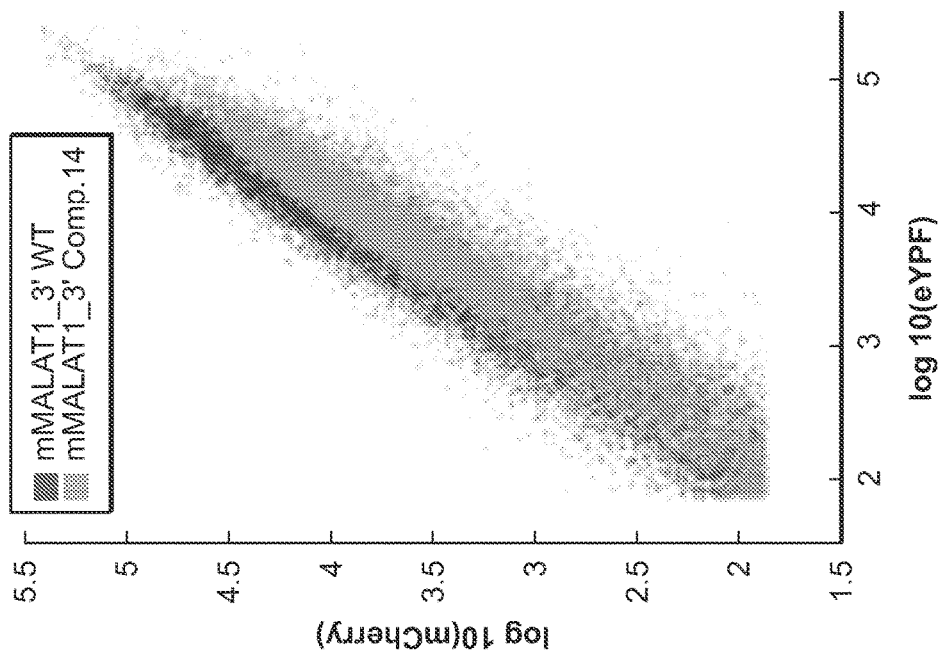
Figure 15C:
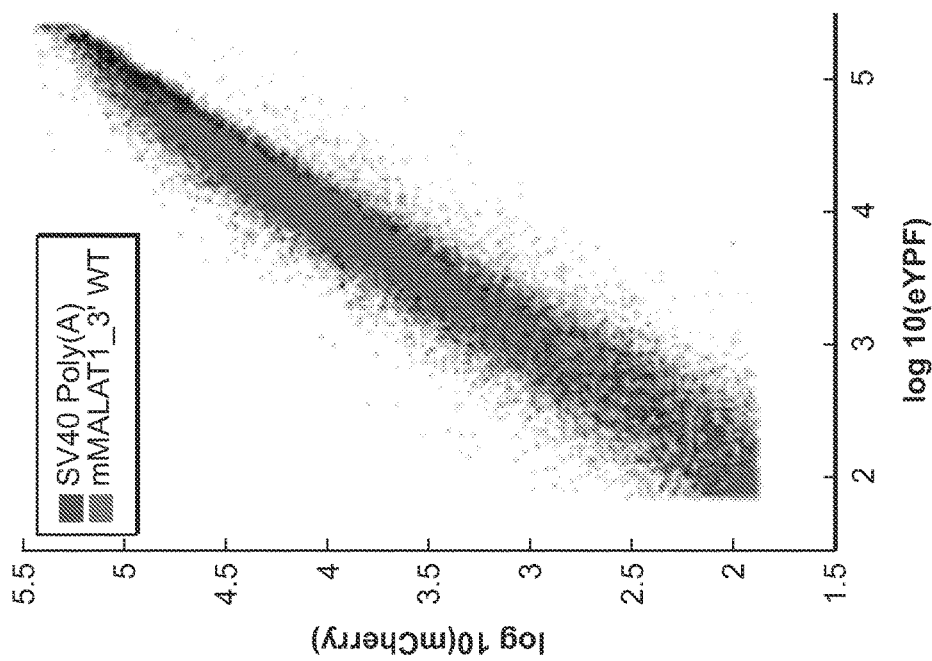
Figure 15E:
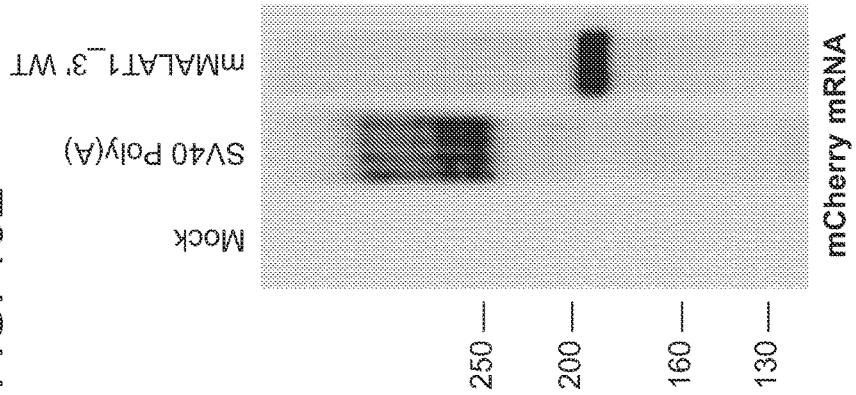
Figure 15D:
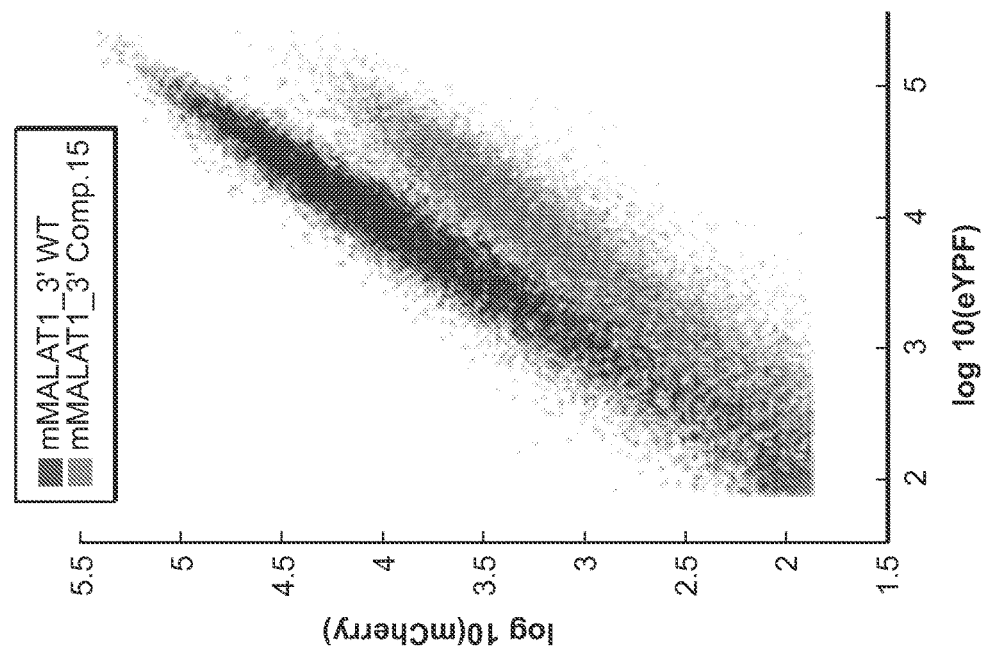
Figure 19A:
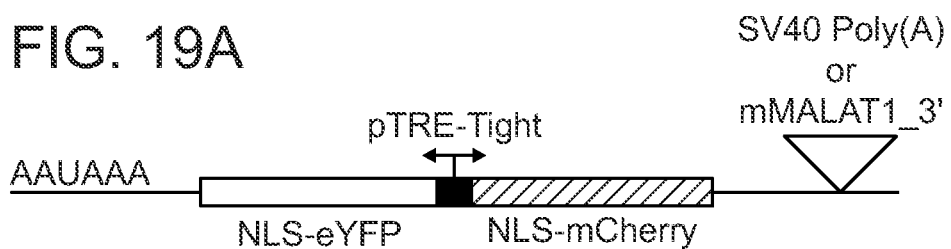
FIGS. 19A-19C are a schematic and graphs showing translation of a triple helix containing mRNA in mesenchymal cells. (19A) Schematic of the two-color fluorescent reporter expression system. (19B) The two-color expression plasmids were transiently transfected into mouse mesenchymal stem cells, and flow cytometry used to measure mCherry and eYFP protein expression in single cells. Shown are box plots of the ratios of mCherry to eYFP protein expression measured in individual transfected cells (horizontal line, median; box, $25^{th}$ through $75^{th}$ percentile; error bars, 1.5× interquartile range) from a representative experiment (n=3). (19C) Scatter plot comparing the eYFP and mCherry intensities for each cell transfected with dual-color vectors in which mCherry ended in the SV40 polyadenylation signal or the mMALAT1_3' region as designated. Cells expressing only background levels of fluorescence were removed.
Figure 19B:
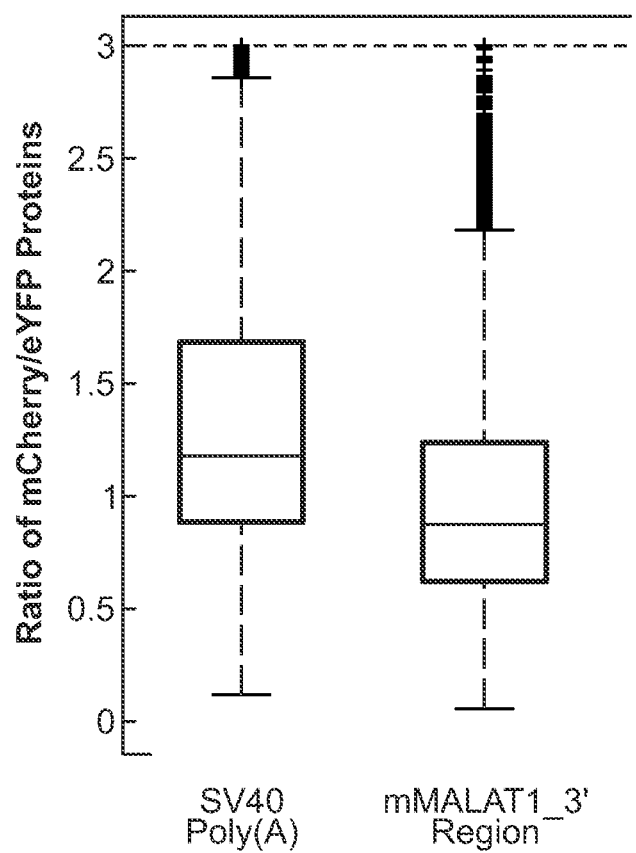
Figure 19C:
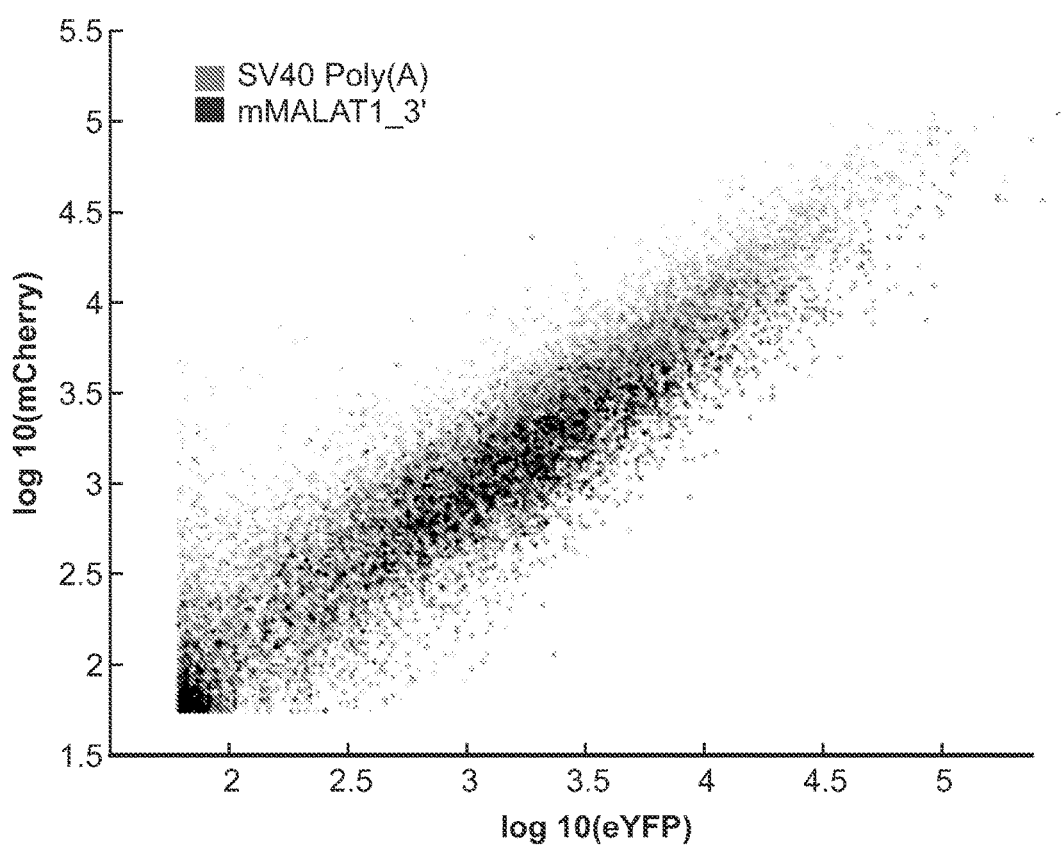

To better quantitate the translational output obtained from a transcript ending in the MALAT1 3' end versus that obtained from a transcript ending in a poly-A tail, a two-color fluorescent reporter system, was used to allow measurements of gene expression in single mammalian cells (Mukherji et al. 2011). This construct consists of a bidirectional Tet-inducible promoter that drives expression of the fluorescent proteins mCherry and enhanced yellow fluorescent protein (eYFP) tagged with nuclear localization sequences (FIG. 5B). In the 3' UTR of mCherry, either the SV40 polyadenylation signal or the mMALAT1_3' region was inserted. In contrast, the 3' UTR of eYFP always ended with the SV40 polyadenylation signal, allowing eYFP expression to serve as an internal normalization control as it is a sensitive reporter of transcriptional and translational activity from the bidirectional promoter. Using flow cytometry to monitor protein expression in single cells, the levels of mCherry and eYFP protein obtained were compared when both transcripts terminated in a canonical poly-A tail. By calculating the ratio of mCherry to eYFP protein detected in each analyzed cell, it was found that the expression of the fluorescent proteins is, as expected, highly correlated (Ratio of 0.91+/−0.05) (FIG. 5C and FIG. 15A). This correlation was mirrored on the transcript level when measured across the population of cells by quantitative PCR (QPCR) (FIG. 5D). Next compared were the levels of mCherry and eYFP proteins and mRNAs obtained when the mMALAT1_3' region was inserted downstream of mCherry. Consistent with the results with the cGFP reporter in FIG. 5A, the mMALAT1_3' region supported strong translation (mCherry/eYFP protein ratio of 1.00+/−0.05) (FIG. 5C, D and FIG. 15B). Northern blots confirmed that the mCherry transcript ended in the mMALAT1_3' region as generated by RNase P, thus eliminating the possibility that a cryptic polyadenylation signal was responsible for the efficient translation observed (FIG. 15E). The two color fluorescent reporter (FIG. 5B) was next transfected into mouse mesenchymal stem cells to determine the ability of a triple helix to support translation in an additional, unrelated cell type. Using flow cytometry to monitor protein expression in single cells, the levels of mChery and eYFP protein obtained were compared when both transcripts terminated in a canonical poly(A) tail or when the mMALAT1_3' region was inserted downstream of mCherry. In both cases, the expression of the fluorescent proteins was found to be highly correlated (FIG. 19), indicating that the MALAT1 triple helix promotes efficient translation in both HeLa cells and mouse mesenchymal stem cells.

Figure 5F:
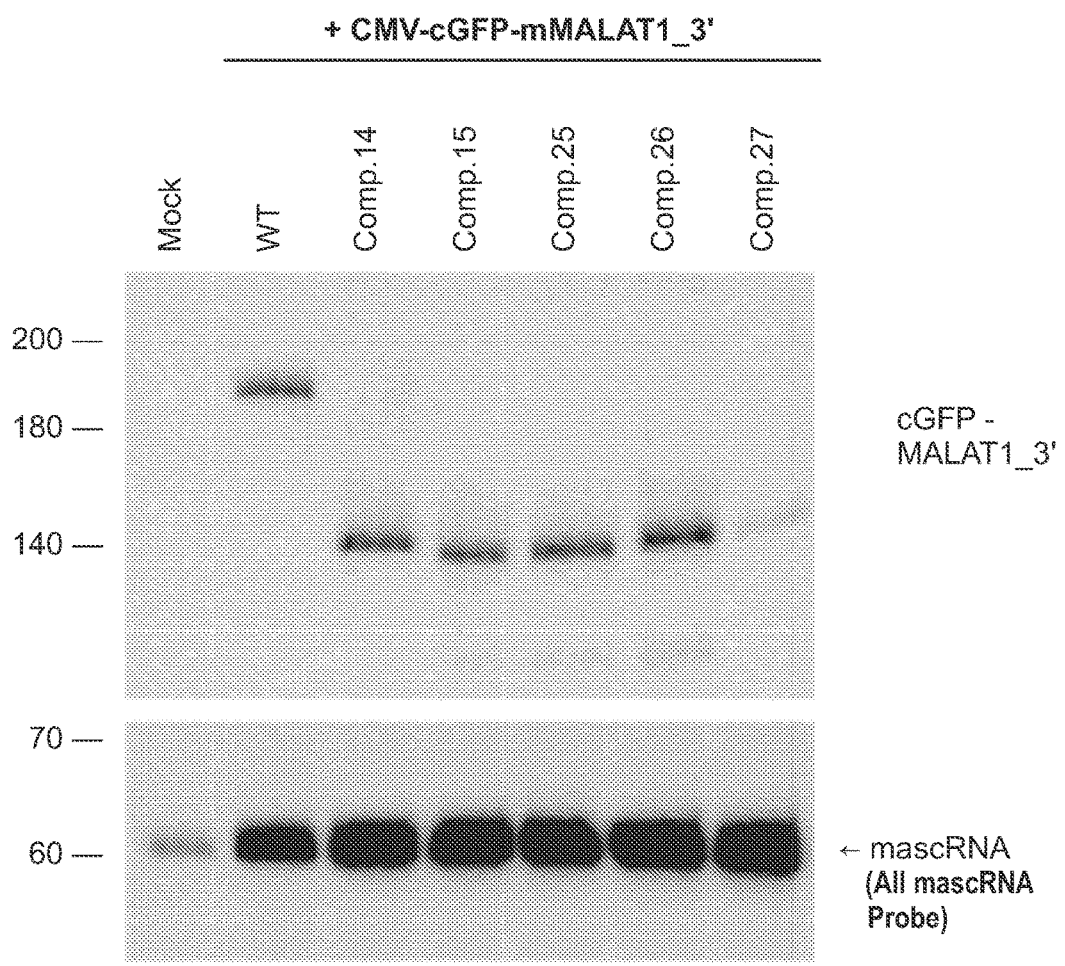
Figure 5G:
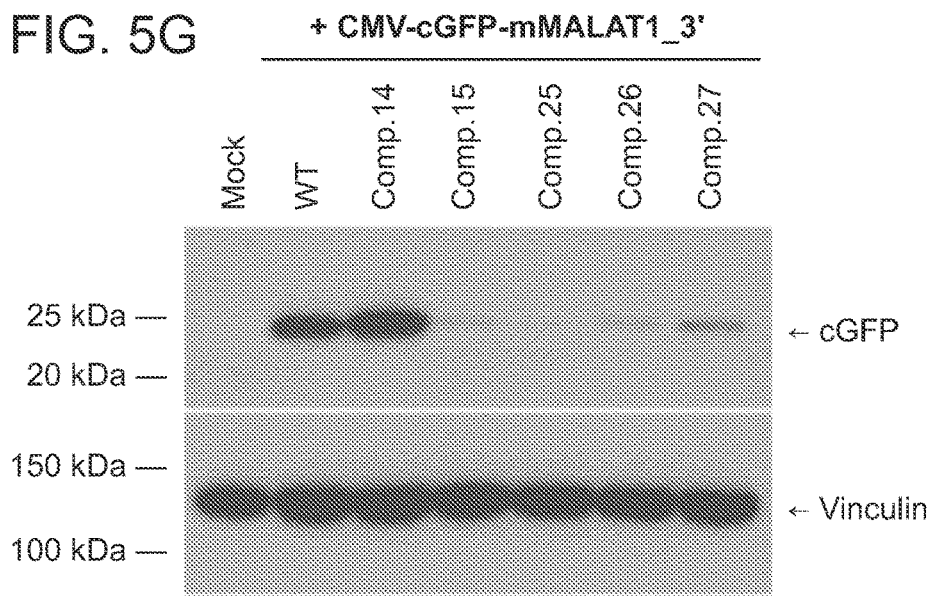
Figure 5H:
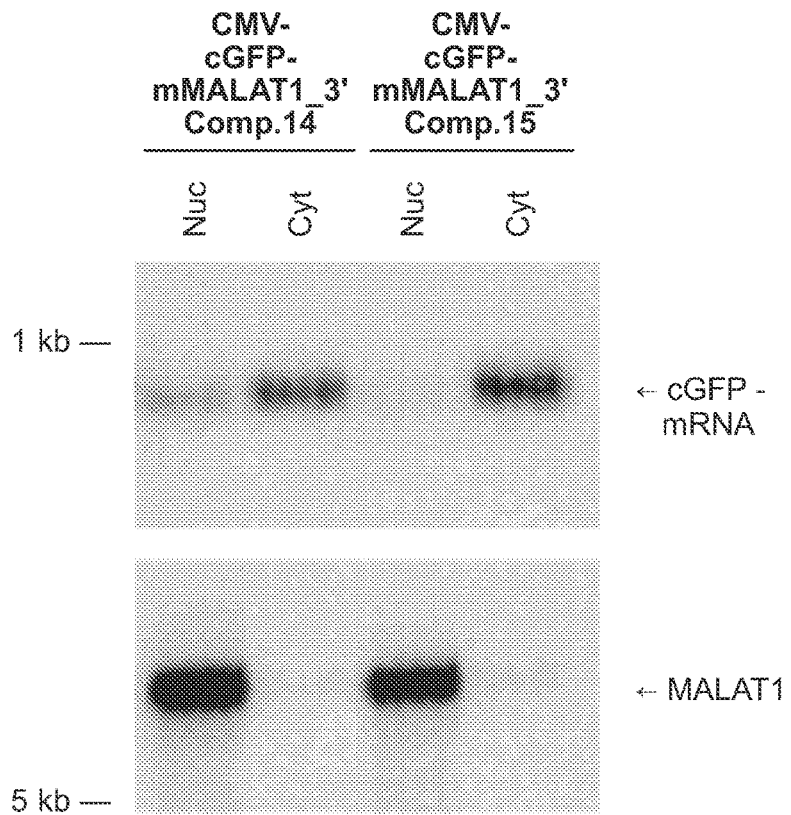
Figure 51:
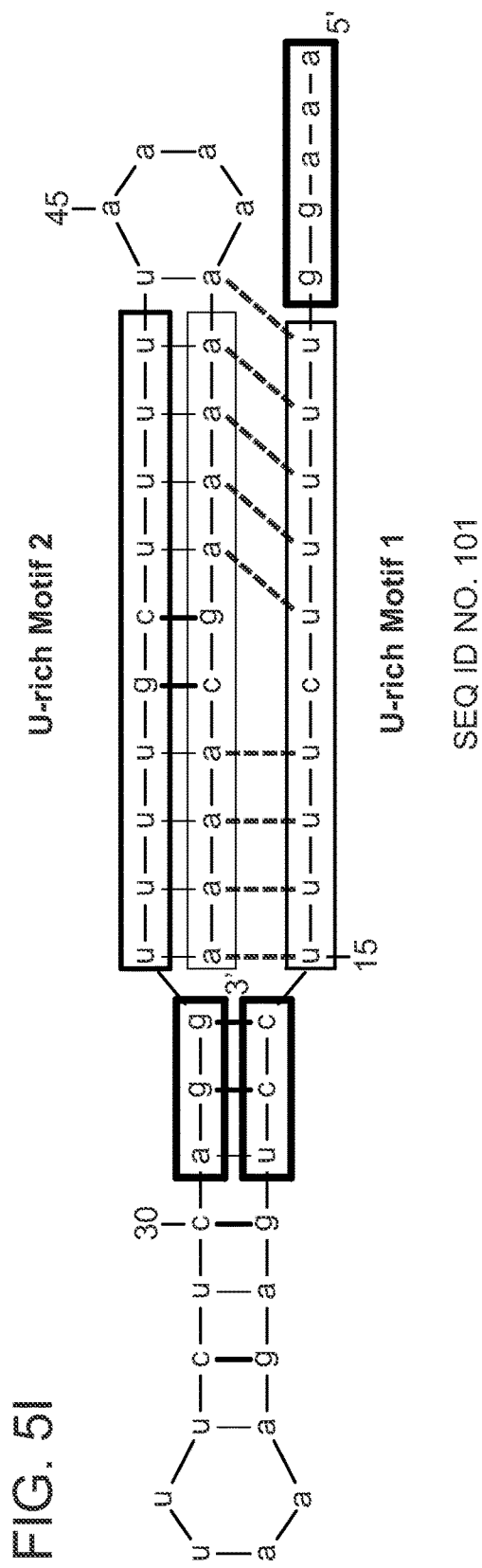

To determine the sequence elements in the mMALAT1_3' region required for efficient translation, the cGFP-MALAT1_3' Comp. 14 transcript was mutated (FIG. 2D), which contains the minimal elements required for RNA stability (FIG. 2G and FIG. 5F) and efficient translation (FIG. 5G), to test if a transcript that is stable but poorly translated could be identified. By mutating every nucleotide at the 3' end of MALAT1 not present in the core triple helical region (while maintaining base pairing in the conserved stem loop) (Comp. 15 shown in, FIG. 5E), a cGFP transcript that is stable (FIG. 5F) but poorly translated (FIG. 5G) was identified. The transcript depicted as Comp. 15 was exported to the cytoplasm as efficiently as Comp. 14, indicating that this decrease in translational efficiency is not due to increased nuclear retention of the transcript (FIG. 5H). Confirming these results, when the mMALAT1_3' Comp. 15 region was placed downstream of mCherry in the two-color fluorescent reporter system (FIG. 5B), a ~5-fold decrease in translational efficiency was observed when compared to the WT mMALAT1_3' region, while the level of mRNA decreased only ~2-fold. (FIG. 5C,D and FIG. 15C,D).

Additional mutagenesis was then performed to determine which of the 27 mutations present in the Comp. 15 region were required for this decrease in translational efficiency (FIG. 5E). Interestingly, this analysis revealed that certain subsets of the 27 mutations (Comp. 27, FIG. 5E) caused the transcript to no longer be stable (FIG. 5F). Nevertheless, it was possible to identify other subsets of mutations (Comp. 25 and Comp. 26, FIG. 5E) that generated a stable cGFP transcript (FIG. 5F) that was poorly translated (FIG. 5G). This shows that the nucleotides immediately flanking each side of the core triple helical region have critical roles in promoting translation (FIG. 5I).

Figure 6:
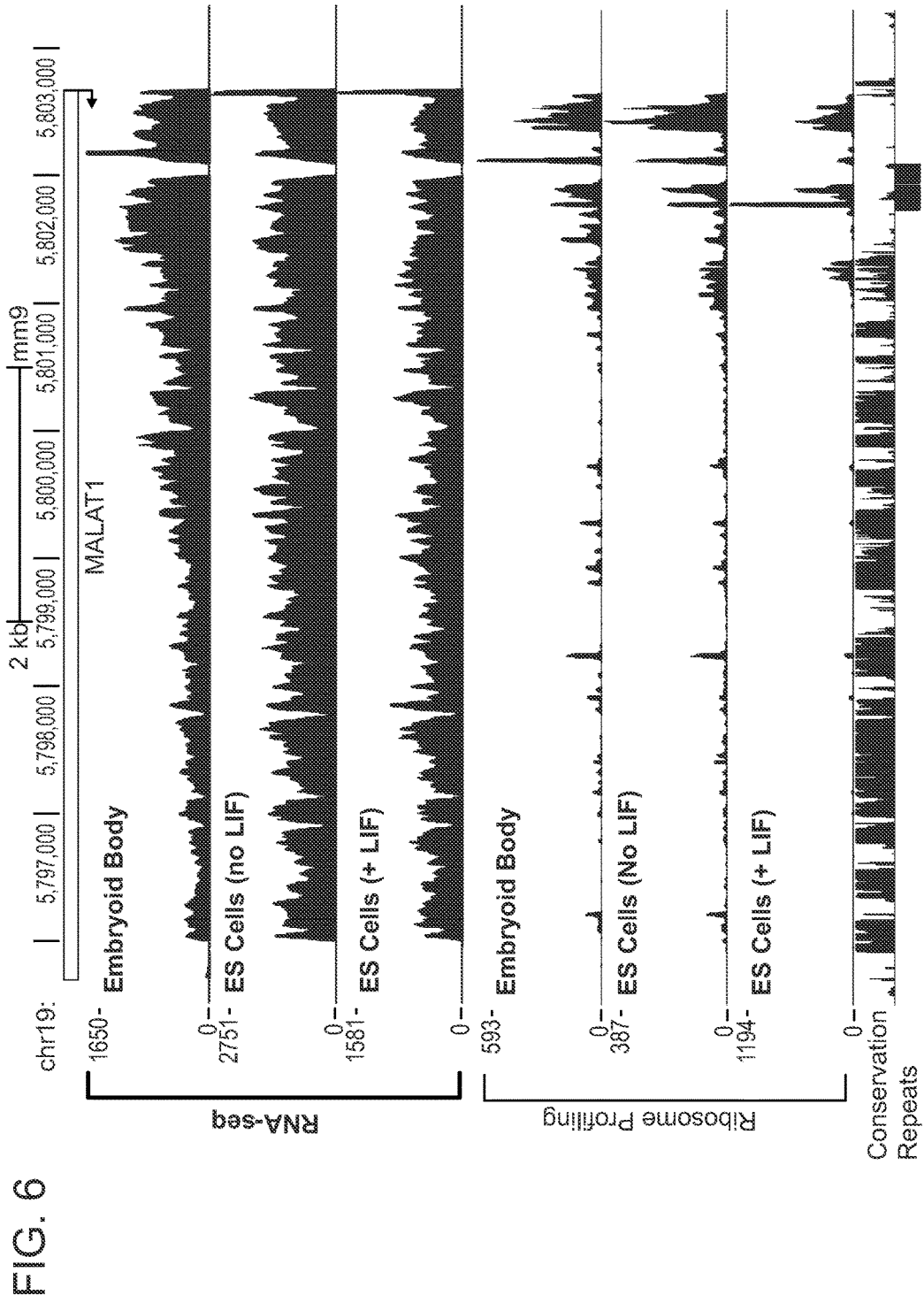
FIG. 6 shows that ribosome footprints are observed near the 5' end of MALAT1 in mouse embryonic stem cells. The mRNA-seq and ribosome footprint profiles of MALAT1 in mouse embryoid bodies and mouse embryonic stem cells (grown in the presence or absence of Leukemia Inhibitory Factor, LIF) as determined by Ingolia et al. 2011 are shown. The MALAT1 transcription start site is denoted by an arrow on the right side of the figure.

As these results indicate that a strong translational enhancer element is present at the 3' end of MALAT1 and MEN β, it was investigated if there was any evidence of translation of these endogenous noncoding RNAs. Although the MEN β transcript is lowly expressed in mouse embryonic stem (ES) cells (data not shown), MALAT1 is highly expressed and ribosome profiling (Ingolia et al. 2011) suggests that reproducible and non-random regions near the 5' end of MALAT1 are protected by ribosomes (FIG. 6). We were unable to identify obvious well-conserved open reading frames in these regions, although it may be that species-specific short peptides are produced from the 5' end of MALAT1 as there are potential start codons in mouse near several of the regions where ribosomes are concentrated.

The Triple Helix Structure Promotes RNA Stability and Translation of the Human LINE-1 mRNA.

To determine if the MALAT1 triple helix can functionally replace the poly(A) tail at the 3' ends of a variety of messenger RNA sequences, several reporter mRNAs were tested. As already shown, when the triple helix was placed at the 3' ends of two different mRNAs encoding fluorescent reporter proteins, GFP (FIG. 5A) or mCherry (FIG. 5C), a level of translation indistinguishable from that obtained with a polyadenylated version of the reporter mRNA was observed.

Figure 20A:
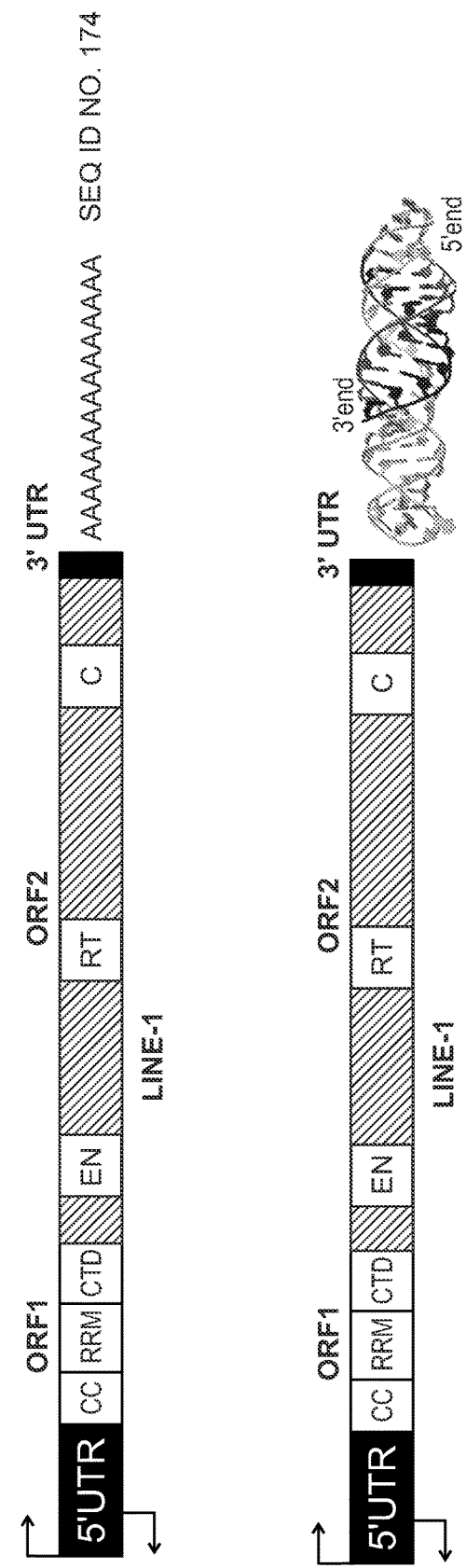

The MALAT1 triple helix was then tested downstream of the human Long Interspersed Element-1 (LINE-1 or L1) mRNA. L1 sequences are the predominant class of autonomous retrotransposons in the human genome. Although greater than 99.9% of L1 elements are no longer capable of mobilization by retrotransposition, the average human genome harbors approximately 80-100 retrotransposition-competent L1 elements (reviewed in Beck et al. 2011). A replication-competent L1 is approximately 6 kb in length, contains two non-overlapping open reading frames (ORF1 and ORF2) and ends with a 3' UTR that is followed by a poly(A) tail (FIG. 20A). To determine the effect of replacing the L1 poly(A) tail with the MALAT1 triple helix, a previously described L1 episome-based expression vector (pAD2TE1) (Doucet et al. 2010) was used. This vector contains a T7 epitope tag at the C-terminus of ORF1 and a TAP tag at the C-terminus of ORF2, facilitating detection of ORF1 and ORF2 protein expression.

Figure 20C:
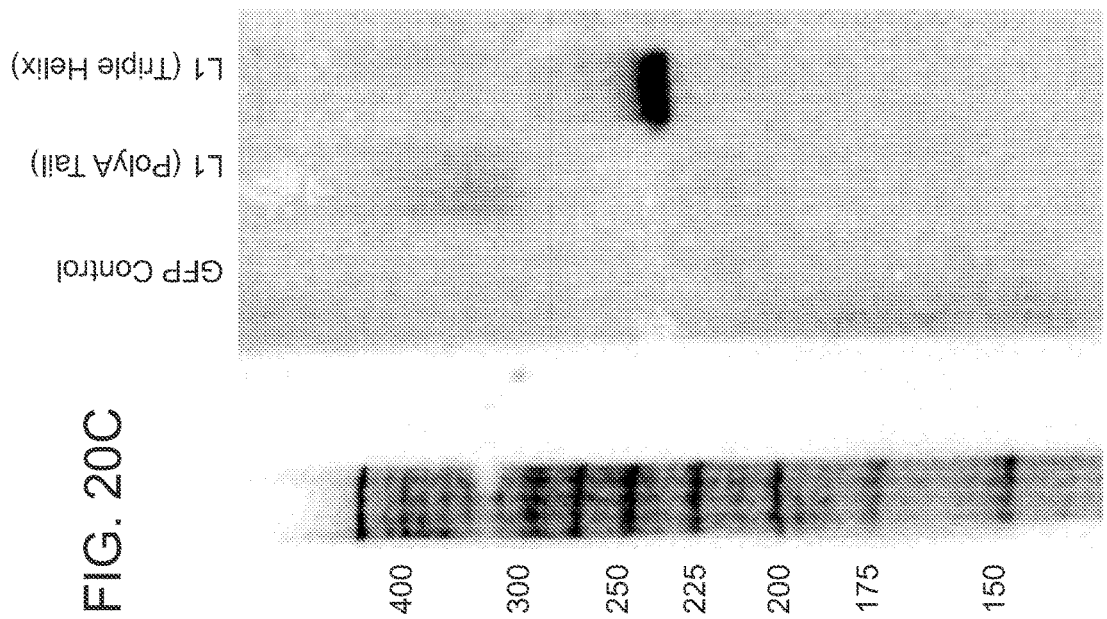
Figure 20B:
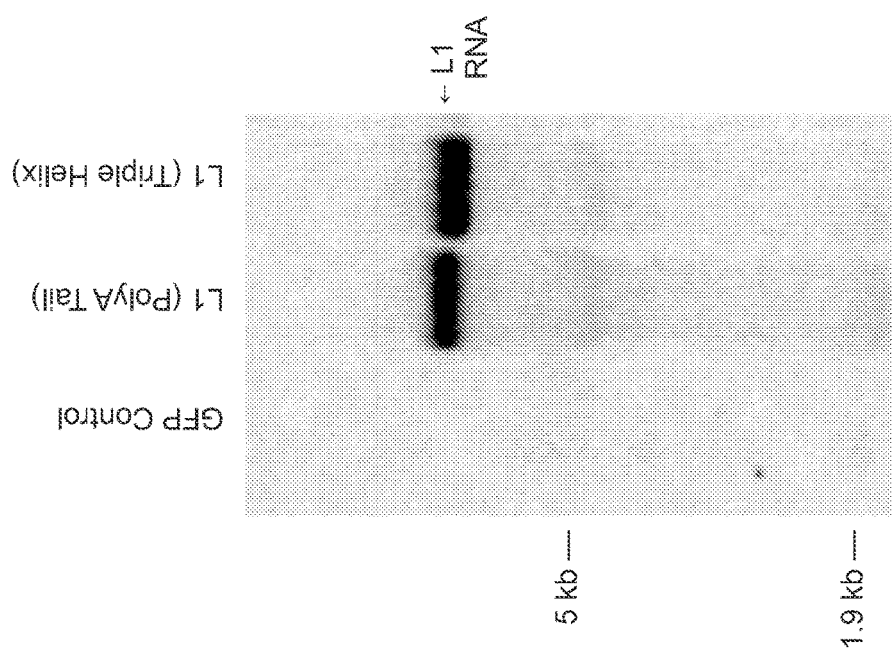

The pAD2TE1 L1 expression vector or a modified version in which the L1 polyadenylation signal was replaced with the mMALAT1_3' sequence (to generate a L1 mRNA ending in a triple helix) were transfected into HeLa cells and total RNA isolated using Trizol. As determined by Northern blot analysis, L1 mRNA ending in the MALAT1 triple helix accumulated to a similar level as the polyadenylated L1 mRNA (FIG. 20B, Probe Sequence (SEQ ID NO. 172): 5'-GCGCCTGAGCACCATTTAGC). To verify that the L1-MALAT1_3' RNA was properly processed by RNase P at its 3' end in vivo, total RNA from the transfections was first hybridized to an oligo (5'-GCGCTTTGGCTTGGGT-CATC) (SEQ ID NO. 173) near the 3' end of ORF2 and subjected to RNase H digestion. Cleavage of the transcript to a smaller size allowed Northern blots with a high resolution to be performed to verify the accuracy of RNase P cleavage. A single band of the expected size (234 nt) was observed for the L1-MALAT1_3' RNA (FIG. 20C). In contrast, a smear was observed for the polyadenylated L1 mRNA, indicative of variations in the length of the poly(A) tails added. These results indicate that the MALAT1 triple helix is able to efficiently stabilize the L1 mRNA.

Figure 20D:
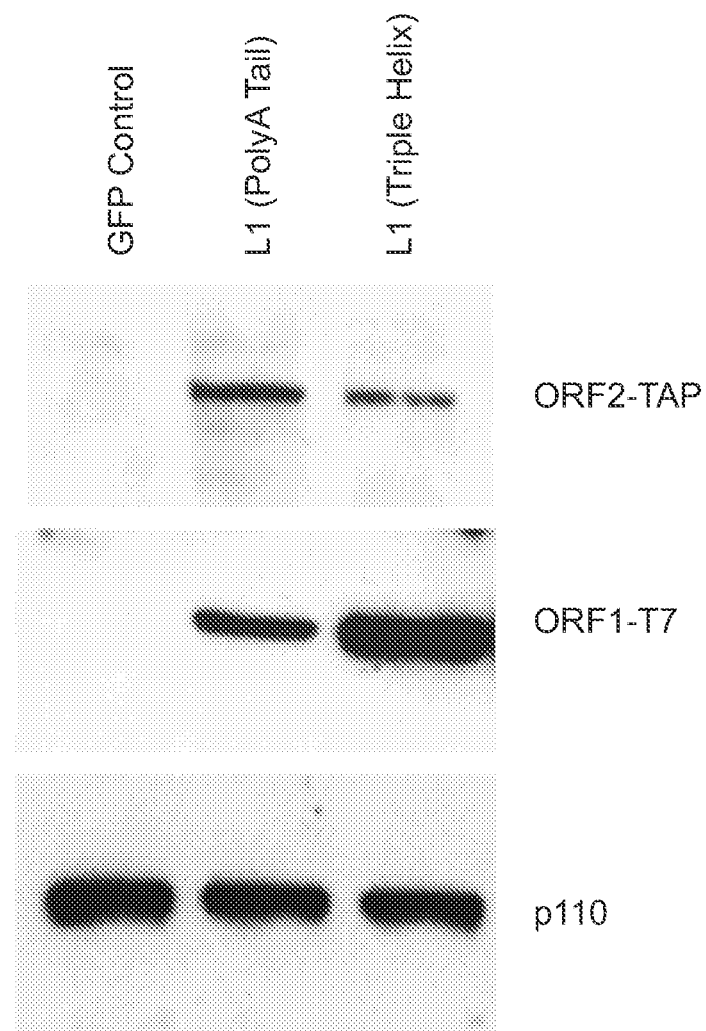
Figure 21:
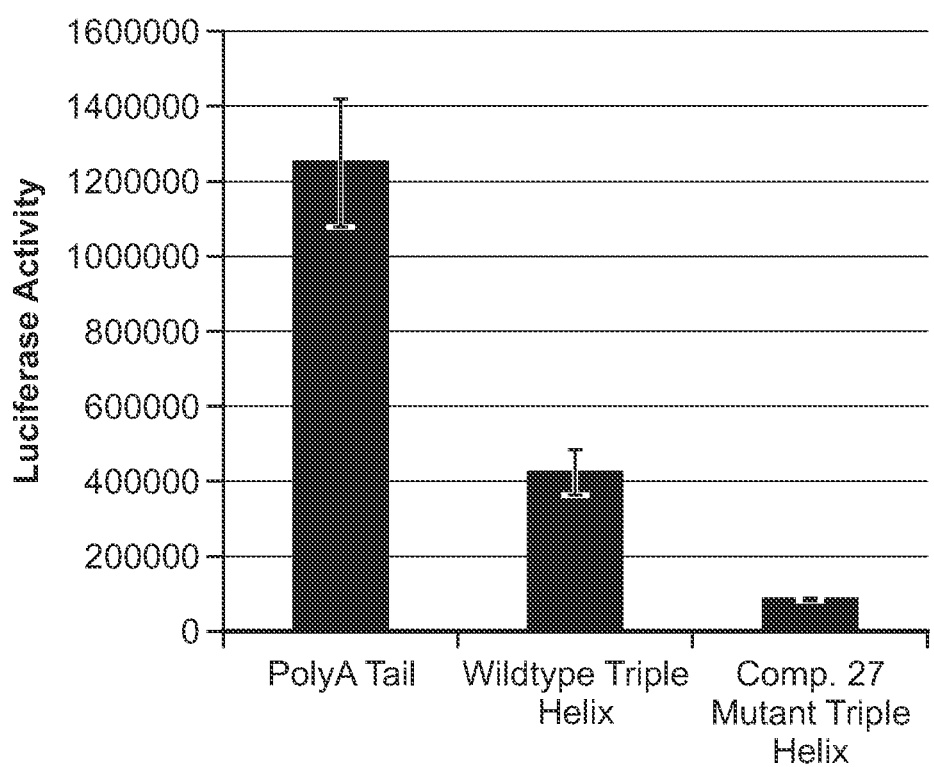
FIG. 21 is a graph showing that in vitro transcribed GFP mRNA ending in a triple helix can be translated in vitro. Equal amounts of in vitro transcribed capped (5'-m$^7$GpppG) luciferase mRNAs were incubated in wildtype yeast extracts. The luciferase mRNA terminated at its 3' end in a poly(A) tail, the wildtype MALAT1 triple helix, or the Comp. 27 mutant MALAT1 triple helix as indicated. Mean luciferase activity from translation of capped mRNAs is shown. Error bars represent standard deviations.

To then determine whether the MALAT1 triple helix is able to support L1 mRNA translation, production of the ORF1 and ORF2 proteins was quantified. To ensure that only proteins translated from the L1 expression vectors (and not from any endogenous L1 element in the genome) were quantified, immunoblotting and immunofluorescence were performed using antibodies that recognize the T7 or TAP epitope tags (to measure expression of ORF1 protein or ORF2 protein, respectively). As shown by the immunoblots in FIG. 20D, similar levels of ORF1 and ORF2 proteins were observed when the L1 transcript ended in a poly(A) tail or the MALAT1 triple helix. These results were confirmed by immunofluorescence, which demonstrated that the ORF1 and ORF2 proteins accumulate to high levels in the cytoplasm of cells regardless of the 3' terminal sequence on the L1 mRNA (FIG. 20E). In total, these results indicate that a triple helix is able to stabilize the 3' end of the L1 mRNA as well as ensure efficient production of both encoded L1 proteins.

Example 5: A Transcript Ending in the MALAT1 Triple Helix is Efficiently Repressed by microRNAs As most long transcripts lacking a poly-A tail are rapidly degraded in cells, it has generally been difficult to define regulatory roles for the poly-A tail or poly-A binding protein (PABP) in vivo. Now, the expression system built around the 3' end of MALAT1 represents a unique and valuable tool to address these issues as it generates in vivo stable transcripts that lack a poly-A tail. It is unlikely that transcripts with mMALAT1_3' sequences at their 3' ends interact with PABP since this protein requires at least 12 consecutive A residues for binding (Sachs et al. 1987). To demonstrate the utility of this system for investigating how non-polyadenylated transcripts are regulated in vivo, it was investigated whether microRNAs repress a transcript ending in the MALAT1 triple helix as efficiently as they do a polyadenylated transcript. MicroRNAs function as part of RISC (RNA-induced silencing complex) and bind to partially complementary sites in target mRNAs, causing translational repression and/or transcript degradation (Bartel 2009). As the core RISC protein component GW182 can directly interact with PABP as well as deadenylases (Braun et al. 2011), a model has emerged in which an interaction between RISC and PABP is required for maximum repression by microRNAs (Fabian et al. 2009; Huntzinger et al. 2010; Moretti et al. 2012). However, the functional importance of these interactions has been debated (Fukaya and Tomari 2011; Mishima et al. 2012).

Figure 7A:
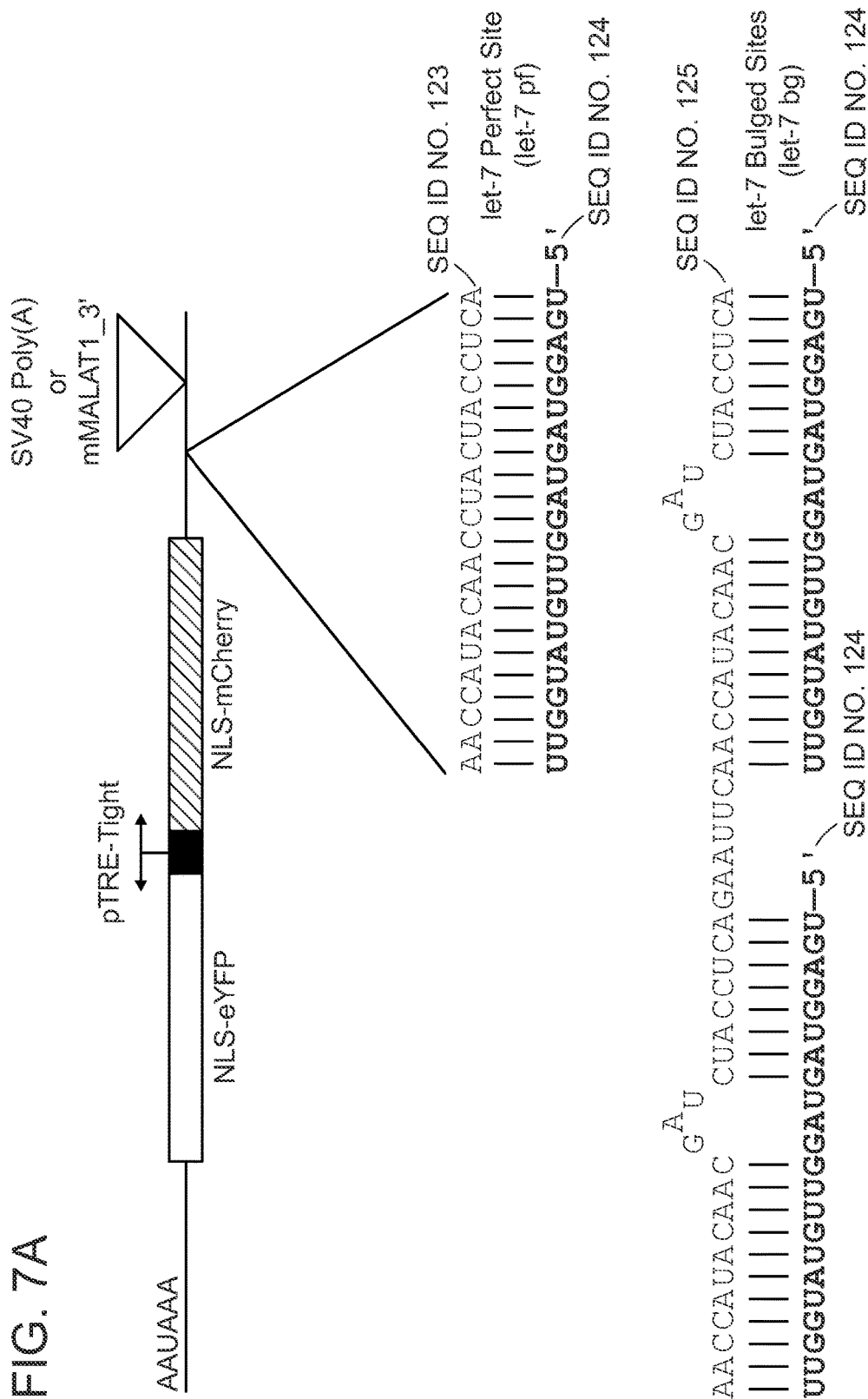
Figure 7B:
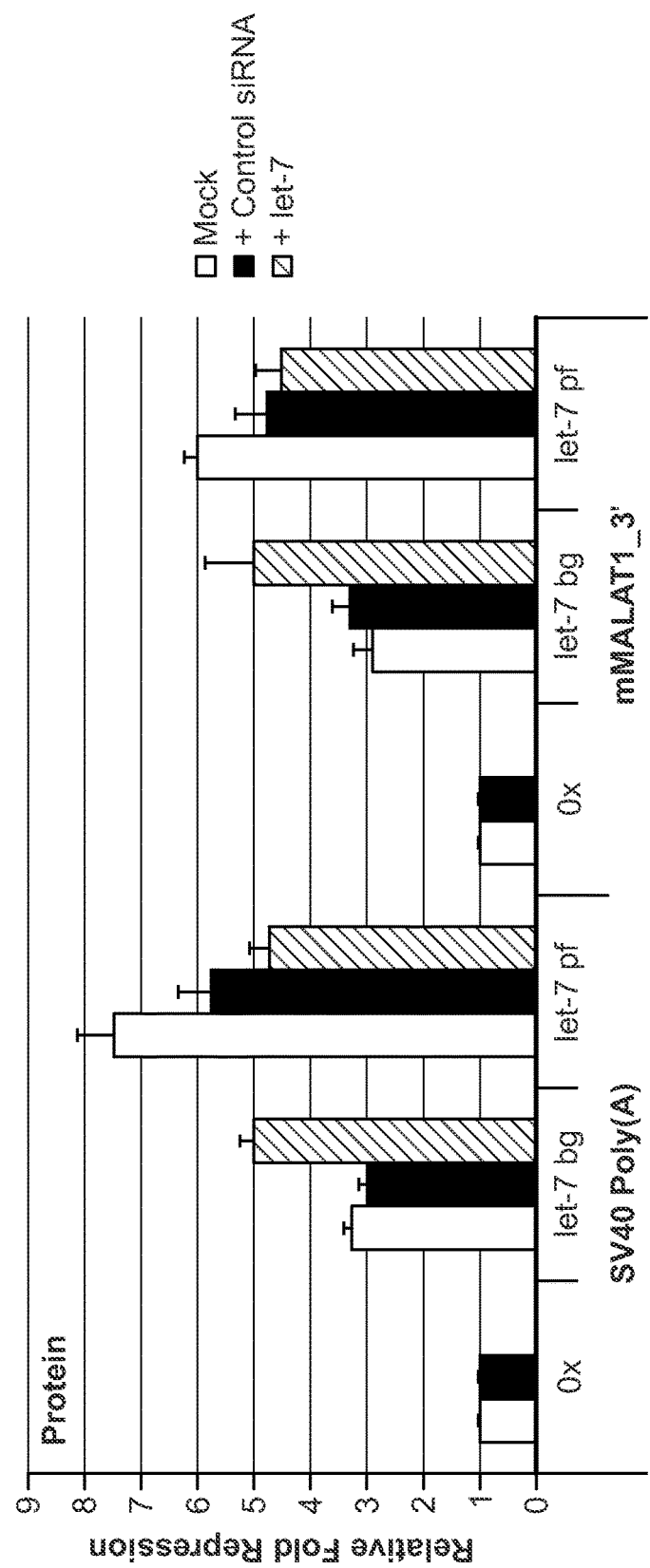
Figure 16A:
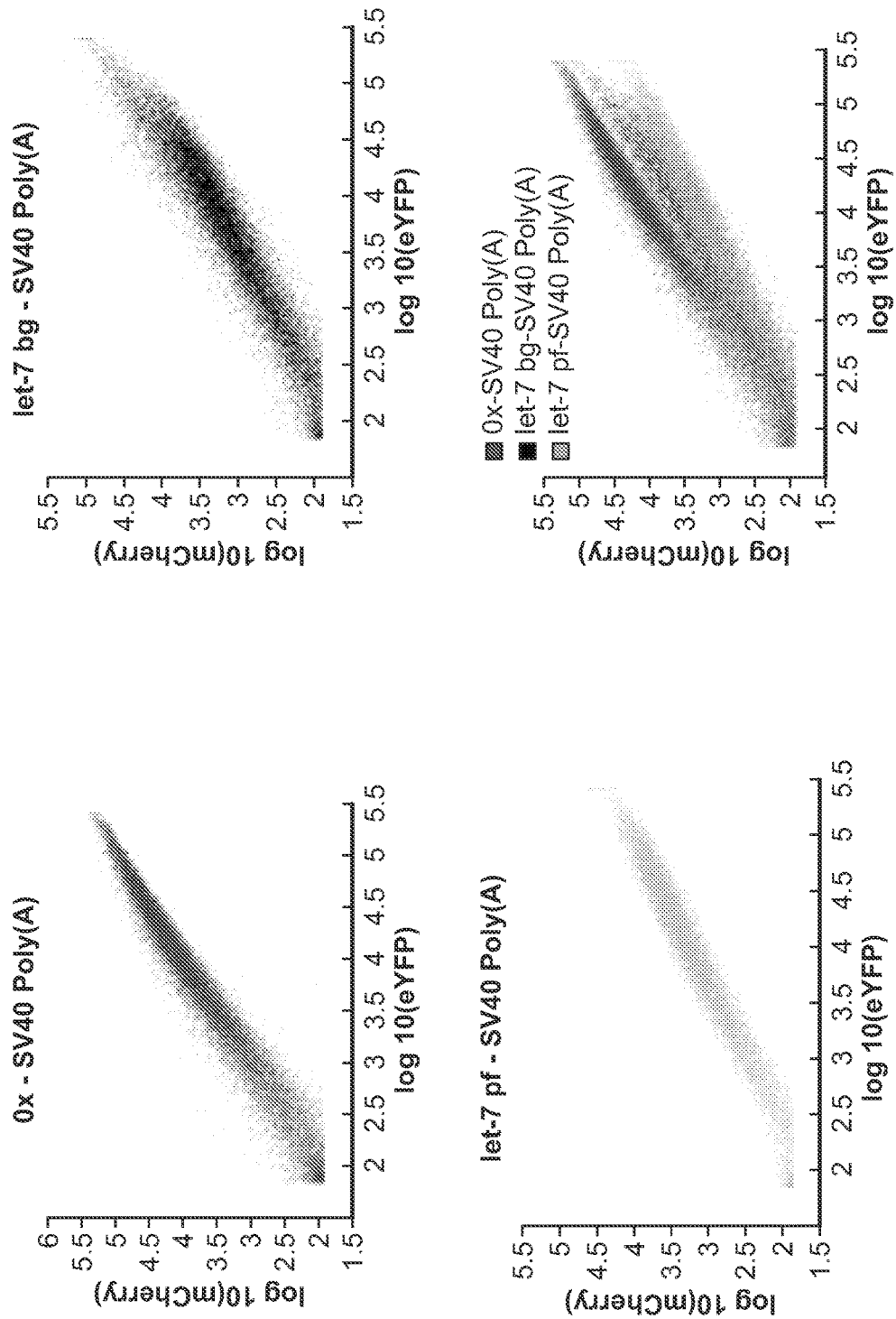
FIGS. 16A and 16B show that a transcript ending in the MALAT1 triple helix is efficiently repressed by microRNAs. After transfecting HeLa cells with the designated dual-color fluorescent reporter vectors (the sequence downstream of mCherry is noted for each plot), flow cytometry was used to determine each cell's raw eYFP and mCherry intensities. The mCherry transcript ended in the SV40 polyadenylation signal (16A) or the mMALAT1_3' region (16B). Cells expressing only background levels of fluorescence were removed from all analyses and are not shown.
Figure 16B:
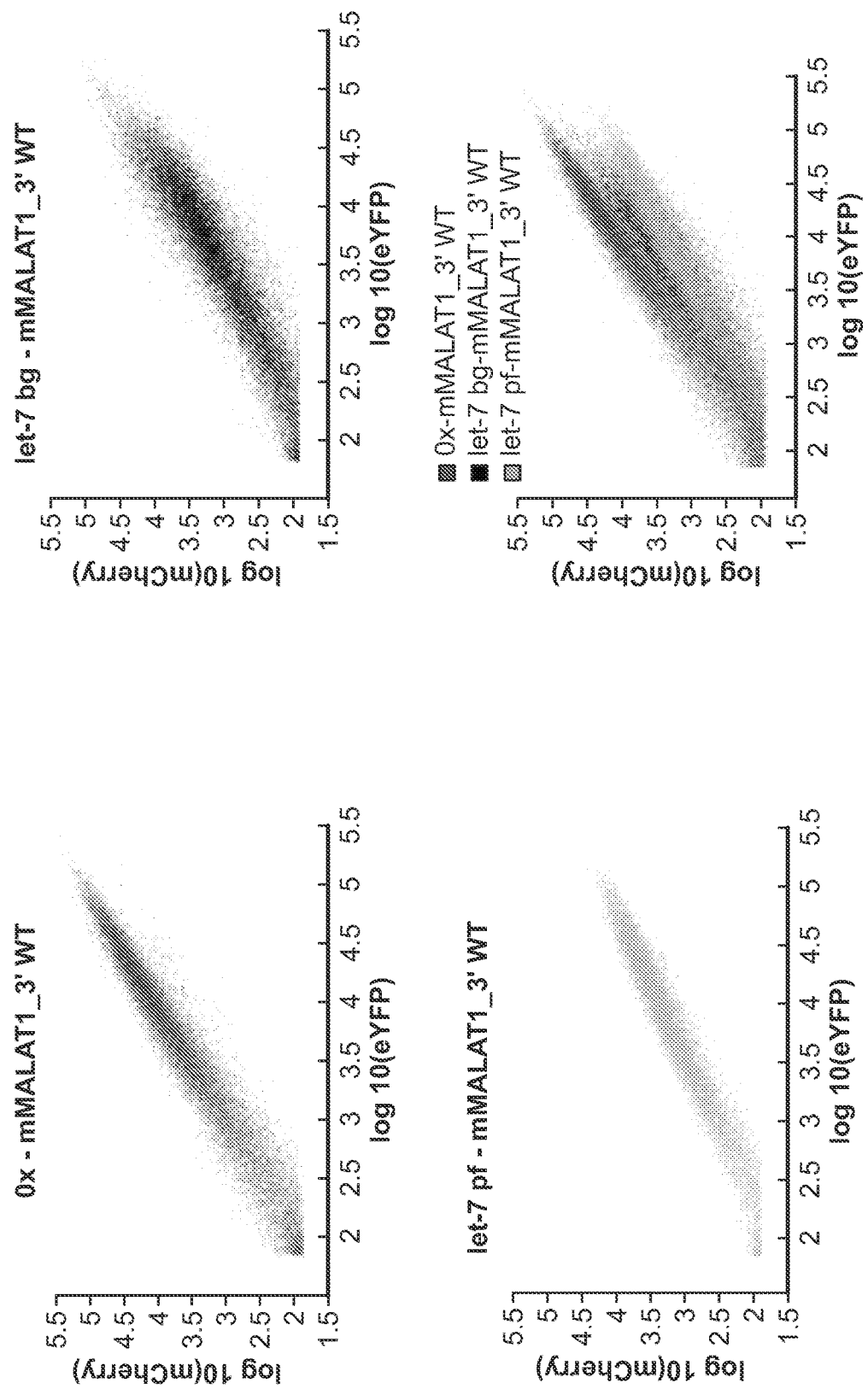
Figure 17B:
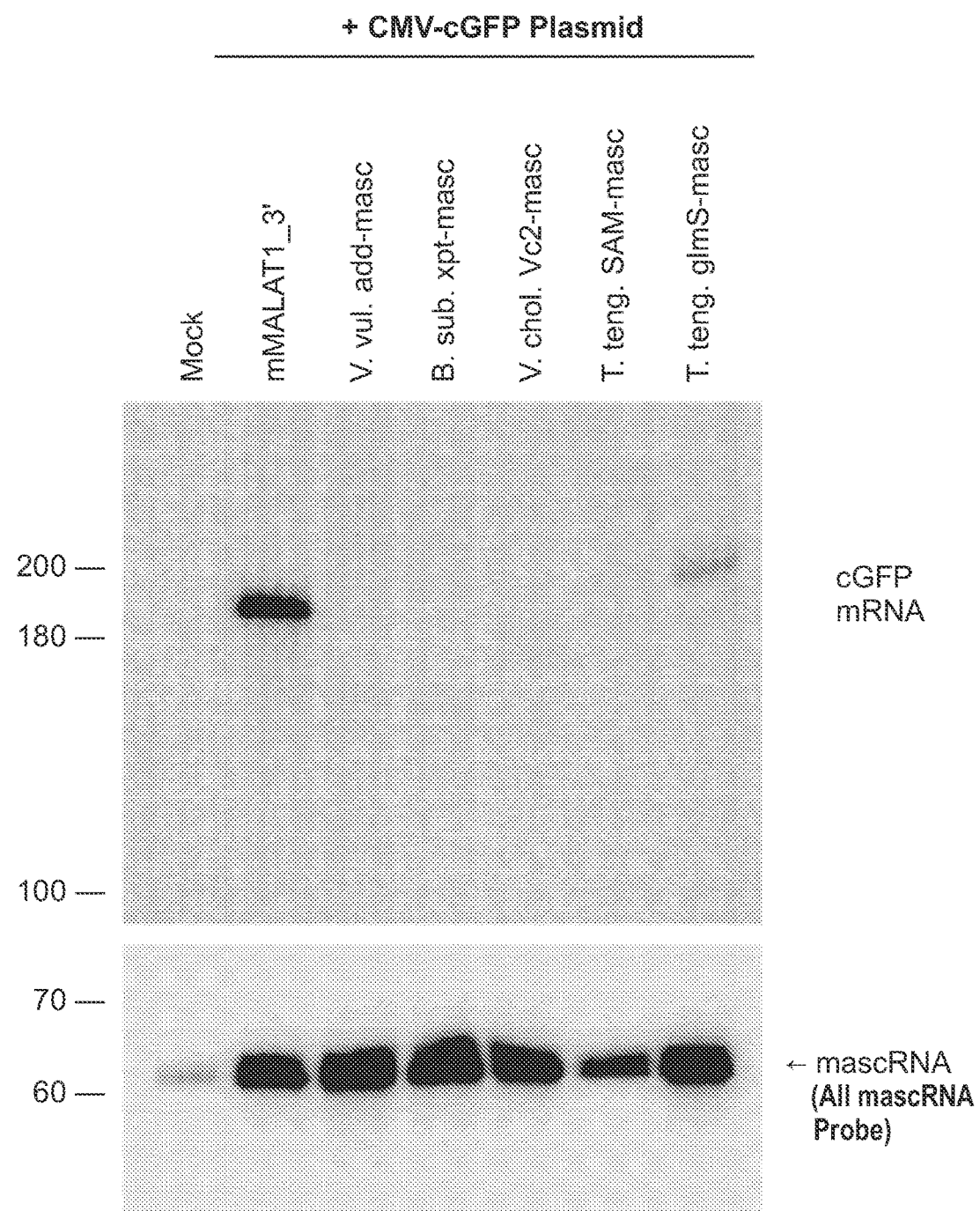
Figure 17C:
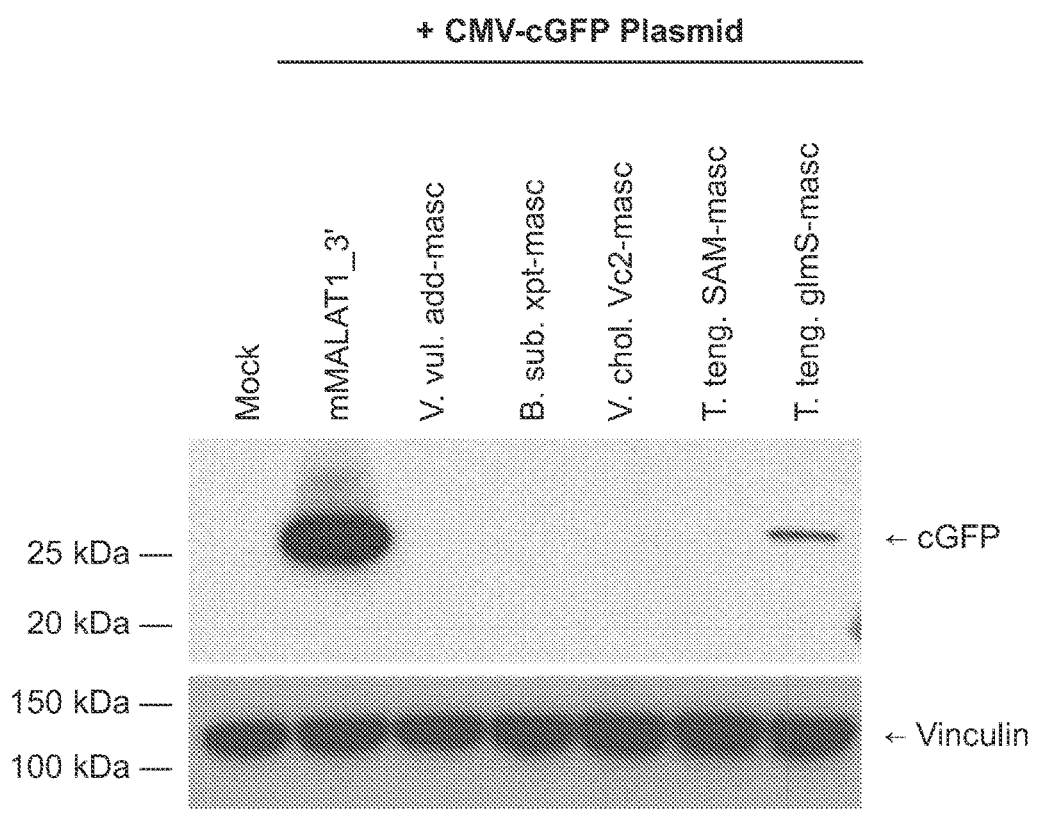

To investigate the role of the poly-A tail in microRNA-mediated repression in vivo, the two-color fluorescent reporter system was taken advantage of, and microRNA binding sites were inserted into the 3' UTR of mCherry, upstream of either the SV40 polyadenylation signal or the mMALAT1_3' region (FIG. 7A). In particular, either two bulged let-7 binding sites (denoted let-7 bg) or a sequence that is perfectly complementary to let-7 (denoted let-7 pf) were inserted, thus converting the interaction between target and microRNA into a catalytic, RNA interference-type repression. Using HeLa cells which naturally express let-7 microRNA, it was found that when mCherry ended in a canonical poly-A tail, the addition of two bulged let-7 binding sites caused 3.2+/−0.2-fold repression as measured by protein expression (FIG. 7B and FIG. 16A). Surprisingly, 2.9+/−0.4 fold repression was observed when two bulged let-7 sites were added to mCherry ending in the MALAT1 triple helix (FIG. 7B and FIG. 16B), a level of repression that is not statistically different from that obtained when a poly-A tail was present. Regardless if mCherry ended in a poly-A tail or in the MALAT1 triple helix, these effects were mirrored on the transcript level (FIG. 7C), indicating that the effects on protein production are likely at least partially due to decreased RNA levels. Upon transfecting synthetic let-7 to increase the level of the microRNA in HeLa cells, the levels of microRNA-mediated repression observed increased consistently regardless of the 3' terminal sequence present (FIG. 7B,C). These results suggest that a poly-A tail is not necessary for maximum repression by microRNAs in vivo and thus that microRNAs may also efficiently target non-polyadenylated transcripts in cells. Although the mechanism by which non-polyadenylated transcripts are degraded in response to microRNAs is unclear, these results suggest that deadenylation may not always be required for efficient microRNA-mediated silencing.

Example 6: Half-Life Measurement

HeLa cells were transiently transfected with the CMV-cGFP-mMALAT1_3' reporter plasmid for 24 hr. To then estimate the half life of the cGFP reporter mRNA ending in the MALAT1 triple helix, 1 µM actinomycin D (ActD), a transcriptional inhibitor, was added to the media and cells were harvested at 0, 1, 2, 4, 6, 8, and 10 hr after transcriptional inhibition. Northern blots indicated the half-life of the cGFP transcript ending in a triple helix to be ~5 hr in HeLa cells. The results are shown in FIG. 18. Previous work has estimated the half-life of a GFP transcript ending in a poly(A) tail to be ~4.8 hr (Kudla, G., et al. (2006). High guanine and cytosine content increases mRNA levels in mammalian cells. PLoS Biol. 4: e180.), indicating that a triple helix on the tested RNA molecule and a poly(A) tail were able to stabilize the 3' end of a transcript to similar extents.

Example 7: In Vitro Transcribed mRNAs Ending in a Triple Helix can be Translated in Cell Extracts Large amounts of mRNAs can be synthesized in vitro from DNA templates using RNA polymerases isolated from phages (for example, SP6, T3, or T7). When transfected into cells or incubated in cellular extracts, in vitro synthesized mRNAs ending in a poly(A) tail can be efficiently translated using the endogenous cellular translation machinery. To determine if an in vitro transcribed mRNA ending in a triple helix can likewise be translated upon incubation with the cellular translation machinery, a well-characterized *Saccharomyces cerevisiae* in vitro translation assay was used (Gilbert et al. 2007; Rojas-Duran and Gilbert 2012). As previously described (Rojas-Duran and Gilbert 2012), reporter constructs were generated containing the Firefly luciferase open reading frame (ORF) under control of the T7 promoter. Inserted downstream of the luciferase ORF in the DNA template was either (i) a poly(A) tail of 62 nucleotides, (ii) the wildtype MALAT1 triple helix, or (iii) the Comp. 27 version of the MALAT1 triple helix that contains mutations that significantly destabilize the triple helical structure and thus targets the mRNA for rapid degradation (FIG. 5E).

Capped luciferase mRNAs were synthesized in vitro by run-off transcription with T7 polymerase followed by capping with Vaccinia capping enzyme. Purified $m^7G$-capped mRNAs were quantified by densitometry of agarose gels. Equal amounts of each mRNA were then added to wildtype yeast extracts and translation assays were performed as per (Rojas-Duran and Gilbert 2012). Using luciferase activity to determine translation activity per mRNA, both a poly(A) tail and the wildtype MALAT1 triple helix were found to promote significant translation over background levels (as determined by the Comp. 27 mutant) (FIG. 2I). These results thus indicate that in vitro transcribed mRNAs ending in a triple helix can be added to cellular extracts to obtain significant levels of protein production.

Discussion

Despite lacking a poly-A tail, the long noncoding RNA MALAT1 is a stable transcript that is expressed at a level comparable or higher than many protein-coding genes in vivo (Wilusz et al. 2008; Zhang et al. 2012). In the present study, we demonstrated that the 3' end of MALAT1 is protected from degradation by an evolutionarily conserved triple helix. We further identified a highly similar triple helical structure that stabilizes the 3' end of the MEN β long noncoding RNA. Surprisingly, these triple helical regions also function as strong translational enhancer elements, allowing a non-polyadenylated mRNA to be translated as efficiently as an mRNA with a canonical poly-A tail. These results have been observed in multiple cell lines. Transcripts ending in a triple helix are efficiently repressed by microRNAs, arguing that a poly-A tail is not required for efficient microRNA-mediated silencing in vivo. Our data provide new insights into how MALAT1, MEN β, and likely other transcripts that lack poly-A tails are stabilized and regulated in vivo.

A Growing Role for Uridylation in RNA Degradation

Disrupting the integrity of the MALAT1 triple helix causes the transcript to be efficiently degraded. We surprisingly found numerous cGFP-MALAT1_3' transcripts ending in post-transcriptionally added short U-rich tails when the transcript was undergoing degradation (FIG. 2F and FIG. 11C), implicating uridylation in the decay process. Oligouridylation has been linked to the degradation of numerous classes of small RNAs, including tRNAs (FIG. 8), microRNA precursors (Heo et al. 2009), mature micoRNAs (Li et al. 2005), and transcription start site-associated RNAs (Choi et al. 2012). Although there is currently less evidence for U-tails on long transcripts in vivo, uridylation can promote mRNA decapping (Song and Kiledjian 2007; Rissland and Norbury 2009) and U-tails have been observed on the products of microRNA-directed cleavage (Shen and Goodman 2004). Interestingly, histone mRNAs are subjected to uridylation and degradation following the completion of DNA synthesis (Mullen and Marzluff 2008). Analogous to what we observed at the highly structured 3' end of MALAT1 (FIG. 2F and FIG. 11C), Mullen and Marzluff observed short U-tails on histone mRNAs that appeared to have been shortened previously by 3'-5' exonucleases. We further observed a similar phenomenon at the 3' end of a mutant mascRNA transcript targeted for degradation (FIG. 8). These results suggest that oligouridylation may play a much more significant role in the degradation of regions of extensive RNA secondary structure than we currently appreciate. In particular, we suggest that when a 3'-5' exonuclease stalls at a region of extensive secondary structure, an oligo (U) tail can be added to provide a single-stranded tail that is subsequently recognized by decay factors and used to re-start the degradation process.

Implications of the Triple Helix for the Functions of MALAT1 and MEN β

Unlike many long noncoding RNAs which are rapidly degraded and thus expressed at near undetectable levels (Wyers et al. 2005; Preker et al. 2008), MALAT1 and MEN β are stable transcripts with half-lives of greater than 12 hours (Wilusz et al. 2008; Sunwoo et al. 2009). By preventing degradation from the 3' ends of these noncoding RNAs, the triple helices play a critical role in not only ensuring RNA stability but also in allowing these transcripts to perform important cellular functions. For example, the MEN β noncoding RNA is an essential structural component of paraspeckles in the nucleus (Sunwoo et al. 2009). When MEN β is depleted from cells, this subnuclear domain is no longer observed and paraspeckle-associated proteins and RNAs instead are dispersed. The exact cellular function of MALAT1 is currently a matter of contention as conflicting results have been published (Tripathi et al. 2010; Yang et al. 2011b; Eissmann et al. 2012; Zhang et al. 2012). Nevertheless, MALAT1 is commonly over-expressed in many cancers, suggesting a possible role in a malignant phenotype.

Our finding that the MALAT1 and MEN β triple helices function as strong translational enhancer elements adds an additional unexpected twist into how these nuclear-retained transcripts may function. Considering that the Xist long noncoding RNA evolved from a protein-coding gene (Duret et al. 2006), it may be that the same is true for MALAT1 and MEN β and thus their associated translation control elements are simply relics of their evolutionary pasts. Alternatively, these noncoding RNAs may interact with ribosomes, possibly producing short peptides, as has been shown for other transcripts that were once considered noncoding (Galindo et al. 2007; Ingolia et al. 2011). Reproducible and non-random ribosome footprints were found on MALAT1 in mouse embryonic stem cells (FIG. 6), although no obvious well-conserved open reading frames were identified. It is also possible that MALAT1 and MEN β may simply interact with components of the translation machinery, thereby serving as a "sponge" that prevents the binding of these factors to mRNAs.

Finally, the availability of expression vectors that produce stable cytoplasmic mRNAs without a poly-A tail will allow the in vivo testing of mechanisms for translational control involving this non-template encoded structure. For example, we find that microRNAs regulate the expression of target mRNAs with a poly-A tail as efficiently as mRNAs ending with the MALAT1 triple helix.

In summary, we have identified highly conserved triple helical structures at the 3' ends of the non-polyadenylated MALAT1 and MEN β long noncoding RNAs, which function to prevent RNA decay. When placed downstream of an open reading frame, the triple helices additionally function to promote efficient translation. We have demonstrated that in vitro transcribed mRNA ending in a triple helix also can be translated in vitro. Our findings thus reveal novel paradigms for how transcripts that lack a canonical poly-A tail can be stabilized, regulated, and translated. Considering the complexity of the human transcriptome and the presence of many other long transcripts that may lack a poly-A tail, it is likely that triple helices and other RNA structural elements may have additional unappreciated roles in ensuring transcript stability and regulating gene expression.

REFERENCES

Bartel D P. 2009. MicroRNAs: target recognition and regulatory functions. *Cell* 136: 215-233.

Borah S, Darricarrere N, Darnell A, Myoung J, Steitz J A. 2011. A viral nuclear noncoding RNA binds re-localized poly-A binding protein and is required for late KSHV gene expression. *PLoS Pathog* 7: e1002300.

Box J A, Bunch J T, Tang W, Baumann P. 2008. Spliceosomal cleavage generates the 3' end of telomerase RNA. *Nature* 456: 910-914.

Braun J E, Huntzinger E, Fauser M, Izaurralde E. 2011. GW182 proteins directly recruit cytoplasmic deadenylase complexes to miRNA targets. *Mol Cell* 44: 120-133.

Cheng J, Kapranov P, Drenkow J, Dike S, Brubaker S, Patel S, Long J, Stern D, Tammana H, Helt G et al. 2005. Transcriptional maps of 10 human chromosomes at 5-nucleotide resolution. *Science* 308: 1149-1154.

Choi Y S, Patena W, Leavitt A D, McManus M T. 2012. Widespread RNA 3'-end oligouridylation in mammals. *RNA* 18: 394-401.

Colgan D F, Manley J L. 1997. Mechanism and regulation of mRNA polyadenylation. *Genes Dev* 11: 2755-2766.

Das R, Baker D. 2007. Automated de novo prediction of native-like RNA tertiary structures. *Proc Natl Acad Sci USA* 104: 14664-14669.

Das R, Karanicolas J, Baker D. 2010. Atomic accuracy in predicting and designing noncanonical RNA structure. *Nat Methods* 7: 291-294.

Davis I J, Hsi B L, Arroyo J D, Vargas S O, Yeh Y A, Motyckova G, Valencia P, Perez-Atayde A R, Argani P, Ladanyi M et al. 2003. Cloning of an Alpha-TFEB fusion in renal tumors harboring the t(6;11)(p21;q13) chromosome translocation. *Proc Natl Acad Sci USA* 100: 6051-6056.

Duret L, Chureau C, Samain S, Weissenbach J, Avner P. 2006. The Xist RNA gene evolved in eutherians by pseudogenization of a protein-coding gene. *Science* 312: 1653-1655.

Eissmann M, Gutschner T, Hammerle M, Gunther S, Caudron-Herger M, Gross M, Schirmacher P, Rippe K, Braun T, Zornig M et al. 2012. Loss of the abundant nuclear non-coding RNA MALAT1 is compatible with life and development. *RNA Biol* 9.

Ellis M J, Ding L, Shen D, Luo J, Suman V J, Wallis J W, Van Tine B A, Hoog J, Goiffon R J, Goldstein T C et al. 2012. Whole-genome analysis informs breast cancer response to aromatase inhibition. *Nature* 486: 353-360.

Fabian M R, Mathonnet G, Sundermeier T, Mathys H, Zipprich J T, Svitkin Y V, Rivas F, Jinek M, Wohlschlegel J, Doudna J A et al. 2009. Mammalian miRNA RISC recruits CAF1 and PABP to affect PABP-dependent deadenylation. *Mol Cell* 35: 868-880.

Fechter P, Rudinger-Thirion J, Florentz C, Giege R. 2001. Novel features in the tRNA-like world of plant viral RNAs. *Cell Mol Life Sci* 58: 1547-1561.

Felsenfeld G, Davies D R, Rich A. 1957. Formation of a three-stranded polynucleotide molecule. *J Am Chem Soc* 79: 2023-2024.

Fukaya T, Tomari Y. 2011. PABP is not essential for microRNA-mediated translational repression and deadenylation in vitro. *EMBO J* 30: 4998-5009.

Galindo M I, Pueyo J I, Fouix S, Bishop S A, Couso J P. 2007. Peptides encoded by short ORFs control development and define a new eukaryotic gene family. *PLoS Biol* 5: e106.

Gutschner T, Baas M, Diederichs S. 2011. Noncoding RNA gene silencing through genomic integration of RNA destabilizing elements using zinc finger nucleases. *Genome Res* 21: 1944-1954.

Heo I, Joo C, Kim Y K, Ha M, Yoon M J, Cho J, Yeom K H, Han J, Kim V N. 2009. TUT4 in concert with Lin28 suppresses microRNA biogenesis through pre-microRNA uridylation. *Cell* 138: 696-708.

Houseley J, LaCava J, Tollervey D. 2006. RNA-quality control by the exosome. *Nat Rev Mol Cell Biol* 7: 529-539.

Huntzinger E, Braun J E, Heimstadt S, Zekri L, Izaurralde E. 2010. Two PABPC1-binding sites in GW182 proteins promote miRNA-mediated gene silencing. *EMBO J* 29: 4146-4160.

Hutchinson J N, Ensminger A W, Clemson C M, Lynch C R, Lawrence J B, Chess A. 2007. A screen for nuclear transcripts identifies two linked noncoding RNAs associated with SC35 splicing domains. *BMC Genomics* 8: 39.

Ingolia N T, Lareau L F, Weissman J S. 2011. Ribosome profiling of mouse embryonic stem cells reveals the complexity and dynamics of mammalian proteomes. *Cell* 147: 789-802.

Ji P, Diederichs S, Wang W, Boing S, Metzger R, Schneider P M, Tidow N, Brandt B, Buerger H, Bulk E et al. 2003. MALAT-1, a novel noncoding RNA, and thymosin beta4 predict metastasis and survival in early-stage non-small cell lung cancer. *Oncogene* 22: 8031-8041.

Kirsebom L A. 2007. RNase P RNA mediated cleavage: substrate recognition and catalysis. *Biochimie* 89: 1183-1194.

Klein D J, Ferre-D'Amare A R. 2006. Structural basis of glmS ribozyme activation by glucosamine-6-phosphate. *Science* 313: 1752-1756.

Kuiper R P, Schepens M, Thijssen J, van Asseldonk M, van den Berg E, Bridge J, Schuuring E, Schoenmakers E F, van Kessel A G. 2003. Upregulation of the transcription factor TFEB in t(6;11)(p21;q13)-positive renal cell carcinomas due to promoter substitution. *Hum Mol Genet* 12: 1661-1669.

Lai M C, Yang Z, Zhou L, Zhu Q Q, Xie H Y, Zhang F, Wu L M, Chen L M, Zheng S S. 2011. Long non-coding RNA MALAT-1 overexpression predicts tumor recurrence of hepatocellular carcinoma after liver transplantation. *Med Oncol.* 29: 1810-1816.

Li J, Yang Z, Yu B, Liu J, Chen X. 2005. Methylation protects miRNAs and siRNAs from a 3'-end uridylation activity in *Arabidopsis*. *Curr Biol* 15: 1501-1507.

Lin R, Maeda S, Liu C, Karin M, Edgington T S. 2007. A large noncoding RNA is a marker for murine hepatocellular carcinomas and a spectrum of human carcinomas. *Oncogene* 26: 851-858.

Lutz C S, Moreira A. 2011. Alternative mRNA polyadenylation in eukaryotes: an effective regulator of gene expression. *Wiley Interdiscip Rev RNA* 2: 23-31.

Marzluff W F, Wagner E J, Duronio R J. 2008. Metabolism and regulation of canonical histone mRNAs: life without a poly-A tail. *Nat Rev Genet* 9: 843-854.

Mishima Y, Fukao A, Kishimoto T, Sakamoto H, Fujiwara T, Inoue K. 2012. Translational inhibition by deadenylation-independent mechanisms is central to microRNA-mediated silencing in zebrafish. *Proc Natl Acad Sci USA* 109: 1104-1109.

Mitton-Fry R M, DeGregorio S J, Wang J, Steitz T A, Steitz J A. 2010. Poly-A tail recognition by a viral RNA element through assembly of a triple helix. *Science* 330: 1244-1247.

Miyagawa R, Tano K, Mizuno R, Nakamura Y, Ijiri K, Rakwal R, Shibato J, Masuo Y, Mayeda A, Hirose T et al. 2012. Identification of cis- and trans-acting factors involved in the localization of MALAT-1 noncoding RNA to nuclear speckles. *RNA* 18: 738-751.

Montange R K, Batey R T. 2006. Structure of the S-adenosylmethionine riboswitch regulatory mRNA element. *Nature* 441: 1172-1175.

Moore C L, Sharp P A. 1985. Accurate cleavage and polyadenylation of exogenous RNA substrate. *Cell* 41: 845-855.

Moretti F, Kaiser C, Zdanowicz-Specht A, Hentze M W. 2012. PABP and the poly-A tail augment microRNA repression by facilitated miRISC binding. *Nat Struct Mol Biol* 19: 603-608.

Mukherji S, Ebert M S, Zheng G X, Tsang J S, Sharp P A, van Oudenaarden A. 2011. MicroRNAs can generate thresholds in target gene expression. *Nat Genet* 43: 854-859.

Mullen T E, Marzluff W F. 2008. Degradation of histone mRNA requires oligouridylation followed by decapping and simultaneous degradation of the mRNA both 5' to 3' and 3' to 5'. *Genes Dev* 22: 50-65.

Nakagawa S, Ip J Y, Shioi G, Tripathi V, Zong X, Hirose T, Prasanth K V. 2012. Malat1 is not an essential component of nuclear speckles in mice. *RNA* 18: 1487-1499.

Preker P, Nielsen J, Kammler S, Lykke-Andersen S, Christensen M S, Mapendano C K, Schierup M H, Jensen T H. 2008. RNA exosome depletion reveals transcription upstream of active human promoters. *Science* 322: 1851-1854.

Proudfoot N. 2004. New perspectives on connecting messenger RNA 3' end formation to transcription. *Curr Opin Cell Biol* 16: 272-278.

Qiao F, Cech T R. 2008. Triple-helix structure in telomerase RNA contributes to catalysis. *Nat Struct Mol Biol* 15: 634-640.

Rajaram V, Knezevich S, Bove K E, Perry A, Pfeifer J D. 2007. DNA sequence of the translocation breakpoints in undifferentiated embryonal sarcoma arising in mesenchymal hamartoma of the liver harboring the t(11;19)(q11;q13.4) translocation. *Genes Chromosomes Cancer* 46: 508-513.

Rissland O S, Norbury C J. 2009. Decapping is preceded by 3' uridylation in a novel pathway of bulk mRNA turnover. *Nat Struct Mol Biol* 16: 616-623.

Sachs A B, Davis R W, Kornberg R D. 1987. A single domain of yeast poly-A-binding protein is necessary and sufficient for RNA binding and cell viability. *Mol Cell Biol* 7: 3268-3276.

Serganov A, Patel D J. 2012. Metabolite recognition principles and molecular mechanisms underlying riboswitch function. *Annu Rev Biophys* 41: 343-370.

Serganov A, Yuan Y R, Pikovskaya O, Polonskaia A, Malinina L, Phan A T, Hobartner C, Micura R, Breaker R R, Patel D J. 2004. Structural basis for discriminative regulation of gene expression by adenine- and guanine-sensing mRNAs. Chem Biol 11: 1729-1741.

Shen B, Goodman H M. 2004. Uridine addition after microRNA-directed cleavage. *Science* 306: 997.

Song M G, Kiledjian M. 2007. 3' Terminal oligo U-tract-mediated stimulation of decapping. *RNA* 13: 2356-2365.

Sudarsan N, Lee E R, Weinberg Z, Moy R H, Kim J N, Link K H, Breaker R R. 2008. Riboswitches in eubacteria sense the second messenger cyclic di-GMP. Science 321: 411-413.

Sunwoo H, Dinger M E, Wilusz J E, Amaral P P, Mattick J S, Spector D L. 2009. MEN epsilon/beta nuclear-retained non-coding RNAs are up-regulated upon muscle differentiation and are essential components of paraspeckles. *Genome Res* 19: 347-359.

Tripathi V, Ellis J D, Shen Z, Song D Y, Pan Q, Watt A T, Freier S M, Bennett C F, Sharma A, Bubulya P A et al. 2010. The nuclear-retained noncoding RNA MALAT1 regulates alternative splicing by modulating SR splicing factor phosphorylation. *Mol Cell* 39: 925-938.

Tycowski K T, Shu M D, Borah S, Shi M, Steitz J A. 2012. Conservation of a Triple-Helix-Forming RNA Stability Element in Noncoding and Genomic RNAs of Diverse Viruses. *Cell Rep* 2: 26-32.

Wilusz J E, Freier S M, Spector D L. 2008. 3' end processing of a long nuclear-retained noncoding RNA yields a tRNA-like cytoplasmic RNA. *Cell* 135: 919-932.

Wilusz J E, Spector D L. 2010. An unexpected ending: noncanonical 3' end processing mechanisms. *RNA* 16: 259-266.

Wilusz J E, Sunwoo H, Spector D L. 2009. Long noncoding RNAs: functional surprises from the RNA world. *Genes Dev* 23: 1494-1504.

Wilusz J E, Whipple J M, Phizicky E M, Sharp P A. 2011. tRNAs marked with CCACCA are targeted for degradation. *Science* 334: 817-821.

Wu Q, Kim Y C, Lu J, Xuan Z, Chen J, Zheng Y, Zhou T, Zhang M Q, Wu C I, Wang S M. 2008. Poly A-transcripts expressed in HeLa cells. *PLoS One* 3: e2803.

Wyers F, Rougemaille M, Badis G, Rousselle J C, Dufour M E, Boulay J, Regnault B, Devaux F, Namane A, Seraphin B et al. 2005. Cryptic pol II transcripts are degraded by a nuclear quality control pathway involving a new poly-A polymerase. *Cell* 121: 725-737.

Yang L, Duff M O, Graveley B R, Carmichael G G, Chen L L. 2011a. Genomewide characterization of non-polyadenylated RNAs. *Genome Biol* 12: R16.

Yang L, Lin C, Liu W, Zhang J, Ohgi K A, Grinstein J D, Dorrestein P C, Rosenfeld M G. 2011b. ncRNA- and Pc2 methylation-dependent gene relocation between nuclear structures mediates gene activation programs. *Cell* 147: 773-788.

Zhang B, Arun G, Mao Y S, Lazar Z, Hung G, Bhattacharjee G, Xiao X, Booth C J, Wu J, Zhang C et al. 2012. The lncRNA Malat1 Is Dispensable for Mouse Development but Its Transcription Plays a cis-Regulatory Role in the Adult. *Cell Rep* 2: 111-123.

Zhao J, Hyman L, Moore C. 1999. Formation of mRNA 3' ends in eukaryotes: mechanism, regulation, and interrelationships with other steps in mRNA synthesis. *Microbiol Mol Biol Rev* 63: 405-445.

---

We claim:

1. A hybrid nucleic acid comprising:
   an RNA molecule lacking a poly-A tail, linked to a heterologous RNA stabilizing terminal sequence, wherein the heterologous RNA stabilizing terminal sequence has a triple helix conformation.

2. The hybrid nucleic acid of claim 1, wherein the RNA molecule is a cytoplasmic RNA or a nuclear RNA.

3. The hybrid nucleic acid of claim 1, wherein the RNA molecule is a mRNA which lacks a poly-A tail.

4. The hybrid nucleic acid of claim 1, wherein the RNA molecule is a noncoding RNA.

5. The hybrid nucleic acid of claim 1, wherein the RNA molecule is a eukaryotic RNA.

6. The hybrid nucleic acid of claim 1, wherein the RNA molecule is a mammalian RNA.

7. The hybrid nucleic acid of claim 1, wherein the RNA molecule is a plant RNA.

8. The hybrid nucleic acid of claim 1, wherein the RNA molecule is a human RNA.

9. A hybrid nucleic acid comprising:
   an RNA molecule lacking a poly-A tail, linked to a heterologous RNA stabilizing terminal sequence, wherein the heterologous RNA stabilizing terminal sequence is a MALAT1 terminal sequence.

10. The hybrid nucleic acid of claim 1, wherein the heterologous RNA stabilizing terminal sequence is a MEN β terminal sequence.

11. The hybrid nucleic acid of claim 1, wherein the heterologous RNA stabilizing terminal sequence is a U-rich sequence.

12. The hybrid nucleic acid of claim 1, wherein the heterologous RNA stabilizing terminal sequence is an A-rich sequence.

13. The hybrid nucleic acid of claim 1, wherein the heterologous RNA stabilizing terminal sequence is a U-rich and A-rich sequence.

14. The hybrid nucleic acid of claim 1, wherein the heterologous RNA stabilizing terminal sequence is a C-rich and G-rich sequence.

15. The hybrid nucleic acid of claim 1, wherein the RNA molecule corresponds to a reporter molecule.

16. A vector comprising: a nucleic acid encoding an RNA molecule, a promoter upstream of the nucleic acid encoding the RNA molecule and a terminal nucleic acid sequence downstream of the nucleic acid encoding the RNA molecule, wherein the vector includes a nucleic acid sequence that produces the hybrid nucleic acid of claim 1.

17. The hybrid nucleic acid of claim 1, wherein nucleic acid includes at least one chemical or natural modification.

18. A method for enhancing translation of an RNA, comprising,
   expressing in a cell an isolated cytoplasmic RNA lacking a poly A tail, wherein the cytoplasmic RNA has a 3' terminal sequence effective for enhancing translation of the RNA in the cell, wherein the cytoplasmic RNA is the hybrid nucleic acid of claim 1.

19. A method for expressing an RNA lacking a poly-A tail, comprising:
   expressing in a cell an isolated nucleic acid comprising an RNA having a 3' heterologous terminal sequence and lacking a poly A tail, wherein the RNA is the hybrid nucleic acid of claim 1.

20. A composition comprising:
   an RNA molecule, lacking a poly-A tail, linked to a heterologous RNA stabilizing terminal sequence, formulated in a nanoparticle, wherein the heterologous RNA stabilizing terminal sequence has a triple helix conformation.

21. The composition of claim 20, wherein RNA includes at least one chemical or natural modification.

\* \* \* \* \*